US007816499B2

(12) United States Patent
Richon et al.

(10) Patent No.: US 7,816,499 B2
(45) Date of Patent: Oct. 19, 2010

(54) ANTIBODIES THAT SELECTIVELY BIND HDAC9

(75) Inventors: Victoria M. Richon, Rye, NY (US); Xianbo Zhou, Dobbs Ferry, NY (US); Richard A. Rifkind, New York, NY (US); Paul A. Marks, Washington, CT (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 477 days.

(21) Appl. No.: 11/809,899

(22) Filed: May 31, 2007

(65) Prior Publication Data

US 2008/0221308 A1 Sep. 11, 2008

Related U.S. Application Data

(62) Division of application No. 11/202,268, filed on Aug. 10, 2005, now Pat. No. 7,244,604, which is a division of application No. 10/173,539, filed on Jun. 14, 2002, now Pat. No. 7,063,973.

(60) Provisional application No. 60/298,173, filed on Jun. 14, 2001, provisional application No. 60/311,686, filed on Aug. 10, 2001, provisional application No. 60/316,995, filed on Sep. 4, 2001.

(51) Int. Cl.
*C07K 16/40* (2006.01)

(52) U.S. Cl. ................................................ 530/388.26

(58) Field of Classification Search ....................... None
See application file for complete search history.

(56) References Cited

U.S. PATENT DOCUMENTS

| | | | | |
|---|---|---|---|---|
| 5,659,016 | A | 8/1997 | Nakamura et al. | 530/358 |
| 5,763,182 | A | 6/1998 | Nakamura et al. | 435/6 |
| 6,287,843 | B1 | 9/2001 | Baldwin et al. | 435/252.3 |
| 6,673,587 | B1 | 1/2004 | Evans et al. | 435/196 |
| 7,063,973 | B2 | 6/2006 | Richon et al. | 435/196 |
| 7,244,604 | B2 | 7/2007 | Richon et al. | 435/196 |
| 2001/0010909 | A1 | 8/2001 | Cahoon et al. | 435/6 |
| 2001/0012836 | A1 | 8/2001 | Hu et al. | 514/44 |
| 2003/0161830 | A1 | 8/2003 | Jackson et al. | 424/146.1 |

FOREIGN PATENT DOCUMENTS

| | | | |
|---|---|---|---|
| WO | WO 97/35990 | | 10/1997 |
| WO | WO 00/10583 | | 3/2000 |
| WO | WO 01/18045 | A1 | 3/2001 |
| WO | WO 01/18171 | A3 | 3/2001 |
| WO | WO 01/42437 | A2 | 6/2001 |
| WO | WO 02/36786 | A2 | 5/2002 |
| WO | WO 02/102323 | A2 | 12/2002 |

OTHER PUBLICATIONS

Attwood, Science 290: 471-473, 2000.*
Skolnick et al., Trends in Biotech. 18: 34-39, 2000.*
Lederman et al., Molecular Immunology 28: 1171-1181, 1991.*
Li et al., PNAS 77: 3211-3214, 1980.*
Buggy, et al. "Cloning and Characterization of a Novel Human Histone Deacetylase, HDAC8", *Biochem. J.*, 350:199-205, (2000).
Cress, et al. "Histone Deacetylases, Transcriptional Control, and Cancer", *Journal of Cellular Physiology*, 184:1-16, (2000).
Dangond, et al. "Differential Display Cloning of a Novel Human Histone Deacetylase (HDAC3) cDNA from PHA-activated Immune Cells", *Biochem. Biophys. Res. Commun.*, 243(3):648-652, (1998).
Emiliani, et al. "Characterization of a Human RPD3 Ortholog, HDAC3", *Proc. Natl. Acad. Sci. USA*, 95:2795-2800, (1998).
Fischle, et al. "A New Family of Human Histone Deacetylases Related to *Saccharomyces cerevisiae* HDA1p", *The Journal of Biological Chemistry*, 274(17):11713-11720, (1999).
Grozinger, et al. "Three Proteins Define a Class of Human Histone Deacetylases Related to Yeast HDa1p", *Proc. Natl. Acad. Sci. USA*, 96:4868-4873, (1999).
Hegde, et al. (2000) "EST380989 MAGE Resequences, MAGJ *Homo sapiens* cDNA, mRNA Sequence", Database EMBL Acc. No. AW968913, Abstract.
Hu, et al. "Cloning and Characterization of a Novel Human Class I Histone Deacetylase That Functions as a Transcriptional Repressor", *The Journal of Biological Chemistry*, 275(20):15254-15264, (2000).
Macleod, et al. (2000) "Human Histone Deacetylase HDAC-5 Coding Sequence", Database EMBL Acc. No. AAC89558, Abstract.
Macleod, et al. (2001) "Human Histone Deacetylase HDAC-5 Coding Sequence", Database EMBL Acc. No. AAC89557, Abstract.
Marks, et al. "Historic Deacetylase Inhibitors as New Cancer Drugs", *Curr. Opin. Oncol.*, 13:477-483, (2001).
Marks, et al. "Histone Deacetylases and Cancer: Causes and Therapies", *Nat. Rev. Cancer*, 1:194-202, (2001).
Miska, et al, "HDAC4 Deacetylase Associates With and Represses the MEF2 Transcription Factor". *The EMBO Journal*, 18:5099-5107 (1999).

(Continued)

*Primary Examiner*—Phillip Gambel
(74) *Attorney, Agent, or Firm*—Ivor R. Elrifi; Mintz, Levin, Cohn, Ferris, Glovsky and Popeo, P.C.

(57) ABSTRACT

The present invention features, inter alia, purified antibodies that selectively bind an isolated or recombinant histone deacetylase polypeptide comprising the amino acid sequence as set forth in SEQ ID NO: 2, which comprises a histone deacetylase catalytic domain at amino acids 635 to 953 of SEQ ID NO: 2, purified antibodies that selectively bind a biologically active fragment of the polypeptide of SEQ ID NO: 2, which fragment exhibits histone deacetylase activity, transcription repression activity, and the ability to deacetylate cellular substrates, purified antibodies that selectively bind an isolated or recombinant histone deacetylase polypeptide encoded by a nucleotide sequence as set forth in SEQ ID NO: 1, purified antibodies that selectively bind an isolated or recombinant histone deacetylase polypeptide comprising the amino acid sequence as set forth in SEQ ID NO: 2 lacking a nuclear localization signal, and purified antibodies that selectively bind an isolated or recombinant histone deacetylase polypeptide having at least 95% amino acid sequence identity to SEQ ID NO: 2 and which exhibits histone deacetylase activity, transcription repression activity, and the ability to deacetylate cellular substrates.

5 Claims, 173 Drawing Sheets

OTHER PUBLICATIONS

Nagase, et al. "Prediction of the Coding Sequences of Unidentified Human Genes. XI. The Complete Sequences of 100 New cDNA Clones from Brain Which Code for Large Proteins in vitro", *DNA Research*, 5:277-286, (1998).
Richon, et al. "A Class of Hybrid Polar Inducers of Transformed Cell Differentiation Inhibits Histone Deacetylases", *Proc. Natl. Acad. Sci. USA*, 95:3003-3007 (1998).
Sparrow, et al. "MEF-2 Function is Modified by a Novel Corepressor, MITR", *The EMBO Journal*, 18:5085:5098, (1999).
Van den Wyngaert, et al. "Cloning and Characterization of Human Histone Deacetylase 8", *FEBS Lett.*, 478:77-83, (2000).
Wang, et al. "HDAC4, a Human Histone Deacetylase Related to Yeast HDA1, Is a Transcriptional Corepressor", *Molecular and Cellular Biology*, 19:7816-7827, (1999).
Yang, et al. "A p300/CBP-associated Factor that Competes With the Adenoviral Oncoprotein E1A", *Nature*, 382:319-324, (1996).
Yang et al. "Isolation and Characterization of cDNAs Corresponding to an Additional Member of the Human Histone Deacetylase Gene Family", *The Journal of Biological Chemistry*, 272:28001-28007, (1997).
Zhang, et al. "The Transcriptional Corepressor MITR is a Signal-responsive Inhibitor of Myogenesis", *Proc. Natl. Acad. Sci. USA*, 98:7354-7359, (2001).
Zhang, et al. "Association of COOH-terminal-binding Protein (CtBP) and MEF2-interacting Transcription Repressor (MITR) Contributes to Transcriptional Repression of the MEF2 Transcription Factor", *The Journal of Biological Chemistry*, 276:35-39, (2001).
Zhang et al. "Mus Musculus MEF2-Interacting Transcription Repressor MITR (Mitr) mRNA, Comp. cds", Database EMBLAcc. No. AF324492, (2001) Abstract.
Zhou, et al., "Identification of a Transcriptional Repressor Related to the Noncatalytic Domain of Histone Deacetylases 4 and 5", *Proc. Natl. Acad. Sci. USA*, 97:1056-1061, (2000).
Zhou, et al. "Cloning and Characterization of a Histone Deacetylase, HDAC9", *PNAS*, 98:10572-10577, (2001).
Zhou et al. "Mus Musculus Historic Deacetylase Related Protein mRNA", Database EMBL Acc. No. AF235053, (2001) Abstract.
European Search Report dated Sep. 20, 2005.
Sequence Search Alignment Between Applicants' SEQ ID No. 1 of USP 7,244,604 and SEQ ID No. 1 of USP 6,673,587, Apr. 2006.

* cited by examiner

| FIG. 1A |
|---|
| FIG. 1B |
| FIG. 1C |
| FIG. 1D |
| FIG. 1E |
| FIG. 1F |
| FIG. 1G |
| FIG. 1H |
| FIG. 1I |
| FIG. 1J |
| FIG. 1K |
| FIG. 1L |
| FIG. 1M |
| FIG. 1N |
| FIG. 1O |

HDAC9 3186 bp Coding 151-3186

Exon 1

1 ggggaagaga ggcacagaca cagataggag aagggcaccg gctggagcca cttgcaggac tgagggtttt tgcaacaaaa ccctagcagc ctgaagaact

2

101 ctaagccaga tggggtggct ggacgagagc agctcttggc tcagcaaaga ATGCACAGTA TGATCAGCTC AGTGGATGTG AAGTCAGAAG TTCCTGTGGG 201 CCTGGAGCCC ATCTCACCTT TAGACCTAAG GACAGACCTC AGGATGATGA TGCCCGTGGT GGACCCTGTT GTCCGTGAGA AGCAATTGCA GCAGGAATTA

3

301 CTTCTTATCC AGCAGCAGCA ACAAATCCAG AAGCAGCTTC TGATAGCAGA GTTTCAGAAA CAGCATGAGA ACTTGACACG GCAGCACCAG GCTCAGCTTC

4

401 AGGAGCATAT CAAGGAACTT CTAGCCATAA AACAGCAACA AGAACTCCTA GAAAAGGAGC AGAAACTGGA GCAGCAGAGG CAAGAACAGG AAGTAGAGAG

501 GCATCGCAGA GAACAGCAGC TTCCTCCTCT CAGAGGCAAA GATAGAGGAC GAGAAAGGGC AGTGGCAAGT ACAGAAGTAA AGCAGAAGCT TCAAGAGTTC

5

601 CTACTGAGTA AATCAGCAAC GAAAGACACT CCAACTAATG GAAAAAATCA TTCCGTGAGC CGCCATCCCA AGCTCTGGTA CACGGCTGCC CACCACACAT

6

701 CATTGGATCA AAGCTCTCCA CCCCTTAGTG GAACATCTCC ATCCTACAAG TACACATTAC CAGGAGCACA AGATGCAAAG GATGATTTCC CCCTTCGAAA

7

801 AACTGCCTCT GAGCCCAACT TGAAGGTGCG GTCCAGGTTA AAACAGAAAG TGGCAGAGAG GAGAAGCAGC CCCTTACTCA GGCGGAAGGA TGGAAATGTT

FIG. 1A

```
                                                        8
901  GTCACTTCAT TCAAGAAGCG AATGTTTGAG GTGACAGAAT CCTCAGTCAG TAGCAGTTCT CCAGGCTCTG GTCCCAGTTC ACCAAACAAT GGGCCAACTG
                                                                                 9
001  GAAGTGTTAC TGAAAATGAG ACTTCGGTTT TGCCCCCTAC CCCTCATGCC GAGCAAATGG TTTCACAGCA ACGCATTCTA ATTCATGAAG ATTCCATGAA

101  CCTGCTAAGT CTTTATACCT CTCCTTCTTT GCCCAACATT ACCTTGGGGC TTCCCGCAGT GCCATCCCAG CTCAATGCTT CGAATTCACT CAAAGAAAAG

201  CAGAAGTGTG AGACGCAGAC GCTTAGGCAA GGTGTTCCTC TGCCTGGGCA GTATGGAGGC AGCATCCCGG CATCTTCCAG CCACCCTCAT GTTACTTTAG
                                                                   10
301  AGGGAAAGCC ACCCAACAGC AGCCACCAGG CTCTCCTGCA GCATTTATTA TTGAAAGAAC AAATGCGACA GCAAAAGCTT CTTGTAGCTG GTGGAGTTCC

401  CTTACATCCT CAGTCTCCCT TGGCAACAAA AGAGAGAATT TCACCTGGCA TTAGAGGTAC CCACAAATTG CCCCGTCACA GACCCCTGAA CCGAACCCAG
                                                       11
501  TCTGCACCTT TGCCTCAGAG CACGTTGGCT CAGCTGGTCA TTCAACAGCA ACACCAGCAA TTCTTGGAGA AGCAGAAGCA ATACCAGCAG CAGATCCACA

601  TGAACAAACT GCTTTCGAAA TCTATTGAAC AACTGAAGCA ACCAGGCAGT CACCTTGAGG AAGCAGAGGA AGAGCTTCAG GGGGACCAGG CGATGCAGGA
                                                   12
701  AGACAGAGCG CCCTCTAGTG GCAACAGCAC TAGGAGCGAC AGCAGTGCTT GTGTGGATGA CACACTGGGA CAAGTTGGGG CTGTGAAGGT CAAGGAGGAA

801  CCAGTGGACA GTGATGAAGA TGCTCAGATC CAGGAAATGG AATCTGGGGA GCAGGCTGCT TTTATGCAAC AGCCTTTCCT GGAACCCACG CACACACGTG
```

FIG. 1B

```
901 CGCTCTCTGT GCGCCAAGCT CCGCTGGCTG CGGTTGGCAT GGATGGATTA GAGAAACACC GTCTCGTCTC CAGGACTCAC TCTTCCCCTG CTGCCTCTGT
                                  14
001 TTTACCTCAC CCAGCAATGG ACCGCCCCCT CCAGCCTGGC TCTGCAACTG GAATTGCCTA TGACCCCTTG ATGCTGAAAC ACCAGTGCGT TTGTGGCAAT
                                                                     15
101 TCCACCACCC ACCCTGAGCA TGCTGGACGA ATACAGAGTA TCTGGTCACG ACTGCAAGAA ACTGGGCTGC TAAATAAATG TGAGCGAATT CAAGGTCGAA
                                                 16
201 AAGCCAGCCT GGAGGAAATA CAGCTTGTTC ATTCTGAACA TCACTCACTG TTGTATGGCA CCAACCCCCT GGACGGACAG AAGCTGGACC CCAGGATACT
                                     17
301 CCTAGGTGAT GACTCTCAAA AGTTTTTTTC CTCATTACCT TGTGGTGGAC TTGGGGTGGA CAGTGACACC ATTTGGAATG AGCTACACTC GTCCGGTGCT
                                      18                                                             19
401 GCACGCATGG CTGTTGGCTG TGTCATCGAG CTGGCTTCCA AAGTGGCCTC AGGAGAGCTG AAGAATGGGT TTGCTGTTGT GAGGCCCCCT GGCCATCACG
                                                                 20
501 CTGAAGAATC CACAGCCATG GGGTTCTGCT TTTTTAATTC AGTTGCAATT ACCGCCAAAT ACTTGAGAGA CCAACTAAAT ATAAGCAAGA TATTGATTGT
                                                    21
601 AGATCTGGAT GTTCACCATG GAAACGGTAC CCAGCAGGCC TTTTATGCTG ACCCCAGCAT CCTGTACATT TCACTCCATC GCTATGATGA AGGGAACTTT
                                                                      23
701 TTCCCTGGCA GTGGAGCCCC AAATGAGGTT GGAACAGGCC TTGGAGAAGG GTACAATATA AATATTGCCT GGACAGGTGG CCTTGATCCT CCCATGGGAG
                                                      24
801 ATGTTGAGTA CCTTGAAGCA TTCAGGAcca TCGTGAAGCC TGTGGCCAAA GAGTTTGATC CAGACATGGT CTTAGTATCT GCTGGATTTG ATGCATTGGA
                                                                           25
901 AGGCCACACC CCTCCTCTAG GAGGGTACAA AGTGACGGCA AAATGTTTTG GTCATTTGAC GAAGCAATTG ATGACATTGG CTGATGGACG TGTGGTGTTG
001 GCTCTAGAAG GAGGACATGA TCTCACAGCC ATCTGTGATG CATCAGAAGC CTGTGTAAAT GCCCTTCTAG GAAATGAGCT GGAGCCACTT GCAGAAGATA
                                                     26
101 TTCTCCACCA AAGCCCGAAT ATGAATGCTG TTATTTCTTT ACAGAAGATC ATTGAAATTC AAAGTATGTC TTTAAAGTTC TCTTAA
```

FIG. 1C

HDAC9a 3499 bp (Coding 151-2790)
Exon
    1

1 ggggaagaga ggcacagaca cagataggag aagggcaccg gctggagcca cttgcaggac tgagggtttt tgcaacaaaa ccctagcagc ctgaagaact
                                                                                                    2
101 ctaagccaga tggggtggct ggacgagagc agtcttggc tcagcaaaga ATGCACAGTA TGATCAGCTC AGTGGATGTG AAGTCAGAAG TTCCTGTGGG
                                                                     3
201 CCTGGAGCCC ATCTTCACCTT TAGACCTAAG GACAGACCTC AGGATGATGA TGCCCGTGGT GGACCCTGTT GTCCGTGAGA AGCAATTGCA GCAGGAATTA
301 CTTCTTATCC AGCAGCAGCA ACAAATCCAG AAGCAGCTTC TGATAGCAGA GTTTCAGAAA CAGCATGAGA ACTTGACACG GCAGCAGAGG AAGTAGAGAG
                       4
401 AGGAGCATAT CAAGGAACTT CTAGCCATAA AACAGCAACA AGAACTCCTA GAAAAGGAGC AGAAACTGGA GCAGCAGAGG CAAGAACAGG AAGTAGAGAG
501 GCATCGGCGA GAACAGCAGC TTCCTCCTCT CAGAGGCAAA GATAGAGGAC GAGAAAGGGC AGTGGCAAGT ACAGAAGTAA AGCAGAAGCT TCAAGAGTTC

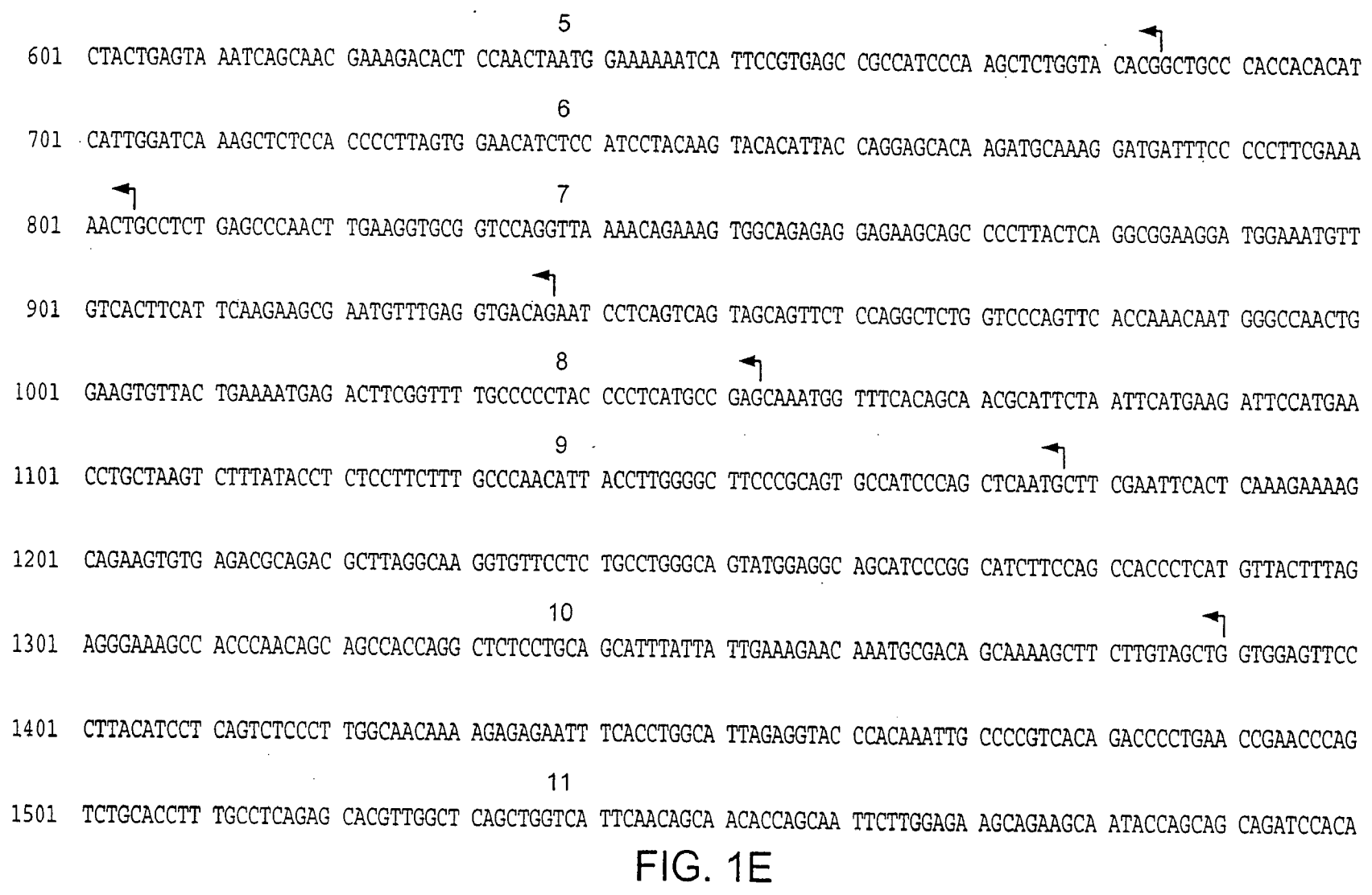

601 CTACTGAGTA AATCAGCAAC GAAAGACACT CCAACTAATG GAAAAAATCA TTCCGTGAGC CGCCATCCCA AGCTCTGGTA CACGGCTGCC CACCACACAT

6

701 CATTGGATCA AAGCTCTCCA CCCCTTAGTG GAACATCTCC ATCCTACAAG TACACATTAC CAGGAGCACA AGATGCAAAG GATGATTTCC CCCTTCGAAA

7

801 AACTGCCTCT GAGCCCAACT TGAAGGTGCG GTCCAGGTTA AAACAGAAAG TGGCAGAGAG GAGAAGCAGC CCCTTACTCA GGCGGAAGGA TGGAAATGTT

901 GTCACTTCAT TCAAGAAGCG AATGTTTGAG GTGACAGAAT CCTCAGTCAG TAGCAGTTCT CCAGGCTCTG GTCCCAGTTC ACCAAACAAT GGGCCAACTG

8

1001 GAAGTGTTAC TGAAAATGAG ACTTCGGTTT TGCCCCCTAC CCCTCATGCC GAGCAAATGG TTTCACAGCA ACGCATTCTA ATTCATGAAG ATTCCATGAA

9

1101 CCTGCTAAGT CTTTATACCT CTCCTTCTTT GCCCAACATT ACCTTGGGGC TTCCCGCAGT GCCATCCCAG CTCAATGCTT CGAATTCACT CAAAGAAAAG

1201 CAGAAGTGTG AGACGCAGAC GCTTAGGCAA GGTGTTCCTC TGCCTGGGCA GTATGGAGGC AGCATCCCGG CATCTTCCAG CCACCCTCAT GTTACTTTAG

10

1301 AGGGAAAGCC ACCCAACAGC AGCCACCAGG CTCTCCTGCA GCATTTATTA TTGAAAGAAC AAATGCGACA GCAAAAGCTT CTTGTAGCTG GTGGAGTTCC

1401 CTTACATCCT CAGTCTCCCT TGGCAACAAA AGAGAGAATT TCACCTGGCA TTAGAGGTAC CCACAAATTG CCCCGTCACA GACCCCTGAA CCGAACCCAG

11

1501 TCTGCACCTT TGCCTCAGAG CACGTTGGCT CAGCTGGTCA TTCAACAGCA ACACCAGCAA TTCTTGGAGA AGCAGAAGCA ATACCAGCAG CAGATCCACA

FIG. 1E

```
601  TGAACAAACT GCTTTCGAAA TCTATTGAAC AACTGAAGCA ACCAGGCAGT CACCTTGAGG AAGCAGAGGA AGAGCTTCAG GGGGACCAGG CGATGCAGGA
                                    12
701  AGACAGAGCG CCCTCTAGTG GCAACAGCAC TAGGAGCGAC AGCAGTGCTT GTGTGGATGA CACACTGGGA CAAGTTGGGG CTGTGAAGGT CAAGGAGGAA

801  CCAGTGGACA GTGATGAAGA TGCTCAGATC CAGGAAATGG AATCTGGGGA GCAGGCTGCT TTTATGCAAC AGCCTTTCCT GGAACCCACG CACACACGTG
                                    14
901  CGCTCTCTGT GCGCCAAGCT CCGCTGGCTG CGGTTGGCAT GGATGGATTA GAGAAACACC GTCTCGTCTC CAGGACTCAC TCTTCCCCTG CTGCCTCTGT

001  TTTACCTCAC CCAGCAATGG ACCGCCCCCT CCAGCCTGGC TCTGCAACTG GAATTGCCTA TGACCCCTTG ATGCTGAAAC ACCAGTGCGT TTGTGGCAAT
                                    15
101  TCCACCACCC ACCCTGAGCA TGCTGGACGA ATACAGAGTA TCTGGTCACG ACTGCAAGAA ACTGGGCTGC TAAATAAATG TGAGCGAATT CAAGGTCGAA
                                    16
201  AAGCCAGCCT GGAGGAAATA CAGCTTGTTC ATTCTGAACA TCACTCACTG TTGTATGGCA CCAACCCCCT GGACGGACAG AAGCTGGACC CCAGGATACT
                                    17
301  CCTAGGTGAT GACTCTCAAA AGTTTTTTTC CTCATTACCT TGTGGTGGAC TTGGGGTGGA CAGTGACACC ATTTGGAATG AGCTACACTC GTCCGGTGCT
                                    18                                            19
401  GCACGCATGG CTGTTGGCTG TGTCATCGAG CTGGCTTCCA AAGTGGCCTC AGGAGAGCTG AAGAATGGGT TTGCTGTTGT GAGGCCCCCT GGCCATCACG
                                    20
501  CTGAAGAATC CACAGCCATG GGGTTCTGCT TTTTTAATTC AGTTGCAATT ACCGCCAAAT ACTTGAGAGA CCAACTAAAT ATAAGCAAGA TATTGATTGT
```

2601 AGATCTGGAT GTTCACCATG GAAACGGTAC CCAGCAGGCC TTTTATGCTG ACCCCAGCAT CCTGTACATT TCACTCCATC GCTATGATGA AGGGAACTTT

2701 TTCCCTGGCA GTGGAGCCCC AAATGAGGTT CGGTTTATTT CTTTAGAGCC CCACTTTTAT TTGTATCTTT CAGGTAATTG CATTGCATGA ttacccctaa

STOP CODON

22

2801 ttttcttgtc ctttgctggt gttttaaatt acacgagatt actgaattgt cccatgggac caagaaccag tgcagaacaa gtgcataacc cagagcactg 2901 tttgtcaggg aaggttgggc tgatttgatg tgttgtttga tgtttatttc aagagctccc atgtgcttgt tttcctctct tcttgctttc ttccatttgc

23

3001 tctcttctct gcccaccgtg gtgtgtcttt ctcttcccag gttggaacag gccttggaga agggtacaat ataaatattg cctggacagg tggccttgat 3101 cctcccatgg gagatgttga gtaccttgaa gcattcagga ccatcgtgaa gcctgtggcc aaagagtttg atccagacat ggtcttagta tctgctggat

24

3201 ttgatgcatt ggaaggccac acccctcctc taggagggta caaagtgacg gcaaaatgtt ttggtcattt gacgaagcaa ttgatgacat tggctgatgg

25

3301 acgtgtggtg ttggctctag aaggaggaca tgatctcaca gccatctgtg atgcatcaga agcctgtgta aatgcccttc taggaaatga gctggagcca

26

3401 cttgcagaag atattctcca ccaaagcccg aatatgaatg ctgttatttc tttacagaag atcattgaaa ttcaaagtat gtctttaaag ttctcttaa

FIG. 1G

```
>HDRP (deltaNLS)
   ·1  ggggaagaga ggcacagaca cagataggag aagggcaccg gctggagcca
   51  cttgcaggac tgagggtttt tgcaacaaaa ccctagcagc ctgaagaact
  101  ctaagccaga tggggtggct ggacgagagc agctcttggc tcagcaaaga
  151  atgcacagta tgatcagctc agtggatgtg aagtcagaag ttcctgtggg
  201  cctggagccc atctcacctt tagacctaag gacagacctc aggatgatga
  251  tgcccgtggt ggaccctgtt gtccgtgaga agcaattgca gcaggaatta
  301  cttcttatcc agcagcagca acaaatccag aagcagcttc tgatagcaga
  351  gtttcagaaa cagcatgaga acttgacacg gcagcaccag gctcagcttc
  401  aggagcatat caaggaactt ctagccataa aacagcaaca agaactccta
  451  gaaaaggagc agaaactgga gcagcagagg caagaacagg aagtagagag
  501  gcatcgcaga gaacagcagc ttcctcctct cagaggcaaa gatagaggac
  551  gagaaagggc agtggcaagt acagaagtaa agcagaagct tcaagagttc
  601  ctactgagta aatcagcaac gaaagacact ccaactaatg gaaaaaatca
  651  ttccgtgagc cgccatccca agctctggta cacggctgcc caccacacat
  701  cattggatca aagctctcca ccccttagtg gaacatctcc atcctacaag
  751  tacacattac caggagcaca agatgcaaag gatgatttcc cccttcgaaa
  801  aactgaatcc tcagtcagta gcagttctcc aggctctggt cccagttcac
  851  caaacaatgg gccaactgga agtgttactg aaaatgagac ttcggttttg
  901  ccccctaccc ctcatgccga gcaaatggtt tcacagcaac gcattctaat
  951  tcatgaagat tccatgaacc tgctaagtct ttatacctct ccttctttgc
 1001  ccaacattac cttggggctt cccgcagtgc catcccagct caatgcttcg
```

FIG. 1H

```
1051  aattcactca aagaaaagca gaagtgtgag acgcagacgc ttaggcaagg
1101  tgttcctctg cctgggcagt atggaggcag catcccggca tcttccagcc
1151  accctcatgt tactttagag ggaaagccac ccaacagcag ccaccaggct
1201  ctcctgcagc atttattatt gaaagaacaa atgcgacagc aaaagcttct
1251  tgtagctggt ggagttccct tacatcctca gtctcccttg gcaacaaaag
1301  agagaatttc acctggcatt agaggtaccc acaaattgcc ccgtcacaga
1351  cccctgaacc gaacccagtc tgcacctttg cctcagagca cgttggctca
1401  gctggtcatt caacagcaac accagcaatt cttggagaag cagaagcaat
1451  accagcagca gatccacatg aacaaactgc tttcgaaatc tattgaacaa
1501  ctgaagcaac caggcagtca ccttgaggaa gcagaggaag agcttcaggg
1551  ggaccaggcg atgcaggaag acagagcgcc ctctagtggc aacagcacta
1601  ggagcgacag cagtgcttgt gtggatgaca cactgggaca agttggggct
1651  gtgaaggtca aggaggaacc agtggacagt gatgaagatg ctcagatcca
1701  ggaaatggaa tctggggagc aggctgcttt tatgcaacag gtaataggca
1751  aagatttagc tccaggattt gtaattaaag tcattatctg a
```

FIG. 1I

```
>HDAC9 (deltaNLS)
   1 ggggaagaga ggcacagaca cagataggag aagggcaccg gctggagcca
  51 cttgcaggac tgagggtttt tgcaacaaaa ccctagcagc ctgaagaact
 101 ctaagccaga tggggtggct ggacgagagc agctcttggc tcagcaaaga
 151 atgcacagta tgatcagctc agtggatgtg aagtcagaag ttcctgtggg
 201 cctggagccc atctcacctt tagacctaag gacagacctc aggatgatga
 251 tgcccgtggt ggaccctgtt gtccgtgaga agcaattgca gcaggaatta
 301 cttcttatcc agcagcagca acaaatccag aagcagcttc tgatagcaga
 351 gtttcagaaa cagcatgaga acttgacacg gcagcaccag gctcagcttc
 401 aggagcatat caaggaactt ctagccataa aacagcaaca agaactccta
 451 gaaaaggagc agaaactgga gcagcagagg caagaacagg aagtagagag
 501 gcatcgcaga gaacagcagc ttcctcctct cagaggcaaa gatagaggac
 551 gagaaagggc agtggcaagt acagaagtaa agcagaagct tcaagagttc
 601 ctactgagta aatcagcaac gaaagacact ccaactaatg gaaaaaatca
 651 ttccgtgagc cgccatccca agctctggta cacggctgcc caccacacat
 701 cattggatca aagctctcca ccccttagtg gaacatctcc atcctacaag
 751 tacacattac caggagcaca agatgcaaag gatgatttcc cccttcgaaa
 801 aactgaatcc tcagtcagta gcagttctcc aggctctggt cccagttcac
 851 caaacaatgg gccaactgga agtgttactg aaaatgagac ttcggttttg
 901 cccccctaccc ctcatgccga gcaaatggtt tcacagcaac gcattctaat
 951 tcatgaagat tccatgaacc tgctaagtct ttatacctct ccttctttgc
1001 ccaacattac cttggggctt cccgcagtgc catcccagct caatgcttcg
1051 aattcactca aagaaaagca gaagtgtgag acgcagacgc ttaggcaagg
1101 tgttcctctg cctgggcagt atggaggcag catcccggca tcttccagcc
```

FIG. 1J

| | | | | | |
|---|---|---|---|---|---|
| 1151 | accctcatgt | tactttagag | ggaaagccac | ccaacagcag | ccaccaggct |
| 1201 | ctcctgcagc | atttattatt | gaaagaacaa | atgcgacagc | aaaagcttct |
| 1251 | tgtagctggt | ggagttccct | tacatcctca | gtctcccttg | gcaacaaaag |
| 1301 | agagaatttc | acctggcatt | agaggtaccc | acaaattgcc | ccgtcacaga |
| 1351 | cccctgaacc | gaacccagtc | tgcacctttg | cctcagagca | cgttggctca |
| 1401 | gctggtcatt | caacagcaac | accagcaatt | cttggagaag | cagaagcaat |
| 1451 | accagcagca | gatccacatg | aacaaactgc | tttcgaaatc | tattgaacaa |
| 1501 | ctgaagcaac | caggcagtca | ccttgaggaa | gcagaggaag | agcttcaggg |
| 1551 | ggaccaggcg | atgcaggaag | acagagcgcc | ctctagtggc | aacagcacta |
| 1601 | ggagcgacag | cagtgcttgt | gtggatgaca | cactgggaca | agttggggct |
| 1651 | gtgaaggtca | aggaggaacc | agtggacagt | gatgaagatg | ctcagatcca |
| 1701 | ggaaatggaa | tctggggagc | aggctgcttt | tatgcaacag | cctttcctgg |
| 1751 | aacccacgca | cacacgtgcg | ctctctgtgc | gccaagctcc | gctggctgcg |
| 1801 | gttggcatgg | atggattaga | gaaacaccgt | ctcgtctcca | ggactcactc |
| 1851 | ttcccctgct | gcctctgttt | tacctcaccc | agcaatggac | cgccccctcc |
| 1901 | agcctggctc | tgcaactgga | attgcctatg | accccttgat | gctgaaacac |
| 1951 | cagtgcgttt | gtggcaattc | caccacccac | cctgagcatg | ctggacgaat |
| 2001 | acagagtatc | tggtcacgac | tgcaagaaac | tgggctgcta | aataaatgtg |
| 2051 | agcgaattca | aggtcgaaaa | gccagcctgg | aggaaataca | gcttgttcat |
| 2101 | tctgaacatc | actcactgtt | gtatggcacc | aaccccctgg | acggacagaa |
| 2151 | gctggacccc | aggatactcc | taggtgatga | ctctcaaaag | tttttttcct |
| 2201 | cattaccttg | tggtggactt | ggggtggaca | gtgacaccat | ttggaatgag |
| 2251 | ctacactcgt | ccggtgctgc | acgcatggct | gttggctgtg | tcatcgagct |
| 2301 | ggcttccaaa | gtggcctcag | gagagctgaa | gaatgggttt | gctgttgtga |
| 2351 | ggccccctgg | ccatcacgct | gaagaatcca | cagccatggg | gttctgcttt |
| 2401 | tttaattcag | ttgcaattac | cgccaaatac | ttgagagacc | aactaaatat |

FIG. 1K

```
2451  aagcaagata ttgattgtag atctggatgt tcaccatgga aacggtaccc
2501  agcaggcctt ttatgctgac cccagcatcc tgtacatttc actccatcgc
2551  tatgatgaag ggaacttttt ccctggcagt ggagccccaa atgaggttgg
2601  aacaggcctt ggagaagggt acaatataaa tattgcctgg acaggtggcc
2651  ttgatcctcc catgggagat gttgagtacc ttgaagcatt caggaccatc
2701  gtgaagcctg tggccaaaga gtttgatcca gacatggtct tagtatctgc
2751  tggatttgat gcattggaag gccacacccc tcctctagga gggtacaaag
2801  tgacggcaaa atgttttggt catttgacga agcaattgat gacattggct
2851  gatggacgtg tggtgttggc tctagaagga ggacatgatc tcacagccat
2901  ctgtgatgca tcagaagcct gtgtaaatgc ccttctagga aatgagctgg
2951  agccacttgc agaagatatt ctccaccaaa gcccgaatat gaatgctgtt
3001  atttctttac agaagatcat tgaaattcaa agtatgtctt taaagttctc
3051  ttaa
```

FIG. 1L

```
>HDAC9a (deltaNLS)
   1  ggggaagaga ggcacagaca cagataggag aagggcaccg gctggagcca
  51  cttgcaggac tgagggtttt tgcaacaaaa ccctagcagc ctgaagaact
 101  ctaagccaga tggggtggct ggacgagagc agctcttggc tcagcaaaga
 151  atgcacagta tgatcagctc agtggatgtg aagtcagaag ttcctgtggg
 201  cctggagccc atctcacctt tagacctaag gacagacctc aggatgatga
 251  tgcccgtggt ggaccctgtt gtccgtgaga agcaattgca gcaggaatta
 301  cttcttatcc agcagcagca acaaatccag aagcagcttc tgatagcaga
 351  gtttcagaaa cagcatgaga acttgacacg gcagcaccag gctcagcttc
 401  aggagcatat caaggaactt ctagccataa aacagcaaca agaactccta
 451  gaaaaggagc agaaactgga gcagcagagg caagaacagg aagtagagag
 501  gcatcgcaga gaacagcagc ttcctcctct cagaggcaaa gatagaggac
 551  gagaaagggc agtggcaagt acagaagtaa agcagaagct tcaagagttc
 601  ctactgagta aatcagcaac gaaagacact ccaactaatg gaaaaaatca
 651  ttccgtgagc cgccatccca agctctggta cacggctgcc caccacacat
 701  cattggatca aagctctcca ccccttagtg gaacatctcc atcctacaag
 751  tacacattac caggagcaca agatgcaaag gatgatttcc cccttcgaaa
 801  aactgaatcc tcagtcagta gcagttctcc aggctctggt cccagttcac
 851  caaacaatgg gccaactgga agtgttactg aaaatgagac ttcggttttg
 901  ccccctaccc ctcatgccga gcaaatggtt tcacagcaac gcattctaat
 951  tcatgaagat tccatgaacc tgctaagtct ttatacctct ccttctttgc
1001  ccaacattac cttggggctt cccgcagtgc catcccagct caatgcttcg
1051  aattcactca aagaaaagca gaagtgtgag acgcagacgc ttaggcaagg
1101  tgttcctctg cctgggcagt atggaggcag catcccggca tcttccagcc
1151  accctcatgt tactttagag ggaaagccac ccaacagcag ccaccaggct
```

FIG. 1M

```
1201  ctcctgcagc atttattatt gaaagaacaa atgcgacagc aaaagcttct
1251  tgtagctggt ggagttccct tacatcctca gtctcccttg gcaacaaaag
1301  agagaatttc acctggcatt agaggtaccc acaaattgcc ccgtcacaga
1351  cccctgaacc gaacccagtc tgcacctttg cctcagagca cgttggctca
1401  gctggtcatt caacagcaac accagcaatt cttggagaag cagaagcaat
1451  accagcagca gatccacatg aacaaactgc tttcgaaatc tattgaacaa
1501  ctgaagcaac caggcagtca ccttgaggaa gcagaggaag agcttcaggg
1551  ggaccaggcg atgcaggaag acagagcgcc ctctagtggc aacagcacta
1601  ggagcgacag cagtgcttgt gtggatgaca cactgggaca agttggggct
1651  gtgaaggtca aggaggaacc agtggacagt gatgaagatg ctcagatcca
1701  ggaaatggaa tctggggagc aggctgcttt tatgcaacag cctttcctgg
1751  aacccacgca cacacgtgcg ctctctgtgc gccaagctcc gctggctgcg
1801  gttggcatgg atggattaga gaaacaccgt ctcgtctcca ggactcactc
1851  ttcccctgct gcctctgttt tacctcaccc agcaatggac cgccccctcc
1901  agcctggctc tgcaactgga attgcctatg accccttgat gctgaaacac
1951  cagtgcgttt gtggcaattc caccacccac cctgagcatg ctggacgaat
2001  acagagtatc tggtcacgac tgcaagaaac tgggctgcta aataaatgtg
2051  agcgaattca aggtcgaaaa gccagcctgg aggaaataca gcttgttcat
2101  tctgaacatc actcactgtt gtatggcacc aaccccctgg acggacagaa
2151  gctggacccc aggatactcc taggtgatga ctctcaaaag tttttttcct
2201  cattaccttg tggtggactt ggggtggaca gtgacaccat ttggaatgag
2251  ctacactcgt ccggtgctgc acgcatggct gttggctgtg tcatcgagct
2301  ggcttccaaa gtggcctcag gagagctgaa gaatgggttt gctgttgtga
2351  ggccccctgg ccatcacgct gaagaatcca cagccatggg gttctgcttt
2401  tttaattcag ttgcaattac cgccaaatac ttgagagacc aactaaatat
```

FIG. 1N

```
2451  aagcaagata ttgattgtag atctggatgt tcaccatgga aacggtaccc
2501  agcaggcctt ttatgctgac cccagcatcc tgtacatttc actccatcgc
2551  tatgatgaag ggaacttttt ccctggcagt ggagccccaa atgaggttcg
2601  gtttatttct ttagagcccc acttttattt gtatctttca ggtaattgca
2651  ttgcatgatt accccctaatt ttcttgtcct ttgctggtgt tttaaattac
2701  acgagattac tgaattgtcc catgggacca agaaccagtg cagaacaagt
2751  gcataaccca gagcactgtt tgtcagggaa ggttgggctg atttgatgtg
2801  ttgtttgatg tttatttcaa gagctcccat gtgcttgttt tcctctcttc
2851  ttgctttctt ccatttgctc tcttctctgc ccaccgtggt gtgtctttct
2901  cttcccaggt tggaacaggc cttggagaag ggtacaatat aaatattgcc
2951  tggacaggtg gccttgatcc tcccatggga gatgttgagt accttgaagc
3001  attcaggacc atcgtgaagc ctgtggccaa agagtttgat ccagacatgg
3051  tcttagtatc tgctggattt gatgcattgg aaggccacac ccctcctcta
3101  ggagggtaca aagtgacggc aaaatgtttt ggtcatttga cgaagcaatt
3151  gatgacattg gctgatggac gtgtggtgtt ggctctagaa ggaggacatg
3201  atctcacagc catctgtgat gcatcagaag cctgtgtaaa tgcccttcta
3251  ggaaatgagc tggagccact tgcagaagat attctccacc aaagcccgaa
3301  tatgaatgct gttatttctt tacagaagat cattgaaatt caaagtatgt
3351  ctttaaagtt ctcttaa
```

FIG. 1O

| |
|---|
| FIG. 2A |
| FIG. 2B |
| FIG. 2C |
| FIG. 2D |
| FIG. 2E |

FIG. 2

>HDAC9 (1011 amino acids)
MHSMISSVDVKSEVPVGLEPISPLDLRTDLRMMMPVVDPVVREKQLQQELLLIQQQQQI
QKQLLIAEFQKQHENLTRQHQAQLQEHIKELLAIKQQQELLEKEQKLEQQRQEQEVERH
RREQQLPPLRGKDRGRERAVASTEVKQKLQEFLLSKSATKDTPTNGKNHSVSRHPKLWY
TAAHHTSLDQSSPPLSGTSPSYKYTLPGAQDAKDDFPLRKTASEPNLKVRSRLKQKVAE
RRSSPLLRRKDGNVVTSFKKRMFEVTESSVSSSSPGSGPSSPNNGPTGSVTENETSVLP
PTPHAEQMVSQQRILIHEDSMNLLSLYTSPSLPNITLGLPAVPSQLNASNSLKEKQKCE
TQTLRQGVPLPGQYGGSIPASSSHPHVTLEGKPPNSSHQALLQHLLLKEQMRQQKLLVA
GGVPLHPQSPLATKERISPGIRGTHKLPRHRPLNRTQSAPLPQSTLAQLVIQQQHQQFL
EKQKQYQQQIHMNKLLSKSIEQLKQPGSHLEEAEEELQGDQAMQEDRAPSSGNSTRSDS
SACVDDTLGQVGAVKVKEEPVDSDEDAQIQEMESGEQAAFMQQPFLEPTHTRALSVRQA
PLAAVGMDGLEKHRLVSRTHSSPAASVLPHPAMDRPLQPGSATGIAYDPLMLKHQCVCG
NSTTHPEHAGRIQSIWSRLQETGLLNKCERIQGRKASLEEIQLVHSEHHSLLYGTNPLD
GQKLDPRILLGDDSQKFFSSLPCGGLGVDSDTIWNELHSSGAARMAVGCVIELASKVAS
GELKNGFAVVRPPGHHAEESTAMGFCFFNSVAITAKYLRDQLNISKILIVDLDVHHGNG
TQQAFYADPSILYISLHRYDEGNFFPGSGAPNEVGTGLGEGYNINIAWTGGLDPPMGDV
EYLEAFRTIVKPVAKEFDPDMVLVSAGFDALEGHTPPLGGYKVTAKCFGHLTKQLMTLA
DGRVVLALEGGHDLTAICDASEACVNALLGNELEPLAEDILHQSPNMNAVISLQKIIEI
QSMSLKFS

FIG. 2A

>HDAC9a (879 amino acids)
MHSMISSVDVKSEVPVGLEPISPLDLRTDLRMMMPVVDPVVREKQLQQELLLIQQQQQI
QKQLLIAEFQKQHENLTRQHQAQLQEHIKELLAIKQQQELLEKEQKLEQQRQEQEVERH
RREQQLPPLRGKDRGRERAVASTEVKQKLQEFLLSKSATKDTPTNGKNHSVSRHPKLWY
TAAHHTSLDQSSPPLSGTSPSYKYTLPGAQDAKDDFPLRKTASEPNLKVRSRLKQKVAE
RRSSPLLRRKDGNVVTSFKKRMFEVTESSVSSSSPGSGPSSPNNGPTGSVTENETSVLP
PTPHAEQMVSQQRILIHEDSMNLLSLYTSPSLPNITLGLPAVPSQLNASNSLKEKQKCE
TQTLRQGVPLPGQYGGSIPASSSHPHVTLEGKPPNSSHQALLQHLLLKEQMRQQKLLVA
GGVPLHPQSPLATKERISPGIRGTHKLPRHRPLNRTQSAPLPQSTLAQLVIQQQHQQFL
EKQKQYQQQIHMNKLLSKSIEQLKQPGSHLEEAEEELQGDQAMQEDRAPSSGNSTRSDS
SACVDDTLGQVGAVKVKEEPVDSDEDAQIQEMESGEQAAFMQQPFLEPTHTRALSVRQA
PLAAVGMDGLEKHRLVSRTHSSPAASVLPHPAMDRPLQPGSATGIAYDPLMLKHQCVCG
NSTTHPEHAGRIQSIWSRLQETGLLNKCERIQGRKASLEEIQLVHSEHHSLLYGTNPLD
GQKLDPRILLGDDSQKFFSSLPCGGLGVDSDTIWNELHSSGAARMAVGCVIELASKVAS
GELKNGFAVVRPPGHHAEESTAMGFCFFNSVAITAKYLRDQLNISKILIVDLDVHHGNG
TQQAFYADPSILYISLHRYDEGNFFPGSGAPNEVRFISLEPHFYLYLSGNCIA

FIG. 2B

>HDAC9 (ΔNLS) (967 amino acids)

MHSMISSVDVKSEVPVGLEPISPLDLRTDLRMMMPVVDPVVREKQLQQELLLIQQQQQI
QKQLLIAEFQKQHENLTRQHQAQLQEHIKELLAIKQQQELLEKEQKLEQQRQEQEVERH
RREQQLPPLRGKDRGRERAVASTEVKQKLQEFLLSKSATKDTPTNGKNHSVSRHPKLWY
TAAHHTSLDQSSPPLSGTSPSYKYTLPGAQDAKDDFPLRKTESSVSSSSPGSGPSSPNN
GPTGSVTENETSVLPPTPHAEQMVSQQRILIHEDSMNLLSLYTSPSLPNITLGLPAVPS
QLNASNSLKEKQKCETQTLRQGVPLPGQYGGSIPASSSHPHVTLEGKPPNSSHQALLQH
LLLKEQMRQQKLLVAGGVPLHPQSPLATKERISPGIRGTHKLPRHRPLNRTQSAPLPQS
TLAQLVIQQQHQQFLEKQKQYQQQIHMNKLLSKSIEQLKQPGSHLEEAEEELQGDQAMQ
EDRAPSSGNSTRSDSSACVDDTLGQVGAVKVKEEPVDSDEDAQIQEMESGEQAAFMQQP
FLEPTHTRALSVRQAPLAAVGMDGLEKHRLVSRTHSSPAASVLPHPAMDRPLQPGSATG
IAYDPLMLKHQCVCGNSTTHPEHAGRIQSIWSRLQETGLLNKCERIQGRKASLEEIQLV
HSEHHSLLYGTNPLDGQKLDPRILLGDDSQKFFSSLPCGGLGVDSDTIWNELHSSGAAR
MAVGCVIELASKVASGELKNGFAVVRPPGHHAEESTAMGFCFFNSVAITAKYLRDQLNI
SKILIVDLDVHHGNGTQQAFYADPSILYISLHRYDEGNFFPGSGAPNEVGTGLGEGYNI
NIAWTGGLDPPMGDVEYLEAFRTIVKPVAKEFDPDMVLVSAGFDALEGHTPPLGGYKVT
AKCFGHLTKQLMTLADGRVVLALEGGHDLTAICDASEACVNALLGNELEPLAEDILHQS
PNMNAVISLQKIIEIQSMSLKFS

FIG. 2C

>HDAC9a (ΔNLS) (835 amino acids)
MHSMISSVDVKSEVPVGLEPISPLDLRTDLRMMMPVVDPVVREKQLQQELLLIQQQQQI
QKQLLIAEFQKQHENLTRQHQAQLQEHIKELLAIKQQQELLEKEQKLEQQRQEQEVERH
RREQQLPPLRGKDRGRERAVASTEVKQKLQEFLLSKSATKDTPTNGKNHSVSRHPKLWY
TAAHHTSLDQSSPPLSGTSPSYKYTLPGAQDAKDDFPLRKTESSVSSSSPGSGPSSPNN
GPTGSVTENETSVLPPTPHAEQMVSQQRILIHEDSMNLLSLYTSPSLPNITLGLPAVPS
QLNASNSLKEKQKCETQTLRQGVPLPGQYGGSIPASSSHPHVTLEGKPPNSSHQALLQH
LLLKEQMRQQKLLVAGGVPLHPQSPLATKERISPGIRGTHKLPRHRPLNRTQSAPLPQS
TLAQLVIQQQHQQFLEKQKQYQQQIHMNKLLSKSIEQLKQPGSHLEEAEEELQGDQAMQ
EDRAPSSGNSTRSDSSACVDDTLGQVGAVKVKEEPVDSDEDAQIQEMESGEQAAFMQQP
FLEPTHTRALSVRQAPLAAVGMDGLEKHRLVSRTHSSPAASVLPHPAMDRPLQPGSATG
IAYDPLMLKHQCVCGNSTTHPEHAGRIQSIWSRLQETGLLNKCERIQGRKASLEEIQLV
HSEHHSLLYGTNPLDGQKLDPRILLGDDSQKFFSSLPCGGLGVDSDTIWNELHSSGAAR
MAVGCVIELASKVASGELKNGFAVVRPPGHHAEESTAMGFCFFNSVAITAKYLRDQLNI
SKILIVDLDVHHGNGTQQAFYADPSILYISLHRYDEGNFFPGSGAPNEVRFISLEPHFY
LYLSGNCIA

FIG. 2D

>HDRPa (HDRP ΔNLS)(546 amino acids)
MHSMISSVDVKSEVPVGLEPISPLDLRTDLRMMMPVVDPVVREKQLQQELLLIQQQQI
QKQLLIAEFQKQHENLTRQHQAQLQEHIKELLAIKQQQELLEKEQKLEQQRQEQEVERH
RREQQLPPLRGKDRGRERAVASTEVKQKLQEFLLSKSATKDTPTNGKNHSVSRHPKLWY
TAAHHTSLDQSSPPLSGTSPSYKYTLPGAQDAKDDFPLRKTESSVSSSSPGSGPSSPNN
GPTGSVTENETSVLPPTPHAEQMVSQQRILIHEDSMNLLSLYTSPSLPNITLGLPAVPS
QLNASNSLKEKQKCETQTLRQGVPLPGQYGGSIPASSSHPHVTLEGKPPNSSHQALLQH
LLLKEQMRQQKLLVAGGVPLHPQSPLATKERISPGIRGTHKLPRHRPLNRTQSAPLPQS
TLAQLVIQQQHQQFLEKQKQYQQQIHMNKLLSKSIEQLKQPGSHLEEAEEELQGDQAMQ
EDRAPSSGNSTRSDSSACVDDTLGQVGAVKVKEEPVDSDEDAQIQEMESGEQAAFMQQV
IGKDLAPGFVIKVII

FIG. 2E

| |
|---|
| FIG. 3A |
| FIG. 3B |
| FIG. 3C |

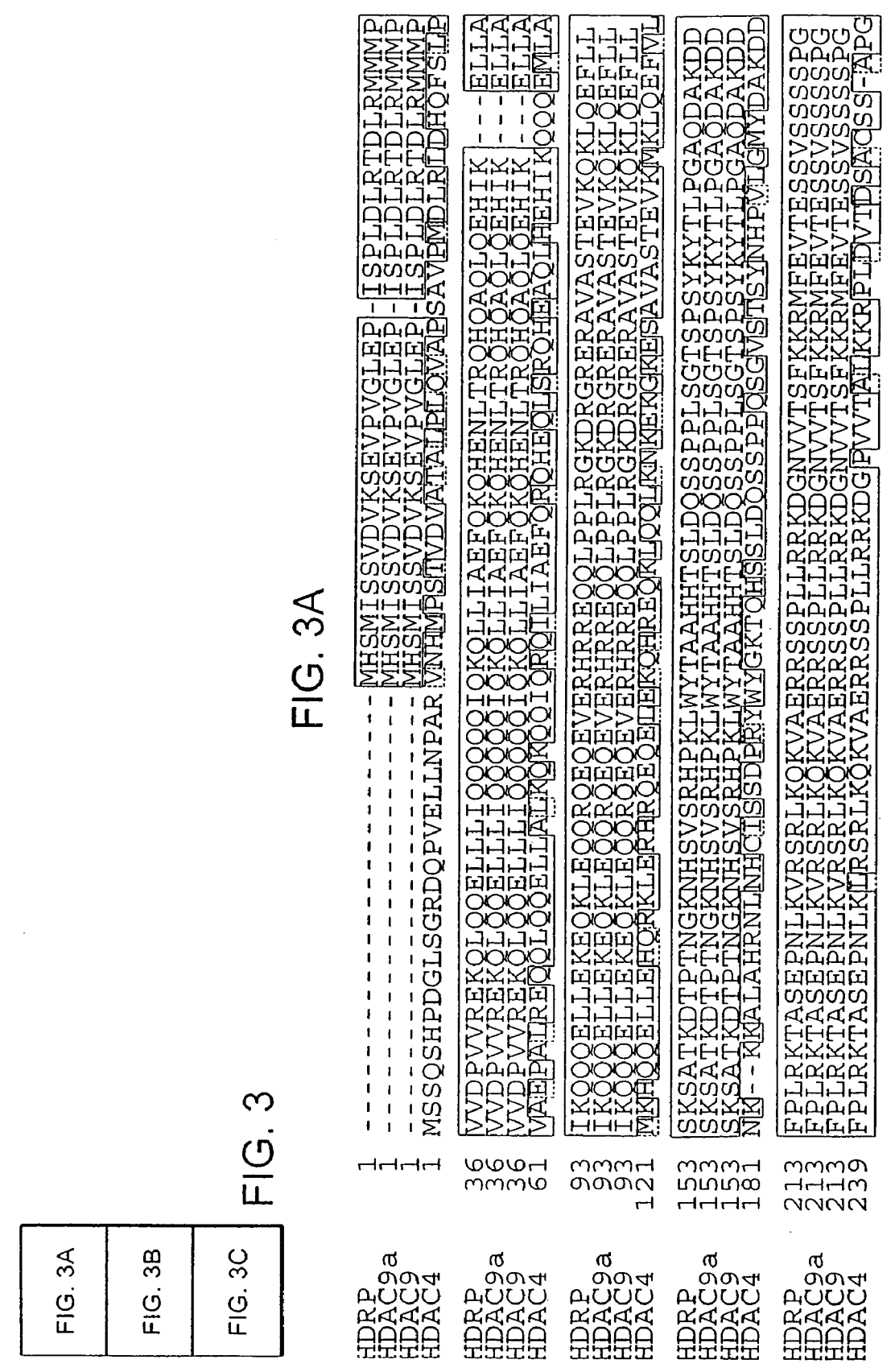

```
HDRP      1 ------------------------MHSMISSVDVKSEVPVGLEP-ISPLDLRTDLRMMMP
HDAC9a    1 ------------------------MHSMISSVDVKSEVPVGLEP-ISPLDLRTDLRMMMP
HDAC9     1 ------------------------MHSMISSVDVKSEVPVGLEP-ISPLDLRTDLRMMMP
HDAC4     1 MSSQSHPDGLSGRDQPVELLNPARVNHMPSTVDVATALPLQVAPSAVPMDLRLDHQFSLP

HDRP     36 VVDPVVREKQLQQELLLIQQQQQIQKQLLIAEFQKQHENLTRQHQAQLQEHIK---ELLA
HDAC9a   36 VVDPVVREKQLQQELLLIQQQQQIQKQLLIAEFQKQHENLTRQHQAQLQEHIK---ELLA
HDAC9    36 VVDPVVREKQLQQELLLIQQQQQIQKQLLIAEFQKQHENLTRQHQAQLQEHIK---ELLA
HDAC4    61 VAEPALREQQLQQELLALKQKQQIQRQILIAEFQRQHEQLSRQHEAQLHEHIKQQQEMLA

HDRP     93 IKQQQELLEKEQKLEQQRQEQEVERHRREQQLPPLRGKDRGRERAVASTEVKQKLQEFLL
HDAC9a   93 IKQQQELLEKEQKLEQQRQEQEVERHRREQQLPPLRGKDRGRERAVASTEVKQKLQEFLL
HDAC9    93 IKQQQELLEKEQKLEQQRQEQEVERHRREQQLPPLRGKDRGRERAVASTEVKQKLQEFLL
HDAC4   121 MKHQQELLEHQRKLERHRQEQELEKQHREQKLQQLKNKEKGKESAVASTEVKMKLQEFVL

HDRP    153 SKSATKDTPTNGKNHSVSRHPKLWYTAAHHTSLDQSSPPLSGTSPSYKYTLPGAQDAKDD
HDAC9a  153 SKSATKDTPTNGKNHSVSRHPKLWYTAAHHTSLDQSSPPLSGTSPSYKYTLPGAQDAKDD
HDAC9   153 SKSATKDTPTNGKNHSVSRHPKLWYTAAHHTSLDQSSPPLSGTSPSYKYTLPGAQDAKDD
HDAC4   181 NK--KKALAHRNLNHCISSDPRYWYGKTQHSSLDQSSPPQSGVSTSYNHPVLGMYDAKDD

HDRP    213 FPLRKTASEPNLKVRSRLKQKVAERRSSPLLRRKDGNVVTSFKKRMFEVTESSVSSSSPG
HDAC9a  213 FPLRKTASEPNLKVRSRLKQKVAERRSSPLLRRKDGNVVTSFKKRMFEVTESSVSSSSPG
HDAC9   213 FPLRKTASEPNLKVRSRLKQKVAERRSSPLLRRKDGNVVTSFKKRMFEVTESSVSSSSPG
HDAC4   239 FPLRKTASEPNLKLRSRLKQKVAERRSSPLLRRKDGPVVTALKKRPLDVTDSACSS-APG
```

```
HDRP    273  SGPSSPNNGPTGSVTENETSVLPPTPHAEQMVSQQRILIHEDSMNLLSLYTSPSLPNITL
HDAC9a  273  SGPSSPNNGPTGSVTENETSVLPPTPHAEQMVSQQRILIHEDSMNLLSLYTSPSLPNITL
HDAC9   273  SGPSSPNNGPTGSVTENETSVLPPTPHAEQMVSQQRILIHEDSMNLLSLYTSPSLPNITL
HDAC4   298  SGPSSPNNSSGSVSAENGIAPAVPSIPAETSLAHR-LVAREGSAAPLPLYTSPSLPNITL

HDRP    333  GLPAVPSQLNASNSLKEKQKCETQTLRQGVPLPGQYGGSIPASSSHPHVTLEGKPPNSSH
HDAC9a  333  GLPAVPSQLNASNSLKEKQKCETQTLRQGVPLPGQYGGSIPASSSHPHVTLEGKPPNSSH
HDAC9   333  GLPAVPSQLNASNSLKEKQKCETQTLRQGVPLPGQYGGSIPASSSHPHVTLEGKPPNSSH
HDAC4   357  GLPATGPSAGTAGQQ-DTERLTLPALQQRLSLFPGTHLTPYLSTS--PLERDG---GAAH

HDRP    393  QALLQHLLLKEQMRQQKLLVAGG--VPLHPQSPLATKERISPGIRGTHKLPRHRPLNRTQ
HDAC9a  393  QALLQHLLLKEQMRQQKLLVAGG--VPLHPQSPLATKERISPGIRGTHKLPRHRPLNRTQ
HDAC9   393  QALLQHLLLKEQMRQQKLLVAGG--VPLHPQSPLATKERISPGIRGTHKLPRHRPLNRTQ
HDAC4   411  SPLLQHMVLLEQPPAQAPLVTGLGALPLHAQS-LVGADRVSP---SIHKLRQHRPLGRTQ

HDRP    451  SAPLPQ--STLAQLVIQQQHQQFLEKQKQ--YQQQIHMNKLLSKSIEQLKQPGSHLEEAE
HDAC9a  451  SAPLPQ--STLAQLVIQQQHQQFLEKQKQ--YQQQIHMNKLLSKSIEQLKQPGSHLEEAE
HDAC9   451  SAPLPQ--STLAQLVIQQQHQQFLEKQKQ--YQQQIHMNKLLSKSIEQLKQPGSHLEEAE
HDAC4   467  SAPLPQNAQALQHLVIQQQHQQFLEKHKQQFQQQQLQMNKIIPKPSEPARQPESHPEETE

HDRP    507  EELQGDQAMQEDRAPSSGNSTR-SDSSACVDDTLGQVGAVKVKEEPVDSDEDAQIQEMES
HDAC9a  507  EELQGDQAMQEDRAPSSGNSTR-SDSSACVDDTLGQVGAVKVKEEPVDSDEDAQIQEMES
HDAC9   507  EELQGDQAMQEDRAPSSGNSTR-SDSSACVDDTLGQVGAVKVKEEPVDSDEDAQIQEMES
HDAC4   527  EELREHQALLDEPYLDRLPGQKEAHAQAGVQVKQEPIESDEEEAEPPREVEPGQRQPSEQ

HDRP    566  GEQAAFMQQVIGKDLAPGFVIKVII-----------------------------------
HDAC9a  566  GEQAAFMQQPFLEPTHTRALSVRQAPLAAVGMDGLEKHRLVSRTHSSPAASVLPHPAMDR
HDAC9   566  GEQAAFMQQPFLEPTHTRALSVRQAPLAAVGMDGLEKHRLVSRTHSSPAASVLPHPAMDR
HDAC4   587  ELLFRQQALLLEQQRIHQLRNYQASMEAAGIPVSFGGHRPLSRAQSSPASATFPVSVQEP
```

FIG. 3B

```
HDRP          ------------------------------------------------------------
HDAC9a   626  PLQPGSATGIAYDPLMLKHQCVCGNSTTHPEHAGRIQSIWSRLQETGLLNKCERIQGRKA
HDAC9    626  PLQPGSATGIAYDPLMLKHQCVCGNSTTHPEHAGRIQSIWSRLQETGLLNKCERIQGRKA
HDAC4    647  PTKPRFTTGLVYDTLMLKHQCTCGSSSSHPEHAGRIQSIWSRLQETGLRGKCECIRGRKA

HDRP          ------------------------------------------------------------
HDAC9a   686  SLEEIQLVHSEHHSLLYGTNPLDGQKLDPRILLGDDSQKFFSSLPCGGLGVDSDTIWNEL
HDAC9    686  SLEEIQLVHSEHHSLLYGTNPLDGQKLDPRILLGDDSQKFFSSLPCGGLGVDSDTIWNEL
HDAC4    707  TLEELQTVHSEAHTLLYGTNPLNRQKLDSKKLLGSLASVFVR-LPCGGVGVDSDTIWNEV

HDRP          ------------------------------------------------------------
HDAC9a   746  HSSGAARMAVGCVIELASKVASGELKNGFAVVRPPGHHAEESTAMGFCFFNSVAITAKYL
HDAC9    746  HSSGAARMAVGCVIELASKVASGELKNGFAVVRPPGHHAEESTAMGFCFFNSVAITAKYL
HDAC4    766  HSAGAARLAVGCVVELVFKVATGELKNGFAVVRPPGHHAEESTPMGFCYFNSVAVAAKLL

HDRP          ------------------------------------------------------------
HDAC9a   806  RDQLNISKILIVDLDVHHGNGTQQAFYADPSILYISLHRYDEGNFFPGSGAPNEV RFISL
HDAC9    806  RDQLNISKILIVDLDVHHGNGTQQAFYADPSILYISLHRYDEGNFFPGSGAPNEVGTG LG
HDAC4    826  QQRLSVSKILIVDWDVHHGNGTQQAFYSDPSVLYMSLHRYDDGNFFPGSGAPDEVGTGPG

HDRP          ------------------------------------------------------------
HDAC9a   866  EPHFYLYLSGNCIA----------------------------------------------
HDAC9    866  EGYNINIAWTGGLDPPMGDVEYLEAFRTIVKPVAKEFDPDMVLVSAGFDALEGHTPPLGG
HDAC4    886  VGFNVNMAFTGGLDPPMGDAEYLAAFRTVVMPIASEFAPDVVLVSSGFDAVEGHPTPLGG

HDRP          ------------------------------------------------------------
HDAC9a        ------------------------------------------------------------
HDAC9    926  YKVTAKCFGHLTKQLMTLADGRVVLALEGGHDLTAICDASEACVNALLGNELEPLAEDIL
HDAC4    946  YNLSARCFGYLTKQLMGLAGGRIVLALEGGHDLTAICDASEACVSALLGNELDPLPEKVL

HDRP          ------------------------------------------------------------
HDAC9a        ------------------------------------------------------------
HDAC9    986  HQSPNMNAVISLQKIIEIQSMSLKFS----------------------------------
HDAC4   1006  QQRPNANAVRSMEKVMEIHSKYWRCLQRTTSTAGRSLIEAQTCENEEAETVTAMASLSVG

HDRP          -------------------
HDAC9a        -------------------
HDAC9         -------------------
HDAC4   1066  VKPAEKRPDEEPMEEEPPL
```

FIG. 3C

1 /[1]ggggaagaga ggcacagaca cagataggag aagggcaccg gctggagcca cttgcaggac tgagggtttt tgcaacaaaa ccctagcagc ctgaagaact 101 ctaagccag/[2]a tggggtggct ggacgagagc agctcttggc tcagcaaaga ATGCACAGTA TGATCAGCTC AGT/[3]GGATGTG AAGTCAGAAG TTCCTGTGGG 201 CCTGGAGCCC ATCTCACCTT TAGACCTAAG GACAGACCTC AGGATGATGA TGCCCGTGGT GGACCCTGTT GTCCGTGAGA AGCAATTGCA GCAGGAATTA 301 CTTCTTATCC AGCAGCAGCA ACAAATCCAG AAGCAGCTTC TGATAGCAGA GTTTCAGAAA CAGCATGAGA ACTTGACACG GCAGCACCAG GCTCAGCTTC 401 AGGAGCATAT CAAG/[4]GAACTT CTAGCCATAA AACAGCAACA AGAACTCCTA GAAAAGGAGC AGAAACTGGA GCAGCAGAGG CAAGAACAGG AAGTAGAGAG 501 GCATCGCAGA GAACAGCAGC TTCCTCCTCT CAGAGGCAAA GATAGAGGAC GAGAAAG /[5]GGC AGTGGCAAGT ACAGAAGTAA AGCAGAAGCT TCAAGAGTTC 601 CTACTGAGTA AATCAGCAAC GAAAGACACT CCAACTAATG GAAAAAATCA TTCCGTGAGC CGCCATCCCA AGCTCTGGTA CACG/[6]GCTGCC CACCACACAT 701 CATTGGATCA AAGCTCTCCA CCCCTTAGTG GAACATCTCC ATCCTACAAG TACACATTAC CAGGAGCACA AGATGCAAAG GATGATTTCC CCCTTCGAAA

FIG. 5A

801 AACT/[7]GCCTCT GAGCCCAACT TGAAGGTGCG GTCCAGGTTA AAACAGAAAG TGGCAGAGAG GAGAAGCAGC CCCTTACTCA GGCGGAAGGA TGGAAATGTT

901 GTCACTTCAT TCAAGAAGCG AATGTTTGAG GTGACAG/[8]AAT CCTCAGTCAG TAGCAGTTCT CCAGGCTCTG GTCCCAGTTC ACCAAACAAT GGGCCAACTG

1001 GAAGTGTTAC TGAAAATGAG ACTTCGGTTT TGCCCCCTAC CCCTCATGCC GAG /[9]CAAATGG TTTCACAGCA ACGCATTCTA ATTCATGAAG ATTCCATGAA

1101 CCTGCTAAGT CTTTATACCT CTCCTTCTTT GCCCAACATT ACCTTGGGGC TTCCCGCAGT GCCATCCCAG CTCAATG /[10]CTT CGAATTCACT CAAAGAAAAG

1201 CAGAAGTGTG AGACGCAGAC GCTTAGGCAA GGTGTTCCTC TGCCTGGGCA GTATGGAGGC AGCATCCCGG CATCTTCCAG CCACCCTCAT GTTACTTTAG

1301 AGGGAAAGCC ACCCAACAGC AGCCACCAGG CTCTCCTGCA GCATTTATTA TTGAAAGAAC AAATGCGACA GCAAAAGCTT CTTGTAGCTG/[11] GTGGAGTTCC

1401 CTTACATCCT CAGTCTCCCT TGGCAACAAA AGAGAGAATT TCACCTGGCA TTAGAGGTAC CCACAAATTG CCCCGTCACA GACCCCTGAA CCGAACCCAG

1501 TCTGCACCTT TGCCTCAGAG CACGTTGGCT CAGCTGGTCA TTCAACAGCA ACACCAGCAA TTCTTGGAGA AGCAGAAGCA ATACCAGCAG CAGATCCACA

1601 TGAACAAA/[12]CT GCTTTCGAAA TCTATTGAAC AACTGAAGCA ACCAGGCAGT CACCTTGAGG AAGCAGAGGA AGAGCTTCAG GGGGACCAGG CGATGCAGGA

FIG. 5B

1701 AGACAGAGCG CCCTCTAGTG GCAACAGCAC TAGGAGCGAC AGCAGTGCTT GTGTGGATGA CACACTGGGA CAAGTTGGGG
CTGTGAAGGT CAAGGAGGAA

1801 CCAGTGGACA GTGATGAAGA TGCTCAGATC CAGGAAATGG AATCTGGGGA GCAGGCTGCT TTTATGCAAC AG
/[13]GTAATAGG CAAAGATTTA GCTCCAGGAT TTGTAATTAA AGTCATTATC TGA...... /[14]CCTTTCCT GGAACCCACG CACACACGTG

1901 CGCTCTCTGT GCGCCAAGCT CCGCTGGCTG CGGTTGGCAT GGATGGATTA GAGAAACACC GTCTCGTCTC CAGGACTCAC
TCTTCCCCTG CTGCCTCTGT

2001 TTTACCTCAC CCAGCAATGG ACCGCCCCCT CCAGCCTGGC TCTGCAACTG /[15]GAATTGCCTA TGACCCCTTG ATGCTGAAAC
ACCAGTGCGT TTGTGGCAAT

2101 TCCACCACCC ACCCTGAGCA TGCTGGACGA ATACAGAGTA TCTGGTCACG ACTGCAAGAA ACTGGGCTGC TAAATAAATG
TGAG/[16]CGAATT CAAGGTCGAA

2201 AAGCCAGCCT GGAGGAAATA CAGCTTGTTC ATTCTGAACA TCACTCACTG TTGTATGGCA CCAACCCCCT GGACGGACAG
AAGCTGGACC CCAGGATACT

2301 CCTAG/[17]GTGAT GACTCTCAAA AGTTTTTTTC CTCATTACCT TGTGGTGGAC TTGGG/[18]GTGGA CAGTGACACC ATTTGGAATG
AGCTACACTC GTCCGGTGCT

2401 GCACGCATGG CTGTTGGCTG TGTCATCGAG CTGGCTTCCA AAGTGGCCTC AGGAGAGCTG AAGA /[19]ATGGGT TTGCTGTTGT
GAGGCCCCCT GGCCATCACG

2501 CTGAAGAATC CACAGCCATG /[20]GGGTTCTGCT TTTTTAATTC AGTTGCAATT ACCGCCAAAT ACTTGAGAGA CCAACTAAAT
ATAAGCAAGA TATTGATTGT

FIG. 5C

2601 AGATCTG/[21]GAT GTTCACCATG GAAACGGTAC CCAGCAGGCC TTTTATGCTG ACCCCAGCAT CCTGTACATT TCACTCCATC GCTATGATGA AGGGAACTTT

2701 TTCCCTGGCA GTGGAGCCCC AAATGAGG/[22]TT CGGTTTATTT CTTTAGAGCC CCACTTTTAT TTGTATCTTT CAGGTAATTG CATTGCATGA ttacccctaa 2801 ttttcttgtc ctttgctggt gttttaaatt acacgagatt actgaattgt cccatgggac caagaaccag tgcagaacaa gtgcataacc cagagcactg 2901 tttgtcaggg aaggttgggc tgatttgatg tgttgtttga tgtttatttc aagagctccc atgtgcttgt tttcctctct tcttgctttc ttccatttgc 3001 tctcttctct gcccaccgtg gtgtgtcttt ctcttcccag /[23]gttggaacag gccttggaga agggtacaat ataaatattg cctggacagg tggccttgat 3101 cctcccatgg gagatgttga gtaccttgaa gcattcag/[24]ga ccatcgtgaa gcctgtggcc aaagagtttg atccagacat ggtcttagta tctgctggat 3201 ttgatgcatt ggaaggccac acccctcctc taggagggta caaagtgacg gcaaaatg/[25]tt ttggtcattt gacgaagcaa ttgatgacat tggctgatgg 3301 acgtgtggtg ttggctctag aaggaggaca tgatctcaca gccatctgtg atgcatcaga agcctgtgta aatgcccttc taggaaatga g/[26]ctggagcca 3401 cttgcagaag atattctcca ccaaagcccg aatatgaatg ctgttatttc tttacagaag atcattgaaa ttcaaagtat gtctttaaag ttctcttaa......

FIG. 5D

| |
|---|
| FIG. 11A |
| FIG. 11B |
| FIG. 11C |
| FIG. 11D |
| FIG. 11E |
| FIG. 11F |

FIG. 11

FIG. 11A cccattcgccattcaggctgcgcaactgttgggaagggcgatcggtgcgggcctcttcgctattacgccagctggcgaaaggg
ggatgtgctgcaaggcgattaagttgggtaacgcccagggttttcccagtcacgacgttgtaaaacgacggccagtgccaagct
gatctaatcaatattggccattagccatattattcattggttatatagcataaatcaatattggctattggccattgcatacgttgtatcca
tatcataatatgtacatttatattggctcatgtccaacattaccgccatgttgacattgattattgactagttattaatagtaatcaattacg
gggtcattagttcatagcccatatatggagttccgcgttacataacttacggtaaatggcccgcctggcgaccgcccagcgaccc
ccgcccgttgacgtcaatagtgacgtatgttcccatagtaacgccaatagggactttccattgacgtcaatgggtggagtatttacg gtaaactgcccacttggcagtacatcaagtgtatcatatgccaagtccgccccctattgacgtcaatgacggtaaatggcccgcct
agcattatgcccagtacatgaccttacgggagtttcctacttggcagtacatctacgtattagtcatcgctattaccatggtgatgcg
gttttggcagtacaccaatgggcgtggatagcggtttgactcacggggatttccaagtctccaccccattgacgtcaatgggagtt
tgttttggcaccaaaatcaacgggactttccaaaatgtcgtaataaccccgccccgttgacgcaaatgggcggtaggcgtgtacg
gtgggaggtctatataagcagagctcgtttagtgaaccgtcagaattcaagcttgcggccgcagatctatcgatctgcaggatatc
(EcoRV)
*acc*

ATGCACAGTATGATCAGCTCAGTGGATGTGAAGTCAGAAGTTCCTGTGGG
CCTGGAGCCCATCTCACCTTTAGACCTAAGGACAGACCTCAGGATGATGA
TGCCCGTGGTGGACCCTGTTGTCCGTGAGAAGCAATTGCAGCAGGAATTA
CTTCTTATCCAGCAGCAGCAACAAATCCAGAAGCAGCTTCTGATAGCAGA
GTTTCAGAAACAGCATGAGAACTTGACACGGCAGCACCAGGCTCAGCTTC
AGGAGCATATCAAGGAACTTCTAGCCATAAAACAGCAACAAGAACTCCTA
GAAAAGGAGCAGAAACTGGAGCAGCAGAGGCAAGAACAGGAAGTAGAGAG
GCATCGCAGAGAACAGCAGCTTCCTCCTCTCAGAGGCAAAGATAGAGGAC
GAGAAAGGGCAGTGGCAAGTACAGAAGTAAAGCAGAAGCTTCAAGAGTTC
CTACTGAGTAAATCAGCAACGAAAGACACTCCAACTAATGGAAAAAATCA
TTCCGTGAGCCGCCATCCCAAGCTCTGGTACACGGCTGCCCACCACACAT
CATTGGATCAAAGCTCTCCACCCCTTAGTGGAACATCTCCATCCTACAAG

FIG. 11B

TACACATTACCAGGAGCACAAGATGCAAAGGATGATTTCCCCCTTCGAAA
AACTGCCTCTGAGCCCAACTTGAAGGTGCGGTCCAGGTTAAAACAGAAAG
TGGCAGAGAGGAGAAGCAGCCCCTTACTCAGGCGGAAGGATGGAAATGTT
GTCACTTCATTCAAGAAGCGAATGTTTGAGGTGACAGAATCCTCAGTCAG
TAGCAGTTCTCCAGGCTCTGGTCCCAGTTCACCAAACAATGGGCCAACTG
GAAGTGTTACTGAAAATGAGACTTCGGTTTTGCCCCCTACCCCTCATGCC
GAGCAAATGGTTTCACAGCAACGCATTCTAATTCATGAAGATTCCATGAA
CCTGCTAAGTCTTTATACCTCTCCTTCTTTGCCCAACATTACCTTGGGGC
TTCCCGCAGTGCCATCCCAGCTCAATGCTTCGAATTCACTCAAAGAAAAG
CAGAAGTGTGAGACGCAGACGCTTAGGCAAGGTGTTCCTCTGCCTGGGCA
GTATGGAGGCAGCATCCCGGCATCTTCCAGCCACCCTCATGTTACTTTAG
AGGGAAAGCCACCCAACAGCAGCCACCAGGCTCTCCTGCAGCATTTATTA
TTGAAAGAACAAATGCGACAGCAAAAGCTTCTTGTAGCTGGTGGAGTTCC
CTTACATCCTCAGTCTCCCTTGGCAACAAAAGAGAGAATTTCACCTGGCA
TTAGAGGTACCCACAAATTGCCCCGTCACAGACCCCTGAACCGAACCCAG
TCTGCACCTTTGCCTCAGAGCACGTTGGCTCAGCTGGTCATTCAACAGCA
ACACCAGCAATTCTTGGAGAAGCAGAAGCAATACCAGCAGCAGATCCACA
TGAACAAACTGCTTTCGAAATCTATTGAACAACTGAAGCAACCAGGCAGT
CACCTTGAGGAAGCAGAGGAAGAGCTTCAGGGGGACCAGGCGATGCAGGA
AGACAGAGCGCCCTCTAGTGGCAACAGCACTAGGAGCGACAGCAGTGCTT
GTGTGGATGACACACTGGGACAAGTTGGGGCTGTGAAGGTCAAGGAGGAA
CCAGTGGACAGTGATGAAGATGCTCAGATCCAGGAAATGGAATCTGGGGA
GCAGGCTGCTTTTATGCAACAGCCTTTCCTGGAACCCACGCACACACGTG
CGCTCTCTGTGCGCCAAGCTCCGCTGGCTGCGGTTGGCATGGATGGATTA

FIG. 11C

GAGAAACACCGTCTCGTCTCCAGGACTCACTCTTCCCCTGCTGCCTCTGT
TTTACCTCACCCAGCAATGGACCGCCCCCTCCAGCCTGGCTCTGCAACTG
GAATTGCCTATGACCCCTTGATGCTGAAACACCAGTGCGTTTGTGGCAAT
TCCACCACCCACCCTGAGCATGCTGGACGAATACAGAGTATCTGGTCACG
ACTGCAAGAAACTGGGCTGCTAAATAAATGTGAGCGAATTCAAGGTCGAA
AAGCCAGCCTGGAGGAAATACAGCTTGTTCATTCTGAACATCACTCACTG
TTGTATGGCACCAACCCCCTGGACGGACAGAAGCTGGACCCCAGGATACT
CCTAGGTGATGACTCTCAAAAGTTTTTTCCTCATTACCTTGTGGTGGAC
TTGGGGTGGACAGTGACACCATTTGGAATGAGCTACACTCGTCCGGTGCT
GCACGCATGGCTGTTGGCTGTGTCATCGAGCTGGCTTCCAAAGTGGCCTC
AGGAGAGCTGAAGAATGGGTTTGCTGTTGTGAGGCCCCCTGGCCATCACG
CTGAAGAATCCACAGCCATGGGGTTCTGCTTTTTTAATTCAGTTGCAATT
ACCGCCAAATACTTGAGAGACCAACTAAATATAAGCAAGATATTGATTGT
AGATCTGGATGTTCACCATGGAAACGGTACCCAGCAGGCCTTTTATGCTG
ACCCCAGCATCCTGTACATTTCACTCCATCGCTATGATGAAGGGAACTTT
TTCCCTGGCAGTGGAGCCCCAAATGAGGTTGGAACAGGCCTTGGAGAAGG
GTACAATATAAATATTGCCTGGACAGGTGGCCTTGATCCTCCCATGGGAG
ATGTTGAGTACCTTGAAGCATTCAGGAccaTCGTGAAGCCTGTGGCCAAA
GAGTTTGATCCAGACATGGTCTTAGTATCTGCTGGATTTGATGCATTGGA
AGGCCACACCCCTCCTCTAGGAGGGTACAAAGTGACGGCAAAATGTTTTG
GTCATTTGACGAAGCAATTGATGACATTGGCTGATGGACGTGTGGTGTTG
GCTCTAGAAGGAGGACATGATCTCACAGCCATCTGTGATGCATCAGAAGC
CTGTGTAAATGCCCTTCTAGGAAATGAGCTGGAGCCACTTGCAGAAGATA
TTCTCCACCAAAGCCCGAATATGAATGCTGTTATTTCTTTACAGAAGATC
ATTGAAATTCAAAGTATGTCTTTAAAGTTCTCT

FIG. 11D (BamHI)ggatccggtaccagattacaaggacgacgatgacaagtagatcccgggtggcatccctgtgacccctccccagtg
cctctcctggccttggaagttgccactccagtgcccaccagccttgtcctaataaaattaagttgcatcattttgtctgactaggtgtc
ctctataatattatggggtggaggggggtggtatggagcaaggggcccaagttgggaagacaacctgtagggcctgcggggtc
tattcgggaaccaagctggagtgcagtggcacaatcttggctcactgcaatctccgcctcctgggttcaagcgattctcctgcctc
agcctcccgagttgttgggattccaggcatgcatgaccaggctcagctaattttgtttttttggtagagacggggtttcaccatattg
gccaggctggtctccaactcctaatctcaggtgatctacccaccttggcctcccaaattgctgggattacaggcgtgaaccactgc
tcccttccctgtccttctgattttaaaataactataccagcaggaggacgtccagacacagcataggctacctgccatggcccaac
cggtgggacatttgagttgcttgcttggcactgtcctctcatgcgttgggtccactcagtagatgcctgttgaattgggtacgcggc
cagcttctgtggaatgtgtgtcagttagggtgtggaaagtccccaggctccccagcaggcagaagtatgcaaagcatgcatctca
attagtcagcaaccaggtgtggaaagtccccaggctccccagcaggcagaagtatgcaaagcatgcatctcaattagtcagca
accatagtcccgcccctaactccgcccatcccgcccctaactccgcccagttccgcccattctccgccccatggctgactaatttt
tttatttatgcagaggccgaggccgcctcggcctctgagctattccagaagtagtgaggaggcttttttggaggcctaggcttttgc
aaaaagctcctcgaggaactgaaaaaccagaaagttaattccctatagtgagtcgtattaaattcgtaatcatggtcatagctgtttc
ctgtgtgaaattgttatccgctcacaattccacacaacatacgagccggaagcataaagtgtaaagcctggggtgcctaatgagt
gagctaactcacattaattgcgttgcgctcactgcccgctttccagtcgggaaacctgtcgtgccagctgcattaatgaatcggcc
aacgcgcggggagaggcggtttgcgtattgggcgctcttccgcttcctcgctcactgactcgctgcgctcggtcgttcggctgcg
gcgagcggtatcagctcactcaaaggcggtaatacggttatccacagaatcaggggataacgcaggaaagaacatgtgagca
aaaggccagcaaaaggccaggaaccgtaaaaaggccgcgttgctggcgtttttccataggctccgcccccctgacgagcatca
caaaaatcgacgctcaagtcagaggtggcgaaacccgacaggactataaagataccaggcgtttccccctggaagctccctcg
tgcgctctcctgttccgaccctgccgcttaccggatacctgtccgcctttctcccttcgggaagcgtggcgctttctcaatgctcac

FIG. 11E gctgtaggtatctcagttcggtgtaggtcgttcgctccaagctgggctgtgtgcacgaaccccccgttcagcccgaccgctgcgc
cttatccggtaactatcgtcttgagtccaacccggtaagacacgacttatcgccactggcagcagccactggtaacaggattagc
agagcgaggtatgtaggcggtgctacagagttcttgaagtggtggcctaactacggctacactagaagaacagtatttggtatct
gcgctctgctgaagccagttaccttcggaaaaagagttggtagctcttgatccggcaaacaaaccaccgctggtagcggtggttt
ttttgtttgcaagcagcagattacgcgcagaaaaaaaggatctcaagaagatcctttgatcttttctacggggtctgacgctcagtg
gaacgaaaactcacgttaagggattttggtcatgagattatcaaaaaggatcttcacctagatccttttaaattaaaaatgaagtttta aatcaatctaaagtatatatgagtaaacttggtctgacagttaccaatgcttaatcagtgaggcacctatctcagcgatctgtctatttc
gttcatccatagttgcctgactccccgtcgtgtagataactacgatacgggagggcttaccatctggccccagtgctgcaatgata
ccgcgagacccacgctcaccggctccagatttatcagcaataaaccagccagccggaagggccgagcgcagaagtggtcct
gcaactttatccgcctccatccagtctattaattgttgccgggaagctagagtaagtagttcgccagttaatagtttgcgcaacgttgt
tgccattgctacaggcatcgtggtgtcacgctcgtcgtttggtatggcttcattcagctccggttcccaacgatcaaggcgagttac
atgatcccccatgttgtgcaaaaaagcggttagctccttcggtcctccgatcgttgtcagaagtaagttggccgcagtgttatcact
catggttatggcagcactgcataattctcttactgtcatgccatccgtaagatgcttttctgtgactggtgagtactcaaccaagtcatt
ctgagaatagtgtatgcggcgaccgagttgctcttgcccggcgtcaatacgggataataccgcgccacatagcagaactttaaaa
gtgctcatcattggaaaacgttcttcggggcgaaaactctcaaggatcttaccgctgttgagatccagttcgatgtaacccactcgt
gcacccaactgatcttcagcatcttttactttcaccagcgtttctgggtgagcaaaaacaggaaggcaaaatgccgcaaaaaagg
gaataagggcgacacggaaatgttgaatactcatactcttcctttttcaatattattgaagcatttatcagggttattgtctcatgagcg
gatacatatttgaatgtatttagaaaaataaacaaataggggttccgcgcacatttccccgaaaagtgccacctgacgcgccctgt
agcggcgcattaagcgcggcgggtgtggtggttacgcgcagcgtgaccgctacacttgccagcgccctagcgcccgctccttt
cgctttcttcccttcctttctcgccacgttcgccggctttccccgtcaagctctaaatcgggggcatccctttagggttccgatttagtgc
tttacggcacctcgaccccaaaaaacttgattagggtgatggttcacgtagtgggccatcgccctgatagacggtttttcgccctttg
acgttggagtccacgttctttaatagtggactcttgttccaaactggaacaacactcaaccctatctcggtctattcttttgatttataa
gggattttgccgatttcggcctattggttaaaaaatgagctgatttaacaaaaatttaacgcgaattttaacaaaatattaaacgtttac
aattt

FIG. 11F pFLAG-CMV-5b-HDAC9

7699 base pairs

Graphic map | Table by enzyme name

```
                                             BstMCI
                  AviII                      PvuI BsiEI     EarI        MspA1I
            BglI  FspI                       BsaOI          Eam1104I    PvuII
cccattcgccattcaggctgcgcaactgttgggaagggcgatcggtgcgggcctcttcgctattacgccagctgg
base pairs
gggtaagcggtaagtccgacgcgttgacaacccttcccgctagccacgcccggagaagcgataatgcggtcgacc
1 to 75
                                                                     NspBII
                  Acc16I                     BspCI          Ksp632I
                                             Bsh1285I
                                             Ple19I


cgaaagggggatgtgctgcaaggcgattaagttgggtaacgcccagggttttcccagtcacgacgttgtaaaacg
base pairs
gctttccccctacacgacgttccgctaattcaacccattgcgggtcccaaaagggtcagtgctgcaacattttgc
76 to 150
```

FIG. 12-1

```
                                      MscI
                                    CfrI
                                 SspI MluNI
  EaeI
acggccagtgccaagctgatctaatcaatattggccattagccatattattcattggttatatagcataaatcaa
base pairs
tgccggtcacggttcgactagattagttataaccggtaatcggtataataagtaaccaatatatcgtatttagtt
151 to 225
  CfrI                              EaeI
                                      BalI


              MscI
              MluNI                                    SspBI
 SspI       EaeI     BsrDI                             Bsp1407I
tattggctattggccattgcatacgttgtatccatatcataatatgtacatttatattggctcatgtccaacatt
base pairs
ataaccgataaccggtaacgtatgcaacataggtatagtattatacatgtaaatataaccgagtacaggttgtaa
226 to 300
           CfrI                                        BsrGI
             BalI
```

FIG. 12-2

```
                                    VspI
           HincII          SpeI     PshBI
accgccatgttgacattgattattgactagttattaatagtaatcaattacggggtcattagttcatagcccata
base pairs
tggcggtacaactgtaactaataactgatcaataattatcattagttaatgccccagtaatcaagtatcgggtat
301 to 375
           HindII          AclNI    AsnI
                                    AseI
```

```
                                                                        HinlI
                                                 BstMCI                  AcyI
                                          BglI   BsaOI                 HincII
tatggagttccgcgttacataacttacggtaaatggcccgcctggcgaccgcccagcgacccccgcccgttgacg
base pairs
atacctcaaggcgcaatgtattgaatgccatttaccgggcggaccgctggcgggtcgctgggggcgggcaactgc
376 to 450
                                                 Bsh1285I              HindII
                                                 BsiEI
```

FIG. 12-3

```
   AatII                                                     BbiII
   BbiII                                                     Hin1I
                                                             AcyI AatII
tcaatagtgacgtatgttcccatagtaacgccaatagggactttccattgacgtcaatgggtggagtatttacgg
base pairs
agttatcactgcatacaagggtatcattgcggttatccctgaaaggtaactgcagttacccacctcataaatgcc
451 to 525
   Hsp92I                                                    Msp17I
                                                             BsaHI
                                                             Hsp92I

                                                                     BbiII
                                                                     Hin1I
             BglI                    NdeI                            AcyI AatII
taaactgcccacttggcagtacatcaagtgtatcatatgccaagtccgcccctattgacgtcaatgacggtaaa
base pairs
atttgacgggtgaaccgtcatgtagttcacatagtatacggttcaggcgggggataactgcagttactgccattt
526 to 600
                                     FauNDI                          Msp17I
                                                                     BsaHI
                                                                     Hsp92I
```

FIG. 12-4

```
                                                                                    BstSNI
                                                                                    SnaBI
tggcccgcctagcattatgcccagtacatgaccttacgggagtttcctacttggcagtacatctacgtattagtc
base pairs
accgggcggatcgtaatacgggtcatgtactggaatgccctcaaaggatgaaccgtcatgtagatgcataatcag
601 to 675
                                                                                    BsaAI
                                                                                   Eco105I


            NcoI Bsp19I
            StyI BstDSI
            EcoT14I
atcgctattaccatggtgatgcggttttggcagtacaccaatgggcgtggatagcggtttgactcacggggattt
base pairs
tagcgataatggtaccactacgccaaaaccgtcatgtggttacccgcacctatcgccaaactgagtgcccctaaa
676 to 750
            BssT1I
            ErhI Eco130I
            DsaI MslI
```

FIG. 12-5

```
                    BbiII
                    Hin1I                    AccB1I
                    AcyI AatII               BshNI
ccaagtctccaccccattgacgtcaatgggagtttgttttggcaccaaaatcaacgggactttccaaaatgtcgt
base pairs
ggttcagaggtggggtaactgcagttaccctcaaacaaaaccgtggttttagttgccctgaaaggttttacagca
751 to 825
                    Msp17I                   BanI
                    BsaHI                    Eco64I
                    Hsp92I

                                                                        BanII
                                                                        Eco24I
                 HincII                                                 EcoICRI
aataaccccgccccgttgacgcaaatgggcggtaggcgtgtacggtgggaggtctatataagcagagctcgttta
base pairs
ttattggggcggggcaactgcgtttacccgccatccgcacatgccaccctccagatatattcgtctcgagcaaat
826 to 900
                 HindII                                                 Ecl136II
                                                                         SacI
```

FIG. 12-6

```
FriOI
SstI
BsiHKAI                    EagI XmaIII BstYI BspDI BcgI Eco32I
 Bbv12I     AcsI           CciNI Bsh1285I BstX2I BanIII PstI          BclI
AspHI       ApoI  HindIII BstZI BstMCI MflI Bsa29I SfcI              Ksp22I
gtgaaccgtcagaattcaagcttgcggccgcagatctatcgatctgcaggatatcaccatgcacagtatgatcag
base pairs
cacttggcagtcttaagttcgaacgccggcgtctagatagctagacgtcctatagtggtacgtgtcatactagtc
901 to 975
 Psp124BI   EcoRI          EaeI Eco52I BglII BscI BspXI BstSFI        FbaI
                           CfrI EclXI BsiEI BseCI Bsu15I EcoRV
Alw21I                     NotI BsaOI XhoII ClaI Bsp106I

                                           FriOI            CvnI       CvnI
                                          Eco24I            AocI       AocI
                                         BpmI               Bsu36I     Bsu36I
ctcagtggatgtgaagtcagaagttcctgtgggcctggagcccatctcacctttagacctaaggacagacctcag
base pairs
gagtcacctacacttcagtcttcaaggacacccggacctcgggtagagtggaaatctggattcctgtctggagtc
976 to 1050
                                         GsuI               Eco81I     Eco81I
                                           BanII            Bse21I     Bse21I
```

FIG. 12-7

```
               DsaI              DrdI              MfeI                Asp700I
gatgatgatgcccgtggtggaccctgttgtccgtgagaagcaattgcagcaggaattacttcttatccagcagca
base pairs
ctactactacgggcaccacctgggacaacaggcactcttcgttaacgtcgtccttaatgaagaataggtcgtcgt
1051 to 1125
               BstDSI                              MunI                XmnI
```

FIG. 12-8

```
                      AlwNI
gcaacaaatccagaagcagcttctgatagcagagtttcagaaacagcatgagaacttgacacggcagcaccaggc
base pairs
cgttgtttaggtcttcgtcgaagactatcgtctcaaagtctttgtcgtactcttgaactgtgccgtcgtggtccg
1126 to 1200


BlpI
CelII     Eco57I                                          EcoNI
                                                                   AlwNI
tcagcttcaggagcatatcaaggaacttctagccataaacagcaacaagaactcctagaaaggagcagaaact
base pairs
agtcgaagtcctcgtatagttccttgaagatcggtatttgtcgttgttcttgaggatctttcctcgtctttga
1201 to 1275
Bsp1720I
Bpu1102I
```

FIG. 12-9

```
    BpmI                                                        BseRI
ggagcagcagaggcaagaacaggaagtagagaggcatcgcagagaacagcagcttcctcctctcagaggcaaaga
base pairs
cctcgtcgtctccgttcttgtccttcatctctccgtagcgtctcttgtcgtcgaaggaggagagtctccgtttct
1276 to 1350
    GsuI                                                         EcoNI

                                             HindIII
tagaggacgagaaagggcagtggcaagtacagaagtaaagcag aagcttcaagagttcctactgagtaaatcagc
base pairs
atctcctgctctttcccgtcaccgttcatgtcttcatttcgtc ttcgaagttctcaaggatgactcatttagtcg
1351 to 1425
```

FIG. 12-10

```
                    Van91I                                Van91I
                    AccB7I                                AccB7I
aacgaaagacactccaactaatggaaaaaatcattccgtgagccgccatcccaagctctggtacacggctgccca
base pairs
ttgctttctgtgaggttgattaccttttttagtaaggcactcggcggtagggttcgagaccatgtgccgacgggt
1426 to 1500
                    Esp1396I                              Esp1396I
                    PflMI                                 PflMI
```

```
ccacacatcattggatcaaagctctccaccccttagtggaacatctccatcctacaagtacacattaccaggagc
base pairs
ggtgtgtagtaacctagtttcgagaggtggggaatcaccttgtagaggtaggatgttcatgtgtaatggtcctcg
1501 to 1575
```

FIG. 12-11

```
                                        BstBI
 Alw21I                                 Bpu14I                  FriOI
 AspHI                                  Csp45I                 Eco24I
acaagatgcaaaggatgatttccccttcgaaaaactgcctctgagcccaacttgaaggtgcggtccaggttaaa
base pairs
tgttctacgtttcctactaaaggggaagcttttgacggagactcgggttgaacttccacgccaggtccaattt
1576 to 1650
 BsiHKAI                                SfuI Bsp119I            BanII
 Bbv12I                                 NspV
                                        LspI


                        BseRI          EcoNI
acagaaagtggcagagaggagaagcagccccttactcaggcggaaggatggaaatgttgtcacttcattcaagaa
base pairs
tgtctttcaccgtctctcctcttcgtcggggaatgagtccgccttcctacctttacaacagtgaagtaagttctt
1651 to 1725
```

FIG. 12-12

```
                                                    Van91I
                                                    AccB7I                 Van91I
                                               BpmI PflMI                  AccB7I
gcgaatgtttgaggtgacagaatcctcagtcagtagcagttctccaggctctggtcccagttcaccaaacaatgg
base pairs
cgcttacaaactccactgtcttaggagtcagtcatcgtcaagaggtccgagaccagggtcaagtggtttgttacc
1726 to 1800
                                                                         Esp1396I
                                                    GsuI                    PflMI
                                                  Esp1396I
                                                    AlwNI

gccaactggaagtgttactgaaaatgagacttcggttttgccccctacccctcatgccgagcaaatggtttcaca
base pairs
cggttgaccttcacaatgacttttactctgaagccaaaacgggggatggggagtacggctcgtttaccaaagtgt
1801 to 1875
```

FIG. 12-13

```
          BsaMI
          Mva1269I                 BspMI                               XcmI
gcaacgcattctaattcatgaagattccatgaacctgctaagtctttatacctctccttctttgcccaacattac
base pairs
cgttgcgtaagattaagtacttctaaggtacttggacgattcagaaatatggagaggaagaaacgggttgtaatg
1876 to 1950
          BsmI RcaI
               BspHI



                                       BstBI AcsI
ErhI                                   Bpu14I
BssT1I                                 Csp45I
                                                                      Esp3I
cttggggcttcccgcagtgccatcccagctcaatgcttc gaattcactcaaagaaaagcagaagtgtgagacgca
base pairs
gaaccccgaagggcgtcacggtagggtcgagttacgaag cttaagtgagtttcttttcgtcttcacactctgcgt
1951 to 2025
EcoT14I                                SfuI Bsp119I
                                                                      BsmBI
StyI                                   NspV ApoI
Eco130I                                LspI EcoRI
```

FIG. 12-14

```
                                                                             MslI
gacgcttaggcaaggtgttcctctgcctgggcagtatggaggcagcatcccggcatcttccagccaccctcatgt
base pairs
ctgcgaatccgttccacaaggagacggacccgtcatacctccgtcgtagggccgtagaaggtcggtgggagtaca
2026 to 2100

                                                         PstI
                                                     SfcI
tactttagagggaaagccacccaacagcagccaccaggctctc ctgcagcatttattattgaaagaacaaatgcg
base pairs
atgaaatctccctttcggtgggttgtcgtcggtggtccgagag gacgtcgtaaataataactttcttgtttacgc
2101 to 2175
                                                     BstSFI
```

FIG. 12-15

```
                                                   Eco130I
                                                    StyI
        HindIII                                     EcoT14I          ApoI
acagcaaaagcttcttgtagctggtggagttcccttacatcctcagtctcccttggcaacaaaagagagaatttc
base pairs
tgtcgttttcgaagaacatcgaccacctcaagggaatgtaggagtcagagggaaccgttgttttctctcttaaag
2176 to 2250
                                                   BssT1I            AcsI
                                                    ErhI


              Asp718I
              Acc65I
              BshNI                                              BsgI
acctggcattagaggtacccacaaattgccccgtcacagacccctgaaccgaacccagtctgcacctttgcctca
base pairs
tggaccgtaatctccatgggtgtttaacggggcagtgtctggggacttggcttgggtcagacgtggaaacggagt
2251 to 2325
              BanI KpnI
              AccB1I
              Eco64I
```

FIG. 12-16

```
            Bpu1102I
     Alw21I Bsp1720I
     AspHI  CelII
gagcacgttggctcagctggtcattcaacagcaacaccagcaattcttggagaagcagaagcaataccagcagca
base pairs
ctcgtgcaaccgagtcgaccagtaagttgtcgttgtggtcgttaagaacctcttcgtcttcgttatggtcgtcgt
2326 to 2400
     BsiHKAI    PvuII
     Bbv12I BlpI MspA1I
                NspBII

                       BstBI
MflI                   Bpu14I
XhoII                  Csp45I                 Eco57I
gatccacatgaacaaactgctttcgaaatctattgaacaactgaagcaaccaggcagtcaccttgaggaagcaga
base pairs
ctaggtgtacttgtttgacgaaagctttagataacttgttgacttcgttggtccgtcagtggaactccttcgtct
2401 to 2475
BstYI                  SfuI Bsp119I
BstX2I                 NspV
                       LspI
```

FIG. 12-17

```
      EarI
      Eam1104I                           Bbv16II
     Asp700I                             BbsI   Bsp143II
ggaagagcttcaggggaccaggcgatgcaggaagacagagcgccctctagtggcaacagcactaggagcgacag
base pairs
ccttctcgaagtcccctggtccgctacgtccttctgtctcgcgggagatcaccgttgtcgtgatcctcgctgtc
2476 to 2550
     XmnI   Eco57I                       BpiI   HaeII
      Ksp632I                            BpuAI  BstH2I
       SapI
```

```
     BcgI
cagtgcttgtgtggatgacacactgggacaagttggggctgtgaaggtcaaggaggaaccagtggacagtgatga
base pairs
gtcacgaacacacctactgtgtgaccctgttcaaccccgacacttccagttcctccttggtcacctgtcactact
2551 to 2625
```

FIG. 12-18

```
         MflI      Van91I
         XhoII     AccB7I
agatgctcagatccaggaaatggaatctggggagcaggctgcttttatgcaacagcctttcctggaacccacgca
base pairs
tctacgagtctaggtcctttaccttagacccctcgtccgacgaaaatacgttgtcggaaaggaccttgggtgcgt
2626 to 2700
         BstYI     Esp1396I
         BstX2I    PflMI


     PmaCI
     PmlI
  AflIII                       NspBII
                                                                        Esp3I
cacacgtgcgctctctgtgcgccaagctccgctggctgcggttggcatggatggattagagaaacaccgtctcgt
base pairs
gtgtgcacgcgagagacacgcggttcgaggcgaccgacgccaaccgtacctacctaatctctttgtggcagagca
2701 to 2775
   MslI Eco72I                 MspA1I
                                                                        BsmBI
     BsaAI
     BbrPI
```

FIG. 12-19

```
                 EarI
     BpmI        Eam1104I                                    BsrDI            BpmI
ctccaggactcactcttcccctgctgcctctgttttacctcacccagcaatggaccgccccctccagcctggctc
base pairs
gaggtcctgagtgagaaggggacgacggagacaaaatggagtgggtcgttacctggcgggggaggtcggaccgag
2776 to 2850
     GsuI        Ksp632I                                                      GsuI


                                                       XcmI
tgcaactggaattgcctatgaccccttgatgctgaaacaccagtgcgtttgtggcaattccaccacccaccctga
base pairs
acgttgaccttaacggatactggggaactacgactttgtggtcacgcaaacaccgttaaggtggtgggtgggact
2851 to 2925
```

FIG. 12-20

```
     SphI                                                          AcsI
     BbuI                                                          ApoI
gcatgctggacgaatacagagtatctggtcacgactgcaagaaactgggctgctaaataaatgtgagc gaattca
base pairs
cgtacgacctgcttatgtctcatagaccagtgctgacgttctttgacccgacgatttatttacactcg cttaagt
2926 to 3000
     PaeI                                                          EcoRI
     NspI
```

```
                                                               AccB1I
                    BpmI                                        BshNI
aggtcgaaaagccagcctggaggaaatacagcttgttcattctgaacatcactcactgttgtatggcaccaaccc
base pairs
tccagcttttcggtcggacctcctttatgtcgaacaagtaagacttgtagtgagtgacaacataccgtggttggg
3001 to 3075
                    GsuI                                        BanI
                                                               Eco64I
```

FIG. 12-21

```
                                                       ErhI
                                                       StyI Eco130I
 BstXI                   AlwNI                         EcoT14I
cctggacggacagaagctggaccccaggatactcctaggtgatgactctcaaaagtttttttcctcattaccttg
base pairs
ggacctgcctgtcttcgacctggggtcctatgaggatccactactgagagttttcaaaaaaaggagtaatggaac
3076 to 3150
                                                       BssT1I
                                                       AvrII
                                                       BlnI

                                                                            BsaWI           BsgI
tggtggacttggggtggacagtgacaccatttggaatgagctacactcgtccggtgctgcacgcatggctgttgg
base pairs
accacctgaaccccacctgtcactgtggtaaaccttactcgatgtgagcaggccacgacgtgcgtaccgacaacc
3151 to 3225
```

FIG. 12-22

```
                                      CvnI
                                      AocI                                      CfrI
                                      Bsu36I          Eco57I               DraII EaeI
ctgtgtcatcgagctggcttccaaagtggcctcaggagagctgaagaatgggtttgctgttgtgaggccccctgg
base pairs
gacacagtagctcgaccgaaggtttcaccggagtcctctcgacttcttacccaaacgacaacactccgggggacc
3226 to 3300
                                      Eco81I                              EcoO109I
                                      Bse21I


MscI                            ErhI Eco130I
                                BssT1I BstXI
              Eco57I            MslI DsaI
ccatcacgctgaagaatccacagccatggggttctgctttttaattcagttgcaattaccgccaaatacttgag
base pairs
ggtagtgcgacttcttaggtgtcggtaccccaagacgaaaaattaagtcaacgttaatggcggtttatgaactc
3301 to 3375
MluNI                           EcoT14I
BalI                            StyI BstDSI
                                NcoI Bsp19I
```

FIG. 12-23

```
                     BstX2I          NcoI Bsp19I Asp718I   SseBI
                     BstYI           StyI BstDSI AccB1I
                                                      Eco147I
   BsaI              XhoII           EcoT14I  BshNI       StuI
agaccaactaaatataagcaagatattgattgtagatctggatgttcaccatggaaacggtacccagcaggcctt
base pairs
tctggttgatttatattcgttctataactaacatctagacctacaagtggtacctttgccatgggtcgtccggaa
3376 to 3450
   Eco31I            BglII           BssT1I   BanI KpnI   AatI
                     MflI            ErhI Eco130I Eco64I  Pme55I
                                     DsaI     Acc65I
```

```
           SspBI
           Bsp1407I        MslI            Asp700I
ttatgctgaccccagcatcctgtacatttcactccatcgctatgatgaagggaactttttccctggcagtggagc
base pairs
aatacgactggggtcgtaggacatgtaaagtgaggtagcgatactacttcccttgaaaaagggaccgtcacctcg
3451 to 3525
           BsrGI                           XmnI
```

FIG. 12-24

```
                     SseBI ErhI
 FriOI               Eco147I
 Eco24I              StuI BssT1I                SspI
cccaaatgaggttggaacaggccttggagaagggtacaatataaatattgcctggacaggtggccttgatcctcc
base pairs
gggtttactccaaccttgtccggaacctcttcccatgttatatttataacggacctgtccaccggaactaggagg
3526 to 3600
 BanII               AatI StyI
                     Pme55I Eco130I
                      EcoT14I

NcoI Bsp19I                                           MscI
StyI BstDSI                    BsaMI                  MluNI
                                                                      AspI
EcoT14I                        Mva1269I             EaeI
                                                                      AtsI
catgggagatgttgagtaccttgaagcattcaggaccatcgtgaagcctgtggccaaagagtttgatccagacat
base pairs
gtaccctctacaactcatggaacttcgtaagtcctggtagcacttcggacaccggtttctcaaactaggtctgta
3601 to 3675
BssT1I                         BsmI                 CfrI
DsaI                                                                 Tth111I
ErhI Eco130I                                          BalI
```

FIG. 12-25

```
                    Mph1103I
                    EcoT22I
                Ppu10I                      EcoNI
ggtcttagtatctgctggatttgatgcattggaaggccacacccctcctctaggagggtacaaagtgacggcaaa
base pairs
ccagaatcatagacgacctaaactacgtaaccttccggtgtggggaggagatcctcccatgtttcactgccgttt
3676 to 3750
                    NsiI                      BseRI
                    Zsp2I

                MfeI                      AflIII        XbaI
atgttttggtcatttgacgaagcaattgatgacattggctgatggacgtgtggtgttggctctagaaggaggaca
base pairs
tacaaaaccagtaaactgcttcgttaactactgtaaccgactacctgcacaccacaaccgagatcttcctcctgt
3751 to 3825
                MunI
```

FIG. 12-26

```
                    Mph1103I
                    EcoT22I
                 Ppu10I                                         BpmI
tgatctcacagccatctgtgatgcatcagaagcctgtgtaaatgcccttctaggaaatgagctggagccacttgc
base pairs
actagagtgtcggtagacactacgtagtcttcggacacatttacgggaagatcctttactcgacctcggtgaacg
3826 to 3900
                    NsiI                                        GsuI
                    Zsp2I

                                    BsaMI
     Asp700I                        Mva1269I                 ApoI
agaagatattctccaccaaagcccgaatatgaatgctgttatttctttacagaagatcattgaaattcaaagtat
base pairs
tcttctataagaggtggtttcgggcttatacttacgacaataaagaaatgtcttctagtaactttaagtttcata
3901 to 3975
     XmnI                           BsmI                     AcsI
```

FIG. 12-27

```
                      MflI  AccB1I                                          AvaI  BcoI
                      BstI  BsaWI  KpnI                                 MflI  Eco88I  PspALI
      DraI            BamHI  BshNI                                      XhoII  Cfr9I  SmaI  MslI
gtctttaaagttctctggatccggtaccagattacaaggacgacgatgacaagtagatcccgggtggcatccctg
base pairs
cagaaatttcaagagacctaggccatggtctaatgttcctgctgctactgttcatctagggcccaccgtagggac
3976 to 4050
                      XhoII  BanI  Eco64I                              BstYI  Ama87I
                      BstYI  Acc65I                                     BstX2I  BsoBI
                      BstX2I  Asp718I                                       XmaI  PspAI

                              Eco130I
                              StyI                  GsuI
                              EcoT14I           MslI
tgacccctccccagtgcctctcctggccttggaagttgccactccagtgcccaccagccttgtcctaataaaatt
base pairs
actggggaggggtcacggagaggaccggaaccttcaacggtgaggtcacgggtggtcggaacaggattatttaa
4051 to 4125
                              BssT1I                BpmI
                              ErhI
```

FIG. 12-28

```
            AspEI                                   DraII
           Eam1105I                  SspI           PspOMI
aagttgcatcattttgtctgactaggtgtcctctataatattatggggtggagggggtggtatggagcaagggg
base pairs
ttcaacgtagtaaaacagactgatccacaggagatattataataccccacctcccccaccatacctcgttcccc
4126 to 4200
            EclHKI
                                                    Bsp120I
            AhdI
                                                      EcoO1

  Eco24I          SfcI
    BanII      Bbv16II
     FriOI     BbsI     DraII                    BpmI  BsgI
cccaagttgggaagacaacctgtagggcctgcggggtctattcgggaaccaagctggagtgcagtggcacaatct
base pairs
gggttcaacccttctgttggacatcccggacgccccagataagcccttggttcgacctcacgtcaccgtgttaga
4201 to 4275
               BpiI     EcoO109I                 GsuI
   09I         BpuAI
  ApaI            BstSFI
```

FIG. 12-29

```
                                                                  BcoI
                                                                 Ama87I
                                                        BcgI      AvaI
tggctcactgcaatctccgcctcctgggttcaagcgattctcctgcctcagcctcccgagttgttgggattccag
base pairs
accgagtgacgttagaggcggaggacccaagttcgctaagaggacggagtcggagggctcaacaaccctaaggtc
4276 to 4350
                                                                 Eco88I
                                                                 BsoBI

      NspI         BlpI                                                     MscI
     PaeI Mph1103I                                                         MluNI
   Ppu10I EcoT22I                                        Esp3I           EaeI
gcatgcatgaccaggctcagctaattttgtttttttggtagagacggggtttcaccatattggccaggctggtc
base pairs
cgtacgtactggtccgagtcgattaaaacaaaaaaaccatctctgccccaaagtggtataaccggtccgaccag
4351 to 4425
     BbuI Zsp2I CelII                                     BsmBI          CfrI
     SphI       Bsp1720I                                                   BalI
       NsiI     Bpu1102I
```

FIG. 12-30

```
                              Eco130I
                              StyI
  BsaI                        EcoT14I          BstXI
tccaactcctaatctcaggtgatctacccaccttggcctcccaaattgctgggattacaggcgtgaaccactgct
base pairs
aggttgaggattagagtccactagatgggtggaaccggagggtttaacgaccctaatgtccgcacttggtgacga
4426 to 4500
  Eco31I                      BssT1I
                              ErhI
```

FIG. 12-31

```
                                                BbiII
                                                                      NcoI
                                                Hin1I                 StyI
                    DraI                        AcyI  AatII          EcoT14I
cccttccctgtccttctgatttaaaataactataccagcaggaggacgtccagacacagcataggctacctgcc
base pairs
gggaagggacaggaagactaaaatttattgatatggtcgtcctcctgcaggtctgtgtcgtatccgatggacgg
4501 to 4575
                                               Msp17I                BssT1I

                                                                      ErhI
                                                BsaHI
                                                                     BspMI

                                               Hsp92I


    Eco130I BsrFI PflMI
    DsaI AgeI Bse118I
         BsaWI AccB7I
atggcccaaccggtgggacatttgagttgcttgcttggcactgtcctctcatgcgttgggtccactcagtagatg
base pairs
taccgggttggccaccctgtaaactcaacgaacgaaccgtgacaggagagtacgcaacccaggtgagtcatctac
4576 to 4650
         BssAI Esp1396I
    BstDSI PinAI Van91I
     Bsp19I Cfr10I
```

FIG. 12-32

```
                   EaeI     AlwNI
cctgttgaattgggtacgcggccagcttctgtggaatgtgtgtcagttagggtgtggaaagtccccaggctcccc
base pairs
ggacaacttaacccatgcgccggtcgaagacaccttacacacagtcaatcccacacctttcaggggtccgagggg
4651 to 4725
                   CfrI


                        NspI
                        PaeI Mph1103I
                      Ppu10I EcoT22I       SexAI
agcaggcagaagtatgcaaagcatgcatctcaattagtcagcaaccaggtgtggaaaagtccccaggctccccag
base pairs
tcgtccgtcttcatacgtttcgtacgtagagttaatcagtcgttggtccacaccttttcaggggtccgaggggtc
4726 to 4800
                        BbuI Zsp2I
                        SphI
                          NsiI
```

FIG. 12-33

```
                 NspI
                 PaeI Mph1103I
               Ppu10I EcoT22I
caggcagaagtatgcaaagcatgcatctcaattagtcagcaaccatagtcccgcccctaactccgcccatcccgc
base pairs
gtccgtcttcatacgtttcgtacgtagagttaatcagtcgttggtatcagggcggggattgaggcgggtagggcg
4801 to 4875
                 BbuI Zsp2I
                 SphI
                   NsiI

                                   NcoI Bsp19I
                                   StyI  BstDSI
                                   EcoT14I
ccctaactccgcccagttccgcccattctccgccccatggctgactaattttttttatttatgcagaggccgagg
base pairs
gggattgaggcgggtcaaggcgggtaagaggcggggtaccgactgattaaaaaaaataaatacgtctccggctcc
4876 to 4950
                                   BssT1I
                                   ErhI Eco130I
                                   DsaI
```

FIG. 12-34

```
                                                        SseBI AvrII
                                                       Eco147I  BlnI
      BglI                                BseRI         StuI BssT1I
ccgcctcggcctctgagctattccagaagtagtgaggaggcttttttggaggcctaggcttttgcaaaaagctc c
base pairs
ggcggagccggagactcgataaggtcttcatcactcctccgaaaaacctccggatccgaaaacgtttttcgagg
4951 to 5025
      SfiI                                              AatI StyI
                                                       Pme55I  ErhI
                                                        EcoT14I Eco130I

Ama87I
Eco88I BseRI
AvaI BsoBI                        SfcI             ApoI
tcgaggaactgaaaaaccagaaagttaattccctatagtgagtcgtattaaattcgtaatcatggtcatagctgt
base pairs
agctccttgacttttggtctttcaattaagggatatcactcagcataatttaagcattagtaccagtatcgaca
5026 to 5100
XhoI BcoI                         BstSFI           AcsI
Sfr274I
PaeR7I
```

FIG. 12-35

```
                    AccBSI
                    BsrBI
ttcctgtgtgaaattgttatccgctcacaattccacacaacatacgagccggaagcataaagtgtaaagcctggg
base pairs
aaggacacactttaacaataggcgagtgttaaggtgtgttgtatgctcggccttcgtatttcacatttcggaccc
5101 to 5175
                    BstD102I


AccB1I                VspI
BshNI                 PshBI
gtgcctaatgagtgagctaactcacattaattgcgttgcgctcactgcccgctttccagtcgggaaacctgtcgt
base pairs
cacggattactcactcgattgagtgtaattaacgcaacgcgagtgacgggcgaaaggtcagccctttggacagca
5176 to 5250
BanI                  AsnI
Eco64I                AseI
```

FIG. 12-36

```
        VspI                                                          Eam1104I
     MspA1I                                                      BstH2I
     PvuII PshBI    EaeI                                         Bsp143II
gccagctgcattaatgaatcggccaacgcgcggggagaggcggtttgcgtattgggcgctcttccgcttcctcgc
base pairs
cggtcgacgtaattacttagccggttgcgcgcccctctccgccaaacgcataacccgcgagaaggcgaaggagcg
5251 to 5325
     NspBII         CfrI                                          HaeII EarI
        AsnI                                                           SapI
        AseI                                                          Ksp632I

                      BstMCI                AccBSI
                      BsaOI                 BsrBI
tcactgactcgctgcgctcggtcgttcggctgcggcgagcggtatcagctcactcaaaggcggtaatacggttat
base pairs
agtgactgagcgacgcgagccagcaagccgacgccgctcgccatagtcgagtgagtttccgccattatgccaata
5326 to 5400
                      Bsh1285I              BstD102I
                      BsiEI
```

FIG. 12-37

```
                                      NspI
                                  BspLU11I
ccacagaatcaggggataacgcaggaaagaacatgtgagcaaaaggccagcaaaaggccaggaaccgtaaaaagg
base pairs
ggtgtcttagtcccctattgcgtcctttcttgtacactcgttttccggtcgttttccggtccttggcatttttcc
5401 to 5475
                              AflIII
```

```
                                                                DrdI
ccgcgttgctggcgtttttccataggctccgcccccctgacgagcatcacaaaaatcgacgctcaagtcagaggt
base pairs
ggcgcaacgaccgcaaaaaggtatccgaggcggggggactgctcgtagtgtttttagctgcgagttcagtctcca
5476 to 5550
```

FIG. 12-38

```
                                                                         BsiI
ggcgaaacccgacaggactataaagataccaggcgtttccccctggaagctccctcgtgcgctctcctgttccga
base pairs
ccgctttgggctgtcctgatatttctatggtccgcaaagggggaccttcgagggagcacgcgagaggacaaggct
5551 to 5625
                                                                         BssSI
```

```
                                                                   BstH2I
             BsaWI                                                 Bsp143II           SfcI
ccctgccgcttaccggatacctgtccgcctttctcccttcgggaagcgtggcgctttctcaatgctcacgctgta
base pairs
gggacggcgaatggcctatggacaggcggaaagagggaagcccttcgcaccgcgaaagagttacgagtgcgacat
5626 to 5700
                                                                   HaeII              BstSFI
```

FIG. 12-39

```
                                                 BsiHKAI
                                                                   NspBII
                                             Alw44I                BstMCI
                                             VneI Bbv12I            BsaOI
ggtatctcagttcggtgtaggtcgttcgctccaagctgggctgtgtgcacgaaccccccgttcagcccgaccgct
base pairs
ccatagagtcaagccacatccagcaagcgaggttcgacccgacacacgtgcttgggggcaagtcgggctggcga
5701 to 5775
                                             ApaLI
                                                                 Bsh1285I
                                                 AspHI              BsiEI
                                                Alw21I
                                                                   MspA1I

         BsaWI                                                         AlwNI
gcgccttatccggtaactatcgtcttgagtccaacccggtaagacacgacttatcgccactggcagcagccactg
base pairs
cgcggaataggccattgatagcagaactcaggttgggccattctgtgctgaatagcggtgaccgtcgtcggtgac
5776 to 5850
```

FIG. 12-40

SfcI
gtaacaggattagcagagcgaggtatgtaggcggtgctacagagttcttgaagtggtggcctaactacggctaca
base pairs
cattgtcctaatcgtctcgctccatacatccgccacgatgtctcaagaacttcaccaccggattgatgccgatgt
5851 to 5925
BstSFI Eco57I
ctagaagaacagtatttggtatctgcgctctgctgaagccagttaccttcggaaaaagagttggtagctcttgat
base pairs
gatcttcttgtcataaaccatagacgcgagacgacttcggtcaatggaagcctttttctcaaccatcgagaacta
5926 to 6000

FIG. 12-41

```
                  NspBII                                                       MflI
                                                                               XhoII
ccggcaaacaaaccaccgctggtagcggtggtttttttgtttgcaagcagcagattacgcgcagaaaaaaaggat
base pairs
ggccgtttgtttggtggcgaccatcgccaccaaaaaaacaaacgttcgtcgtctaatgcgcgtctttttttccta
6001 to 6075
                  MspA1I                                                       BstYI
                                                                              BstX2I


        MflI
        XhoII
ctcaagaagatcctttgatcttttctacggggtctgacgctcagtggaacgaaaactcacgttaagggattttgg
base pairs
gagttcttctaggaaactagaaaagatgccccagactgcgagtcaccttgcttttgagtgcaattccctaaaacc
6076 to 6150
        BstYI
        BstX2I
```

FIG. 12-42

```
                    MflI        MflI
 RcaI               XhoII       XhoII    DraI                DraI
tcatgagattatcaaaaaggatcttcacctagatcctttaaattaaaaatgaagttttaaatcaatctaaagta
base pairs
agtactctaatagtttttcctagaagtggatctaggaaatttaatttttacttcaaaatttagttagatttcat
6151 to 6225
 BspHI              BstYI       BstYI
                    BstX2I      BstX2I
```

```
                                                    AccB1I
                                                     BshNI
tatatgagtaaacttggtctgacagttaccaatgcttaatcagtgaggcacctatctcagcgatctgtctatttc
base pairs
atatactcatttgaaccagactgtcaatggttacgaattagtcactccgtggatagagtcgctagacagataaag
6226 to 6300
                                                     BanI
                                                    Eco64I
```

FIG. 12-43

```
                        Eam1105I
                        AspEI
gttcatccatagttgcctgactccccgtcgtgtagataactacgatacgggagggcttaccatctggccccagtg
base pairs
caagtaggtatcaacggactgaggggcagcacatctattgatgctatgccctcccgaatggtagaccggggtcac
6301 to 6375
                        EclHKI
                        AhdI

                                  Cfr10I
        BsrDI           BsaI      BssAI     BpmI                         BglI
ctgcaatgataccgcgagacccacgctcaccggctccagatttatcagcaataaaccagccagccggaagggccg
base pairs
gacgttactatggcgctctgggtgcgagtggccgaggtctaaatagtcgttatttggtcggtcggccttcccggc
6376 to 6450
                        Eco31I    BsrFI     GsuI
                                  Bse118I
```

FIG. 12-44

```
                                                  VspI
                                                  PshBI
agcgcagaagtggtcctgcaactttatccgcctccatccagtctattaattgttgccgggaagctagagtaagta
base pairs
tcgcgtcttcaccaggacgttgaaataggcggaggtaggtcagataattaacaacggcccttcgatctcattcat
6451 to 6525
                                                  AsnI
                                                  AseI


                     AviII                BstSFI
                     FspI                 SfcI          MslI
gttcgccagttaatagtttgcgcaacgttgttgccattgctacaggcatcgtggtgtcacgctcgtcgtttggta
base pairs
caagcggtcaattatcaaacgcgttgcaacaacggtaacgatgtccgtagcaccacagtgcgagcagcaaaccat
6526 to 6600
                     Acc16I               BsrDI
                         Psp1406I
```

FIG. 12-45

```
               BsaWI
tggcttcattcagctccggttcccaacgatcaaggcgagttacatgatcccccatgttgtgcaaaaaagcggtta
base pairs
accgaagtaagtcgaggccaagggttgctagttccgctcaatgtactagggggtacaacacgttttttcgccaat
6601 to 6675

                   BstMCI
                   PvuI BsiEI
                   BsaOI             EaeI                  MslI
gctccttcggtcctccgatcgttgtcagaagtaagttggccgcagtgttatcactcatggttatggcagcactgc
base pairs
cgaggaagccaggaggctagcaacagtcttcattcaaccggcgtcacaatagtgagtaccaataccgtcgtgacg
6676 to 6750
                   BspCI             CfrI
                   Bsh1285I
                   Ple19I
```

FIG. 12-46

```
                                                      Acc113I
                                                      Eco255I
ataattctcttactgtcatgccatccgtaagatgcttttctgtgactggtgagtactcaaccaagtcattctgag
base pairs
tattaagagaatgacagtacggtaggcattctacgaaaagacactgaccactcatgagttggttcagtaagactc
6751 to 6825
                                                       ScaI

                                        BbiII
                 BstMCI                 Hin1I
                 BsaOI    BcgI          AcyI
aatagtgtatgcggcgaccgagttgctcttgcccggcgtcaatacgggataataccgcgccacatagcagaactt
base pairs
ttatcacatacgccgctggctcaacgagaacgggccgcagttatgccctattatggcgcggtgtatcgtcttgaa
6826 to 6900
                 Bsh1285I               Msp17I
                 BsiEI                  BsaHI
                                        Hsp92I
```

FIG. 12-47

```
          Alw21I       XmnI                        MflI              MflI
 DraI     AspHI        Psp1406I                    XhoII     NspBII XhoII
taaaagtgctcatcattggaaaacgttcttcggggcgaaaactctcaaggatcttaccgctgttgagatccagtt
base pairs
attttcacgagtagtaaccttttgcaagaagccccgcttttgagagttcctagaatggcgacaactctaggtcaa
6901 to 6975
          BsiHKAI      Asp700I                     BstYI     MspA1I BstYI
          Bbv12I                                  BstX2I            BstX2I

                BssSI
               Alw44I Bbv12I
               VneI BsiHKAI         Eco57I
cgatgtaacccactcgtgcacccaactgatcttcagcatcttttactttcaccagcgtttctgggtgagcaaaaa
base pairs
gctacattgggtgagcacgtgggttgactagaagtcgtagaaaatgaaagtggtcgcaaagacccactcgtttttt
6976 to 7050
               ApaLI Alw21I
                 BsiI
                   AspHI
```

FIG. 12-48

```
                                                                        EarI
                                               MslI                     Eam1104I
caggaaggcaaaatgccgcaaaaaagggaataagggcgacacggaaatgttgaatactcatactcttcctttttc
base pairs
gtccttccgttttacggcgtttttcccttattcccgctgtgcctttacaacttatgagtatgagaaggaaaaag
7051 to 7125
                                                                       Ksp632I

                                               AccBSI
   SspI                                RcaI    BsrBI
aatattattgaagcatttatcagggttattgtctcatgagcggatacatatttgaatgtatttagaaaaataaac
base pairs
ttataataacttcgtaaatagtcccaataacagagtactcgcctatgtataaacttacataaatctttttatttg
7126 to 7200
                                       BspHI   BstD102I
```

FIG. 12-49

```
                                                  SfcI
aaataggggttccgcgcacatttccccgaaaagtgccacctgacgcgccctgtagcggcgcattaagcgcggcgg
base pairs
tttatccccaaggcgcgtgtaaaggggcttttcacggtggactgcgcgggacatcgccgcgtaattcgcgccgcc
7201 to 7275
                                                  BstSFI

                                                              AccBSI
                                          BstH2I   HaeII BstD102I
                                          Bsp143II       BsrBI
gtgtggtggttacgcgcagcgtgaccgctacacttgccagcgccctagcgcccgctcctttcgctttcttccctt
base pairs
cacaccaccaatgcgcgtcgcactggcgatgtgaacggtcgcgggatcgcgggcgaggaaagcgaaagaagggaa
7276 to 7350
                                          HaeII   Bsp143II
                                                 BstH2I
```

FIG. 12-50

```
                    BsrFI
                    BssAI NaeI
                    MroNI Bse118I
cctttctcgccacgttcgccggctttccccgtcaagctctaaatcggggcatccctttagggttccgatttagtg
base pairs
ggaaagagcggtgcaagcggccgaaaggggcagttcgagatttagccccgtagggaaatcccaaggctaaatcac
7351 to 7425
                    NgoAIV
                    NgoMI
                    Cfr10I


       AccB1I
       BshNI                                               BsaAI
ctttacggcacctcgaccccaaaaaacttgattagggtgatggttcacgtagtgggccatcgccctgatagacgg
base pairs
gaaatgccgtggagctggggtttttgaactaatcccactaccaagtgcatcacccggtagcgggactatctgcc
7426 to 7500
       BanI                                                   DraIII
       Eco64I
```

FIG. 12-51

```
                    DrdI
tttttcgccctttgacgttggagtccacgttctttaatagtggactcttgttccaaactggaacaacactcaacc
base pairs
aaaaagcgggaaactgcaacctcaggtgcaagaaattatcacctgagaacaaggtttgaccttgttgtgagttgg
7501 to 7575
```

```
ctatctcggtctattcttttgatttataagggatttgccgatttcggcctattggttaaaaaaatgagctgattt
base pairs
gatagagccagataagaaaactaaatattccctaaacggctaaagccggataaccaatttttttactcgactaaa
7576 to 7650
```

FIG. 12-52

```
      ApoI        ApoI            SspI  Psp1406I
aacaaaaatttaacgcgaattttaacaaaatattaaacgtttacaattt  base pairs
ttgtttttaaattgcgcttaaaattgttttataatttgcaaatgttaaa  7651 to 7699
      AcsI        AcsI
```

Table by Enzyme Name

| Enzyme name | No. cuts | Positions of sites | Recognition sequence | |
|---|---|---|---|---|
| AatI | 3 | 3446 3546 5002 | agg/cct | More info |
| AatII | 5 | 451 504 587 773 4550 | gacgt/c | More info |
| Acc113I | 1 | 6804 | agt/act | More info |
| Acc16I | 2 | 21 6546 | tgc/gca | More info |
| Acc65I | 3 | 2264 3434 3998 | g/ gtacc | More info |
| AccB1I | 8 | 791 2264 3065 3434 3998 5175 6272 7432 | g/ gyrcc | More info |
| AccB7I | 6 | 1445 1482 1775 1796 2644 4587 | ccannnn/ntgg | More info |
| AccBSI | 4 | 5126 5367 7168 7332 | gagcgg | More info |
| AclNI | 1 | 326 | a/ ctagt | More info |
| AcsI | 8 | 912 1990 2244 2994 3963 5075 7656 7667 | r/ aatty | More info |
| AcyI | 6 | 448 501 584 770 4547 6861 | gr/cgyc | More info |

FIG. 12-53

| | | | | |
|---|---|---|---|---|
| AflIII | 3 | 2702 3796 5431 | a/ crygt | More info |
| AgeI | 1 | 4584 | a/ ccggt | More info |
| AhdI | 2 | 4150 6324 | gacnnn/nngtc | More info |
| Alw21I | 6 | 894 1576 2330 5749 6910 6995 | gwgcw/c | More info |
| Alw44I | 2 | 5745 6991 | g/ tgcac | More info |
| AlwNI | 6 | 1147 1273 1775 3091 4678 5847 | cagnnn/ctg | More info |
| Ama87I | 3 | 4034 4330 5025 | c/ ycgrg | More info |
| AocI | 3 | 1034 1046 3256 | cc/ tnagg | More info |
| ApaI | 1 | 4202 | gggcc/c | More info |
| ApaLI | 2 | 5745 6991 | g/ tgcac | More info |
| ApoI | 8 | 912 1990 2244 2994 3963 5075 7656 7667 | r/ aatty | More info |
| AseI | 4 | 334 5202 5261 6496 | at/ taat | More info |
| AsnI | 4 | 334 5202 5261 6496 | at/ taat | More info |
| Asp700I | 5 | 1107 2481 3506 3906 6923 | gaann/nnttc | More info |
| Asp718I | 3 | 2264 3434 3998 | g/ gtacc | More info |

FIG. 12-54

| | | | | |
|---|---|---|---|---|
| AspEI | 2 | 4150 6324 | gacnnn/nngtc | More info |
| AspHI | 6 | 894 1576 2330 5749 6910 6995 | gwgcw/c | More info |
| AspI | 1 | 3674 | gacn/nngtc | More info |
| AtsI | 1 | 3674 | gacn/nngtc | More info |
| AvaI | 3 | 4034 4330 5025 | c/ ycgrg | More info |
| AviII | 2 | 21 6546 | tgc/gca | More info |
| AvrII | 2 | 3109 5003 | c/ ctagg | More info |
| BalI | 5 | 184 238 3300 3653 4414 | tgg/cca | More info |
| BamHI | 1 | 3992 | g/ gatcc | More info |
| BanI | 8 | 791 2264 3065 3434 3998 5175 6272 7432 | g/ gyrcc | More info |
| BanII | 5 | 894 1017 1623 3526 4202 | grgcy/c | More info |
| BanIII | 1 | 939 | at/ cgat | More info |
| BbiII | 6 | 448 501 584 770 4547 6861 | gr/cgyc | More info |
| BbrPI | 1 | 2705 | cac/gtg | More info |
| BbsI | 2 | 2512 4216 | gaagac | More info |
| BbuI | 4 | 2930 4355 4750 4823 | gcatg/c | More info |
| Bbv12I | 6 | 894 1576 2330 5749 6910 6995 | gwgcw/c | More info |
| Bbv16II | 2 | 2512 4216 | gaagac | More info |
| BcgI | 4 | 941 2556 4321 6851 | cgannnnnntgc | More info |

FIG. 12-55

| | | | | |
|---|---|---|---|---|
| BclI | 1 | 969 | t/ gatca | More info |
| BcoI | 3 | 4034 4330 5025 | c/ ycgrg | More info |
| BglI | 5 | 14 417 538 4956 6444 | gccnnnn/nggc | More info |
| BglII | 2 | 932 3409 | a/ gatct | More info |
| BlnI | 2 | 3109 5003 | c/ ctagg | More info |
| BlpI | 3 | 1200 2337 4366 | gc/tnagc | More info |
| BpiI | 2 | 2512 4216 | gaagac | More info |
| BpmI | 10 | 1015 1279 1772 2781 2842 3022 3892 4097 4259 6414 | ctggag | More info |
| Bpu1102I | 3 | 1200 2337 4366 | gc/tnagc | More info |
| Bpu14I | 3 | 1603 1988 2423 | tt/cgaa | More info |
| BpuAI | 2 | 2512 4216 | gaagac | More info |
| Bsa29I | 1 | 939 | at/ cgat | More info |
| BsaAI | 3 | 666 2705 7473 | yac/gtr | More info |
| BsaHI | 6 | 448 501 584 770 4547 6861 | gr/cgyc | More info |
| BsaI | 3 | 3380 4427 6396 | ggtctc | More info |
| BsaMI | 3 | 1886 3631 3936 | gaatgc | More info |
| BsaOI | 7 | 42 424 928 5347 5771 6694 6843 | cgry/cg | More info |
| BsaWI | 6 | 3200 3995 4584 5637 5784 6615 | w/ ccggw | More info |
| BscI | 1 | 939 | at/ cgat | More info |

FIG. 12-56

| | | | | |
|---|---|---|---|---|
| Bse118I | 3 | 4584 6404 7368 | r/ ccggy | More info |
| Bse21I | 3 | 1034 1046 3256 | cc/ tnagg | More info |
| BseCI | 1 | 939 | at/ cgat | More info |
| BseRI | 5 | 1337 1671 3725 4989 5027 | gaggag | More info |
| BsgI | 3 | 2315 3212 4264 | gtgcag | More info |
| Bsh1285I | 7 | 42 424 928 5347 5771 6694 6843 | cgry/cg | More info |
| BshNI | 8 | 791 2264 3065 3434 3998 5175 6272 7432 | g/ gyrcc | More info |
| BsiEI | 7 | 42 424 928 5347 5771 6694 6843 | cgry/cg | More info |
| BsiHKAI | 6 | 894 1576 2330 5749 6910 6995 | gwgcw/c | More info |
| BsiI | 2 | 5609 6993 | ctcgtg | More info |
| BsmBI | 3 | 2023 2773 4397 | cgtctc | More info |
| BsmI | 3 | 1886 3631 3936 | gaatgc | More info |
| BsoBI | 3 | 4034 4330 5025 | c/ ycgrg | More info |
| Bsp106I | 1 | 939 | at/ cgat | More info |
| Bsp119I | 3 | 1603 1988 2423 | tt/cgaa | More info |
| Bsp120I | 1 | 4198 | g/ ggccc | More info |
| Bsp1407I | 2 | 270 3471 | t/ gtaca | More info |
| Bsp143II | 5 | 2519 5309 5679 7318 7326 | rgcgc/y | More info |
| Bsp1720I | 3 | 1200 2337 4366 | gc/tnagc | More info |
| Bsp19I | 6 | 686 3324 3424 3600 4574 4910 | c/ catgg | More info |

FIG. 12-57

| | | | | |
|---|---|---|---|---|
| BspCI | 2 | 42 6694 | cgat/cg | More info |
| BspDI | 1 | 939 | at/ cgat | More info |
| BspHI | 3 | 1891 6151 7159 | t/ catga | More info |
| BspLU11I | 1 | 5431 | a/ catgt | More info |
| BspMI | 2 | 1913 4574 | acctgc | More info |
| BspXI | 1 | 939 | at/ cgat | More info |
| BsrBI | 4 | 5126 5367 7168 7332 | gagcgg | More info |
| BsrDI | 4 | 245 2827 6383 6565 | gcaatg | More info |
| BsrFI | 3 | 4584 6404 7368 | r/ ccggy | More info |
| BsrGI | 2 | 270 3471 | t/ gtaca | More info |
| BssAI | 3 | 4584 6404 7368 | r/ ccggy | More info |
| BssSI | 2 | 5609 6993 | ctcgtg | More info |
| BssT1I | 13 | 686 1950 2226 3109 3324 3424 3547 3600 4077 4456 4574 4910 5003 | c/ cwwgg | More info |
| BstBI | 3 | 1603 1988 2423 | tt/cgaa | More info |
| BstD102I | 4 | 5126 5367 7168 7332 | gagcgg | More info |
| BstDSI | 7 | 686 1062 3324 3424 3600 4574 4910 | c/ crygg | More info |
| BstH2I | 5 | 2519 5309 5679 7318 7326 | rgcgc/y | More info |

FIG. 12-58

| | | | | |
|---|---|---|---|---|
| BstI | 1 | 3992 | g/ gatcc | More info |
| BstMCI | 7 | 42 424 928 5347 5771 6694 6843 | cgry/cg | More info |
| BstSFI | 8 | 944 2144 4220 5058 5696 5887 6565 7250 | c/ tryag | More info |
| BstSNI | 1 | 666 | tac/gta | More info |
| BstX2I | 12 | 932 2400 2634 3409 3992 4030 6072 6083 6169 6181 6949 6966 | r/ gatcy | More info |
| BstXI | 3 | 3076 3325 4473 | ccannnnn/ntgg | More info |
| BstYI | 12 | 932 2400 2634 3409 3992 4030 6072 6083 6169 6181 6949 6966 | r/ gatcy | More info |
| BstZI | 1 | 925 | c/ ggccg | More info |
| Bsu15I | 1 | 939 | at/ cgat | More info |
| Bsu36I | 3 | 1034 1046 3256 | cc/ tnagg | More info |
| CciNI | 1 | 925 | gc/ggccgc | More info |
| CelII | 3 | 1200 2337 4366 | gc/tnagc | More info |
| Cfr10I | 3 | 4584 6404 7368 | r/ ccggy | More info |
| Cfr9I | 1 | 4034 | c/ ccggg | More info |
| CfrI | 10 | 152 182 236 925 3298 3651 4412 4669 5270 6712 | y/ ggccr | More info |
| ClaI | 1 | 939 | at/ cgat | More info |
| Csp45I | 3 | 1603 1988 2423 | tt/cgaa | More info |
| CvnI | 3 | 1034 1046 3256 | cc/ tnagg | More info |

FIG. 12-59

| | | | | |
|---|---|---|---|---|
| DraI | 5 | 3981 4523 6190 6209 6901 | ttt/aaa | More info |
| DraII | 3 | 3291 4198 4225 | rg/gnccy | More info |
| DraIII | 1 | 7476 | cacnnn/gtg | More info |
| DrdI | 3 | 1076 5539 7520 | gacnnnn/nngtc | More info |
| DsaI | 7 | 686 1062 3324 3424 3600 4574 4910 | c/ crygg | More info |
| EaeI | 10 | 152 182 236 925 3298 3651 4412 4669 5270 6712 | y/ ggccr | More info |
| | | | | More info |
| EagI | 1 | 925 | c/ ggccg | More info |
| Eam1104I | 5 | 58 2482 2793 5314 7118 | ctcttc | More info |
| Eam1105I | 2 | 4150 6324 | gacnnn/nngtc | More info |
| EarI | 5 | 58 2482 2793 5314 7118 | ctcttc | More info |
| Ecl136II | 1 | 892 | gag/ ctc | More info |
| EclHKI | 2 | 4150 6324 | gacnnn/nngtc | More info |
| EclXI | 1 | 925 | c/ ggccg | More info |
| Eco105I | 1 | 666 | tac/gta | More info |
| Eco130I | 13 | 686 1950 2226 3109 3324 3424 3547 3600 4077 4456 4574 4910 5003 | c/ cwwgg | More info |
| Eco147I | 3 | 3446 3546 5002 | agg/cct | More info |

FIG. 12-60

| | | | | |
|---|---|---|---|---|
| Eco24I | 5 | 894 1017 1623 3526 4202 | grgcy/c | More info |
| Eco255I | 1 | 6804 | agt/act | More info |
| Eco31I | 3 | 3380 4427 6396 | ggtctc | More info |
| Eco32I | 1 | 952 | gat/ atc | More info |
| Eco52I | 1 | 925 | c/ ggccg | More info |
| Eco57I | 7 | 1210 2446 2488 3271 3314 5963 7011 | ctgaag | More info |
| Eco64I | 8 | 791 2264 3065 3434 3998 5175 6272 7432 | g/ gyrcc | More info |
| Eco72I | 1 | 2705 | cac/gtg | More info |
| Eco81I | 3 | 1034 1046 3256 | cc/ tnagg | More info |
| Eco88I | 3 | 4034 4330 5025 | c/ ycgrg | More info |
| EcoICRI | 1 | 892 | gag/ ctc | More info |
| EcoNI | 4 | 1259 1338 1684 3723 | cctnn/nnnagg | More info |
| EcoO109I | 3 | 3291 4198 4225 | rg/gnccy | More info |
| EcoRI | 3 | 912 1990 2994 | g/ aattc | More info |
| EcoRV | 1 | 952 | gat/ atc | More info |
| EcoT14I | 13 | 686 1950 2226 3109 3324 3424 3547 3600 4077 4456 4574 4910 5003 | c/ cwwgg | More info |
| EcoT22I | 5 | 3703 3850 4357 4752 4825 | atgca/t | More info |

FIG. 12-61

| | | | | |
|---|---|---|---|---|
| ErhI | 13 | 686 1950 2226 3109 3324 3424 3547 3600 4077 4456 4574 4910 5003 | c/ cwwgg | More info |
| Esp1396I | 6 | 1445 1482 1775 1796 2644 4587 | ccannnn/ntgg | More info |
| Esp3I | 3 | 2023 2773 4397 | cgtctc | More info |
| FauNDI | 1 | 560 | ca/ tatg | More info |
| FbaI | 1 | 969 | t/ gatca | More info |
| FriOI | 5 | 894 1017 1623 3526 4202 | grgcy/c | More info |
| FspI | 2 | 21 6546 | tgc/gca | More info |
| GsuI | 10 | 1015 1279 1772 2781 2842 3022 3892 4097 4259 6414 | ctggag | More info |
| HaeII | 5 | 2519 5309 5679 7318 7326 | rgcgc/y | More info |
| Hin1I | 6 | 448 501 584 770 4547 6861 | gr/cgyc | More info |
| HincII | 3 | 311 446 842 | gty/rac | More info |
| HindII | 3 | 311 446 842 | gty/rac | More info |
| HindIII | 3 | 918 1394 2183 | a/ agctt | More info |
| Hsp92I | 6 | 448 501 584 770 4547 6861 | gr/cgyc | More info |
| KpnI | 3 | 2268 3438 4002 | ggtac/c | More info |
| Ksp22I | 1 | 969 | t/ gatca | More info |
| Ksp632I | 5 | 58 2482 2793 5314 7118 | ctcttc | More info |
| LspI | 3 | 1603 1988 2423 | tt/cgaa | More info |
| MfeI | 2 | 1091 3773 | c/ aattg | More info |
| MflI | 12 | 932 2400 2634 3409 3992 4030 | r/gatcy | More info |

FIG. 12-62

| | | | | |
|---|---|---|---|---|
| | | 6072 6083 6169 6181 6949 6966 | | |
| MluNI | 5 | 184 238 3300 3653 4414 | tgg/cca | More info |
| Mph1103I | 5 | 3703 3850 4357 4752 4825 | atgca/t | More info |
| MroNI | 1 | 7368 | g/ ccggc | More info |
| MscI | 5 | 184 238 3300 3653 4414 | tgg/cca | More info |
| MslI | 10 | 691 2094 2703 3323 3489 4047 4094 6576 6735 7094 | caynn/nnrtg | More info |
| Msp17I | 6 | 448 501 584 770 4547 6861 | gr/cgyc | More info |
| MspA1I | 7 | 71 2341 2731 5255 5773 6018 6959 | cmg/ckg | More info |
| MunI | 2 | 1091 3773 | c/ aattg | More info |
| Mva1269I | 3 | 1886 3631 3936 | gaatgc | More info |
| NaeI | 1 | 7370 | gcc/ggc | More info |
| NcoI | 6 | 686 3324 3424 3600 4574 4910 | c/ catgg | More info |
| NdeI | 1 | 560 | ca/ tatg | More info |
| NgoAIV | 1 | 7368 | g/ ccggc | More info |
| NgoMI | 1 | 7368 | g/ ccggc | More info |
| NotI | 1 | 925 | gc/ggccgc | More info |
| NsiI | 5 | 3703 3850 4357 4752 4825 | atgca/t | More info |
| NspBII | 7 | 71 2341 2731 5255 5773 6018 6959 | cmg/ckg | More info |
| NspI | 5 | 2930 4355 4750 4823 5435 | rcatg/y | More info |
| NspV | 3 | 1603 1988 2423 | tt/cgaa | More info |
| PaeI | 4 | 2930 4355 4750 4823 | gcatg/c | More info |
| PaeR7I | 1 | 5025 | c/ tcgag | More info |

FIG. 12-63

| | | | | |
|---|---|---|---|---|
| PflMI | 6 | 1445 1482 1775 1796 2644 4587 | ccannnn/ntgg | More info |
| PinAI | 1 | 4584 | a/ ccggt | More info |
| Ple19I | 2 | 42 6694 | cgat/cg | More info |
| PmaCI | 1 | 2705 | cac/gtg | More info |
| Pme55I | 3 | 3446 3546 5002 | agg/cct | More info |
| PmlI | 1 | 2705 | cac/gtg | More info |
| Ppu10I | 5 | 3699 3846 4353 4748 4821 | a/ tgcat | More info |
| PshBI | 4 | 334 5202 5261 6496 | at/ taat | More info |
| Psp124BI | 1 | 894 | gagct/c | More info |
| Psp1406I | 3 | 6550 6923 7687 | aa/cgtt | More info |
| PspAI | 1 | 4034 | c/ccggg | More info |
| PspALI | 1 | 4036 | ccc/ggg | More info |
| PspOMI | 1 | 4198 | g/ggccc | More info |
| PstI | 2 | 948 2148 | ctgca/g | More info |
| PvuI | 2 | 42 6694 | cgat/cg | More info |
| PvuII | 3 | 71 2341 5255 | cag/ctg | More info |
| RcaI | 3 | 1891 6151 7159 | t/ catga | More info |
| SacI | 1 | 894 | gagct/c | More info |
| SapI | 2 | 2483 5314 | gctcttc | More info |
| ScaI | 1 | 6804 | agt/act | More info |
| SexAI | 1 | 4769 | a/ ccwggt | More info |
| SfcI | 8 | 944 2144 4220 5058 5696 5887 | c/ tryag | More info |

FIG. 12-64

| | | | | |
|---|---|---|---|---|
| | | 6565 7250 | | |
| SfiI | 1 | 4956 | ggccnnnn/nggcc | More info |
| Sfr274I | 1 | 5025 | c/ tcgag | More info |
| SfuI | 3 | 1603 1988 2423 | tt/cgaa | More info |
| SmaI | 1 | 4036 | ccc/ggg | More info |
| SnaBI | 1 | 666 | tac/gta | More info |
| SpeI | 1 | 326 | a/ ctagt | More info |
| SphI | 4 | 2930 4355 4750 4823 | gcatg/c | More info |
| SseBI | 3 | 3446 3546 5002 | agg/cct | More info |
| SspBI | 2 | 270 3471 | t/ gtaca | More info |
| SspI | 6 | 179 226 3571 4164 7128 7681 | aat/att | More info |
| SstI | 1 | 894 | gagct/c | More info |
| StuI | 3 | 3446 3546 5002 | agg/cct | More info |
| StyI | 13 | 686 1950 2226 3109 3324 3424 3547 3600 4077 4456 4574 4910 5003 | c/ cwwgg | More info |
| Tth111I | 1 | 3674 | gacn/nngtc | More info |
| Van91I | 6 | 1445 1482 1775 1796 2644 4587 | ccannnn/ntgg | More info |
| VneI | 2 | 5745 6991 | g/ tgcac | More info |
| VspI | 4 | 334 5202 5261 6496 | at/ taat | More info |
| XbaI | 1 | 3811 | t/ ctaga | More info |
| XcmI | 2 | 1948 2897 | ccannnnn/nnnntgg | More info |

FIG. 12-65

| | | | | |
|---|---|---|---|---|
| XhoI | 1 | 5025 | c/ tcgag | More info |
| XhoII | 12 | 932 2400 2634 3409 3992 4030 6072 6083 6169 6181 6949 6966 | r/ gatcy | More info |
| XmaI | 1 | 4034 | c/ ccggg | More info |
| XmaIII | 1 | 925 | c/ ggccg | More info |
| XmnI | 5 | 1107 2481 3506 3906 6923 | gaann/nnttc | More info |
| Zsp2I | 5 | 3703 3850 4357 4752 4825 | atgca/t | More info |

The following endonucleases were selected but don't cut this sequence:
AccI, AccIII, AfeI, AflII, Aor51HI, AscI, BbeI, BfrI, BsaBI, Bse8I, BseAI, BsePI, Bsh1365I, BsiMI, BsiWI, Bsp13I, Bsp68I, BspEI, BspTI, BsrBRI, BssHII, Bst1107I, Bst98I, BstEII, BstPI, Cfr42I, CpoI, CspI, Eco47III, Eco91I, EcoO65I, EheI, FseI, HpaI, KasI, Kpn2I, KspI, MamI, MluI, MroI, MspCI, NarI, NheI, NruI, PacI, Pfl23II, PmeI, PpuMI, PshAI, Psp5II, PspEI, PspLI, PstNHI, RsrII, SacII, SalI, SbfI, Sfr303I, SgfI, SgrAI, SmiI, SplI, SrfI, Sse8387I, SstII, SunI, SwaI, Vha464I

FIG. 12-66

| |
|---|
| FIG. 13A |
| FIG. 13B |
| FIG. 13C |
| FIG. 13D |
| FIG. 13E |

FIG. 13 cccattcgccattcaggctgcgcaactgttgggaagggcgatcggtgcgggcctcttcgctattacgccagctggcgaaaggg
ggatgtgctgcaaggcgattaagttgggtaacgcccagggttttcccagtcacgacgttgtaaaacgacggccagtgccaagct
gatctaatcaatattggccattagccatattattcattggttatatagcataaatcaatattggctattggccattgcatacgttgtatcca
tatcataatatgtacatttatattggctcatgtccaacattaccgccatgttgacattgattattgactagttattaatagtaatcaattacg
gggtcattagttcatagcccatatatggagttccgcgttacataacttacggtaaatggcccgcctggcgaccgcccagcgaccc
ccgcccgttgacgtcaatagtgacgtatgttcccatagtaacgccaatagggactttccattgacgtcaatgggtggagtatttacg
gtaaactgcccacttggcagtacatcaagtgtatcatatgccaagtccgccccctattgacgtcaatgacggtaaatggcccgcct
agcattatgcccagtacatgaccttacgggagtttcctacttggcagtacatctacgtattagtcatcgctattaccatggtgatgcg
gttttggcagtacaccaatgggcgtggatagcggtttgactcacggggatttccaagtctccaccccattgacgtcaatgggagtt
tgttttggcaccaaaatcaacgggactttccaaaatgtcgtaataaccccgccccgttgacgcaaatgggcggtaggcgtgtacg
gtgggaggtctatataagcagagctcgtttagtgaaccgtcagaattcaagcttgcggccgcagatctatcgatctgcaggatatc
(EcoRV)
*acc*

FIG. 13A

ATGCACAGTATGATCAGCTCAGTGGATGTGAAGTCAGAAGTTCCTGTGGCCTGGAGCCCATCTCACCTTTA
GACCTAAGGACAGACCTCAGGATGATGATGCCCGTGGTGGACCCTGTTGTCCGTGAGAAGCAATTGCAGCAG
GAATTACTTCTTATCCAGCAGCAGCAACAAATCCAGAAGCAGCTTCTGATAGCAGAGTTTCAGAAACAGCAT
GAGAACTTGACACGGCAGCACCAGGCTCAGCTTCAGGAGCATATCAAGGAACTTCTAGCCATAAAACAGCAA
CAAGAACTCCTAGAAAAGGAGCAGAAACTGGAGCAGCAGAGGCAAGAACAGGAAGTAGAGAGGCATCGCAGA
GAACAGCAGCTTCCTCCTCTCAGAGGCAAAGATAGAGGACGAGAAAGGGCAGTGGCAAGTACAGAAGTAAAG
CAGAAGCTTCAAGAGTTCCTACTGAGTAAATCAGCAACGAAAGACACTCCAACTAATGGAAAAAATCATTCC
GTGAGCCGCCATCCCAAGCTCTGGTACACGGCTGCCCACCACACATCATTGGATCAAAGCTCTCCACCCCTT
AGTGGAACATCTCCATCCTACAAGTACACATTACCAGGAGCACAAGATGCAAAGGATGATTTCCCCCTTCGA
AAAACTGCCTCTGAGCCCAACTTGAAGGTGCGGTCCAGGTTAAAACAGAAAGTGGCAGAGAGGAGAAGCAGC
CCCTTACTCAGGCGGAAGGATGGAAATGTTGTCACTTCATTCAAGAAGCGAATGTTTGAGGTGACAGAATCC
TCAGTCAGTAGCAGTTCTCCAGGCTCTGGTCCCAGTTCACCAAACAATGGGCCAACTGGAAGTGTTACTGAA
AATGAGACTTCGGTTTTGCCCCCTACCCCTCATGCCGAGCAAATGGTTTCACAGCAACGCATTCTAATTCAT
GAAGATTCCATGAACCTGCTAAGTCTTTATACCTCTCCTTCTTTGCCCAACATTACCTTGGGGCTTCCCGCA
GTGCCATCCCAGCTCAATGCTTCGAATTCACTCAAAGAAAAGCAGAAGTGTGAGACGCAGACGCTTAGGCAA
GGTGTTCCTCTGCCTGGGCAGTATGGAGGCAGCATCCCGGCATCTTCCAGCCACCCTCATGTTACTTTAGAG
GGAAAGCCACCCAACAGCAGCCACCAGGCTCTCCTGCAGCATTTATTATTGAAAGAACAAATGCGACAGCAA
AAGCTTCTTGTAGCTGGTGGAGTTCCCTTACATCCTCAGTCTCCCTTGGCAACAAAAGAGAGAATTTCACCT
GGCATTAGAGGTACCCACAAATTGCCCCGTCACAGACCCCTGAACCGAACCCAGTCTGCACCTTTGCCTCAG
AGCACGTTGGCTCAGCTGGTCATTCAACAGCAACACCAGCAATTCTTGGAGAAGCAGAAGCAATACCAGCAG
CAGATCCACATGAACAAACTGCTTTCGAAATCTATTGAACAACTGAAGCAACCAGGCAGTCACCTTGAGGAA
GCAGAGGAAGAGCTTCAGGGGGACCAGGCGATGCAGGAAGACAGAGCGCCCTCTAGTGGCAACAGCACTAGG
AGCGACAGCAGTGCTTGTGTGGATGACACACTGGGACAAGTTGGGGCTGTGAAGGTCAAGGAGGAACCAGTG
GACAGTGATGAAGATGCTCAGATCCAGGAAATGGAATCTGGGGAGCAGGCTGCTTTTATGCAACAGCCTTTC

FIG. 13B

CTGGAACCCACGCACACACGTGCGCTCTCTGTGCGCCAAGCTCCGCTGGCTGCGGTTGGCATGGATGGATTA
GAGAAACACCGTCTCGTCTCCAGGACTCACTCTTCCCCTGCTGCCTCTGTTTTACCTCACCCAGCAATGGAC
CGCCCCCTCCAGCCTGGCTCTGCAACTGGAATTGCCTATGACCCCTTGATGCTGAAACACCAGTGCGTTTGT
GGCAATTCCACCACCCACCCTGAGCATGCTGGACGAATACAGAGTATCTGGTCACGACTGCAAGAAACTGGG
CTGCTAAATAAATGTGAGCGAATTCAAGGTCGAAAAGCCAGCCTGGAGGAAATACAGCTTGTTCATTCTGAA
CATCACTCACTGTTGTATGGCACCAACCCCCTGGACGGACAGAAGCTGGACCCCAGGATACTCCTAGGTGAT
GACTCTCAAAAGTTTTTTTCCTCATTACCTTGTGGTGGACTTGGGGTGGACAGTGACACCATTTGGAATGAG
CTACACTCGTCCGGTGCTGCACGCATGGCTGTTGGCTGTGTCATCGAGCTGGCTTCCAAAGTGGCCTCAGGA
GAGCTGAAGAATGGGTTTGCTGTTGTGAGGCCCCCTGGCCATCACGCTGAAGAATCCACAGCCATGGGGTTC
TGCTTTTTTAATTCAGTTGCAATTACCGCCAAATACTTGAGAGACCAACTAAATATAAGCAAGATATTGATT
GTAGATCTGGATGTTCACCATGGAAACGGTACCCAGCAGGCCTTTTATGCTGACCCCAGCATCCTGTACATT
TCACTCCATCGCTATGATGAAGGGAACTTTTTCCCTGGCAGTGGAGCCCCAAATGAGGTTCGGTTTATTTCT
TTAGAGCCCCACTTTTATTTGTATCTTTCAGGTAATTGCATTGCA

FIG. 13C (BamHI)<u>ggatcc</u>ggtaccagattacaaggacgacgatgacaagtagatcccgggtggcatccctgtgacccctccccagtg
cctctcctggccttggaagttgccactccagtgcccaccagccttgtcctaataaaattaagttgcatcattttgtctgactaggtgtc
ctctataatattatggggtggaggggggtggtatggagcaaggggcccaagttgggaagacaacctgtagggcctgcggggtc
tattcgggaaccaagctggagtgcagtggcacaatcttggctcactgcaatctccgcctcctgggttcaagcgattctcctgcctc
agcctcccgagttgttgggattccaggcatgcatgaccaggctcagctaatttttgtttttttggtagagacggggtttcaccatattg
gccaggctggtctccaactcctaatctcaggtgatctacccaccttggcctcccaaattgctgggattacaggcgtgaaccactgc
tcccttccctgtccttctgattttaaaataactataccagcaggaggacgtccagacacagcataggctacctgccatggcccaac
cggtgggacatttgagttgcttgcttggcactgtcctctcatgcgttgggtccactcagtagatgcctgttgaattgggtacgcggc
cagcttctgtggaatgtgtgtcagttagggtgtggaaagtccccaggctccccagcaggcagaagtatgcaaagcatgcatctca
attagtcagcaaccaggtgtggaaaagtccccaggctccccagcaggcagaagtatgcaaagcatgcatctcaattagtcagca
accatagtcccgcccctaactccgcccatcccgcccctaactccgcccagttccgcccattctccgccccatggctgactaattttt
tttatttatgcagaggccgaggccgcctcggcctctgagctattccagaagtagtgaggaggcttttttggaggcctaggcttttgc
aaaaagctcctcgaggaactgaaaaaccagaaagttaattccctatagtgagtcgtattaaattcgtaatcatggtcatagctgtttc
ctgtgtgaaattgttatccgctcacaattccacacaacatacgagccggaagcataaagtgtaaagcctggggtgcctaatgagt
gagctaactcacattaattgcgttgcgctcactgcccgctttccagtcgggaaacctgtcgtgccagctgcattaatgaatcggcc
aacgcgcggggagaggcggtttgcgtattgggcgctcttccgcttcctcgctcactgactcgctgcgctcggtcgttcggctgcg
gcgagcggtatcagctcactcaaaggcggtaatacggttatccacagaatcaggggataacgcaggaaagaacatgtgagca
aaaggccagcaaaaggccaggaaccgtaaaaaggccgcgttgctggcgtttttccataggctccgcccccctgacgagcatca
caaaaatcgacgctcaagtcagaggtggcgaaacccgacaggactataaagataccaggcgtttccccctggaagctccctcg
tgcgctctcctgttccgaccctgccgcttaccggatacctgtccgcctttctcccttcgggaagcgtggcgctttctcaatgctcac
gctgtaggtatctcagttcggtgtaggtcgttcgctccaagctgggctgtgtgcacgaaccccccgttcagcccgaccgctgcgc
cttatccggtaactatcgtcttgagtccaacccggtaagacacgacttatcgccactggcagcagccactggtaacaggattagc
agagcgaggtatgtaggcggtgctacagagttcttgaagtggtggcctaactacggctacactagaagaacagtatttggtatct
gcgctctgctgaagccagttaccttcggaaaaagagttggtagctcttgatccggcaaacaaaccaccgctggtagcggtggttt

FIG. 13D ttttgtttgcaagcagcagattacgcgcagaaaaaaaggatctcaagaagatcctttgatcttttctacggggtctgacgctcagtg
gaacgaaaactcacgttaagggattttggtcatgagattatcaaaaaggatcttcacctagatccttttaaattaaaaatgaagtttta
aatcaatctaaagtatatatgagtaaacttggtctgacagttaccaatgcttaatcagtgaggcacctatctcagcgatctgtctatttc
gttcatccatagttgcctgactccccgtcgtgtagataactacgatacgggagggcttaccatctggccccagtgctgcaatgata
ccgcgagacccacgctcaccggctccagatttatcagcaataaaccagccagccggaagggccgagcgcagaagtggtcct
gcaactttatccgcctccatccagtctattaattgttgccgggaagctagagtaagtagttcgccagttaatagtttgcgcaacgttgt
tgccattgctacaggcatcgtggtgtcacgctcgtcgtttggtatggcttcattcagctccggttcccaacgatcaaggcgagttac
atgatcccccatgttgtgcaaaaaagcggttagctccttcggtcctccgatcgttgtcagaagtaagttggccgcagtgttatcact
catggttatggcagcactgcataattctcttactgtcatgccatccgtaagatgcttttctgtgactggtgagtactcaaccaagtcatt
ctgagaatagtgtatgcggcgaccgagttgctcttgcccggcgtcaatacgggataataccgcgccacatagcagaactttaaaa
gtgctcatcattggaaaacgttcttcggggcgaaaactctcaaggatcttaccgctgttgagatccagttcgatgtaacccactcgt
gcacccaactgatcttcagcatcttttactttcaccagcgtttctgggtgagcaaaaacaggaaggcaaaatgccgcaaaaaagg
gaataagggcgacacggaaatgttgaatactcatactcttcctttttcaatattattgaagcatttatcagggttattgtctcatgagcg
gatacatatttgaatgtatttagaaaaataaacaaataggggttccgcgcacatttccccgaaaagtgccacctgacgcgccctgt
agcggcgcattaagcgcggcgggtgtggtggttacgcgcagcgtgaccgctacacttgccagcgccctagcgcccgctccttt
cgctttcttcccttcctttctcgccacgttcgccggctttccccgtcaagctctaaatcggggcatccctttagggttccgatttagtgc
tttacggcacctcgaccccaaaaaacttgattagggtgatggttcacgtagtgggccatcgccctgatagacggtttttcgcccttt
gacgttggagtccacgttctttaatagtggactcttgttccaaactggaacaacactcaaccctatctcggtctattcttttgatttataa
gggattttgccgatttcggcctattggttaaaaaatgagctgatttaacaaaaatttaacgcgaattttaacaaaatattaaacgtttac
aattt

FIG. 13E pFLAG-CMV-5b-HDAC9a

7303 base pairs

Graphic map | Table by enzyme name

```
                                BstMCI
                AviII              PvuI BsiEI      EarI        MspA1I
           BglI FspI               BsaOI           Eam1104I    PvuII
cccattcgccattcaggctgcgcaactgttgggaagggcgatcggtgcgggcctcttcgctattacgccagctgg
base pairs
gggtaagcggtaagtccgacgcgttgacaacccttcccgctagccacgcccggagaagcgataatgcggtcgacc
1 to 75
                Acc16I             BspCI           Ksp632I     NspBII
                                   Bsh1285I
                                   Ple19I
```

FIG. 14-1

```
cgaaagggggatgtgctgcaaggcgattaagttgggtaacgcccagggttttcccagtcacgacgttgtaaaacg
base pairs
gctttcccctacacgacgttccgctaattcaacccattgcgggtcccaaaagggtcagtgctgcaacattttgc
76 to 150



                                  MscI
                                CfrI
  EaeI                       SspI MluNI
acggccagtgccaagctgatctaatcaatattggccattagccatattattcattggttatatagcataaatcaa
base pairs
tgccggtcacggttcgactagattagttataaccggtaatcggtataataagtaaccaatatatcgtatttagtt
151 to 225
  CfrI                          EaeI
                                  BalI
```

FIG. 14-2

```
               MscI
               MluNI                                    SspBI
 SspI       EaeI      BsrDI                             Bsp1407I
tattggctattggccattgcatacgttgtatccatatcataatatgtacatttatattggctcatgtccaacatt
base pairs
ataaccgataaccggtaacgtatgcaacataggtatagtattatacatgtaaatataaccgagtacaggttgtaa
226 to 300
           CfrI                                         BsrGI
             BalI


                                         VspI
           HincII           SpeI         PshBI
accgccatgttgacattgattattgactagttattaatagtaatcaattacggggtcattagttcatagcccata
base pairs
tggcggtacaactgtaactaataactgatcaataattatcattagttaatgccccagtaatcaagtatcgggtat
301 to 375
           HindII           AclNI        AsnI
                                         AseI
```

FIG. 14-3

```
                                                                                    HinlI
                                                     BstMCI                          AcyI
                                               BglI  BsaOI                         HincII
tatggagttccgcgttacataacttacggtaaatggcccgcctggcgaccgcccagcgacccccgcccgttgacg
base pairs
atacctcaaggcgcaatgtattgaatgccatttaccgggcggaccgctggcgggtcgctgggggcgggcaactgc
376 to 450
                                                     Bsh1285I                      HindII
                                                     BsiEI                         Hsp92I
                                                                                   Msp17I

   BsaHI                                                   BbiII
   AatII                                                   HinlI
   BbiII                                                   AcyI AatII
tcaatagtgacgtatgttcccatagtaacgccaatagggactttccattgacgtcaatgggtggagtatttacgg
base pairs
agttatcactgcatacaagggtatcattgcggttatccctgaaaggtaactgcagttacccacctcataaatgcc
451 to 525
                                                           Msp17I
                                                           BsaHI
                                                           Hsp92I
```

FIG. 14-4

```
                                                                    BbiII
                                                                   Hin1I
             BglI                  NdeI                             AcyI AatII
taaactgcccacttggcagtacatcaagtgtatcatatgccaagtccgcccctattgacgtcaatgacggtaaa
base pairs
atttgacgggtgaaccgtcatgtagttcacatagtatacggttcaggcggggataactgcagttactgccattt
526 to 600
                                   FauNDI                          Msp17I
                                                                    BsaHI
                                                                   Hsp92I

                                                                           BstSNI
                                                                           SnaBI
tggcccgcctagcattatgcccagtacatgaccttacgggagtttcctacttggcagtacatctacgtattagtc
base pairs
accgggcggatcgtaatacgggtcatgtactggaatgccctcaaaggatgaaccgtcatgtagatgcataatcag
601 to 675
                                                                           BsaAI
                                                                          Eco105I
```

FIG. 14-5

```
        NcoI Bsp19I
        StyI BstDSI
        EcoT14I
atcgctattaccatggtgatgcggttttggcagtacaccaatgggcgtggatagcggtttgactcacggggattt
base pairs
tagcgataatggtaccactacgccaaaaccgtcatgtggttacccgcacctatcgccaaactgagtgcccctaaa
676 to 750
        BssT1I
        ErhI Eco130I
        DsaI MslI

               BbiII
               Hin1I                AccB1I
               AcyI AatII           BshNI
ccaagtctccaccccattgacgtcaatgggagtttgttttggcaccaaaatcaacgggactttccaaaatgtcgt
base pairs
ggttcagaggtggggtaactgcagttaccctcaaacaaaaccgtggttttagttgccctgaaaggttttacagca
751 to 825
               Msp17I               BanI
               BsaHI                Eco64I
               Hsp92I
```

FIG. 14-6

```
                                                                              Eco24I
                 HincII                                                      EcoICRI
aataaccccgccccgttgacgcaaatgggcggtaggcgtgtacggtgggaggtctatataagca gagctcgttta
base pairs
ttattggggcggggcaactgcgtttacccgccatccgcacatgccaccctccagatatattcgt ctcgagcaaat
826 to 900
                 HindII                                                      Ecl136II
                                                                             Bbv12I
                                                                             AspHI
                                                                             Psp124BI
SacI
FriOI
SstI
BanII
BsiHKAI                     EagI XmaIII BstYI BspDI BcgI Eco32I
           AcsI             CciNI Bsh1285I BstX2I BanIII PstI               BclI
           ApoI  HindIII BstZI BstMCI MflI Bsa29I SfcI                      Ksp22I
gtgaaccgtcagaattcaagcttgcggccgcagatctatcgat ctgcaggatatcaccatgcacagtatgatcag
base pairs
cacttggcagt cttaagttcgaacgccggcgtctagatagcta gacgtcctatagtggtacgtgtcatactagtc
901 to 975
           EcoRI            EaeI Eco52I BglII BscI BspXI BstSFI             FbaI
                            CfrI EclXI BsiEI BseCI Bsu15I EcoRV
Alw21I                      NotI BsaOI XhoII ClaI Bsp106I
```

FIG. 14-7

```
                                            FriOI           CvnI        CvnI
                                           Eco24I           AocI        AocI
                                          BpmI             Bsu36I      Bsu36I
ctcagtggatgtgaagtcagaagttcctgtgggcctggagcccatctcacctttagacctaaggacagacctcag
base pairs
gagtcacctacacttcagtcttcaaggacacccggacctcgggtagagtggaaatctggattcctgtctggagtc
976 to 1050
                                          GsuI             Eco81I      Eco81I
                                            BanII          Bse21I      Bse21I


           DsaI         DrdI          MfeI          Asp700I
gatgatgatgcccgtggtggaccctgttgtccgtgagaagcaattgcagcaggaattacttcttatccagcagca
base pairs
ctactactacgggcaccacctgggacaacaggcactcttcgttaacgtcgtccttaatgaagaataggtcgtcgt
1051 to 1125
           BstDSI                     MunI          XmnI
```

FIG. 14-8

```
                          AlwNI
gcaacaaatccagaagcagcttctgatagcagagtttcagaaacagcatgagaacttgacacggcagcaccaggc
base pairs
cgttgtttaggtcttcgtcgaagactatcgtctcaaagtctttgtcgtactcttgaactgtgccgtcgtggtccg
1126 to 1200
```

```
BlpI
CelII     Eco57I                                                EcoNI    AlwNI
tcagcttcaggagcatatcaaggaacttctagccataaaacagcaacaagaactcctagaaaggagcagaaact
base pairs
agtcgaagtcctcgtatagttccttgaagatcggtattttgtcgttgttcttgaggatctttcctcgtctttga
1201 to 1275
Bsp1720I
Bpu1102I
```

FIG. 14-9

```
    BpmI                                                        BseRI
ggagcagcagaggcaagaacaggaagtagagaggcatcgcagagaacagcagcttcctcctctcagaggcaaaga
base pairs
cctcgtcgtctccgttcttgtccttcatctctccgtagcgtctcttgtcgtcgaaggaggagagtctccgtttct
1276 to 1350
    GsuI                                                         EcoNI
```

```
                                               HindIII
tagaggacgagaaagggcagtggcaagtacagaagtaaagcag aagcttcaagagttcctactgagtaaatcagc
base pairs
atctcctgctctttcccgtcaccgttcatgtcttcatttcgtc ttcgaagttctcaaggatgactcatttagtcg
1351 to 1425
```

FIG. 14-10

Van91I Van91I
AccB7I AccB7I
aacgaaagacactccaactaatggaaaaaatcattccgtgagccgccatcccaagctctggtacacggctgccca
base pairs
ttgctttctgtgaggttgattaccttttttagtaaggcactcggcggtagggttcgagaccatgtgccgacgggt
1426 to 1500
Esp1396I Esp1396I
PflMI PflMI ccacacatcattggatcaaagctctccaccccttagtggaacatctccatcctacaagtacacattaccaggagc
base pairs
ggtgtgtagtaacctagtttcgagaggtggggaatcaccttgtagaggtaggatgttcatgtgtaatggtcctcg
1501 to 1575

FIG. 14-11

```
                           BstBI
 Alw21I                    Bpu14I             FriOI
 AspHI                     Csp45I            Eco24I
acaagatgcaaaggatgatttccccttcgaaaactgcctctgagcccaacttgaaggtgcggtccaggttaaa
base pairs
tgttctacgtttcctactaaaggggaagcttttgacggagactcgggttgaacttccacgccaggtccaattt
1576 to 1650
 BsiHKAI                   SfuI Bsp119I       BanII
 Bbv12I                    NspV
                           LspI



                    BseRI        EcoNI
acagaaagtggcagagaggagaagcagccccttactcaggcggaaggatggaaatgttgtcacttcattcaagaa
base pairs
tgtctttcaccgtctctcctcttcgtcggggaatgagtccgccttcctacctttacaacagtgaagtaagttctt
1651 to 1725
```

FIG. 14-12

```
                                                Van91I
                                                AccB7I              Van91I
                                              BpmI PflMI             AccB7I
gcgaatgtttgaggtgacagaatcctcagtcagtagcagttctccaggctctggtcccagttcaccaaacaatgg
base pairs
cgcttacaaactccactgtcttaggagtcagtcatcgtcaagaggtccgagaccagggtcaagtggtttgttacc
1726 to 1800
                                              GsuI
                                                                  Esp1396I
                                                                     PflMI
                                                AlwNI

                                                Esp1396I


gccaactggaagtgttactgaaaatgagacttcggttttgccccctacccctcatgccgagcaaatggtttcaca
base pairs
cggttgaccttcacaatgacttttactctgaagccaaaacgggggatggggagtacggctcgtttaccaaagtgt
1801 to 1875
```

FIG. 14-13

```
          BsaMI
          Mva1269I                    BspMI                         XcmI
gcaacgcattctaattcatgaagattccatgaacctgctaagtctttatacctctccttctttgcccaacattac
base pairs
cgttgcgtaagattaagtacttctaaggtacttggacgattcagaaatatggagaggaagaaacgggttgtaatg
1876 to 1950
          BsmI RcaI
               BspHI


ErhI                                  BstBI AcsI
BssT1I                                Bpu14I
                                      Csp45I
                                                                     Esp3I
cttggggcttcccgcagtgccatcccagctcaatgcttc gaattcactcaaagaaaagcagaagtgtgagacgca
base pairs
gaaccccgaagggcgtcacggtagggtcgagttacgaag cttaagtgagtttcttttcgtcttcacactctgcgt
1951 to 2025
EcoT14I                               SfuI Bsp119I
                                                                     BsmBI
StyI                                  NspV ApoI
Eco130I                               LspI EcoRI
```

FIG. 14-14

MslI
gacgcttaggcaaggtgttcctctgcctgggcagtatggaggcagcatcccggcatcttccagccaccctcatgt
base pairs
ctgcgaatccgttccacaaggagacggacccgtcatacctccgtcgtagggccgtagaaggtcggtgggagtaca
2026 to 2100

PstI
SfcI
tactttagagggaaagccacccaacagcagccaccaggctctc ctgcagcatttattattgaaagaacaaatgcg
base pairs
atgaaatctccctttcggtgggttgtcgtcggtggtccgagag gacgtcgtaaataataactttcttgtttacgc
2101 to 2175
BstSFI

FIG. 14-15

```
                                                Eco130I
                                                StyI
      HindIII                                   EcoT14I          ApoI
acagcaaaagcttcttgtagctggtggagttcccttacatcctcagtctcccttggcaacaaaagagagaatttc
base pairs
tgtcgttttcgaagaacatcgaccacctcaagggaatgtaggagtcagagggaaccgttgttttctctcttaaag
2176 to 2250
                                                BssT1I           AcsI
                                                ErhI

           Asp718I
           Acc65I
           BshNI                                              BsgI
acctggcattagaggtacccacaaattgccccgtcacagacccctgaaccgaacccagtctgcacctttgcctca
base pairs
tggaccgtaatctccatgggtgtttaacggggcagtgtctggggacttggcttgggtcagacgtggaaacggagt
2251 to 2325
           BanI KpnI
           AccB1I
           Eco64I
```

FIG. 14-16

```
           Bpu1102I
     Alw21I Bsp1720I
     AspHI  CelII
gagcacgttggctcagctggtcattcaacagcaacaccagcaattcttggagaagcagaagcaataccagcagca
base pairs
ctcgtgcaaccgagtcgaccagtaagttgtcgttgtggtcgttaagaacctcttcgtcttcgttatggtcgtcgt
2326 to 2400
     BsiHKAI    PvuII
     Bbv12I BlpI MspA1I
                NspBII

                       BstBI
MflI                   Bpu14I
XhoII                  Csp45I                 Eco57I
gatccacatgaacaaactgctttcgaaatctattgaacaactgaagcaaccaggcagtcaccttgaggaagcaga
base pairs
ctaggtgtacttgtttgacgaaagctttagataacttgttgacttcgttggtccgtcagtggaactccttcgtct
2401 to 2475
BstYI                  SfuI Bsp119I
BstX2I                 NspV
                       LspI
```

FIG. 14-17

```
      EarI
      Eam1104I                           Bbv16II
     Asp700I                             BbsI   Bsp143II
ggaagagcttcaggggaccaggcgatgcaggaagacagagcgccctctagtggcaacagcactaggagcgacag
base pairs
ccttctcgaagtcccctggtccgctacgtccttctgtctcgcgggagatcaccgttgtcgtgatcctcgctgtc
2476 to 2550
     XmnI   Eco57I                       BpiI   HaeII
      Ksp632I                            BpuAI  BstH2I
       SapI


     BcgI
cagtgcttgtgtggatgacacactgggacaagttggggctgtgaaggtcaaggaggaaccagtggacagtgatga
base pairs
gtcacgaacacacctactgtgtgaccctgttcaaccccgacacttccagttcctccttggtcacctgtcactact
2551 to 2625
```

FIG. 14-18

```
         MflI       Van91I
         XhoII      AccB7I
agatgctcagatccaggaaatggaatctggggagcaggctgcttttatgcaacagcctttcctggaacccacgca
base pairs
tctacgagtctaggtcctttaccttagacccctcgtccgacgaaaatacgttgtcggaaaggaccttgggtgcgt
2626 to 2700
         BstYI      Esp1396I
         BstX2I     PflMI


     PmaCI
     PmlI
  AflIII                      NspBII
                                                                         Esp3I
cacacgtgcgctctctgtgcgccaagctccgctggctgcggttggcatggatggattagagaaacaccgtctcgt
base pairs
gtgtgcacgcgagagacacgcggttcgaggcgaccgacgccaaccgtacctacctaatctctttgtggcagagca
2701 to 2775
   MslI Eco72I                MspA1I
                                                                         BsmBI
     BsaAI
     BbrPI
```

FIG. 14-19

```
                  EarI
      BpmI        Eam1104I                                 BsrDI          BpmI
ctccaggactcactcttcccctgctgcctctgttttacctcacccagcaatggaccgcccctccagcctggctc
base pairs
gaggtcctgagtgagaaggggacgacggagacaaaatggagtgggtcgttacctggcggggaggtcggaccgag
2776 to 2850
      GsuI        Ksp632I                                                 GsuI


                                                     XcmI
tgcaactggaattgcctatgaccccttgatgctgaaacaccagtgcgtttgtggcaattccaccacccaccctga
base pairs
acgttgaccttaacggatactggggaactacgactttgtggtcacgcaaacaccgttaaggtggtgggtgggact
2851 to 2925
```

FIG. 14-20

```
     SphI                                                              AcsI
     BbuI                                                              ApoI
gcatgctggacgaatacagagtatctggtcacgactgcaagaaactgggctgctaaataaatgtgagc gaattca
base pairs
cgtacgacctgcttatgtctcatagaccagtgctgacgttctttgacccgacgatttatttacactcg cttaagt
2926 to 3000
     PaeI                                                              EcoRI
     NspI

                                                                   AccB1I
                      BpmI                                          BshNI
aggtcgaaaagccagcctggaggaaatacagcttgttcattctgaacatcactcactgttgtatggcaccaaccc
base pairs
tccagcttttcggtcggacctcctttatgtcgaacaagtaagacttgtagtgagtgacaacataccgtggttggg
3001 to 3075
                      GsuI                                          BanI
                                                                   Eco64I
```

FIG. 14-21

```
                                              ErhI
                                              StyI Eco130I
 BstXI              AlwNI                     EcoT14I
cctggacggacagaagctggaccccaggatactcctaggtgatgactctcaaaagtttttttcctcattaccttg
base pairs
ggacctgcctgtcttcgacctggggtcctatgaggatccactactgagagtttcaaaaaaaggagtaatggaac
3076 to 3150
                                              BssT1I
                                              AvrII
                                              BlnI

                                                                 BsaWI          BsgI
tggtggacttggggtggacagtgacaccatttggaatgagctacactcgtccggtgctgcacgcatggctgttgg
base pairs
accacctgaaccccacctgtcactgtggtaaaccttactcgatgtgagcaggccacgacgtgcgtaccgacaacc
3151 to 3225
```

FIG. 14-22

```
                    CvnI
                    AocI                                      CfrI
                    Bsu36I       Eco57I              DraII    EaeI
ctgtgtcatcgagctggcttccaaagtggcctcaggagagctgaagaatgggtttgctgttgtgaggccccctgg
base pairs
gacacagtagctcgaccgaaggtttcaccggagtcctctcgacttcttacccaaacgacaacactccgggggacc
3226 to 3300
                    Eco81I                                  EcoO109I
                    Bse21I

MscI                     ErhI Eco130I
                         BssT1I BstXI
              Eco57I    MslI DsaI
ccatcacgctgaagaatccacagccatggggttctgctttttaattcagttgcaattaccgccaaatacttgag
base pairs
ggtagtgcgacttcttaggtgtcggtaccccaagacgaaaaattaagtcaacgttaatggcggtttatgaactc
3301 to 3375
MluNI                    EcoT14I
BalI                     StyI BstDSI
                         NcoI Bsp19I
```

FIG. 14-23

```
                                    BstX2I         NcoI Bsp19I Asp718I   SseBI
                                    BstYI          StyI BstDSI AccB1I
Eco147I
     BsaI                           XhoII          EcoT14I   BshNI       StuI
agaccaactaaatataagcaagatattgattgtagatctggatgttcaccatggaaacggtacccagcaggcctt
base pairs
tctggttgatttatattcgttctataactaacatctagacctacaagtggtacctttgccatgggtcgtccggaa
3376 to 3450
     Eco31I                         BglII          BssT1I    BanI KpnI   AatI
                                    MflI           ErhI Eco130I Eco64I   Pme55I
                                                   DsaI      Acc65I


                      SspBI
                      Bsp1407I          MslI              Asp700I
ttatgctgaccccagcatcctgtacatttcactccatcgctatgatgaagggaactttttccctggcagtggagc
base pairs
aatacgactggggtcgtaggacatgtaaagtgaggtagcgatactacttcccttgaaaaagggaccgtcacctcg
3451 to 3525
                      BsrGI                               XmnI
```

FIG. 14-24

```
                                                                           BstYI
 FriOI                             FriOI                                   XhoII
 Eco24I                            Eco24I                                BsrDI
cccaaatgaggttcggtttatttctttagagccccactttatttgtatctttcaggtaattgcattgca ggatc
base pairs
gggtttactccaagccaaataaagaaatctcggggtgaaataaacatagaaagtccattaacgtaacgt cctag
3526 to 3600
 BanII                             BanII                                   BamHI
                                                                           BstI
                                                                           MflI


Acc65I                                AvaI BcoI
  BanI Eco64I                       MflI Eco88I PspALI
BstX2I Asp718I                      XhoII Cfr9I SmaI MslI
cggtaccagattacaaggacgacgatgacaagtagat cccgggtggcatccctgtgacccctccccagtgcctct
base pairs
gccatggtctaatgttcctgctgctactgttcatcta gggcccaccgtagggacactggggaggggtcacggaga
3601 to 3675
  BshNI                             BstYI Ama87I
 BsaWI KpnI                        BstX2I BsoBI
  AccB1I                                XmaI PspAI
```

FIG. 14-25

```
     Eco130I
     StyI                GsuI
     EcoT14I          MslI
cctggccttggaagttgccactccagtgcccaccagccttgtcctaataaattaagttgcatcattttgtctga
base pairs
ggaccggaaccttcaacggtgaggtcacgggtggtcggaacaggattatttaattcaacgtagtaaaacagact
3676 to 3750
     BssT1I              BpmI
     ErhI

                                                          Eco24I
                                                                       SfcI
   Eam1105I                                            DraII BanII     Bbv16II
   AspEI        SspI                                   PspOMI FriOI    BbsI
ctaggtgtcctctataatattatggggtggagggggtggtatggagcaaggggcccaagttgggaagacaacct
base pairs
gatccacaggagatattataataccccacctcccccaccatacctcgttccccgggttcaacccttctgttgga
3751 to 3825
   EclHKI                                              Bsp120I         BpiI
   AhdI                                                EcoO109I        BpuAI
                                                           ApaI       BstSFI
```

FIG. 14-26

```
    DraII                              BpmI BsgI
gtagggcctgcggggtctattcgggaaccaagctggagtgcagtggcacaatcttggctcactgcaatctccgcc
base pairs
catcccggacgccccagataagcccttggttcgacctcacgtcaccgtgttagaaccgagtgacgttagaggcgg
3826 to 3900
    EcoO109I                           GsuI

                                          BcoI                    NspI      BlpI
                                          Ama87I                  PaeI Mph1103I
                                 BcgI     AvaI                  Ppu10I EcoT22I
tcctgggttcaagcgattctcctgcctcagcctcccgagttgttgggattccaggcatgcatgaccaggctcagc
base pairs
aggacccaagttcgctaagaggacggagtcggagggctcaacaaccctaaggtccgtacgtactggtccgagtcg
3901 to 3975
                                          Eco88I                  BbuI Zsp2I CelII
                                          BsoBI                   SphI      Bsp172
                                                                    NsiI    Bpu11
```

FIG. 14-27

```
                                            MscI
                                            MluNI
                        Esp3I             EaeI               BsaI
taatttttgtttttttggtagagacggggtttcaccatattggccaggctggtctccaactcctaatctcaggtg
base pairs
attaaaaacaaaaaaaccatctctgccccaaagtggtataaccggtccgaccagaggttgaggattagagtccac
3976 to 4050
                        BsmBI             CfrI               Eco31I
 0I                                         BalI
02I

          Eco130I
          StyI
          EcoT14I          BstXI
atctacccaccttggcctcccaaattgctgggattacaggcgtgaaccactgctcccttccctgtccttctgatt
base pairs
tagatgggtggaaccggagggtttaacgaccctaatgtccgcacttggtgacgagggaagggacaggaagactaa
4051 to 4125
          BssT1I
          ErhI
```

FIG. 14-28

```
                         BbiII                   NcoI Eco130I BsrFI PflMI
                         Hin1I                   StyI DsaI AgeI Bse118I
  DraI                   AcyI AatII              EcoT14I   BsaWI AccB7I
ttaaaataactataccagcaggaggacgtccagacacagcataggctacctgccatggcccaaccggtgggacat
base pairs
aatttattgatatggtcgtcctcctgcaggtctgtgtcgtatccgatggacggtaccgggttggccaccctgta
4126 to 4200
                         Msp17I                  BssT1I    BssAI Esp1396I
                         BsaHI                   ErhI BstDSI PinAI Van91I
                         Hsp92I                  BspMI Bsp19I Cfr10I

                                                                        EaeI
ttgagttgcttgcttggcactgtcctctcatgcgttgggtccactcagtagatgcctgttgaattgggtacgcgg
base pairs
aactcaacgaacgaaccgtgacaggagagtacgcaacccaggtgagtcatctacggacaacttaacccatgcgcc
4201 to 4275
                                                                        CfrI
```

FIG. 14-29

```
      AlwNI
ccagcttctgtggaatgtgtgtcagttagggtgtggaaagtccccaggctccccagcaggcagaagtatgcaaag
base pairs
ggtcgaagacaccttacacacagtcaatcccacacctttcaggggtccgaggggtcgtccgtcttcatacgtttc
4276 to 4350
```

```
    NspI
    PaeI Mph1103I
  Ppu10I EcoT22I       SexAI
catgcatctcaattagtcagcaaccaggtgtggaaaagtccccaggctccccagcaggcagaagtatgcaaagca
base pairs
gtacgtagagttaatcagtcgttggtccacaccttttcaggggtccgaggggtcgtccgtcttcatacgtttcgt
4351 to 4425
    BbuI Zsp2I
    SphI
      NsiI
```

FIG. 14-30

```
  NspI
  PaeI Mph1103I
Ppu10I EcoT22I
tgcatctcaattagtcagcaaccatagtcccgcccctaactccgcccatcccgcccctaactccgcccagttccg
base pairs
acgtagagttaatcagtcgttggtatcagggcggggattgaggcgggtagggcggggattgaggcgggtcaaggc
4426 to 4500
  BbuI Zsp2I
  SphI
    NsiI

              NcoI Bsp19I
              StyI BstDSI
              EcoT14I                              BglI
cccattctccgccccatggctgactaattttttttatttatgcagaggccgaggccgcctcggcctctgagctat
base pairs
gggtaagaggcggggtaccgactgattaaaaaaaataaatacgtctccggctccggcggagccggagactcgata
4501 to 4575
              BssT1I                               SfiI
              ErhI Eco130I
              DsaI
```

FIG. 14-31

```
                               SseBI AvrII           Ama87I
                               Eco147I  BlnI         Eco88I  BseRI
                  BseRI        StuI BssT1I           AvaI BsoBI
tccagaagtagtgaggaggctttttggaggcctaggcttttgcaaaagctc ctcgaggaactgaaaaaccaga
base pairs
aggtcttcatcactcctccgaaaaacctccggatccgaaaacgttttcgag gagctccttgactttttggtct
4576 to 4650
                               AatI StyI             XhoI BcoI
                               Pme55I  ErhI          Sfr274I
                                EcoT14I Eco130I      PaeR7I

          SfcI         ApoI
aagttaattccctatagtgagtcgtattaaattcgtaatcatggtcatagctgtttcctgtgtgaaattgttatc
base pairs
ttcaattaagggatatcactcagcataatttaagcattagtaccagtatcgacaaaggacacactttaacaatag
4651 to 4725
          BstSFI       AcsI
```

FIG. 14-32

```
     AccBSI                                                 AccB1I
     BsrBI                                                  BshNI
cgctcacaattccacacaacatacgagccggaagcataaagtgtaaagcctggggtgcctaatgagtgagctaac
base pairs`
gcgagtgttaaggtgtgttgtatgctcggccttcgtatttcacatttcggaccccacggattactcactcgattg
4726 to 4800
     BstD102I                                               BanI
                                                           Eco64I

                                                                  VspI
      VspI                                                  MspA1I
      PshBI                                                  PvuII PshBI
                                                                       EaeI
tcacattaattgcgttgcgctcactgcccgctttccagtcgggaaacctgtcgtgccagctgcattaatgaatcg
base pairs
agtgtaattaacgcaacgcgagtgacgggcgaaaggtcagccctttggacagcacggtcgacgtaattacttagc
4801 to 4875
      AsnI                                                   NspBII
                                                                       CfrI
      AseI                                                        AsnI
                                                                  AseI
```

FIG. 14-33

```
                                                Eam1104I
                                           BstH2I
                                           Bsp143II
gccaacgcgcggggagaggcggtttgcgtattgggcgctcttccgcttcctcgctcactgactcgctgcgctcgg
base pairs
cggttgcgcgcccctctccgccaaacgcataacccgcgagaaggcgaaggagcgagtgactgagcgacgcgagcc
4876 to 4950
                                           HaeII EarI
                                                SapI
                                                Ksp632I


 BstMCI                 AccBSI
 BsaOI                  BsrBI
tcgttcggctgcggcgagcggtatcagctcactcaaaggcggtaatacggttatccacagaatcaggggataacg
base pairs
agcaagccgacgccgctcgccatagtcgagtgagtttccgccattatgccaataggtgtcttagtcccctattgc
4951 to 5025
 Bsh1285I               BstD102I
 BsiEI
```

FIG. 14-34

```
             NspI
         BspLU11I
caggaaagaacatgtgagcaaaaggccagcaaaaggccaggaaccgtaaaaaggccgcgttgctggcgtttttcc
base pairs
gtcctttcttgtacactcgttttccggtcgttttccggtccttggcatttttccggcgcaacgaccgcaaaaagg
5026 to 5100
         AflIII
```

```
                                             DrdI
ataggctccgcccccctgacgagcatcacaaaaatcgacgctcaagtcagaggtggcgaaacccgacaggactat
base pairs
tatccgaggcggggggactgctcgtagtgtttttagctgcgagttcagtctccaccgctttgggctgtcctgata
5101 to 5175
```

FIG. 14-35

```
                                        BsiI                       BsaWI
aaagataccaggcgtttccccctggaagctccctcgtgcgctctcctgttccgaccctgccgcttaccggatacc
base pairs
tttctatggtccgcaaagggggaccttcgagggagcacgcgagaggacaaggctgggacggcgaatggcctatgg
5176 to 5250
                                        BssSI
```

```
                                  BstH2I
                                  Bsp143II          SfcI
tgtccgcctttctcccttcgggaagcgtggcgctttctcaatgctcacgctgtaggtatctcagttcggtgtagg
base pairs
acaggcggaaagagggaagcccttcgcaccgcgaaagagttacgagtgcgacatccatagagtcaagccacatcc
5251 to 5325
                                  HaeII             BstSFI
```

FIG. 14-36

```
                BsiHKAI                        NspBII
            Alw44I                           BstMCI
            VneI Bbv12I                      BsaOI          BsaWI
tcgttcgctccaagctgggctgtgtgcacgaaccccccgttcagcccgaccgctgcgccttatccggtaactatc
base pairs
agcaagcgaggttcgacccgacacacgtgcttgggggcaagtcgggctggcgacgcggaataggccattgatag
5326 to 5400
            ApaLI                            Bsh1285I
                AspHI                        BsiEI
                Alw21I                        MspA1I


                                              AlwNI
gtcttgagtccaacccggtaagacacgacttatcgccactggcagcagccactggtaacaggattagcagagcga
base pairs
cagaactcaggttgggccattctgtgctgaatagcggtgaccgtcgtcggtgaccattgtcctaatcgtctcgct
5401 to 5475
```

FIG. 14-37

```
                SfcI
ggtatgtaggcggtgctacagagttcttgaagtggtggcctaactacggctacactagaagaacagtatttggta
base pairs
ccatacatccgccacgatgtctcaagaacttcaccaccggattgatgccgatgtgatcttcttgtcataaaccat
5476 to 5550
                BstSFI


                 Eco57I
                                                                     NspBII
tctgcgctctgctgaagccagttaccttcggaaaaagagttggtagctcttgatccggcaaacaaaccaccgctg
base pairs
agacgcgagacgacttcggtcaatggaagcctttttctcaaccatcgagaactaggccgtttgtttggtggcgac
5551 to 5625
                                                                     MspA1I
```

FIG. 14-38

```
                                                MflI      MflI
                                                XhoII     XhoII
gtagcggtggtttttttgtttgcaagcagcagattacgcgcagaaaaaaaggatctcaagaagatcctttgatct
base pairs
catcgccaccaaaaaaacaaacgttcgtcgtctaatgcgcgtcttttttttcctagagttcttctaggaaactaga
5626 to 5700
                                                BstYI     BstYI
                                                BstX2I    BstX2I
```

```
                                                    RcaI             MflI
                                                                XhoII
tttctacggggtctgacgctcagtggaacgaaaactcacgttaagggattttggtcatgagattatcaaaaagga
base pairs
aaagatgccccagactgcgagtcaccttgcttttgagtgcaattccctaaaaccagtactctaatagtttttcct
5701 to 5775
                                                    BspHI       BstYI
                                                                BstX2I
```

FIG. 14-39

```
          MflI
          XhoII    DraI                DraI
tcttcacctagatccttttaaattaaaaatgaagttttaaatcaatctaaagtatatatgagtaaacttggtctg
base pairs
agaagtggatctaggaaaatttaatttttacttcaaaatttagttagatttcatatatactcatttgaaccagac
5776 to 5850
          BstYI
          BstX2I
```

```
                          AccB1I
                          BshNI
acagttaccaatgcttaatcagtgaggcacctatctcagcgatctgtctatttcgttcatccatagttgcctgac
base pairs
tgtcaatggttacgaattagtcactccgtggatagagtcgctagacagataaagcaagtaggtatcaacggactg
5851 to 5925
                          BanI
                          Eco64I
```

FIG. 14-40

```
   Eam1105I
   AspEI                                                         BsrDI
tccccgtcgtgtagataactacgatacgggagggcttaccatctggccccagtgctgcaatgataccgcgagacc
base pairs
aggggcagcacatctattgatgctatgccctcccgaatggtagaccggggtcacgacgttactatggcgctctgg
5926 to 6000
   EclHKI
   AhdI
```

```
        Cfr10I
BsaI    BssAI     BpmI                             BglI
cacgctcaccggctccagatttatcagcaataaaccagccagccggaagggccgagcgcagaagtggtcctgcaa
base pairs
gtgcgagtggccgaggtctaaatagtcgttatttggtcggtcggccttcccggctcgcgtcttcaccaggacgtt
6001 to 6075
Eco31I  BsrFI     GsuI
        Bse118I
```

FIG. 14-41

```
                        VspI
                        PshBI
ctttatccgcctccatccagtctattaattgttgccgggaagctagagtaagtagttcgccagttaatagtttgc
base pairs
gaaataggcggaggtaggtcagataattaacaacggcccttcgatctcattcatcaagcggtcaattatcaaacg
6076 to 6150
                        AsnI
                        AseI


AviII             BstSFI
FspI              SfcI         MslI                                      BsaWI
gcaacgttgttgccattgctacaggcatcgtggtgtcacgctcgtcgtttggtatggcttcattcagctccggtt
base pairs
cgttgcaacaacggtaacgatgtccgtagcaccacagtgcgagcagcaaaccataccgaagtaagtcgaggccaa
6151 to 6225
Acc16I            BsrDI
    Psp1406I
```

FIG. 14-42

```
                                                                            BsiEI
                                                                             PvuI
                                                                           BstMCI
                                                                            BsaOI
cccaacgatcaaggcgagttacatgatcccccatgttgtgcaaaaaagcggttagctccttcggtcctccgatcg
base pairs
gggttgctagttccgctcaatgtactagggggtacaacacgttttttcgccaatcgaggaagccaggaggctagc
6226 to 6300
                                                                            BspCI
                                                                         Bsh1285I
                                                                           Ple19I

               EaeI                  MslI
ttgtcagaagtaagttggccgcagtgttatcactcatggttatggcagcactgcataattctcttactgtcatgc
base pairs
aacagtcttcattcaaccggcgtcacaatagtgagtaccaataccgtcgtgacgtattaagagaatgacagtacg
6301 to. 6375
               CfrI
```

FIG. 14-43

```
                                   Acc113I
                                                                          BstMCI
                                   Eco255I                                 BsaOI
catccgtaagatgcttttctgtgactggtgagtactcaaccaagtcattctgagaatagtgtatgcggcgaccga
base pairs
gtaggcattctacgaaaagacactgaccactcatgagttggttcagtaagactcttatcacatacgccgctggct
6376 to 6450
                                   ScaI
                                                                         Bsh1285I
                                                                          BsiEI

              BbiII
              Hin1I                                                  Alw21I
    BcgI      AcyI                                         DraI       AspHI
gttgctcttgcccggcgtcaatacgggataataccgcgccacatagcagaactttaaaagtgctcatcattggaa
base pairs
caacgagaacgggccgcagttatgccctattatggcgcggtgtatcgtcttgaaattttcacgagtagtaacctt
6451 to 6525
              Msp17I                                                  BsiHKAI
              BsaHI                                                  Bbv12I
              Hsp92I
```

FIG. 14-44

```
                                                                           BssSI
  XmnI                       MflI             MflI                        Alw44I
  Psp1406I                   XhoII     NspBII XhoII                       VneI
aacgttcttcggggcgaaaactctcaaggatcttaccgctgttgagatccagttcgatgtaacccactcgtgcac
base pairs
ttgcaagaagccccgcttttgagagttcctagaatggcgacaactctaggtcaagctacattgggtgagcacgtg
6526 to 6600
  Asp700I                    BstYI     MspA1I BstYI                        ApaLI
                             BstX2I           BstX2I                        BsiI
                                                                           AspHI


  Bbv12I
BsiHKAI        Eco57I
ccaactgatcttcagcatcttttactttcaccagcgtttctgggtgagcaaaaacaggaaggcaaaatgccgcaa
base pairs
ggttgactagaagtcgtagaaaatgaaagtggtcgcaaagacccactcgtttttgtccttccgttttacggcgtt
6601 to 6675
 Alw21I
```

FIG. 14-45

```
                                              EarI
                     MslI                     Eam1104I  SspI
aaaagggaataagggcgacacggaaatgttgaatactcatactcttcctttttcaatattattgaagcatttatc
base pairs
ttttcccttattcccgctgtgcctttacaacttatgagtatgagaaggaaaaagttataataacttcgtaaatag
6676 to 6750
                                              Ksp632I
```

```
                         AccBSI
                 RcaI    BsrBI
agggttattgtctcatgagcggatacatatttgaatgtatttagaaaaataaacaaataggggttccgcgcacat
base pairs
tcccaataacagagtactcgcctatgtataaacttacataaatctttttatttgtttatccccaaggcgcgtgta
6751 to 6825
                 BspHI   BstD102I
```

FIG. 14-46

```
                                SfcI
ttccccgaaaagtgccacctgacgcgccctgtagcggcgcattaagcgcggcgggtgtggtggttacgcgcagcg
base pairs
aaggggcttttcacggtggactgcgcgggacatcgccgcgtaattcgcgccgcccacaccaccaatgcgcgtcgc
6826 to 6900
                                BstSFI

                                       AccBSI                                BsrFI
                        BstH2I  HaeII  BstD102I                              BssAI
                        Bsp143II       BsrBI                                 MroNI
tgaccgctacacttgccagcgccctagcgcccgctcctttcgctttcttcccttcctttctcgccacgttcgccg
base pairs
actggcgatgtgaacggtcgcgggatcgcgggcgaggaaagcgaaagaagggaaggaaagagcggtgcaagcggc
6901 to 6975                                                                NgoAIV
                        HaeII   Bsp143II                                     NgoMI
                                                                            Bse118I
                                BstH2I
```

FIG. 14-47

```
   NaeI                                                                   AccB1I
                                                                           BshNI
gctttccccgtcaagctctaaatcgggcatccctttagggttccgatttagtgctttacggcacctcgacccca
base pairs
cgaaaggggcagttcgagatttagccccgtagggaaatcccaaggctaaatcacgaaatgccgtggagctggggt
6976 to 7050
                                                                           BanI
 Cfr10I                                                                   Eco64I



                                     BsaAI
                                                                              DrdI
aaaaacttgattagggtgatggttcacgtagtgggccatcgccctgatagacggtttttcgccctttgacgttgg
base pairs
tttttgaactaatcccactaccaagtgcatcacccggtagcgggactatctgccaaaaagcgggaaactgcaacc
7051 to 7125
                                        DraIII
```

FIG. 14-48

```
agtccacgttctttaatagtggactcttgttccaaactggaacaacactcaaccctatctcggtctattcttttg
base pairs
tcaggtgcaagaaattatcacctgagaacaaggtttgaccttgttgtgagttgggatagagccagataagaaaac
7126 to 7200

                                                                 ApoI         ApoI
atttataagggattttgccgatttcggcctattggttaaaaaatgagctgatttaacaaaaatttaacgcgaatt
base pairs
taaatattccctaaaacggctaaagccggataaccaattttttactcgactaaattgtttttaaattgcgcttaa
7201 to 7275
                                                                 AcsI         AcsI

          SspI  Psp1406I
ttaacaaaatattaaacgtttacaattt  base pairs
aattgttttataatttgcaaatgttaaa  7276 to 7303
```

FIG. 14-49

Table by Enzyme Name

| Enzyme name | No. cuts | Positions of sites | Recognition sequence | |
|---|---|---|---|---|
| AatI | 2 | 3446 4606 | agg/cct | More info |
| AatII | 5 | 451 504 587 773 4154 | gacgt/c | More info |
| Acc113I | 1 | 6408 | agt/act | More info |
| Acc16I | 2 | 21 6150 | tgc/gca | More info |
| Acc65I | 3 | 2264 3434 3602 | g/ gtacc | More info |
| AccB1I | 8 | 791 2264 3065 3434 3602 4779 5876 7036 | g/ gyrcc | More info |
| AccB7I | 6 | 1445 1482 1775 1796 2644 4191 | ccannnn/ntgg | More info |
| AccBSI | 4 | 4730 4971 6772 6936 | gagcgg | More info |
| AclNI | 1 | 326 | a/ ctagt | More info |
| AcsI | 7 | 912 1990 2244 2994 4679 7260 7271 | r/ aatty | More info |
| AcyI | 6 | 448 501 584 770 4151 6465 | gr/cgyc | More info |
| AflIII | 2 | 2702 5035 | a/ crygt | More info |
| AgeI | 1 | 4188 | a/ ccggt | More info |
| AhdI | 2 | 3754 5928 | gacnnn/nngtc | More info |
| Alw21I | 6 | 894 1576 2330 5353 6514 6599 | gwgcw/c | More info |
| Alw44I | 2 | 5349 6595 | g/ tgcac | More info |

FIG. 14-50

| | | | | |
|---|---|---|---|---|
| AlwNI | 6 | 1147 1273 1775 3091 4282 5451 | cagnnn/ctg | More info |
| Ama87I | 3 | 3638 3934 4629 | c/ ycgrg | More info |
| AocI | 3 | 1034 1046 3256 | cc/ tnagg | More info |
| ApaI | 1 | 3806 | gggcc/c | More info |
| ApaLI | 2 | 5349 6595 | g/ tgcac | More info |
| ApoI | 7 | 912 1990 2244 2994 4679 7260 7271 | r/ aatty | More info |
| AseI | 4 | 334 4806 4865 6100 | at/ taat | More info |
| AsnI | 4 | 334 4806 4865 6100 | at/ taat | More info |
| Asp700I | 4 | 1107 2481 3506 6527 | gaann/nnttc | More info |
| Asp718I | 3 | 2264 3434 3602 | g/ gtacc | More info |
| AspEI | 2 | 3754 5928 | gacnnn/nngtc | More info |
| AspHI | 6 | 894 1576 2330 5353 6514 6599 | gwgcw/c | More info |
| AvaI | 3 | 3638 3934 4629 | c/ ycgrg | More info |
| AviII | 2 | 21 6150 | tgc/gca | More info |
| AvrII | 2 | 3109 4607 | c/ ctagg | More info |
| BalI | 4 | 184 238 3300 4018 | tgg/cca | More info |
| BamHI | 1 | 3596 | g/ gatcc | More info |
| BanI | 8 | 791 2264 3065 3434 3602 4779 5876 7036 | g/ gyrcc | More info |
| BanII | 6 | 894 1017 1623 3526 3558 3806 | grgcy/c | More info |
| BanIII | 1 | 939 | at/ cgat | More info |
| BbiII | 6 | 448 501 584 770 4151 6465 | gr/cgyc | More info |

FIG. 14-51

| | | | | |
|---|---|---|---|---|
| BbrPI | 1 | 2705 | cac/gtg | More info |
| BbsI | 2 | 2512 3820 | gaagac | More info |
| BbuI | 4 | 2930 3959 4354 4427 | gcatg/c | More info |
| Bbv12I | 6 | 894 1576 2330 5353 6514 6599 | gwgcw/c | More info |
| Bbv16II | 2 | 2512 3820 | gaagac | More info |
| BcgI | 4 | 941 2556 3925 6455 | cgannnnnntgc | More info |
| BclI | 1 | 969 | t/ gatca | More info |
| BcoI | 3 | 3638 3934 4629 | c/ ycgrg | More info |
| BglI | 5 | 14 417 538 4560 6048 | gccnnnn/nggc | More info |
| BglII | 2 | 932 3409 | a/ gatct | More info |
| BlnI | 2 | 3109 4607 | c/ ctagg | More info |
| BlpI | 3 | 1200 2337 3970 | gc/tnagc | More info |
| BpiI | 2 | 2512 3820 | gaagac | More info |
| BpmI | 9 | 1015 1279 1772 2781 2842 3022 3701 3863 6018 | ctggag | More info |
| Bpu1102I | 3 | 1200 2337 3970 | gc/tnagc | More info |
| Bpu14I | 3 | 1603 1988 2423 | tt/cgaa | More info |
| BpuAI | 2 | 2512 3820 | gaagac | More info |
| Bsa29I | 1 | 939 | at/ cgat | More info |
| BsaAI | 3 | 666 2705 7077 | yac/gtr | More info |
| BsaHI | 6 | 448 501 584 770 4151 6465 | gr/cgyc | More info |

FIG. 14-52

| | | | | |
|---|---|---|---|---|
| BsaI | 3 | 3380 4031 6000 | ggtctc | More info |
| BsaMI | 1 | 1886 | gaatgc | More info |
| BsaOI | 7 | 42 424 928 4951 5375 6298 6447 | cgry/cg | More info |
| BsaWI | 6 | 3200 3599 4188 5241 5388 6219 | w/ ccggw | More info |
| BscI | 1 | 939 | at/ cgat | More info |
| Bse118I | 3 | 4188 6008 6972 | r/ ccggy | More info |
| Bse21I | 3 | 1034 1046 3256 | cc/ tnagg | More info |
| BseCI | 1 | 939 | at/ cgat | More info |
| BseRI | 4 | 1337 1671 4593 4631 | gaggag | More info |
| BsgI | 3 | 2315 3212 3868 | gtgcag | More info |
| Bsh1285I | 7 | 42 424 928 4951 5375 6298 6447 | cgry/cg | More info |
| BshNI | 8 | 791 2264 3065 3434 3602 4779 5876 7036 | g/ gyrcc | More info |
| BsiEI | 7 | 42 424 928 4951 5375 6298 6447 | cgry/cg | More info |
| BsiHKAI | 6 | 894 1576 2330 5353 6514 6599 | gwgcw/c | More info |
| BsiI | 2 | 5213 6597 | ctcgtg | More info |
| BsmBI | 3 | 2023 2773 4001 | cgtctc | More info |
| BsmI | 1 | 1886 | gaatgc | More info |
| BsoBI | 3 | 3638 3934 4629 | c/ ycgrg | More info |
| Bsp106I | 1 | 939 | at/ cgat | More info |
| Bsp119I | 3 | 1603 1988 2423 | tt/cgaa | More info |
| Bsp120I | 1 | 3802 | g/ ggccc | More info |
| Bsp1407I | 2 | 270 3471 | t/ gtaca | More info |

FIG. 14-53

| | | | | |
|---|---|---|---|---|
| Bsp143II | 5 | 2519 4913 5283 6922 6930 | rgcgc/y | More info |
| Bsp1720I | 3 | 1200 2337 3970 | gc/tnagc | More info |
| Bsp19I | 5 | 686 3324 3424 4178 4514 | c/ catgg | More info |
| BspCI | 2 | 42 6298 | cgat/cg | More info |
| BspDI | 1 | 939 | at/ cgat | More info |
| BspHI | 3 | 1891 5755 6763 | t/ catga | More info |
| BspLU11I | 1 | 5035 | a/ catgt | More info |
| BspMI | 2 | 1913 4178 | acctgc | More info |
| BspXI | 1 | 939 | at/ cgat | More info |
| BsrBI | 4 | 4730 4971 6772 6936 | gagcgg | More info |
| BsrDI | 5 | 245 2827 3594 5987 6169 | gcaatg | More info |
| BsrFI | 3 | 4188 6008 6972 | r/ ccggy | More info |
| BsrGI | 2 | 270 3471 | t/ gtaca | More info |
| BssAI | 3 | 4188 6008 6972 | r/ ccggy | More info |
| BssSI | 2 | 5213 6597 | ctcgtg | More info |
| BssT1I | 11 | 686 1950 2226 3109 3324 3424 3681 4060 4178 4514 4607 | c/ cwwgg | More info |
| BstBI | 3 | 1603 1988 2423 | tt/cgaa | More info |
| BstD102I | 4 | 4730 4971 6772 6936 | gagcgg | More info |
| BstDSI | 6 | 686 1062 3324 3424 4178 4514 | c/ crygg | More info |
| BstH2I | 5 | 2519 4913 5283 6922 6930 | rgcgc/y | More info |
| BstI | 1 | 3596 | g/ gatcc | More info |

FIG. 14-54

| | | | | |
|---|---|---|---|---|
| BstMCI | 7 | 42 424 928 4951 5375 6298 6447 | cgry/cg | More info |
| BstSFI | 8 | 944 2144 3824 4662 5300 5491 6169 6854 | c/ tryag | More info |
| BstSNI | 1 | 666 | tac/gta | More info |
| BstX2I | 12 | 932 2400 2634 3409 3596 3634 5676 5687 5773 5785 6553 6570 | r/ gatcy | More info |
| BstXI | 3 | 3076 3325 4077 | ccannnnn/ntgg | More info |
| BstYI | 12 | 932 2400 2634 3409 3596 3634 5676 5687 5773 5785 6553 6570 | r/ gatcy | More info |
| BstZI | 1 | 925 | c/ ggccg | More info |
| Bsu15I | 1 | 939 | at/ cgat | More info |
| Bsu36I | 3 | 1034 1046 3256 | cc/ tnagg | More info |
| CciNI | 1 | 925 | gc/ggccgc | More info |
| CelII | 3 | 1200 2337 3970 | gc/tnagc | More info |
| Cfr10I | 3 | 4188 6008 6972 | r/ ccggy | More info |
| Cfr9I | 1 | 3638 | c/ ccggg | More info |
| CfrI | 9 | 152 182 236 925 3298 4016 4273 4874 6316 | y/ ggccr | More info |
| ClaI | 1 | 939 | at/ cgat | More info |
| Csp45I | 3 | 1603 1988 2423 | tt/cgaa | More info |
| CvnI | 3 | 1034 1046 3256 | cc/ tnagg | More info |

FIG. 14-55

| | | | | |
|---|---|---|---|---|
| DraI | 4 | 4127 5794 5813 6505 | ttt/aaa | More info |
| DraII | 3 | 3291 3802 3829 | rg/gnccy | More info |
| DraIII | 1 | 7080 | cacnnn/gtg | More info |
| DrdI | 3 | 1076 5143 7124 | gacnnnn/nngtc | More info |
| DsaI | 6 | 686 1062 3324 3424 4178 4514 | c/ crygg | More info |
| EaeI | 9 | 152 182 236 925 3298 4016 4273 4874 6316 | y/ ggccr | More info |
| EagI | 1 | 925 | c/ ggccg | More info |
| Eam1104I | 5 | 58 2482 2793 4918 6722 | ctcttc | More info |
| Eam1105I | 2 | 3754 5928 | gacnnn/nngtc | More info |
| EarI | 5 | 58 2482 2793 4918 6722 | ctcttc | More info |
| Ecl136II | 1 | 892 | gag/ ctc | More info |
| EclHKI | 2 | 3754 5928 | gacnnn/nngtc | More info |
| EclXI | 1 | 925 | c/ ggccg | More info |
| Eco105I | 1 | 666 | tac/gta | More info |
| Eco130I | 11 | 686 1950 2226 3109 3324 3424 3681 4060 4178 4514 4607 | c/ cwwgg | More info |
| Eco147I | 2 | 3446 4606 | agg/cct | More info |
| Eco24I | 6 | 894 1017 1623 3526 3558 3806 | grgcy/c | More info |
| Eco255I | 1 | 6408 | agt/act | More info |
| Eco31I | 3 | 3380 4031 6000 | ggtctc | More info |
| Eco32I | 1 | 952 | gat/ atc | More info |
| Eco52I | 1 | 925 | c/ ggccg | More info |

FIG. 14-56

| | | | | |
|---|---|---|---|---|
| Eco57I | 7 | 1210 2446 2488 3271 3314 5567 6615 | ctgaag | More info |
| Eco64I | 8 | 791 2264 3065 3434 3602 4779 5876 7036 | g/ gyrcc | More info |
| Eco72I | 1 | 2705 | cac/gtg | More info |
| Eco81I | 3 | 1034 1046 3256 | cc/ tnagg | More info |
| Eco88I | 3 | 3638 3934 4629 | c/ ycgrg | More info |
| EcoICRI | 1 | 892 | gag/ ctc | More info |
| EcoNI | 3 | 1259 1338 1684 | cctnn/nnnagg | More info |
| EcoO109I | 3 | 3291 3802 3829 | rg/gnccy | More info |
| EcoRI | 3 | 912 1990 2994 | g/ aattc | More info |
| EcoRV | 1 | 952 | gat/ atc | More info |
| EcoT14I | 11 | 686 1950 2226 3109 3324 3424 3681 4060 4178 4514 4607 | c/ cwwgg | More info |
| EcoT22I | 3 | 3961 4356 4429 | atgca/t | More info |
| ErhI | 11 | 686 1950 2226 3109 3324 3424 3681 4060 4178 4514 4607 | c/ cwwgg | More info |
| Esp1396I | 6 | 1445 1482 1775 1796 2644 4191 | ccannnn/ntgg | More info |
| Esp3I | 3 | 2023 2773 4001 | cgtctc | More info |
| FauNDI | 1 | 560 | ca/ tatg | More info |
| FbaI | 1 | 969 | t/ gatca | More info |
| FriOI | 6 | 894 1017 1623 3526 3558 3806 | grgcy/c | More info |
| FspI | 2 | 21 6150 | tgc/gca | More info |

FIG. 14-57

| | | | | |
|---|---|---|---|---|
| GsuI | 9 | 1015 1279 1772 2781 2842 3022 3701 3863 6018 | ctggag | More info |
| HaeII | 5 | 2519 4913 5283 6922 6930 | rgcgc/y | More info |
| Hin1I | 6 | 448 501 584 770 4151 6465 | gr/cgyc | More info |
| HincII | 3 | 311 446 842 | gty/rac | More info |
| HindII | 3 | 311 446 842 | gty/rac | More info |
| HindIII | 3 | 918 1394 2183 | a/ agctt | More info |
| Hsp92I | 6 | 448 501 584 770 4151 6465 | gr/cgyc | More info |
| KpnI | 3 | 2268 3438 3606 | ggtac/c | More info |
| Ksp22I | 1 | 969 | t/ gatca | More info |
| Ksp632I | 5 | 58 2482 2793 4918 6722 | ctcttc | More info |
| LspI | 3 | 1603 1988 2423 | tt/cgaa | More info |
| MfeI | 1 | 1091 | c/ aattg | More info |
| MflI | 12 | 932 2400 2634 3409 3596 3634 5676 5687 5773 5785 6553 6570 | r/ gatcy | More info |
| MluNI | 4 | 184 238 3300 4018 | tgg/cca | More info |
| Mph1103I | 3 | 3961 4356 4429 | atgca/t | More info |
| MroNI | 1 | 6972 | g/ ccggc | More info |
| MscI | 4 | 184 238 3300 4018 | tgg/cca | More info |
| MslI | 10 | 691 2094 2703 3323 3489 3651 3698 6180 6339 6698 | caynn/nnrtg | More info |
| Msp17I | 6 | 448 501 584 770 4151 6465 | gr/cgyc | More info |
| MspA1I | 7 | 71 2341 2731 4859 5377 5622 6563 | cmg/ckg | More info |

FIG. 14-58

| | | | | |
|---|---|---|---|---|
| MunI | 1 | 1091 | c/ aattg | More info |
| Mva1269I | 1 | 1886 | gaatgc | More info |
| NaeI | 1 | 6974 | gcc/ggc | More info |
| NcoI | 5 | 686 3324 3424 4178 4514 | c/ catgg | More info |
| NdeI | 1 | 560 | ca/ tatg | More info |
| NgoAIV | 1 | 6972 | g/ ccggc | More info |
| NgoMI | 1 | 6972 | g/ ccggc | More info |
| NotI | 1 | 925 | gc/ggccgc | More info |
| NsiI | 3 | 3961 4356 4429 | atgca/t | More info |
| NspBII | 7 | 71 2341 2731 4859 5377 5622 6563 | cmg/ckg | More info |
| NspI | 5 | 2930 3959 4354 4427 5039 | rcatg/y | More info |
| NspV | 3 | 1603 1988 2423 | tt/cgaa | More info |
| PaeI | 4 | 2930 3959 4354 4427 | gcatg/c | More info |
| PaeR7I | 1 | 4629 | c/ tcgag | More info |
| PflMI | 6 | 1445 1482 1775 1796 2644 4191 | ccannnn/ntgg | More info |
| PinAI | 1 | 4188 | a/ ccggt | More info |
| Ple19I | 2 | 42 6298 | cgat/cg | More info |
| PmaCI | 1 | 2705 | cac/gtg | More info |
| Pme55I | 2 | 3446 4606 | agg/cct | More info |
| PmlI | 1 | 2705 | cac/gtg | More info |
| Ppu10I | 3 | 3957 4352 4425 | a/ tgcat | More info |
| PshBI | 4 | 334 4806 4865 6100 | at/ taat | More info |
| Psp124BI | 1 | 894 | gagct/c | More info |
| Psp1406I | 3 | 6154 6527 7291 | aa/cgtt | More info |

FIG. 14-59

| | | | | |
|---|---|---|---|---|
| PspAI | 1 | 3638 | c/ ccggg | More info |
| PspALI | 1 | 3640 | ccc/ggg | More info |
| PspOMI | 1 | 3802 | g/ ggccc | More info |
| PstI | 2 | 948 2148 | ctgca/g | More info |
| PvuI | 2 | 42 6298 | cgat/cg | More info |
| PvuII | 3 | 71 2341 4859 | cag/ctg | More info |
| RcaI | 3 | 1891 5755 6763 | t/ catga | More info |
| SacI | 1 | 894 | gagct/c | More info |
| SapI | 2 | 2483 4918 | gctcttc | More info |
| ScaI | 1 | 6408 | agt/act | More info |
| SexAI | 1 | 4373 | a/ ccwggt | More info |
| SfcI | 8 | 944 2144 3824 4662 5300 5491 6169 6854 | c/ tryag | More info |
| SfiI | 1 | 4560 | ggccnnnn/nggcc | More info |
| Sfr274I | 1 | 4629 | c/ tcgag | More info |
| SfuI | 3 | 1603 1988 2423 | tt/cgaa | More info |
| SmaI | 1 | 3640 | ccc/ggg | More info |
| SnaBI | 1 | 666 | tac/gta | More info |
| SpeI | 1 | 326 | a/ ctagt | More info |
| SphI | 4 | 2930 3959 4354 4427 | gcatg/c | More info |
| SseBI | 2 | 3446 4606 | agg/cct | More info |
| SspBI | 2 | 270 3471 | t/ gtaca | More info |
| SspI | 5 | 179 226 3768 6732 7285 | aat/att | More info |
| SstI | 1 | 894 | gagct/c | More info |

FIG. 14-60

| | | | | |
|---|---|---|---|---|
| StuI | 2 | 3446 4606 | agg/cct | More info |
| StyI | 11 | 686 1950 2226 3109 3324 3424 3681 4060 4178 4514 4607 | c/ cwwgg | More info |
| Van91I | 6 | 1445 1482 1775 1796 2644 4191 | ccannnn/ntgg | More info |
| VneI | 2 | 5349 6595 | g/ tgcac | More info |
| VspI | 4 | 334 4806 4865 6100 | at/ taat | More info |
| XcmI | 2 | 1948 2897 | ccannnnn/nnnntgg | More info |
| XhoI | 1 | 4629 | c/ tcgag | More info |
| XhoII | 12 | 932 2400 2634 3409 3596 3634 5676 5687 5773 5785 6553 6570 | r/gatcy | More info |
| XmaI | 1 | 3638 | c/ ccggg | More info |
| XmaIII | 1 | 925 | c/ ggccg | More info |
| XmnI | 4 | 1107 2481 3506 6527 | gaann/nnttc | More info |
| Zsp2I | 3 | 3961 4356 4429 | atgca/t | More info |

The following endonucleases were selected but don't cut this sequence:
AccI, AccIII, AfeI, AflII, Aor51HI, AscI, AspI, AtsI, BbeI, BfrI, BsaBI, Bse8I, BseAI, BsePI, Bsh1365I, BsiMI, BsiWI, Bsp13I, Bsp68I, BspEI, BspTI, BsrBRI, BssHII, Bst1107I, Bst98I, BstEII, BstPI, Cfr42I, CpoI, CspI, Eco47III, Eco91I, EcoO65I, EheI, FseI, HpaI, KasI, Kpn2I, KspI, MamI, MluI, MroI, MspCI, NarI, NheI, NruI, PacI, Pfl23II, PmeI, PpuMI, PshAI, Psp5II, PspEI, PspLI, PstNHI, RsrII, SacII, SalI, SbfI, Sfr303I, SgfI, SgrAI, SmiI, SplI, SrfI, Sse8387I, SstII, SunI, SwaI, Tth111I, Vha464I, XbaI

FIG. 14-61

ANTIBODIES THAT SELECTIVELY BIND HDAC9

RELATED APPLICATIONS

This application is a divisional of U.S. application Ser. No. 11/202,268, filed on Aug. 10, 2005, now U.S. Pat. No. 7,244,604, which is a divisional of U.S. application Ser. No. 10/173,539, filed on Jun. 14, 2002, now U.S. Pat. No. 7,063,973, which claims the benefit of U.S. Provisional Application Ser. No. 60/298,173 filed on Jun. 14, 2001, U.S. Provisional Application No. 60/311,686 filed on Aug. 10, 2001 and U.S. Provisional Application No. 60/316,995, filed on Sep. 4, 2001. The entire teachings of the above applications are incorporated herein by reference in their entirety.

GOVERNMENT SUPPORT

The invention was supported, in whole or in part, by grant CA-0974823 from the National Cancer Institute. The Government has certain rights in the invention.

BACKGROUND OF THE INVENTION

The N-terminal tails of core histones are covalently modified by post-translational modifications, including acetylation and phosphorylation. Evidence suggests that these covalent modifications play important roles in several biological activities involving chromatin, e.g., transcription and replication. Histone deacetylases (HDACs) catalyze the removal of the acetyl group from the lysine residues in the N-terminal tails of nucleosomal core histones resulting in a more compact chromatin structure, a configuration that is generally associated with repression of transcription.

Five proteins and/or open reading frames in yeast (RPD3, HDA1, HOS1, HOS2 and HOS3) that share significant homology in the catalytic domain have been identified as HDACs based upon their sequence homology to human HDAC1. To date, eight HDACs have been identified in mammalian cells, and classified into two classes based on their structure and similarity to yeast RPD3 or HDA1 proteins. Recently, Sir2 family proteins that are structurally unrelated to the five proteins aforementioned have been identified as NAD-dependent HDACs. Class I HDACs are the yeast RPD3 homologs HDAC1, 2, 3, and 8, and are composed primarily of a catalytic domain. Class II HDACs are the yeast HDA1 homologs HDAC4, 5, 6, and 7. HDAC4, 5, and 7 contain a long non-catalytic N-terminal end and a C-terminal HDAC catalytic domain while HDAC6 has two HDAC catalytic domains.

It has also been determined that histone deacetylases can be sensitive to small molecules, including trichostatin A (TSA), trapoxin, and butyrate. For example, the yeast RPD3 and HDA1 and mammalian HDAC1, 2, 3, 4, 5, 6, 7 and 8 are sensitive to inhibition by trichostatin A (TSA). The Sir2 family HDACs, yeast HOS3 and *Drosophila melanogaster* dHDAC6, however, appear to be relatively insensitive to TSA. A class of hybrid bipolar compounds, such as suberoylanilide hydroxamic acid (SAHA) have also been shown to inhibit histone deacetylases and induce terminal differentiation and/or apoptosis in various transformed cells. Examples of such compounds can be found in U.S. Pat. No. 5,369,108, issued on Nov. 29, 1994, U.S. Pat. No. 5,700,811, issued on Dec. 23, 1997, and U.S. Pat. No. 5,773,474, issued on Jun. 30, 1998 to Breslow et al., as well as U.S. Pat. No. 5,055,608, issued on Oct. 8, 1991, and U.S. Pat. No. 5,175,191, issued on Dec. 29, 1992 to Marks et al., the entire content of all of which are hereby incorporated by reference.

The identification of the mechanisms by which histones are deacetylated, and the characterization of histone deacetylase function would be of great benefit in understanding how gene transcription is controlled, how the cell cycle is regulated, and how cells are signaled to undergo terminal differentiation and/or apoptosis. Elucidation of such mechanisms can lead to improved therapeutics for many diseases, in particular those characterized by cell proliferation or a lack of cell differentiation or apoptosis, for example, cancer.

SUMMARY OF THE INVENTION

The present invention relates to isolated or recombinant histone deacetylase polypeptides, and isolated histone deacetylase nucleic acid molecules encoding those polypeptides, as well as vectors and cells containing those isolated nucleic acid molecules.

In one aspect of the invention, the isolated or recombinant histone deacetylase polypeptide is selected from a) an isolated or recombinant polypeptide comprising SEQ ID NO: 2, SEQ ID NO: 4, SEQ ID NO: 6, SEQ ID NO: 8, or SEQ ID NO: 10; and b) a polypeptide having at least 60% sequence identity with any one of SEQ ID NO: 2, SEQ ID NO: 4, SEQ ID NO: 6, SEQ ID NO: 8, or SEQ ID NO: 10. In one embodiment, the isolated or recombinant histone deacetylase polypeptide consists of SEQ ID NO: 2, SEQ ID NO: 4, SEQ ID NO: 6, SEQ ID NO: 8, or SEQ ID NO: 10. In another embodiment, the isolated or recombinant histone deacetylase polypeptide is mammalian; preferably, the isolated or recombinant histone deacetylase polypeptide is human.

In another aspect, the invention features an isolated nucleic acid molecule selected from a) an isolated nucleic acid comprising SEQ ID NO: 1, SEQ ID NO: 3, SEQ ID NO: 5, SEQ ID NO: 7, or SEQ ID NO: 9; b) a complement of an isolated nucleic acid comprising SEQ ID NO: 1, SEQ ID NO: 3, SEQ ID NO: 5, SEQ ID NO: 7, or SEQ ID NO: 9; c) an isolated nucleic acid encoding a histone deacetylase polypeptide of SEQ ID NO: 2, SEQ ID NO: 4, SEQ ID NO: 6, SEQ ID NO: 8, or SEQ ID NO: 10; d) a complement of an isolated nucleic acid encoding a histone deacetylase polypeptide of SEQ ID NO: 2, SEQ ID NO: 4, SEQ ID NO: 6, SEQ ID NO: 8, or SEQ ID NO: 10; e) a nucleic acid that is hybridizeable under high stringency conditions to a nucleic acid molecule that encodes any of SEQ ID NO: 2, SEQ ID NO: 4, SEQ ID NO: 6, or SEQ ID NO: 8, or a complement thereof; or f) a nucleic acid molecule that is hybridizeable under high stringency conditions to a nucleic acid comprising SEQ ID NO: 1, SEQ ID NO: 3, SEQ ID NO: 5, or SEQ ID NO: 7; and g) an isolated nucleic acid molecule that has at least 55% sequence identity with any one of SEQ ID NO: 1, SEQ ID NO: 3, SEQ ID NO: 5, SEQ ID NO: 7, SEQ ID NO: 9, or a complement thereof. In one embodiment, the isolated nucleic acid molecule consists of SEQ ID NO: 1, SEQ ID NO: 3, SEQ ID NO: 5, SEQ ID NO: 7, or SEQ ID NO: 9. In another embodiment, the isolated nucleic acid molecule is mammalian; preferably, the isolated nucleic acid molecule is human.

In other aspects, the invention features a vector comprising the isolated histone deacetylase nucleic acid molecule described above, a cell comprising the vector, and a cell comprising the isolated histone deacetylase nucleic acid molecule described above.

In another aspect, the invention features a purified antibody that selectively binds a histone deacetylase polypeptide described above.

In yet another aspect, the invention features a method of identifying a compound that modulates expression of a histone deacetylase nucleic acid molecule described above. The method comprises the steps of a) contacting the nucleic acid molecule with a candidate compound under conditions suitable for expression; and b) assessing the level of expression of the nucleic acid molecule. A candidate compound that increases or decreases expression of the nucleic acid molecule relative to a control is a compound that modulates expression of the nucleic acid molecule. In one embodiment, the method is carried out in a cell or animal. In another embodiment, the method is carried out in a cell free system.

The invention also features a method of treating a cell proliferation disease, an apoptotic disease, or a cell differentiation disease, for example, cancers such as lymphoma, leukemia, melanoma, ovarian cancer, breast cancer, pancreatic cancer, prostate cancer, colon cancer, and lung cancer and myeloproliferative disorders, including polycythemia vera, essential thrombocythemia, agnogenic myeloid metaplasia, and chronic myelogenous leukemia in an individual, comprising administering a compound identified by the above method.

In still another aspect, the invention features a method of identifying a compound that modulates the enzymatic activity of the histone deacetylase polypeptide described above. The method comprises the steps of a) contacting the polypeptide with a candidate compound under conditions suitable for enzymatic reaction; and b) assessing the activity level of the polypeptide. A candidate compound that increases or decreases the activity level of the polypeptide relative to a control is a compound that modulates the enzymatic activity of the polypeptide. In one embodiment, the method is carried out in a cell or animal. In another embodiment, the method is carried out in a cell free system.

In yet another embodiment, the polypeptide is further contacted with a substrate for the polypeptide, wherein the substrate is selected from the group consisting of a cell proliferation disease binding agent, an apoptotic disease binding agent, and a cell differentiation disease binding agent. In one embodiment, the candidate compound is an inhibitor. In another embodiment, candidate compound is an activator.

In another aspect, the invention features a method of identifying a compound that modulates the transcriptional repression activity of the histone deacetylase polypeptide described above. The method comprises the steps of a) contacting the polypeptide with a candidate compound under conditions suitable for a transcriptional repression reaction; and b) assessing the transcriptional repression activity level of the polypeptide. A candidate compound that increases or decreases the transcriptional repression activity level of the polypeptide relative to a control is a compound that modulates the transcriptional repression activity of the polypeptide. In one embodiment, the method is carried out in a cell or animal. In another embodiment, the method is carried out in a cell free system.

In yet another embodiment, the polypeptide is further contacted with a substrate for the polypeptide, wherein the substrate is selected from the group consisting of a cell proliferation disease binding agent, an apoptotic disease binding agent, and a cell differentiation disease binding agent. In one embodiment, the candidate compound is an inhibitor. In another embodiment, candidate compound is an activator.

In another aspect, the invention features a method of identifying a compound that modulates expression of a histone deacetylase nucleic acid molecule described above. The method comprises the steps of a) providing a nucleic acid molecule comprising a promoter region of the histone deacetylase nucleic acid molecule described above, or part of such a promoter region, operably linked to a reporter gene; b) contacting the nucleic acid molecule or with a candidate compound; and c) assessing the level of the reporter gene. A candidate compound that increases or decreases expression of the reporter gene relative to a control is a compound that modulates expression of the histone deacetylase nucleic acid molecule described above. In one embodiment, the method is carried out in a cell.

In still another aspect, the invention features a method of identifying a polypeptide that interacts with a histone deacetylase polypeptide described above in a yeast two-hybrid system. The method comprises the steps of a) providing a first nucleic acid vector comprising a nucleic acid molecule encoding a DNA binding domain and the histone deacetylase polypeptide described above; b) providing a second nucleic acid vector comprising a nucleic acid encoding a transcription activation domain and a nucleic acid encoding a test polypeptide; c) contacting the first nucleic acid vector with the second nucleic acid vector in a yeast two-hybrid system; and d) assessing transcriptional activation in the yeast two-hybrid system. An increase in transcriptional activation relative to a control indicates that the test polypeptide is a polypeptide that interacts with the histone deacetylase polypeptide described above.

The invention also features a pharmaceutical composition comprising a histone deacetylase polypeptide described above.

In addition, the present invention features a method of diagnosing a cell proliferation disease, an apoptotic disease, or a cell differentiation disease in a subject. The method comprises the steps of a) obtaining a sample from the subject; and b) assessing the level of activity or expression of the histone deacetylase polypeptide described above or the level of the nucleic acid molecule described above in the sample. If the level is increased relative to a control, then the subject has an increased likelihood of having a cell proliferation disease, an apoptotic disease, or a cell differentiation disease, and if the level is decreased relative to a control, then the subject has a decreased likelihood of having a cell proliferation disease, an apoptotic disease, or a cell differentiation disease. In one embodiment, the polypeptide level is assayed using immunohistochemistry techniques. In another embodiment, the nucleic acid molecule level is assayed using in situ hybridization techniques.

Compounds and/or polypeptides identified in the above-described screening methods are also part of the present invention.

DESCRIPTION OF THE FIGURES

FIGS. 1A-1C show the cDNA sequence of HDAC9 (SEQ ID NO: 1). The arrows and numbers in the HDAC9 sequence indicate exons. The boxed portion of the sequence indicates the HDAC domain.

FIGS. 1D-1G show the cDNA sequence of HDAC9a (SEQ ID NO: 3). The arrows and numbers in the HDAC9a sequence indicate exons. The boxed portion of the sequence indicates the HDAC domain.

FIGS. 1H-1I show the cDNA sequence of HDRP(ΔNLS) (SEQ ID NO:9).

FIGS. 1J-1L show the cDNA sequence of HDAC9(ΔNLS) (SEQ ID NO:5).

FIGS. 1M-1O show the cDNA sequence of HDAC9a (ΔNLS) (SEQ ID NO:7).

FIG. 2 is a schematic representation of the order in which FIGS. 2A-2E should be viewed.

FIG. 2A shows the amino acid sequence of HDAC9 (SEQ ID NO: 2).

FIG. 2B shows the amino acid sequence of HDAC9a (SEQ ID NO: 4).

FIG. 2C shows the amino acid sequence of HDAC9 (ΔNLS) (SEQ ID NO: 6).

FIG. 2D shows the amino acid sequence of HDAC9a (ΔNLS) (SEQ ID NO: 8).

FIG. 2E shows the amino acid sequence of and HDRP (ΔNLS) (SEQ ID NO: 10).

FIG. 3 is a schematic representation of the order in which FIGS. 3A-3C should be viewed.

FIGS. 3A-3C show an amino acid sequence alignment of HDRP (SEQ ID NO: 11), HDAC9 (SEQ ID NO: 2), HDAC9a (SEQ ID NO: 4), and HDAC4 (SEQ ID NO: 12) polypeptides. Amino acid sequences of HDAC9 (GenBank Accession: AY032737; SEQ ID NO: 2) and HDAC9a (GenBank Accession: AY032738; SEQ ID NO: 4) are aligned with HDRP (GenBank Accession: BAA34464; SEQ D NO: 11) and HDAC4 (GenBank Accession: NP_006028; SEQ ID NO: 12). The identical residues in all proteins are boxed with solid lines. The similar residues are boxed with dotted lines.

FIGS. 5A-5D show the nucleic acid sequence of HDAC9, containing all exons expressed in the various isoforms of HDAC9, HDAC9a, HDAC9(ΔNLS), HDAC9a(ΔNLS), and HDRP(ΔNLS) of the present invention (SEQ ID NO:13).

FIG. 11 is a schematic representation of the order in which FIGS. 11A-11F should be viewed.

FIGS. 11A-11F show the nucleotide sequence of the vector pFLAG-CMV-5b-HDAC9 (VR1) (SEQ ID NO: 14). Lowercase letters are vector backbone, uppercase letters are HDAC9 sequence. "Acc" was added at the beginning of the HDAC9 sequence for translation initiation.

FIGS. 12-1 through 12-66 show the nucleotide sequence of the vector pFLAG-CMV-5b-HDAC9a (VR2), with restriction enzyme sites indicated (SEQ ID NO: 14).

FIG. 13 is a schematic representation of the order in which FIGS. 13A-13E should be viewed.

FIGS. 13A-13E show the nucleotide sequence of the vector pFLAG-CMV-5b-HDAC9a (VR2) (SEQ ID NO: 15). Lowercase letters are vector backbone, uppercase letters are HDAC9a sequence. "Acc" was added at the beginning of the HDAC9a sequence for translation initiation.

FIGS. 14-1 through 14-61 show the nucleotide sequence of the vector pFLAG-CMV-5b-HDAC9a (VR2), with restriction enzyme sites indicated (SEQ ID NO: 15).

DETAILED DESCRIPTION OF THE INVENTION

Figure 1:
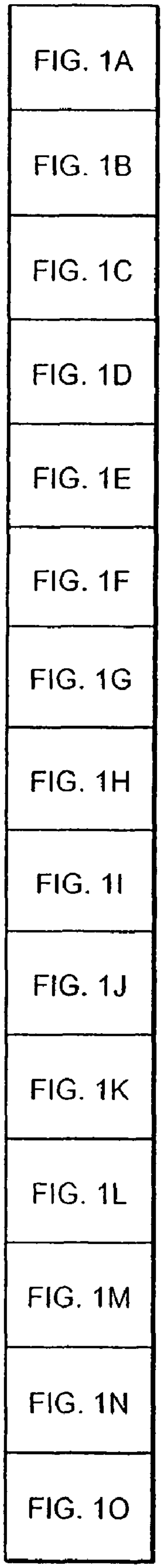
FIG. 1 is a schematic representation of the order in which FIGS. 1A-1O should be viewed.

A protein designated HDRP (See Zhou et al., Proc. Natl. Acad. Sci. USA, 97:1056-1061 (2000)) (also called MITR (See Sparrow et al., EMBO J. 18:5085-5098(1999); Zhang et al, J. Biol. Chem., 276:35-39 (2001); and Zhang et al., Proc. Natl. Acad. Sci. USA, 98:7354-7359 (2001)) that is 50% identical to the N-terminal domains of histone deacetylase 4 (HDAC4) and histone deacetylase 5 (HDAC5) was recently identified. The cloning and characterization of a novel histone deacetylase, HDAC9, of which HDRP is an alternatively spliced isoform is described herein. The cDNA sequence of HDAC9 is shown in FIGS. 1A-1C (SEQ ID NO: 1), and the HDAC9 amino acid sequence is shown in FIG. 2A (SEQ ID NO: 2). In addition to cloning HDAC9, other alternatively spliced isoforms of HDAC9, designated as HDAC9a (a polypeptide that is 132 amino acids shorter at the C-terminal end than HDAC9), and isoforms of HDAC9, HDAC9a, and HDRP polypeptides that lack the nuclear localization signal (NLS) in the N-terminal non-catalytic end of HDAC9, termed HDAC9(ΔNLS), HDAC9a(ΔNLS), and HDRP(ΔNLS), respectively were also identified. The cDNA sequence of HDAC9a is shown in FIGS. 1D-1G (SEQ ID NO: 3), and the HDAC9a amino acid sequence is shown in FIG. 2B (SEQ ID NO: 4). The cDNA sequence of HDAC9 lacking amino acids encoding an NLS (HDAC9(ΔNLS)) is shown in FIGS. 1J-1L (SEQ ID NO: 5), and the HDAC9 lacking an NLS amino acid sequence is shown in FIG. 2C (SEQ ID NO: 6). The cDNA sequence of HDAC9a encoding a polypeptide lacking an NLS (HDAC9a(ΔNLS)) is shown in FIGS. 1M-1O (SEQ ID NO: 7), and the HDAC9a lacking an NLS amino acid sequence is shown in FIG. 2D (SEQ ID NO: 8). The cDNA sequence of HDRP encoding a polypeptide lacking an NLS (HDRP (ΔNLS)) is shown in FIGS. 1H-1I (SEQ ID NO: 9), and the HDRP lacking an NLS amino acid sequence is shown in FIG. 2E (SEQ ID NO: 10).

Polypeptides of the Invention

The present invention features isolated or recombinant HDAC9 polypeptides, HDAC9a polypeptides, HDAC9 (ΔNLS) polypeptides, HDAC9a(ΔNLS) polypeptides, and HDRP(ΔNLS) polypeptides, and fragments, derivatives, and variants thereof, as well as polypeptides encoded by nucleotide sequences described herein (e.g., other variants). As used herein, the term "polypeptide" refers to a polymer of amino acids, and not to a specific length; thus, peptides, oligopeptides, and proteins are included within the definition of a polypeptide.

As used herein, a polypeptide is said to be "isolated," "substantially pure," or "substantially pure and isolated" when it is substantially free of cellular material, when it is isolated from recombinant or non-recombinant cells, or free of chemical precursors or other chemicals when it is chemically synthesized. Typically, the HDAC9, HDAC9a, HDAC9 (ΔNLS), HDAC9a(ΔNLS), or HDRP(ΔNLS) polypeptide is isolated, substantially pure, or substantially pure and isolated when it has a relative increased concentration or activity of HDAC9, HDAC9a, HDAC9(ΔNLS), HDAC9a(ΔNLS), or HDRP(ΔNLS), in comparison to total HDAC concentration or activity. Preferably the increased activity or concentration of the HDAC9, HDAC9a, HDAC9(ΔNLS), HDAC9a (ΔNLS), or HDRP(ΔNLS) is at least 2-fold, more preferably, at least 5-fold, and most preferably, at least 10 fold, in comparison to total HDAC concentration or activity. In addition, a polypeptide can be joined to another polypeptide with which it is not normally associated in a cell (e.g.; in a "fusion protein") and still be "isolated," "substantially pure," or "substantially pure and isolated." An isolated, substantially pure, or substantially pure and isolated polypeptide may be obtained, for example, using affinity purification techniques described herein, as well as other techniques described herein and known to those skilled in the art.

By a "histone deacetylase polypeptide" is meant a polypeptide having histone deacetylase activity, transcription repression activity, and/or the ability to deacetylate other substrates, for example, transcription factors, including p53, CoRest, E2F, GATA-1, TFIIe, and TFIIF that normally have a nuclear or cytoplasmic location in a cell. A histone deacetylase polypeptide is also a polypeptide whose activity can be inhibited by molecules having HDAC inhibitory activity. These molecules fall into four general classes: 1) short-chain fatty acids (e.g., 4-phenylbutyrate and valproic acid); 2) hydroxamic acids (e.g. SAHA, Pyroxamide, trichostatin A (TSA), oxamflatin and CHAPs, such as, CHAP1 and CHAP 31); 3) cyclic tetrapeptides (Trapoxin A, Apicidin and Depsipeptide (FK-228, also known as FR9011228); 4) benzamides (e.g., MS-275); and other compounds such as Scriptaid. Examples of such compounds can be found in U.S. Pat. No. 5,369,108, issued on Nov. 29, 1994, U.S. Pat. No. 5,700, 811, issued on Dec. 23, 1997, and U.S. Pat. No. 5,773,474, issued on Jun. 30, 1998 to Breslow et al., U.S. Pat. No. 5,055,608, issued on Oct. 8, 1991, and U.S. Pat. No. 5,175, 191, issued on Dec. 29, 1992 to Marks et al., as well as, Yoshida et al., Bioessays 17, 423-430 (1995), Saito et al., PNAS USA 96, 4592-4597, (1999), Furamai et al., PNAS USA 98 (1), 87-92 (2001), Komatsu et al., Cancer Res. 61(11), 4459-4466 (2001), Su et al., Cancer Res. 60, 3137-3142 (2000), Lee et al., Cancer Res. 61(3), 931-934 and Suzuki et al. J. Med. Chem. 42(15), 3001-3003 (1999) the entire content of all of which are hereby incorporated by reference. Examples of such histone deacetylase polypeptides include HDAC9, HDAC9a, HDAC9(ΔNLS), HDAC9a (ΔNLS), HDRP(ΔNLS); a substantially pure polypeptide comprising SEQ ID NO: 2, SEQ ID NO: 4, SEQ ID NO: 6, SEQ ID NO: 8, or SEQ ID NO: 10; and a polypeptide having preferably at least 60%, more preferably, 70%, 75%, 80%, 85%, or 90%, and most preferably, 95% sequence identity to any one of SEQ ID NO: 2, SEQ ID NO: 4, SEQ ID NO: 6, SEQ ID NO: 8, or SEQ ID NO: 10, as determined using the BLAST program and parameters described herein.

In one embodiment, the histone deacetylase polypeptide has histone deacetylase activity, transcription repression activity, the ability to deacetylate substrates, or is inhibited by trichostatin A or a hybrid polar compound such as SAHA. In another embodiment, the HDAC9(ΔNLS) polypeptide has any two of the above biological activities. In still another embodiment, the HDAC9(ΔNLS) polypeptide has any three of the above biological activities. In yet another embodiment, the HDAC9(ΔNLS) polypeptide has all of the above biological activities.

An HDAC9 polypeptide is a histone deacetylase polypeptide as described above. An HDAC9 polypeptide preferably has at least 60%, more preferably, 70%, 75%, 80%, 85%, or 90%, and most preferably, 95% sequence identity to SEQ ID NO: 2, as determined using the BLAST program and parameters described herein. An HDAC9 polypeptide is also a polypeptide that comprises the amino acids encoded by exons 23, 24, 25 and/or 26, and that does not comprise the amino acids encoded by exon 13 of the HDAC9 nucleic acid sequence, as shown in FIGS. 1A-1C, FIG. 4, and FIGS. 5A-5D. Preferably, an HDAC9 polypeptide comprises the sequence of SEQ ID NO: 2. More preferably, an HDAC9 polypeptide consists of the sequence of SEQ ID NO: 2. An HDAC polypeptide is also a polypeptide comprising the amino acid sequence of the polypeptide encoded by the nucleic acid sequence of SEQ ID NO: 1.

An HDAC9a polypeptide is a histone deacetylase polypeptide as described above. An HDAC9a polypeptide preferably has at least 60%, more preferably, 70%, 75%, 80%, 85%, or 90%, and most preferably, 95% sequence identity to SEQ ID NO: 4, as determined using the BLAST program and parameters described herein. An HDAC9a polypeptide is also a polypeptide that comprises the amino acids encoded by exon 22, and that does not comprise the amino acids encoded by exons 13, 23, 24, 25, or 26 of the HDAC9 nucleic acid sequence, as shown in FIGS. 1D-1G, FIG. 4, and FIGS.

5A-5D. Preferably, an HDAC9a polypeptide comprises the sequence of SEQ ID NO: 4. More preferably, an HDAC9a polypeptide consists of the sequence of SEQ ID NO: 4. An HDAC9a polypeptide is also a polypeptide comprising the amino acid sequence of the polypeptide encoded by the nucleic acid sequence of SEQ ID NO: 3.

An HDAC9(ΔNLS) is a histone deacetylase polypeptide as described above. An HDAC9(ΔNLS) polypeptide does not comprise a nuclear localization signal (NLS). An HDAC9 (ΔNLS) polypeptide preferably has at least 60%, more preferably, 70%, 75%, 80%, 85%, or 90%, and most preferably, 95% sequence identity to SEQ ID NO: 6, as determined using the BLAST program and parameters described herein. An HDAC9(ΔNLS) polypeptide is also a polypeptide that comprises the amino acids encoded by exons 23, 24, 25, and/or 26, and that does not comprise the amino acids encoded by exons 7 or 13 of the HDAC9 nucleic acid sequence, as shown in FIGS. 1J-1L, and FIGS. 5A-5D. Preferably, an HDAC9 (ΔNLS) polypeptide comprises the sequence of SEQ ID NO: 6. More preferably, an HDAC9(ΔNLS) polypeptide consists of the sequence of SEQ ID NO: 6. An HDAC9(ΔNLS) polypeptide is also a polypeptide comprising the amino acid sequence of the polypeptide encoded by the nucleic acid sequence of SEQ ID NO: 5.

An HDAC9a(ΔNLS) polypeptide is a histone deacetylase polypeptide as described above. An HDAC9a(ΔNLS) does not comprise a nuclear localization signal (NLS). An HDAC9a(ΔNLS) polypeptide preferably has at least 60%, more preferably, 70%, 75%, 80%, 85%, or 90%, and most preferably, 95% sequence identity to SEQ ID NO: 8; as determined using the BLAST program and parameters described herein. An HDAC9a(ΔNLS) polypeptide is also a polypeptide that comprises the amino acids encoded by exon 22, and that does not comprise the amino acids encoded by exons 7, 13, 23, 24, 25, or 26 of the HDAC9 nucleic acid sequence, as shown in FIGS. 1M-1O, and FIGS. 5A-5D. Preferably, an HDAC9a(ΔNLS) polypeptide comprises the sequence of SEQ ID NO: 8. More preferably, an HDAC9a(ΔNLS) polypeptide consists of the sequence of SEQ ID NO: 8. An HDAC9a(ΔNLS) polypeptide is also a polypeptide comprising the amino acid sequence of the polypeptide encoded by the nucleic acid sequence of SEQ ID NO: 7.

An HDRP(ΔNLS) polypeptide is a histone deacetylase polypeptide as described above. An HDRP(ΔNLS) does not comprise a nuclear localization signal (NLS). An HDRP (ΔNLS) polypeptide preferably has at least 60%, more preferably, 70%, 75%, 80%, 85%, or 90%, and most preferably, 95% sequence identity to SEQ ID NO: 10, as determined using the BLAST program and parameters described herein. An HDRP(ΔNLS) polypeptide is also a polypeptide that does not comprise the amino acids encoded by exons 7 or 13-26 of the HDAC9 nucleic acid sequence, as shown in FIGS. 1H-1I and FIGS. 5A-5D. Preferably, an HDRP(ΔNLS) polypeptide comprises the sequence of SEQ ID NO: 10. More preferably, an HDRP(ΔNLS) polypeptide consists of the sequence of SEQ ID NO: 10. An HDRP(ΔNLS) polypeptide is also a polypeptide comprising the amino acid sequence of the polypeptide encoded by the nucleic acid sequence of SEQ ID NO: 9.

The polypeptides of the invention can be purified to homogeneity. It is understood, however, that preparations in which the polypeptide is not purified to homogeneity are useful. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins.

When a polypeptide is recombinantly produced, it can also be substantially free of culture medium, i.e., culture medium represents less than about 20%, less than about 10%, or less than about 5% of the volume of the polypeptide preparation. The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, a polypeptide of the invention comprises an amino acid sequence encoded by a nucleic acid molecule comprising a nucleotide sequence selected from the group consisting of SEQ ID NO: 1, SEQ ID NO: 3, SEQ ID NO: 5, SEQ ID NO: 7, SEQ ID NO: 9, and complements and portions thereof, (e.g., a complement of any one of SEQ ID NO: 1, SEQ ID NO: 3, SEQ ID NO: 5, SEQ ID NO: 7, SEQ ID NO: 9 or a portion of any one of SEQ ID NO: 1 or SEQ ID NO: 3, SEQ ID NO: 5, SEQ ID NO: 7, or SEQ ID NO: 9).

The polypeptides of the invention also encompass fragments and sequence variants. Variants include a substantially homologous polypeptide encoded by the same genetic locus in an organism, i.e., an allelic variant, as well as other variants. Variants also encompass polypeptides derived from other genetic loci in an organism, but having substantial homology to a polypeptide encoded by a nucleic acid molecule comprising a nucleotide sequence selected from the group consisting of SEQ ID NO: 1, SEQ ID NO: 3, SEQ ID NO: 5, SEQ ID NO: 7, SEQ ID NO: 9, and complements and portions thereof, or having substantial homology to a polypeptide encoded by a nucleic acid molecule comprising a nucleotide sequence selected from the group consisting of nucleotide sequences encoding any one of SEQ ID NO: 2, SEQ ID NO: 4, SEQ ID NO: 6, SEQ ID NO: 8, or SEQ ID NO: 10. Variants also include polypeptides substantially homologous or identical to these polypeptides but derived from another organism, i.e., an ortholog. Variants also include polypeptides that are substantially homologous or identical to these polypeptides that are produced by chemical synthesis. Variants also include polypeptides that are substantially homologous or identical to these polypeptides that are produced by recombinant methods.

As used herein, two polypeptides (or a region of the polypeptides) are substantially homologous or identical when the amino acid sequences are at least about 60-65%, typically at least about 70-75%, more typically at least about 80-85%, and most typically greater than about 90-95% or more homologous or identical. A substantially identical or homologous amino acid sequence, according to the present invention, will be encoded by a nucleic acid molecule hybridizing to SEQ ID NO: 1, SEQ ID NO: 3, SEQ ID NO: 5, SEQ ID NO: 7, SEQ ID NO: 9, or a portion thereof, under stringent conditions as more particularly described herein, or will be encoded by a nucleic acid molecule hybridizing to a nucleic acid sequence encoding SEQ ID NO: 2, SEQ ID NO: 4, SEQ ID NO: 6, SEQ ID NO: 8, SEQ ID NO: 10, or portion thereof, under stringent conditions as more particularly described herein.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions×100). In certain embodiments, the length of the HDAC9, HDAC9a, HDAC9(ΔNLS), HDAC9a(ΔNLS), and HDRP (ΔNLS) amino acid or nucleotide sequence aligned for comparison purposes is at least 30%, preferably, at least 40%, more preferably, at least 60%, and even more preferably, at least 70%, 80%, 90%, or 100% of the length of the reference sequence, for example, those sequences provided in FIGS. 1A-1O and 2A-2E. The actual comparison of the two sequences can be accomplished by well-known methods, for example, using a mathematical algorithm. A preferred, non-limiting example of such a mathematical algorithm is described in Karlin et al., Proc. Natl. Acad. Sci. USA, 90:5873-5877 (1993). Such an algorithm is incorporated into the BLASTN and BLASTX programs (version 2.2) as described in Schaffer et al., Nucleic Acids Res., 29:2994-3005 (2001). When utilizing BLAST and Gapped BLAST programs, the default parameters of the respective programs (e.g., BLASTN) can be used. See http://www.ncbi.nlm.nih-.gov, as available on Aug. 10, 2001. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Another preferred, non-limiting example of a mathematical algorithm utilized for the comparison of sequences is the algorithm of Myers and Miller, CABIOS (1989). Such an algorithm is incorporated into the ALIGN program (version 2.0), which is part of the GCG (Accelrys) sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, Comput. Appl. Biosci., 10: 3-5 (1994); and FASTA described in Pearson and Lipman, Proc. Natl. Acad. Sci USA, 85: 2444-8 (1988).

In another embodiment, the percent identity between two amino acid sequences can be accomplished using the GAP program in the GCG software package using either a Blossom 63 matrix or a PAM250 matrix, and a gap weight of 12, 10, 8, 6, or 4 and a length weight of 2, 3 or 4. In yet another embodiment, the percent identity between two nucleic acid sequences can be accomplished using the GAP program in the GCG software package, using a gap weight of 50 and a length weight of 3.

The invention also encompasses HDAC9, HDAC9a, HDAC9(ΔNLS), HDAC9aΔNLS, and HDRP(ΔNLS) polypeptides having a lower degree of identity but having sufficient similarity so as to perform one or more of the same functions performed by an HDAC9, HDAC9a, HDAC9 (ΔNLS), HDAC9aΔNLS, or HDRP(ΔNLS) polypeptide encoded by a nucleic acid molecule of the invention. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247: 1306-1310 (1990).

A variant polypeptide can differ in amino acid sequence by one or more substitutions, deletions, insertions, inversions, fusions, and truncations or a combination of any of these. Further, variant polypeptides can be fully functional or can lack function in one or more activities, for example, in histone deacetylase activity or transcription repression activity. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncations or a substitution, insertion, inversion, or deletion in a critical residue or critical region, such critical regions include the HDAC domains, which provide the polypeptide with deacetylase activity, as shown in the nucleic acid sequences of FIGS. 1A-1G, as well as in the schematic of FIG. 4.

Amino acids that are essential for function can be identified by methods known in the art, such as site-directed mutagenesis or alanine-scanning mutagenesis (Cunningham et al., Science, 244: 1081-1085 (1989)). The latter procedure introduces a single alanine mutation at each of the residues in the molecule (one mutation per molecule). The resulting mutant molecules are then tested for biological activity in vitro. Sites that are critical for polypeptide activity can also be determined by structural analysis, such as crystallization, nuclear magnetic resonance, or photoaffinity labeling (See Smith et al., J. Mol. Biol., 224: 899-904 (1992); and de Vos et al. Science, 255: 306-312 (1992)).

The invention also includes HDAC9, HDAC9a, HDAC9 (ΔNLS), HDAC9a(ΔNLS), and HDRP(ΔNLS) polypeptide fragments of the polypeptides of the invention. Fragments can be derived from a polypeptide comprising SEQ ID NO: 2, SEQ ID NO: 4, SEQ ID NO: 6, SEQ ID NO: 8, or SEQ ID NO: 10, or from a polypeptide encoded by a nucleic acid molecule comprising SEQ ID NO: 1, SEQ ID NO: 3, SEQ ID NO: 5, SEQ ID NO: 7, or SEQ ID NO: 9 or a portion thereof and the complements thereof or other variants. The present invention also encompasses fragments of the variants of the polypeptides described herein. Useful fragments include those that retain one or more of the biological activities of the polypeptide as well as fragments that can be used as an immunogen to generate polypeptide-specific antibodies.

Biologically active fragments (peptides that are, for example, 6, 9, 12, 15, 16, 20, 30, 35, 36, 37, 38, 39, 40, 50, 100, or more amino acids in length) can comprise a domain, segment, or motif, for example, an HDAC domain, that has been identified by analysis of the polypeptide sequence using well-known methods, e.g., signal peptides, extracellular domains, one or more transmembrane segments or loops, ligand binding regions, zinc finger domains, DNA binding domains, acylation sites, glycosylation sites, or phosphorylation sites.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The invention thus provides chimeric or fusion polypeptides. These comprise an HDAC9, HDAC9a, HDAC9 (ΔNLS), HDAC9aΔNLS, or HDRP(ΔNLS) polypeptide of the invention operatively linked to a heterologous protein or polypeptide having an amino acid sequence not substantially homologous to the polypeptide. "Operatively linked" indicates that the polypeptide and the heterologous protein are fused in-frame. The heterologous protein can be fused to the N-terminus or C-terminus of the polypeptide. In one embodiment, the fusion polypeptide does not affect the function of the polypeptide per se. For example, the fusion polypeptide can be a GST-fusion polypeptide in which the polypeptide sequences are fused to the C-terminus of the GST sequences. Other types of fusion polypeptides include, but are not limited to, enzymatic fusion polypeptides, for example, β-galactosidase fusions, yeast two-hybrid GAL fusions, poly-His fusions, and Ig fusions. Such fusion polypeptides, particularly poly-His fusions, can facilitate the purification of recombinant polypeptide. In certain host cells (e.g., mammalian host cells), expression and/or secretion of a polypeptide can be increased by using a heterologous signal sequence. Therefore, in another embodiment, the fusion polypeptide contains a heterologous signal sequence at its N-terminus.

EP-A 0464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. (See Bennett et al., Journal of Molecular Recognition, 8: 52-58 (1995) and Johanson et al., The Journal of Biological Chemistry, 270,16: 9459-9471 (1995)). Thus, this invention also encompasses soluble fusion polypeptides containing a polypeptide of the invention and various portions of the constant regions of heavy or light chains of immunoglobulins of various subclass (IgG, IgM, IgA, IgE).

A chimeric or fusion polypeptide can be produced by standard recombinant DNA techniques. For example, DNA fragments coding for the different polypeptide sequences are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., "Current Protocols in Molecular Biology," John Wiley & Sons, (1998), the entire teachings of which are incorporated by reference herein). Moreover, many expression vectors are commercially available that already encode a fusion moiety (e.g., a GST protein). A nucleic acid molecule encoding a polypeptide of the invention can be cloned into such an expression vector such that the fusion moiety is linked in-frame to the polypeptide.

The substantially pure, isolated, or substantially pure and isolated HDAC9, HDAC9a, HDAC9(ΔNLS), HDAC9aΔNLS, or HDRP(ΔNLS) polypeptide can be purified from cells that naturally express it, purified from cells that have been altered to express it (recombinant), or synthesized using known protein synthesis methods. In one embodiment, the polypeptide is produced by recombinant DNA techniques. For example, a nucleic acid molecule encoding the polypeptide is cloned into an expression vector, the expression vector introduced into a host cell, and the polypeptide expressed in the host cell. The polypeptide can then be isolated from the cells by an appropriate purification scheme using standard protein purification techniques.

In general, HDAC9, HDAC9a, HDAC9(ΔNLS), HDAC9aΔNLS, and HDRP(ΔNLS) polypeptides of the present invention can be used as a molecular weight marker on SDS-PAGE gels or on molecular sieve gel filtration columns using art-recognized methods. The polypeptides of the present invention can be used to raise antibodies or to elicit an immune response. The polypeptides can also be used as a reagent, e.g., a labeled reagent, in assays to quantitatively determine levels of the polypeptide or a molecule to which it binds (e.g., a receptor or a ligand) in biological fluids. The polypeptides can also be used as markers for cells or tissues in which the corresponding polypeptide is preferentially expressed, either constitutively, during tissue differentiation, or in a diseased state. The polypeptides can be used to isolate a corresponding binding agent, and to screen for peptide or small molecule antagonists or agonists of the binding interaction. The polypeptides of the present invention can also be used as therapeutic agents.

Nucleic Acid Molecules of the Invention

The present invention also features isolated HDAC9, HDAC9a, HDAC9(ΔNLS), HDAC9a(ΔNLS), and HDRP (ΔNLS) nucleic acid molecules.

By a "histone deacetylase nucleic acid molecule" is meant a nucleic acid molecule that encodes a histone deacetylase polypeptide. Such histone nucleic acids include, for example, the HDAC9, HDAC9a, HDAC9(ΔNLS), HDAC9a(ΔNLS), or HDRP(ΔNLS) nucleic acid molecule described in detail herein; an isolated nucleic acid comprising SEQ ID NO: 1, SEQ ID NO: 3, SEQ ID NO: 5, SEQ ID NO: 7, or SEQ ID NO: 9; a complement of an isolated nucleic acid comprising SEQ ID NO: 1, SEQ ID NO: 3, SEQ ID NO: 5, SEQ ID NO: 7, or SEQ ID NO: 9; an isolated nucleic acid encoding a histone deacetylase polypeptide of SEQ ID NO: 2, SEQ ID NO: 4, SEQ ID NO: 6, SEQ ID NO: 8, or SEQ ID NO: 10; a complement of an isolated nucleic acid encoding a histone deacetylase polypeptide of SEQ ID NO: 2, SEQ ID NO: 4, SEQ ID NO: 6, SEQ ID NO: 8, or SEQ ID NO: 10; a nucleic acid that is hybridizeable under high stringency conditions to a nucleic acid molecule that encodes any of SEQ ID NO: 2, SEQ ID NO: 4, SEQ ID NO: 6, or SEQ ID NO: 8, or a complement thereof; a nucleic acid molecule that is hybridizeable under high stringency conditions to a nucleic acid comprising SEQ ID NO: 1, SEQ ID NO: 3, SEQ ID NO: 5, or SEQ ID NO: 7; and an isolated nucleic acid molecule that has at least 55%, more preferably, 60%, 65%, 70%, 75%, 80%, 85%, or 90%, and most preferably, 95% or 99% sequence identity with any one of SEQ ID NO: 1, SEQ ID NO: 3, SEQ ID NO: 5, SEQ ID NO: 7, SEQ ID NO: 9, or a complement thereof.

An HDAC9 nucleic acid molecule is a nucleic acid molecule that encodes an HDAC9 polypeptide. In one embodiment, the HDAC9 nucleic acid molecule is selected from: a nucleic acid molecule that comprises the nucleic acid sequence of SEQ ID NO: 1; a complement of an isolated nucleic acid comprising SEQ ID NO: 1; an isolated nucleic acid encoding a histone deacetylase polypeptide of SEQ ID NO: 2; a complement of an isolated nucleic acid encoding a histone deacetylase polypeptide of SEQ ID NO: 2; a nucleic acid that is hybridizeable under high stringency conditions to a nucleic acid molecule that encodes SEQ ID NO: 2; a nucleic acid molecule that is hybridizeable under high stringency conditions to a nucleic acid comprising SEQ ID NO: 1; and an isolated nucleic acid molecule that has preferably, at least 55%, more preferably, 60%, 65%, 70%, 75%, 80%, 85%, or 90%, and most preferably, 95% or 99% sequence identity with SEQ ID NO: 1, as determined using the BLAST program and parameters described herein. In another embodiment, the HDAC9 nucleic acid molecule consists of the nucleic acid sequence of SEQ ID NO: 1.

An HDAC9a nucleic acid molecule is a nucleic acid molecule that encodes an HDAC9a polypeptide. An HDAC9a nucleic acid molecule preferably has at least 55%, sequence identity to SEQ ID NO: 3, In one embodiment, the HDAC9a nucleic acid molecule is selected from: a nucleic acid molecule that comprises the nucleic acid sequence of SEQ ID NO: 3; a complement of an isolated nucleic acid comprising SEQ ID NO: 3; an isolated nucleic acid encoding a histone deacetylase polypeptide of SEQ ID NO: 4; a complement of an isolated nucleic acid encoding a histone deacetylase polypeptide of SEQ ID NO: 4; a nucleic acid that is hybridizeable under high stringency conditions to a nucleic acid molecule that encodes SEQ ID NO: 4; a nucleic acid molecule that is hybridizeable under high stringency conditions to a nucleic acid comprising SEQ ID NO: 3; and an isolated nucleic acid molecule that has preferably, at least 55%, more preferably, 60%, 65%, 70%, 75%, 80%, 85%, or 90%, and most preferably, 95% or 99% sequence identity with SEQ ID NO: 3 or a complement thereof, as determined using the BLAST program and parameters described herein. In another embodiment, the HDAC9a nucleic acid molecule consists of the nucleic acid sequence of SEQ ID NO: 3.

An HDAC9(ΔNLS) nucleic acid molecule is a nucleic acid molecule that encodes an HDAC9(ΔNLS) polypeptide. In one embodiment, the HDAC9(ΔNLS) nucleic acid molecule is selected from: a nucleic acid molecule that comprises the nucleic acid sequence of SEQ ID NO: 5; a complement of an isolated nucleic acid comprising SEQ ID NO: 5; an isolated nucleic acid encoding a histone deacetylase polypeptide of SEQ ID NO: 6; a complement of an isolated nucleic acid encoding a histone deacetylase polypeptide of SEQ ID NO: 6; a nucleic acid that is hybridizeable under high stringency conditions to a nucleic acid molecule that encodes SEQ ID NO: 6; a nucleic acid molecule that is hybridizeable under high stringency conditions to a nucleic acid comprising SEQ ID NO: 5; and an isolated nucleic acid molecule that has preferably, at least 55%, more preferably, 60%, 65%, 70%, 75%, 80%, 85%, or 90%, and most preferably, 95% or 99% sequence identity with SEQ ID NO: 5 or a complement thereof, as determined using the BLAST program and parameters described herein. In another embodiment, the HDAC9 (ΔNLS) nucleic acid molecule consists of the nucleic acid sequence of SEQ ID NO: 5.

An HDAC9a(ΔNLS) nucleic acid molecule is a nucleic acid molecule that encodes an HDAC9a(ΔNLS) polypeptide. In one embodiment, the HDAC9a(ΔNLS) nucleic acid molecule is selected from: a nucleic acid molecule that comprises the nucleic acid sequence of SEQ ID NO: 7; a complement of an isolated nucleic acid comprising SEQ ID NO: 7; an isolated nucleic acid encoding a histone deacetylase polypeptide of SEQ ID NO: 8; a complement of an isolated nucleic acid encoding a histone deacetylase polypeptide of SEQ ID NO: 8; a nucleic acid that is hybridizeable under high stringency conditions to a nucleic acid molecule that encodes SEQ ID NO: 8; a nucleic acid molecule that is hybridizeable under high stringency conditions to a nucleic acid comprising SEQ ID NO: 7; and an isolated nucleic acid molecule that has preferably, at least 55%, more preferably, 60%, 65%, 70%, 75%, 80%, 85%, or 90%, and most preferably, 95% or 99% sequence identity with SEQ ID NO: 7 or a complement thereof, as determined using the BLAST program and parameters described herein. In another embodiment, the HDAC9a (ΔNLS) nucleic acid molecule consists of the nucleic acid sequence of SEQ ID NO: 7.

An "HDRP(ΔNLS) nucleic acid molecule" is a nucleic acid molecule that encodes an HDRP(ΔNLS) polypeptide. In one embodiment, the HDRP(ΔNLS) nucleic acid molecule is selected from: a nucleic acid molecule that comprises the nucleic acid sequence of SEQ ID NO: 9; a complement of an isolated nucleic acid comprising SEQ ID NO: 9; an isolated nucleic acid encoding a histone deacetylase polypeptide of SEQ ID NO: 10; a complement of an isolated nucleic acid encoding a histone deacetylase polypeptide of SEQ ID NO: 10; and an isolated nucleic acid molecule that has preferably, at least 55%, more preferably, 60%, 65%, 70%, 75%, 80%, 85%, or 90%, and most preferably, 95% or 99% sequence identity with SEQ ID NO: 9 or a complement thereof, as determined using the BLAST program and parameters described herein. In another embodiment, the HDRP(ΔNLS) nucleic acid molecule consists of the nucleic acid sequence of SEQ ID NO: 9.

The isolated nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. The nucleic acid molecule can include all or a portion of the coding sequence of the gene and can further comprise additional non-coding sequences such as introns and non-coding 3' and 5' sequences (including regulatory sequences, for example). Additionally, the nucleic acid molecule can be fused to a marker sequence, for example, a sequence that encodes a polypeptide to assist in isolation or purification of the polypeptide. Such sequences include, but are not limited to, those that encode a glutathione-S-transferase (GST) fusion protein and those that encode a hemagglutinin A (HA) polypeptide marker from influenza.

An "isolated," "substantially pure," or "substantially pure and isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA or cDNA library). For example, an isolated nucleic acid of the invention may be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system, or reagent mix. In other circumstances, the material may be purified to essential homogeneity, for example, as determined by agarose gel electrophoresis or column chromatography such as HPLC. Preferably, an isolated nucleic acid molecule comprises at least about 50, 80, or 90% (on a molar basis) of all macromolecular species present.

With regard to genomic DNA, the term "isolated" also can refer to nucleic acid molecules that are separated from the chromosome with which the genomic DNA is naturally associated. For example, the isolated nucleic acid molecule can contain less than about 5 kb, 4 kb, 3 kb, 2 kb, 1 kb, 0.5 kb, or 0.1 kb of nucleotides that flank the nucleic acid molecule in the genomic DNA of the cell from which the nucleic acid molecule is derived.

The HDAC9, HDAC9a, HDAC9(ΔNLS), HDAC9a (ΔNLS), or HDRP(ΔNLS) nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Therefore, recombinant DNA contained in a vector are included in the definition of "isolated" as used herein.

Isolated nucleotide molecules also include recombinant DNA molecules in heterologous organisms, as well as partially or substantially purified DNA molecules in solution. In vivo and in vitro RNA transcripts of the DNA molecules of the present invention are also encompassed by "isolated" nucleotide sequences. Such isolated nucleotide sequences are useful in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis.

The present invention also pertains to variant HDAC9, HDAC9a, HDAC9(ΔNLS), HDAC9a(ΔNLS), and HDRP (ΔNLS) nucleic acid molecules that are not necessarily found in nature but that encode an HDAC9, HDAC9a, HDAC9 (ΔNLS), HDAC9a(ΔNLS), or HDRP(ΔNLS) polypeptide. Thus, for example, DNA molecules that comprise a sequence that is different from the naturally-occurring HDAC9, HDAC9a, HDAC9(ΔNLS), HDAC9a(ΔNLS), or HDRP (ΔNLS) nucleotide sequence but which, due to the degeneracy of the genetic code, encode an HDAC9, HDAC9a, HDAC9(ΔNLS), HDAC9a(ΔNLS), or HDRP(ΔNLS) polypeptide of the present invention are also the subject of this invention.

The invention also encompasses HDAC9, HDAC9a, HDAC9(ΔNLS), HDAC9a(ΔNLS), and HDRP(ΔNLS) nucleotide sequences encoding portions (fragments), or encoding variant polypeptides such as analogues or derivatives of an HDAC9, HDAC9a, HDAC9(ΔNLS), HDAC9a (ΔNLS), or HDRP(ΔNLS) polypeptide. Such variants can be naturally-occurring, such as in the case of allelic variation or single nucleotide polymorphisms, or non-naturally-occurring, such as those induced by various mutagens and mutagenic processes. Intended variations include, but are not limited to, addition, deletion, and substitution of one or more nucleotides that can result in conservative or non-conservative amino acid changes, including additions and deletions. Preferably, the HDAC9, HDAC9a, HDAC9(ΔNLS), HDAC9a(ΔNLS), or HDRP(ΔNLS) nucleotide (and/or resultant amino acid) changes are silent or conserved; that is, they do not alter the characteristics or activity of the HDAC9, HDAC9a, HDAC9(ΔNLS), HDAC9a(ΔNLS), or HDRP (ΔNLS) polypeptide. In one preferred embodiment, the nucleotide sequences are fragments that comprise one or more polymorphic microsatellite markers.

Other alterations of the HDAC9, HDAC9a, HDAC9 (ΔNLS), HDAC9a(ΔNLS), or HDRP(ΔNLS) nucleic acid molecules of the invention can include, for example, labeling, methylation, internucleotide modifications such as uncharged linkages (e.g., methyl phosphonates, phosphotriesters, phosphoamidates, and carbamates), charged linkages (e.g., phosphorothioates or phosphorodithioates), pendent moieties (e.g., polypeptides), intercalators (e.g., acridine or psoralen), chelators, alkylators, and modified linkages (e.g., alpha anomeric nucleic acids). Also included are synthetic molecules that mimic nucleic acid molecules in the ability to bind to a designated sequences via hydrogen bonding and other chemical interactions. Such molecules include, for example, those in which peptide linkages substitute for phosphate linkages in the backbone of the molecule.

The invention also pertains to HDAC9, HDAC9a, HDAC9 (ΔNLS), HDAC9a(ΔNLS), and HDRP(ΔNLS) nucleic acid molecules that hybridize under high stringency hybridization conditions, such as for selective hybridization, to a nucleotide sequence described herein (e.g., nucleic acid molecules that specifically hybridize to a nucleotide sequence encoding polypeptides described herein, and, optionally, have an activity of the polypeptide). In one embodiment, the invention includes variants described herein that hybridize under high stringency hybridization conditions (e.g., for selective hybridization) to a nucleotide sequence comprising a nucleotide sequence selected from SEQ ID NO: 1, SEQ ID NO: 3, SEQ ID NO: 5, SEQ ID NO: 7, SEQ ID NO: 9 and the complement of SEQ ID NO: 1, SEQ ID NO: 3, SEQ ID NO: 5, SEQ ID NO: 7, or SEQ ID NO: 9. In another embodiment, the invention includes variants described herein that hybridize under high stringency hybridization conditions (e.g., for selective hybridization) to a nucleotide sequence encoding an amino acid sequence of SEQ ID NO: 2 (HDAC9), SEQ ID NO: 4 (HDAC9a), SEQ ID NO: 6 (HDAC9(ΔNLS)), SEQ ID NO: 8 (HDAC9a(ΔNLS)), or SEQ ID NO: 10 (HDRP (ΔNLS)). In a preferred embodiment, the variant that hybridizes under high stringency hybridizations encodes a polypeptide that has a biological activity of an HDAC9, HDAC9a, HDAC9(ΔNLS), HDAC9a(ΔNLS), or HDRP(ΔNLS) polypeptide (e.g., histone deacetylase activity or transcription repression activity).

Such nucleic acid molecules can be detected and/or isolated by specific hybridization (e.g., under high stringency conditions). "Specific hybridization," as used herein, refers to the ability of a first nucleic acid to hybridize to a second nucleic acid in a manner such that the first nucleic acid does not hybridize to any nucleic acid other than to the second nucleic acid (e.g., when the first nucleic acid has a higher similarity to the second nucleic acid than to any other nucleic acid in a sample wherein the hybridization is to be performed). "Stringency conditions" for hybridization is a term of art that refers to the incubation and wash conditions, e.g., conditions of temperature and buffer concentration, that permit hybridization of a particular nucleic acid to a second nucleic acid; the first nucleic acid may be perfectly (i.e., 100%) complementary to the second, or the first and second may share some degree of complementarity that is less than perfect (e.g., 70%, 75%, 85%, 95%). For example, certain high stringency conditions can be used that distinguish perfectly complementary nucleic acids from those of less complementarity. "High stringency conditions," "moderate stringency conditions," and "low stringency conditions" for nucleic acid hybridizations are explained on pages 2.10.1-2.10.16 and pages 6.3.1-6.3.6 in Current Protocols in Molecular Biology (See Ausubel et al., supra, the entire teachings of which are incorporated by reference herein). The exact conditions that determine the stringency of hybridization depend not only on ionic strength (e.g., 0.2×SSC or 0.1×SSC), temperature (e.g., room temperature, 42° C. or 68° C.), and the concentration of destabilizing agents such as formamide or denaturing agents such as SDS, but also on factors such as the length of the nucleic acid sequence, base composition, percent mismatch between hybridizing sequences, and the frequency of occurrence of subsets of that sequence within other non-identical sequences. Thus, equivalent conditions can be determined by varying one or more of these parameters while maintaining a similar degree of identity or similarity between the two nucleic acid molecules. Typically, conditions are used such that sequences at least about 60%, at least about 70%, at least about 80%, at least about 90% or at least about 95% or more identical to each other remain hybridized to one another. By varying hybridization conditions from a level of stringency at which no hybridization occurs to a level at which hybridization is first observed, conditions that will allow a given sequence to hybridize (e.g., selectively) with the most similar sequences in the sample can be determined.

Exemplary conditions are described in Krause and Aaronson, Methods in Enzymology, 200:546-556 (1991). Also, in, Ausubel, et al., supra, which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in Tm of 17° C. Using these guidelines, the washing temperature can be determined empirically for high, moderate, or low stringency, depending on the level of mismatch sought.

For example, a low stringency wash can comprise washing in a solution containing 0.2×SSC/0.1% SDS for 10 minutes at room temperature; a moderate stringency wash can comprise washing in a prewarmed solution (42° C.) solution containing 0.2×SSC/0.1% SDS for 15 minutes at 42° C.; and a high stringency wash can comprise washing in prewarmed (68° C.) solution containing 0.1×SSC/0.1% SDS for 15 minutes at 68° C. Furthermore, washes can be performed repeatedly or sequentially to obtain a desired result as known in the art. Equivalent conditions can be determined by varying one or more of the parameters given as an example, as known in the art, while maintaining a similar degree of identity or similarity between the target nucleic acid molecule and the primer or probe used.

To determine the percent homology or identity of two nucleic acid sequences, the sequences are aligned for optimal comparison purposes (e.g., gaps can be introduced in the sequence of one polypeptide or nucleic acid molecule for optimal alignment with the other polypeptide or nucleic acid molecule). The amino acid residues or nucleotides at corresponding amino acid positions or nucleotide positions are then compared, as described above.

The present invention also provides isolated HDAC9, HDAC9a, HDAC9(ΔNLS), HDAC9a(ΔNLS), and HDRP (ΔNLS) nucleic acid molecules that contain a fragment or portion that hybridizes under highly stringent conditions to a nucleotide sequence comprising a nucleotide sequence selected from SEQ ID NO: 1, SEQ ID NO: 3, SEQ ID NO: 5, SEQ ID NO: 7, SEQ ID NO: 9, and the complement of any of SEQ ID NO: 1, SEQ ID NO: 3, SEQ ID NO: 5, SEQ ID NO: 7, or SEQ ID NO: 9 and also provides isolated nucleic acid molecules that contain a fragment or portion that hybridizes under highly stringent conditions to a nucleotide sequence encoding an amino acid sequence selected from SEQ ID NO: 2, SEQ ID NO: 4, SEQ ID NO: 6, SEQ ID NO: 8, and SEQ ID NO: 10. The nucleic acid fragments of the invention are at least about 15, preferably, at least about 18, 20, 23, or 25 nucleotides, and can be 30, 40, 50, 100, 200 or more nucleotides in length. Longer fragments, for example, 30 or more nucleotides in length, that encode antigenic polypeptides described herein are particularly useful, such as for the generation of antibodies as described above.

In a related aspect, the HDAC9, HDAC9a, HDAC9 (ΔNLS), HDAC9a(ΔNLS), and HDRP(ΔNLS) nucleic acid fragments of the invention are used as probes or primers in assays such as those described herein. "Probes" or "primers" are oligonucleotides that hybridize in a base-specific manner to a complementary strand of nucleic acid molecules. Such probes and primers include polypeptide nucleic acids, as described in Nielsen et al., Science, 254, 1497-1500 (1991). As also used herein, the term "primer" in particular refers to a single-stranded oligonucleotide that acts as a point of initiation of template-directed DNA synthesis using well-known methods (e.g., PCR, LCR) including, but not limited to those described herein.

Typically, a probe or primer comprises a region of nucleotide sequence that hybridizes to at least about 15, typically about 20-25, and more typically about 40, 50 or 75, consecutive nucleotides of a nucleic acid molecule comprising a contiguous nucleotide sequence selected from: SEQ ID NO: 1, SEQ ID NO: 3, SEQ ID NO: 5, SEQ ID NO: 7, SEQ ID NO: 9, the complement of any of SEQ ID NO: 1, SEQ ID NO: 3, SEQ ID NO: 5, SEQ ID NO: 7, SEQ ID NO: 9, and a sequence encoding an amino acid sequence of SEQ ID NO: 2, SEQ ID NO: 4, SEQ ID NO: 6, SEQ ID NO: 8, or SEQ ID NO: 10.

In preferred embodiments, a probe or primer comprises 100 or fewer nucleotides, preferably, from 6 to 50 nucleotides, and more preferably, from 12 to 30 nucleotides. In other embodiments, the probe or primer is at least 70% identical to the contiguous nucleotide sequence or to the complement of the contiguous nucleotide sequence, preferably, at least 80% identical, more preferably, at least 90% identical, even more preferably, at least 95% identical, or even capable of selectively hybridizing to the contiguous nucleotide sequence or to the complement of the contiguous nucleotide sequence. Often, the probe or primer further comprises a label, e.g., radioisotope, fluorescent compound, enzyme, or enzyme co-factor.

The nucleic acid molecules of the invention such as those described above can be identified and isolated using standard molecular biology techniques and the sequence information provided in SEQ ID NO: 1, SEQ ID NO; 3, SEQ ID NO: 5, SEQ ID NO: 7, SEQ ID NO: 9, SEQ ID NO: 2, SEQ ID NO: 4, SEQ ID NO: 6, SEQ ID NO: 8, and/or SEQ ID NO: 10. For example, nucleic acid molecules can be amplified and isolated by the polymerase chain reaction using synthetic oligonucleotide primers designed based on one or more of the nucleic acid sequences provided above and/or the complement of those sequences. Or such nucleic acid molecules may be designed based on nucleotide sequences encoding one or more of the amino acid sequences provided in SEQ ID NO: 2, SEQ ID NO: 4, SEQ ID NO: 6, SEQ ID NO: 8, or SEQ ID NO: 10. See generally PCR Technology: Principles and Applications for DNA Amplification (ed. H. A. Erlich, Freeman Press, NY, N.Y., (1992); PCR Protocols: A Guide to Methods and Applications (Eds. Innis et al., Academic Press, San Diego, Calif., (1990); Mattila et al., Nucleic Acids Res., 19: 4967 (1991); Eckert et al., PCR Methods and Applications, 1: 17 (1991); PCR (eds. McPherson et al., IRL Press, Oxford)); and U.S. Pat. No. 4,683,202. The nucleic acid molecules can be amplified using cDNA, mRNA, or genomic DNA as a template, cloned into an appropriate vector and characterized by DNA sequence analysis.

Other suitable amplification methods include the ligase chain reaction (LCR) (See Wu and Wallace, Genomics, 4:560 (1989), Landegren et al., Science, 241:1077 (1988)), transcription amplification (Kwoh et al., Proc. Natl. Acad. Sci. USA, 86:1173 (1989)), and self-sustained sequence replication (See Guatelli et al., Proc. Nat. Acad. Sci. USA, 87:1874 (1990)) and nucleic acid based sequence amplification (NASBA). The latter two amplification methods involve isothermal reactions based on isothermal transcription, that produce both single stranded RNA (ssRNA) and double stranded DNA (dsDNA) as the amplification products in a ratio of about 30 or 100 to 1, respectively.

The amplified DNA can be radiolabeled and used as a probe for screening a cDNA library derived from human cells, mRNA in zap express, ZIPLOX, or other suitable vector. Corresponding clones can be isolated, DNA can be obtained following in vivo excision, and the cloned insert can be sequenced in either or both orientations by art-recognized methods to identify the correct reading frame encoding a polypeptide of the appropriate molecular weight. For example, the direct analysis of the nucleotide sequence of nucleic acid molecules of the present invention can be accomplished using well-known methods that are commercially available. See, for example, Sambrook et al., Molecular Cloning, A Laboratory Manual (2nd Ed., CSHP, New York (1989)); Zyskind et al., Recombinant DNA Laboratory Manual, (Acad. Press, (1988)). Using these or similar methods, the polypeptide and the DNA encoding the polypeptide can be isolated, sequenced, and further characterized.

Antisense nucleic acid molecules of the invention can be designed using the nucleotide sequences of SEQ ID NO: 1, SEQ ID NO: 3, SEQ ID NO: 5, SEQ ID NO: 7, SEQ ID NO: 9 and/or the complement of any of SEQ ID NO: 1, SEQ ID NO: 3, SEQ ID NO: 5, SEQ ID NO: 7, SEQ ID NO: 9 and/or a portion of those sequences, and/or the complement of those portion or sequences, and/or a sequence encoding the amino acid sequence of SEQ ID NO: 2, SEQ ID NO: 4, SEQ ID NO: 6, SEQ ID NO: 8, SEQ ID NO: 10, or encoding a portion of SEQ ID NO: 2, SEQ ID NO: 4, SEQ ID NO: 6, SEQ ID NO: 8, or SEQ ID NO: 10. Such antisense nucleic acid molecules can be constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid molecule can be produced biologically using an expression vector into which a nucleic acid molecule has been subcloned in an antisense orientation (i.e., RNA transcribed from the inserted nucleic acid molecule will be of an antisense orientation to a target nucleic acid of interest).

In general, the isolated HDAC9, HDAC9a, HDAC9 (ΔNLS), HDAC9a(ΔNLS), and HDRP(ΔNLS) nucleic acid sequences of the invention can be used as molecular weight markers on Southern blots, and as chromosome markers that are labeled to map related gene positions. The nucleic acid sequences can also be used to compare with endogenous DNA sequences in patients to identify genetic disorders (e.g., a predisposition for or susceptibility to a cell proliferation disease, an apoptotic disease, or a cell differentiation disease), and as probes, such as to hybridize and discover related DNA sequences or to subtract out known sequences from a sample. The nucleic acid molecules of the present invention can also be used as therapeutic agents.

By a "cell proliferation disease" is meant a disease that is caused by or results in undesirably high levels of cell division, undesirably low levels of apoptosis, or both. For example, cancers such as lymphoma, leukemia, melanoma, ovarian cancer, breast cancer, pancreatic cancer, prostate cancer, colon cancer, and lung cancer are all examples of cell proliferation diseases. Myeloproliferative disorders, including polycythemia vera, essential thrombocythemia, agnogenic myeloid metaplasia, and chronic myelogenous leukemia are also cell proliferation diseases.

By a "cell differentiation disease" is meant a disease that is caused by or results in undesirably low levels of cell differentiation, or by undesirably high levels of cell differentiation. For example, cancers such as lymphoma, leukemia, melanoma, ovarian cancer, breast cancer, pancreatic cancer, prostate cancer, colon cancer, and lung cancer are all examples of cell differentiation diseases. Myeloproliferative disorders, including polycythemia vera, essential thrombocythemia, agnogenic myeloid metaplasia, and chronic myelogenous leukemia are also cell differentiation diseases.

By an "apoptotic disease" is meant a condition in which the apoptotic response is abnormal. This may pertain to a cell or a population of cells that does not undergo cell death under appropriate conditions. For example, normally a cell will die upon exposure to apoptotic-triggering agents, such as chemotherapeutic agents, or ionizing radiation. When, however, a subject has an apoptotic disease, for example, cancer, the cell or a population of cells may not undergo cell death in response to contact with apoptotic-triggering agents. In addition, a subject may have an apoptotic disease when the occurrence of cell death is too low, for example, when the number of proliferating cells exceeds the number of cells undergoing cell death, as occurs in cancer when such cells do not properly differentiate.

An apoptotic disease may also be a condition characterized by the occurrence of undesirably high levels of apoptosis. For example, certain neurodegenerative diseases, including but not limited to Alzheimer's disease, Parkinson's disease, amyotrophic lateral sclerosis, multiple sclerosis, restenosis, stroke, and ischemic brain injury are apoptotic diseases in which neuronal cells undergo undesired cell death.

Other diseases for which the polypeptides and nucleic acid molecules of the present invention may be useful for diagnosing and/or treating include, but are not limited to Huntington's disease.

The HDAC9, HDAC9a, HDAC9(ΔNLS), HDAC9a (ΔNLS), and HDRP(ΔNLS) nucleic acid molecules of the present invention can further be used to derive primers for genetic fingerprinting, to raise anti-polypeptide antibodies using DNA immunization techniques, and as an antigen to raise anti-DNA antibodies or elicit immune responses. Portions or fragments of the nucleotide sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample.

In addition, the HDAC9, HDAC9a, HDAC9(ΔNLS), HDAC9a(ΔNLS), and HDRP(ΔNLS) nucleotide sequences of the invention can be used to identify and express recombinant polypeptides for analysis, characterization, or therapeutic use, or as markers for tissues in which the corresponding polypeptide is expressed, either constitutively, during tissue differentiation, or in diseased states. The nucleic acid sequences can additionally be used as reagents in the screening and/or diagnostic assays described herein, and can also be included as components of kits (e.g., reagent kits) for use in the screening and/or diagnostic assays described herein.

Standard techniques, such as the polymerase chain reaction (PCR) and DNA hybridization, may be used to clone HDAC9, HDAC9a, HDAC9(ΔNLS), HDAC9a(ΔNLS), or HDRP(ΔNLS) homologs in other species, for example, mammalian homologs. HDAC9, HDAC9a, HDAC9(ΔNLS), HDAC9a(ΔNLS), or HDRP(ΔNLS) homologs may be readily identified using low-stringency DNA hybridization or low-stringency PCR with human HDAC9, HDAC9a, HDAC9 (ΔNLS), HDAC9a(ΔNLS), or HDRP(ΔNLS) probes or primers. Degenerate primers encoding human HDAC9, HDAC9a, HDAC9(ΔNLS), HDAC9a(ΔNLS), or HDRP(ΔNLS) polypeptides may be used to clone HDAC9, HDAC9a, HDAC9(ΔNLS), HDAC9a(ΔNLS), or HDRP(ΔNLS) homologs by RT-PCR.

Alternatively, additional HDAC9, HDAC9a, HDAC9 (ΔNLS), HDAC9a(ΔNLS), or HDRP(ΔNLS) homologs can be identified by utilizing consensus sequence information for HDAC9, HDAC9a, HDAC9(ΔNLS), HDAC9a(ΔNLS), or HDRP(ΔNLS) polypeptides to search for similar polypeptides in other species. For example, polypeptide databases for other species can be searched for proteins with the HDAC domains described herein. Candidate polypeptides containing such a motif can then be tested for their HDAC9, HDAC9a, HDAC9(ΔNLS), HDAC9a(ΔNLS), or HDRP (ΔNLS) biological activities, using methods described herein.

Expression of the Nucleic Acid Molecules of the Invention

Another aspect of the invention pertains to nucleic acid constructs containing an HDAC9, HDAC9a, HDAC9 (ΔNLS), HDAC9a(ΔNLS), or HDRP(ΔNLS) nucleic acid molecule, for example, one selected from the group consisting of SEQ ID NO: 1, SEQ ID NO: 3, SEQ ID NO: 5, SEQ ID NO: 7, SEQ ID NO: 9, and the complement of any of SEQ ID NO: 1, SEQ ID NO: 3, SEQ ID NO: 5, SEQ ID NO: 7, or SEQ ID NO: 9 (or portions thereof). Yet another aspect of the invention pertains to HDAC9, HDAC9a, HDAC9(ΔNLS), HDAC9a(ΔNLS), and HDRP(ΔNLS) nucleic acid constructs containing a nucleic acid molecule encoding the amino acid sequence of SEQ ID NO: 2, SEQ ID NO: 4, SEQ ID NO: 6, SEQ ID NO: 8, or SEQ ID NO: 10. The constructs comprise a vector (e.g., an expression vector) into which a sequence of the invention has been inserted in a sense or antisense orientation.

As used herein, the term "vector" or "construct" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences).

It will be appreciated by those skilled in the art that the design of the expression vector can depend on such factors as the choice of the host cell to be transformed and the level of expression of polypeptide desired. The expression vectors of the invention can be introduced into host cells to thereby produce polypeptides, including fusion polypeptides, encoded by nucleic acid molecules as described herein.

The recombinant expression vectors of the invention can be designed for expression of a polypeptide of the invention in prokaryotic or eukaryotic cells, e.g., bacterial cells, such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example, using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a nucleic acid molecule of the invention can be expressed in bacterial cells (e.g., *E. coli*), insect cells, yeast, or mammalian cells (such as Chinese hamster ovary cells (CHO) or COS cells, human 293T cells, HeLa cells, NIH 3T3 cells, and mouse erythroleukemia (MEL) cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing a foreign nucleic acid molecule (e.g., DNA) into a host cell, including calcium phosphate or calcium chloride co-precipitation, DEAE-dextranmediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin, or methotrexate. Nucleic acid molecules encoding a selectable marker can be introduced into a host cell on the same vector as the nucleic acid molecule of the invention or can be introduced on a separate vector. Cells stably transfected with the introduced nucleic acid molecule can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which an HDAC9, HDAC9a, HDAC9(ΔNLS), HDAC9a(ΔNLS), or HDRP(ΔNLS) nucleic acid molecule of the invention has been introduced. Such host cells can then be used to create non-human transgenic animals in which exogenous nucleotide sequences have been introduced into the genome or homologous recombinant animals in which endogenous nucleotide sequences have been altered. Such animals are useful for studying the function and/or activity of the nucleotide sequence and polypeptide encoded by the sequence and for identifying and/or evaluating modulators of their activity.

As used herein, a "transgenic animal" is a non-human animal, preferably, a mammal, more preferably, a rodent such as a rat or mouse, in which one or more of the cells of the animal includes a transgene. Other examples of transgenic animals include non-human primates, sheep, dogs, cows, goats, chickens, and amphibians. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably, a mammal, more preferably, a mouse, in which an endogenous gene has been altered by homologous recombination between the endogenous gene and an exogenous DNA molecule introduced into a cell of the animal, e.g., an embryonic cell of the animal, prior to development of the animal.

Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191, and in Hogan, Manipulating the Mouse Embryo (Cold Spring Harbor Laboratory Press, Cold Spring Harbor, N.Y., (1986)). Methods for constructing homologous recombination vectors and homologous recombinant animals are described further in Bradley, Current Opinion in Bio/Technology, 2:823-829 (1991) and in PCT Publication Nos. WO 90/11354, WO 91/01140, WO 92/0968, and WO 93/04169. Clones of the non-human transgenic animals described herein can also be produced according to the methods described in Wilmut et al., Nature, 385: 810-813 (1997) and PCT Publication Nos. WO 97/07668 and WO 97/07669.

Antibodies of the Invention

Polyclonal and/or monoclonal antibodies that selectively bind one form of an HDAC9, HDAC9a, HDAC9(ΔNLS), HDAC9a(ΔNLS), or HDRP(ΔNLS) polypeptide but not another form of the polypeptide are also provided. Antibodies are also provided that bind a portion of either the variant or reference HDAC9, HDAC9a, HDAC9(ΔNLS), HDAC9a (ΔNLS), or HDRP(ΔNLS) polypeptide that contains the polymorphic site or sites.

In another aspect, the invention provides antibodies to each of the HDAC9, HDAC9a, HDAC9(ΔNLS), HDAC9a (ΔNLS), and HDRP(ΔNLS) polypeptides and polypeptide fragments of the invention, e.g., having an amino acid sequence encoded by SEQ ID NO: 2, SEQ ID NO: 4, SEQ ID NO: 6, SEQ ID NO: 8, SEQ ID NO: 10, or a portion thereof, or having an amino acid sequence encoded by a nucleic acid molecule comprising all or a portion of SEQ ID NO: 1, SEQ ID NO: 3, SEQ ID NO: 5, SEQ ID NO: 7, or SEQ ID NO: 9, (e.g., SEQ ID NO: 2, SEQ ID NO: 4, SEQ ID NO: 6, SEQ ID NO: 8, or SEQ ID NO: 10, or another variant, or portion thereof).

The term "purified antibody" as used herein refers to immunoglobulin molecules and immunologically active portions of immunoglobulin molecules, i.e., molecules that contain an antigen binding site that selectively binds an antigen. A molecule that selectively binds to a polypeptide of the invention is a molecule that binds to that polypeptide or a fragment thereof, but does not substantially bind other molecules in a sample, e.g., a biological sample that naturally contains the polypeptide. Preferably the antibody is at least 60%, by weight, free from proteins and naturally occurring organic molecules with which it naturally associated. More preferably, the antibody preparation is at least 75% or 90%, and most preferably, 99%, by weight, antibody. Examples of immunologically active portions of immunoglobulin molecules include F(ab) and F(ab')2 fragments that can be generated by treating the antibody with an enzyme such as pepsin.

The invention provides polyclonal and monoclonal antibodies that selectively bind to an HDAC9, HDAC9a, HDAC9 (ΔNLS), HDAC9a(ΔNLS), or HDRP(ΔNLS) polypeptide of the invention. The term "monoclonal antibody" or "monoclonal antibody composition," as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., an HDAC9, HDAC9a, HDAC9(ΔNLS), HDAC9a (ΔNLS), or HDRP(ΔNLS) polypeptide of the invention or fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction.

At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, Nature, 256:495-497 (1975), the human B cell hybridoma technique (Kozbor et al., Immunol. Today, 4:72 (1983)), the EBV-hybridoma technique (Cole et al., Monoclonal Antibodies and Cancer Therapy, Alan R. Liss, Inc., pp. 77-96 (1985)) or trioma techniques. The technology for producing hybridomas is well known (see generally Current Protocols in Immunology, Coligan et al., (eds.) John Wiley & Sons, Inc., New York, N.Y. (1994)). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., Current Protocols in Immunology, supra; Galfre et al., (1977) Nature, 266:55052; R. H. Kenneth, in Monoclonal Antibodies: A New Dimension In Biological Analyses, Plenum Publishing Corp., New York, N.Y. (1980); and Lerner, Yale J. Biol. Med., 54:387-402 (1981)). Moreover, the ordinarily skilled worker will appreciate that there are many variations of such methods that also would be useful.

Alternative to preparing monoclonal antibody-secreting hybridomas, a monoclonal antibody to an HDAC9, HDAC9a, HDAC9(ΔNLS), HDAC9a(ΔNLS), or HDRP(ΔNLS) polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., Bio/Technology, 9:1370-1372 (1991); Hay et al., Hum. Antibod. Hybridomas, 3:81-85 (1992); Huse et al., Science, 246: 1275-1281 (1989); and Griffiths et al., EMBO J., 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate an HDAC9, HDAC9a, HDAC9(ΔNLS), HDAC9a(ΔNLS), or HDRP(ΔNLS) polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for an HDAC9, HDAC9a, HDAC9(ΔNLS), HDAC9a (ΔNLS), or HDRP(ΔNLS) polypeptide of the invention can be used to detect the polypeptide (e.g., in a cellular lysate, cell supernatant, or tissue sample) in order to evaluate the abundance and pattern of expression of the polypeptide.

The antibodies of the present invention can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferase, luciferin, and aequorin, and examples of suitable radioactive material include $^{125}I$, $^{131}I$, $^{35}S$, and $^{3}H$.

Diagnostic and Screening Assays of the Invention

The present invention also pertains to diagnostic assays for assessing HDAC 9 HDAC9a, HDAC9(ΔNLS), HDAC9a (ΔNLS), or HDRP(ΔNLS) gene expression, or for assessing activity of HDAC9, HDAC9a, HDAC9(ΔNLS), HDAC9a (ΔNLS), or HDRP(ΔNLS) polypeptides of the invention. In one embodiment, the assays are used in the context of a biological sample (e.g., blood, serum, cells, tissue) to thereby determine whether an individual is afflicted with a cell proliferation disease, an apoptotic disease, or a cell differentiation disease, or is at risk for (has a predisposition for or a susceptibility to) developing a cell proliferation disease, an apoptotic disease, or a cell differentiation disease. The invention also provides for prognostic (or predictive) assays for determining whether an individual is susceptible to developing a cell proliferation disease, an apoptotic disease, or a cell differentiation disease. For example, mutations in the HDAC9, HDAC9a, HDAC9(ΔNLS), HDAC9a(ΔNLS), or HDRP(ΔNLS) nucleic acid molecule can be assayed in a biological sample. Such assays can be used for prognostic or predictive purpose to thereby prophylactically treat an individual prior to the onset of symptoms associated with a cell proliferation disease, an apoptotic disease, or a cell differentiation disease.

Another aspect of the invention pertains to assays for monitoring the influence of agents, or candidate compounds (e.g., drugs or other agents) on the nucleic acid molecule expression or biological activity of polypeptides of the invention, as well as to assays for identifying candidate compounds that bind to an HDAC9, HDAC9a polypeptide, an HDAC9 (ΔNLS) polypeptide, an HDAC9a(ΔNLS) polypeptide, or an HDRP(ΔNLS) polypeptide. These and other assays and agents are described in further detail in the following sections.

Diagnostic Assays

HDAC9, HDAC9a, HDAC9(ΔNLS), HDAC9a(ΔNLS), or HDRP(ΔNLS) nucleic acid molecules, probes, primers, polypeptides, and antibodies to an HDAC9, an HDAC9a protein, an HDAC9(ΔNLS) protein, an HDAC9a(ΔNLS) protein, or an HDRP(ΔNLS) protein can be used in methods of diagnosis of a susceptibility to, or likelihood of having a cell proliferation disease, an apoptotic disease, or a cell differentiation disease, as well as in kits useful for diagnosis of a susceptibility to a cell proliferation disease, an apoptotic disease, or a cell differentiation disease.

In one embodiment of the invention, diagnosis of a decreased susceptibility to a cell proliferation disease, an apoptotic disease, or a cell differentiation disease is made by detecting a polymorphism in HDAC9, HDAC9a, HDAC9 (ΔNLS), HDAC9a(ΔNLS), or HDRP(ΔNLS). The polymorphism can be a mutation in HDAC9, HDAC9a, HDAC9 (ΔNLS), HDAC9a(ΔNLS), or HDRP(ΔNLS), such as the insertion or deletion of a single nucleotide, or of more than one nucleotide, resulting in a frame shift mutation; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of the gene; duplication of all or a part of the gene; transposition of all or a part of the gene; or rearrangement of all or a part of the gene, or a change in the expression pattern of the various HDAC9 isoforms. More than one such mutation may be present in a single nucleic acid molecule.

Such sequence changes cause a mutation in the polypeptide encoded by HDAC9, HDAC9a, HDAC9(NLS), HDAC9a (ΔNLS), or HDRP(ΔNLS). For example, if the mutation is a frame shift mutation, the frame shift can result in a change in the encoded amino acids, and/or can result in the generation of a premature stop codon, causing generation of a truncated polypeptide. Alternatively, a polymorphism associated with a decreased susceptibility to a cell proliferation disease, an apoptotic disease, or a cell differentiation disease can be a synonymous mutation in one or more nucleotides (i.e., a mutation that does not result in a change in the HDAC9, HDAC9a, HDAC9(ΔNLS), HDAC9a(ΔNLS), or HDRP (ΔNLS) polypeptide). Such a polymorphism may alter sites, affect the stability or transport of mRNA, or otherwise affect the transcription or translation of the nucleic acid molecule. HDAC9, HDAC9a, HDAC9(ΔNLS), HDAC9a(ΔNLS), or HDRP(ΔNLS) that has any of the mutations described above is referred to herein as a "mutant nucleic acid molecule."

In a first method of diagnosing a decreased susceptibility to a cell proliferation disease, an apoptotic disease, or a cell differentiation disease, hybridization methods, such as Southern analysis, Northern analysis, or in situ hybridizations, can be used (see Ausubel, et al., supra). For example, a biological sample from a test subject (a "test sample") of genomic DNA, RNA, or cDNA, is obtained from an individual suspected of having, being susceptible to or predisposed for, or carrying a defect for, a cell proliferation disease, an apoptotic disease, or a cell differentiation disease (the "test individual"). The individual can be an adult, child, or fetus. The test sample can be from any source that contains genomic DNA, such as a blood sample, sample of amniotic fluid, sample of cerebrospinal fluid, or tissue sample from skin, muscle, buccal or conjunctival mucosa, placenta, gastrointestinal tract, or other organs. A test sample of DNA from fetal cells or tissue can be obtained by appropriate methods, such as by amniocentesis or chorionic villus sampling. The DNA, RNA, or cDNA sample is then examined to determine whether a polymorphism in HDAC9, HDAC9a, HDAC9 (ΔNLS), HDAC9a(ΔNLS), or HDRP(ΔNLS) is present, and/or to determine which variant(s) encoded by HDAC9, HDAC9a, HDAC9(ΔNLS), HDAC9a(ΔNLS), or HDRP (ΔNLS) is present. The presence of the polymorphism or variant(s) can be indicated by hybridization of the gene in the genomic DNA, RNA, or cDNA to a nucleic acid probe. A "nucleic acid probe," as used herein, can be a DNA probe or an RNA probe; the nucleic acid probe can contain at least one polymorphism in HDAC9, HDAC9a, HDAC9(ΔNLS), HDAC9a(ΔNLS), or HDRP(ΔNLS) or contains a nucleic acid encoding a particular variant of HDAC9, HDAC9a, HDAC9 (ΔNLS), HDAC9a(ΔNLS), or HDRP(ΔNLS). The probe can be any of the nucleic acid molecules described above (e.g., the entire nucleic acid molecule, a fragment, a vector comprising the gene, a probe, or primer, etc.).

To diagnose a decreased susceptibility to a cell proliferation disease, an apoptotic disease, or a cell differentiation disease, a hybridization sample is formed by contacting the test sample containing HDAC9, HDAC9a, HDAC9(ΔNLS), HDAC9a(ΔNLS), or HDRP(ΔNLS), with at least one nucleic acid probe. A preferred probe for detecting mRNA or genomic DNA is a labeled nucleic acid probe capable of hybridizing to HDAC9, HDAC9a, HDAC9(ΔNLS), HDAC9a (ΔNLS), or HDRP(ΔNLS) mRNA or genomic DNA sequences described herein. The nucleic acid probe can be, for example, a full-length nucleic acid molecule, or a portion thereof, such as an oligonucleotide of at least 15, 30, 50, 100, 250, or 500 nucleotides in length and sufficient to specifically hybridize under stringent conditions to appropriate mRNA or genomic DNA. For example, the nucleic acid probe can be all or a portion of SEQ ID NO: 1, SEQ ID NO: 3, SEQ ID NO: 5, SEQ ID NO: 7, SEQ ID NO: 9, or the complement of SEQ ID NO: 1 or SEQ ID NO: 3, SEQ ID NO: 5, SEQ ID NO: 7, SEQ ID NO: 9; or can be a nucleic acid molecule encoding all or a portion of SEQ ID NO: 2, SEQ ID NO: 4, SEQ ID NO: 6, SEQ ID NO: 8, or SEQ ID NO: 10. Other suitable probes for use in the diagnostic assays of the invention are described above (see. e.g., probes and primers discussed under the heading, "Nucleic Acids of the Invention").

The hybridization sample is maintained under conditions that are sufficient to allow specific hybridization of the nucleic acid probe to HDAC9, HDAC9a, HDAC9(ΔNLS), HDAC9a(ΔNLS), or HDRP(ΔNLS). "Specific hybridization," as used herein, indicates exact hybridization (e.g., with no mismatches). Specific hybridization can be performed under high stringency conditions or moderate stringency conditions, for example, as described above. In a particularly preferred embodiment, the hybridization conditions for specific hybridization are high stringency.

Specific hybridization, if present, is then detected using standard methods. If specific hybridization occurs between the nucleic acid probe and HDAC9, HDAC9a, HDAC9 (ΔNLS), HDAC9a(ΔNLS), or HDRP(ΔNLS) in the test sample, then HDAC9, HDAC9a, HDAC9(ΔNLS), HDAC9a (ΔNLS), or HDRP(ΔNLS) has the polymorphism, or is the variant, that is present in the nucleic acid probe. More than one nucleic acid probe can also be used concurrently in this method. Specific hybridization of any one of the nucleic acid probes is indicative of a polymorphism in HDAC9, HDAC9a, HDAC9(ΔNLS), HDAC9a(ΔNLS), or HDRP(ΔNLS), or of the presence of a particular variant encoded by HDAC9, HDAC9a, HDAC9(ΔNLS), HDAC9a(ΔNLS), or HDRP (ΔNLS), and is therefore diagnostic for a decreased susceptibility to a cell proliferation disease, an apoptotic disease, or a cell differentiation disease.

In Northern analysis (see Current Protocols in Molecular Biology, Ausubel, et al., supra), the hybridization methods described above are used to identify the presence of a polymorphism or of a particular variant, associated with a decreased susceptibility to a cell proliferation disease, an apoptotic disease, or a cell differentiation disease. For Northern analysis, a test sample of RNA is obtained from the individual by appropriate means. Specific hybridization of a nucleic acid probe, as described above, to RNA from the individual is indicative of a polymorphism in HDAC9, HDAC9a, HDAC9(ΔNLS), HDAC9a(ΔNLS), or HDRP (ΔNLS), or of the presence of a particular variant encoded by HDAC9, HDAC9a, HDAC9(ΔNLS), HDAC9a(ΔNLS), or HDRP(ΔNLS), and is therefore diagnostic for a decreased susceptibility to a cell proliferation disease, an apoptotic disease, or a cell differentiation disease.

For representative examples of use of nucleic acid probes, see, for example, U.S. Pat. Nos. 5,288,611 and 4,851,330.

Alternatively, a peptide nucleic acid (PNA) probe can be used instead of a nucleic acid probe in the hybridization methods described above. PNA is a DNA mimic having a peptide-like, inorganic backbone, such as N-(2-aminoethyl) glycine units, with an organic base (A, G, C, T, or U) attached to the glycine nitrogen via a methylene carbonyl linker (see, for example, Nielsen et al., Bioconjugate Chemistry, 5 (1994), American Chemical Society, p. 1 (1994)). The PNA probe can be designed to specifically hybridize to a gene having a polymorphism associated with a susceptibility to a cell proliferation disease, an apoptotic disease, or a cell differentiation disease. Hybridization of the PNA probe to HDAC9, HDAC9a, HDAC9(ΔNLS), HDAC9a(ΔNLS), or HDRP(ΔNLS) is diagnostic for a decreased susceptibility to a cell proliferation disease, an apoptotic disease, or a cell differentiation disease.

In another method of the invention, mutation analysis by restriction digestion can be used to detect a mutant nucleic acid molecule, or nucleic acid molecules containing a polymorphism(s), if the mutation or polymorphism in the gene results in the creation or elimination of a restriction site. A test sample containing genomic DNA is obtained from the individual. Polymerase chain reaction (PCR) can be used to amplify HDAC9, HDAC9a, HDAC9(ΔNLS), HDAC9a (ΔNLS), or HDRP(ΔNLS) (and, if necessary, the flanking sequences) in the test sample of genomic DNA from the test individual. RFLP analysis is conducted as described (see Current Protocols in Molecular Biology, supra). The digestion pattern of the relevant DNA fragment indicates the presence or absence of the mutation or polymorphism in HDAC9, HDAC9a, HDAC9(ΔNLS), HDAC9a(ΔNLS), or HDRP (ΔNLS), and therefore indicates the presence or absence of this decreased susceptibility to a cell proliferation disease, an apoptotic disease, or a cell differentiation disease.

Sequence analysis can also be used to detect specific polymorphisms in HDAC9, HDAC9a, HDAC9(ΔNLS), HDAC9a (ΔNLS), or HDRP(ΔNLS). A test sample of DNA or RNA is obtained from the test individual. PCR or other appropriate methods can be used to amplify the nucleic acid molecule, and/or its flanking sequences, if desired. The sequence of HDAC9, HDAC9a, HDAC9(ΔNLS), HDAC9a(ΔNLS), or HDRP(ΔNLS), or HDRP(ΔNLS), or a fragment of the any of those nucleic acid molecules, or an HDAC9, HDAC9a, HDAC9(ΔNLS), HDAC9a(ΔNLS), or HDRP(ΔNLS) cDNA, or a fragment of any of those cDNAs, or an HDAC9, HDAC9a, HDAC9(ΔNLS), HDAC9a(ΔNLS), or HDRP (ΔNLS) mRNA, or a fragment of any of those mRNAs, is determined, using standard methods. The sequence of the above gene, gene fragment, cDNA, cDNA fragment, mRNA, or mRNA fragment is compared with the known nucleic acid sequence of the nucleic acid molecule, cDNA (e.g., SEQ ID NO: 1, SEQ ID NO: 3, SEQ ID NO: 5, SEQ ID NO: 7, SEQ ID NO: 9, or a nucleic acid sequence encoding the protein of SEQ ID NO: 2, SEQ ID NO:4, SEQ ID NO:6, SEQ ID NO:8, SEQ ID NO: 10, or a fragment thereof) or mRNA, as appropriate. The presence of a polymorphism in HDAC9, HDAC9a, HDAC9(ΔNLS), HDAC9a(ΔNLS), or HDRP (ΔNLS) indicates that the individual has a decreased susceptibility to a cell proliferation disease, an apoptotic disease, or a cell differentiation disease.

Allele-specific oligonucleotides can also be used to detect the presence of a polymorphism in HDAC9, HDAC9a, HDAC9(ΔNLS), HDAC9a(ΔNLS), or HDRP(ΔNLS), through the use of dot-blot hybridization of amplified oligonucleotides with allele-specific oligonucleotide (ASO) probes (see, for example, Saiki et al., Nature (London) 324: 163-166 (1986)). An "allele-specific oligonucleotide" (also referred to herein as an "allele-specific oligonucleotide probe") is an oligonucleotide of approximately 10-50 base pairs, preferably approximately 15-30 base pairs, that specifically hybridizes to HDAC9, HDAC9a, HDAC9(ΔNLS), HDAC9a(ΔNLS), or HDRP(ΔNLS), and that contains a polymorphism associated with a decreased susceptibility to a cell proliferation disease, an apoptotic disease, or a cell differentiation disease. An allele-specific oligonucleotide probe that is specific for particular polymorphisms in HDAC9, HDAC9a, HDAC9(ΔNLS), HDAC9a(ΔNLS), or HDRP (ΔNLS) can be prepared, using standard methods (see Current Protocols in Molecular Biology, supra).

To identify polymorphisms in the gene that are associated with a decreased susceptibility to a cell proliferation disease, an apoptotic disease, or a cell differentiation disease a test sample of DNA is obtained from the individual. PCR can be used to amplify all or a fragment of HDAC9, HDAC9a, HDAC9(ΔNLS), HDAC9a(ΔNLS), or HDRP(ΔNLS), and its flanking sequences. The DNA containing the amplified HDAC9, HDAC9a, HDAC9(ΔNLS), HDAC9a(ΔNLS), or HDRP(ΔNLS) (or a fragment of any of those genes) is dot-blotted, using standard methods (see Current Protocols in Molecular Biology, supra), and the blot is contacted with the oligonucleotide probe. The presence of specific hybridization of the probe to the amplified HDAC9, HDAC9a, HDAC9 (ΔNLS), HDAC9a(ΔNLS), or HDRP(ΔNLS) is then detected. Specific hybridization of an allele-specific oligonucleotide probe to DNA from the individual is indicative of a polymorphism in HDAC9, HDAC9a, HDAC9(ΔNLS), HDAC9a(ΔNLS), or HDRP(ΔNLS), and is therefore indicative of a decreased susceptibility to a cell proliferation disease, an apoptotic disease, or a cell differentiation disease.

In another embodiment, arrays of oligonucleotide probes that are complementary to target nucleic acid sequence segments from an individual, can be used to identify polymorphisms in HDAC9, HDAC9a, HDAC9(ΔNLS), HDAC9a (ΔNLS), or HDRP(ΔNLS). For example, in one embodiment, an oligonucleotide array can be used. Oligonucleotide arrays typically comprise a plurality of different oligonucleotide probes that are coupled to a surface of a substrate in different known locations. These oligonucleotide arrays, also described as "GENECHIPS," have been generally described in the art, for example, U.S. Pat. No. 5,143,854 and PCT patent publication Nos. WO 90/15070 and 92/10092. These arrays can generally be produced using mechanical synthesis methods or light directed synthesis methods that incorporate a combination of photolithographic methods and solid phase oligonucleotide synthesis methods. See Fodor et al., Science, 251:767-777 (1991), Pirrung et al., U.S. Pat. No. 5,143,854; PCT Publication No. WO 90/15070; Fodor et al., PCT Publication No. WO 92/10092, and U.S. Pat. No. 5,424,186, the entire teachings of each of which are incorporated by reference herein. Techniques for the synthesis of these arrays using mechanical synthesis methods are described in, e.g., U.S. Pat. No. 5,384,261, the entire teachings of which are incorporated by reference herein.

Once an oligonucleotide array is prepared, a nucleic acid of interest is hybridized to the array and scanned for polymorphisms. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein. In brief, a target nucleic acid sequence that includes one or more previously identified polymorphic markers is amplified by well known amplification techniques, e.g., PCR. Typically, this involves the use of primer sequences that are complementary to the two strands of the target sequence both upstream and downstream from the polymorphism. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Although primarily described in terms of a single detection block, e.g., for detection of a single polymorphism, arrays can include multiple detection blocks, and thus be capable of analyzing multiple, specific polymorphisms. In alternate arrangements, it will generally be understood that detection blocks may be grouped within a single array or in multiple, separate arrays so that varying, optimal conditions may be used during the hybridization of the target to the array. For example, it may often be desirable to provide for the detection of those polymorphisms that fall within G-C rich stretches of a genomic sequence, separately from those falling in A-T rich segments. This allows for the separate optimization of hybridization conditions for each situation.

Additional descriptions of the use of oligonucleotide arrays for detection of polymorphisms can be found, for example, in U.S. Pat. Nos. 5,858,659 and 5,837,832, the entire teachings of which are incorporated by reference herein.

Other methods of nucleic acid analysis can be used to detect polymorphisms in HDAC9, HDAC9a, HDAC9 (ΔNLS), HDAC9a(ΔNLS), or HDRP(ΔNLS) or variants encoded by HDAC9, HDAC9a, HDAC9(ΔNLS), HDAC9a (ΔNLS), or HDRP(ΔNLS). Representative methods include direct manual sequencing (Church and Gilbert Proc. Natl. Acad. Sci. USA 81: 1991-1995, (1988); Sanger et al., Proc. Natl. Acad. Sci. 74: 5463-5467 (1977); Beavis et al., U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield et al., Proc. Natl. Acad. Sci. USA 86: 232-236 (1991)), mobility shift analysis (Orita et al., Proc. Natl. Acad. Sci. USA 86: 2766-2770 (1989)), restriction enzyme analysis (Flavell et al., Cell 15: 25 (1978); Geever, et al., Proc. Natl. Acad. Sci. USA 78: 5081 (1981)); heteroduplex analysis; chemical mismatch cleavage (CMC) (Cotton et al., Proc. Natl. Acad. Sci. USA 85: 4397-4401 (1985)); RNase protection assays (Myers et al., Science 230: 1242 (1985)); use of polypeptides that recognize nucleotide mismatches, such as *E. coli* mutS protein; and allele-specific PCR.

In another embodiment of the invention, diagnosis of a susceptibility to a cell proliferation disease, an apoptotic disease, or a cell differentiation disease can also be made by examining the level of an HDAC9, HDAC9a, HDAC9 (ΔNLS), HDAC9a(ΔNLS), or HDRP(ΔNLS) nucleic acid, for example, using in situ hybridization techniques known to one skilled in the art, or by examining the level of expression, activity, and/or composition of an HDAC9, HDAC9a, HDAC9(ΔNLS), HDAC9a(ΔNLS), or HDRP(ΔNLS) polypeptide, by a variety of methods, including enzyme linked immunosorbent assays (ELISAs), Western blots, immunoprecipitations, immunohistochemistry, and immunofluorescence. A test sample from an individual is assessed for the presence of an alteration in the level of an HDAC9, HDAC9a, HDAC9(ΔNLS), HDAC9a(ΔNLS), or HDRP (ΔNLS) nucleic acid or in the expression and/or an alteration in composition of the polypeptide encoded by HDAC9, HDAC9a, HDAC9(ΔNLS), HDAC9a(ΔNLS), or HDRP (ΔNLS), or for the presence of a particular variant encoded by HDAC9, HDAC9a, HDAC9(ΔNLS), HDAC9a(ΔNLS), or HDRP(ΔNLS). An alteration in expression of a polypeptide encoded by HDAC9, HDAC9a, HDAC9(ΔNLS), HDAC9a (ΔNLS), or HDRP(ΔNLS) can be, for example, an alteration in the quantitative polypeptide expression (i.e., the amount of polypeptide produced); an alteration in the composition of a polypeptide encoded by HDAC9, HDAC9a, HDAC9(ΔNLS), HDAC9a(ΔNLS), or HDRP(ΔNLS), or an alteration in the qualitative polypeptide expression (e.g., expression of a mutant HDAC9, HDAC9a, HDAC9(ΔNLS), HDAC9a (ΔNLS), or HDRP(ΔNLS) polypeptide or variant thereof). In a preferred embodiment, diagnosis of a susceptibility to a cell proliferation disease, an apoptotic disease, or a cell differentiation disease is made by detecting a particular variant encoded by HDAC9, HDAC9a, HDAC9(ΔNLS), HDAC9a (ΔNLS), or HDRP(ΔNLS), or a particular pattern of variants. Preferably, increased levels of HDAC9, HDAC9a, HDAC9 (ΔNLS), HDAC9a(ΔNLS), or HDRP(ΔNLS) or increased expression or activity of an HDAC9, HDAC9a, HDAC9 (ΔNLS), HDAC9a(ΔNLS), or HDRP(ΔNLS) polypeptide, relative to a control sample, for example, a sample known not to be associated with a cell proliferation disease, an apoptotic disease, or a cell differentiation disease, indicates an increased susceptibility or likelihood that the individual has a cell proliferation disease, an apoptotic disease, or a cell differentiation disease. Alternatively, decreased levels of HDAC9, HDAC9a, HDAC9(ΔNLS), HDAC9a(ΔNLS), or HDRP(ΔNLS) or decreased expression or activity of an HDAC9, HDAC9a, HDAC9(ΔNLS), HDAC9a(ΔNLS), or HDRP(ΔNLS) polypeptide, relative to a control sample, for example, a sample known not to be associated with a cell proliferation disease, an apoptotic disease, or a cell differentiation disease, indicates a decreased susceptibility or likelihood that the individual has a cell proliferation disease, an apoptotic disease, or a cell differentiation disease.

Both quantitative and qualitative alterations can also be present. An "alteration" or "modulation" in the polypeptide expression, activity, or composition, as used herein, refers to an alteration in expression or composition in a test sample, as compared with the expression or composition of HDAC9, HDAC9a, HDAC9(ΔNLS), HDAC9a(ΔNLS), or HDRP (ΔNLS) polypeptide in a control sample. A control sample is a sample that corresponds to the test sample (e.g., is from the same type of cells), and is from an individual who is not affected by a cell proliferation disease, an apoptotic disease, or a cell differentiation disease. An alteration in the expression or composition of the polypeptide in the test sample, as compared with the control sample, is indicative of a decreased susceptibility to a cell proliferation disease, an apoptotic disease, or a cell differentiation disease. Similarly, the presence of one or more different variants in the test sample, or the presence of significantly different amounts of different variants in the test sample, as compared with the control sample, is indicative of a decreased susceptibility to a cell proliferation disease, an apoptotic disease, or a cell differentiation disease.

It is understood that alterations or modulations in polypeptide expression or function can occur in varying degrees. For example, an alteration or modulation in expression can be an increase, for example, by at least 1.5-fold to 2-fold, at least 3-fold, or, at least 5-fold, relative to the control. Alternatively, the alteration or modulation in polypeptide expression can be a decrease, for example, by at least 10%, at least 40%, 50%, or 75%, or by at least 90%, relative to the control.

Various means of examining expression or composition of the HDAC9, HDAC9a, HDAC9(ΔNLS), HDAC9a(ΔNLS), or HDRP(ΔNLS) polypeptide can be used, including spectroscopy, colorimetry, electrophoresis, isoelectric focusing, and immunoassays (e.g., David et al., U.S. Pat. No. 4,376,110) such as immunoblotting (see also Ausubel et al., supra; particularly chapter 10). For example, in one embodiment, an antibody capable of binding to the polypeptide (e.g., as described above), preferably an antibody with a detectable label, can be used. Antibodies can be polyclonal, or more preferably, monoclonal. An intact antibody, or a fragment thereof (e.g., Fab or F(ab')2) can be used. The term "labeled," with regard to the antibody, is intended to encompass direct labeling of the antibody by coupling (i.e., physically linking) a detectable substance to the antibody, as well as indirect labeling of the antibody by reacting it with another reagent that is directly labeled. An example of indirect labeling is detection of a primary antibody using a fluorescently labeled secondary antibody.

Western blotting analysis, using an antibody as described above that specifically binds to a mutant HDAC9, HDAC9a, HDAC9(ΔNLS), HDAC9a(ΔNLS), or HDRP(ΔNLS) polypeptide, or an antibody that specifically binds to a non-mutant HDAC9, HDAC9a, HDAC9(ΔNLS), HDAC9a (ΔNLS), or HDRP(ΔNLS) polypeptide, or an antibody that specifically binds to a particular variant encoded by HDAC9, HDAC9a, HDAC9(ΔNLS), HDAC9a(ΔNLS), or HDRP (ΔNLS), can be used to identify the presence in a test sample of a particular variant of a polypeptide encoded by a polymorphic or mutant HDAC9, HDAC9a, HDAC9(ΔNLS), HDAC9a(ΔNLS), or HDRP(ΔNLS), or the absence in a test sample of a particular variant or of a polypeptide encoded by a non-polymorphic or non-mutant gene. The presence of a polypeptide encoded by a polymorphic or mutant gene, or the absence of a polypeptide encoded by a non-polymorphic or non-mutant gene, is diagnostic for a decreased susceptibility to a cell proliferation disease, an apoptotic disease, or a cell differentiation disease, as is the presence (or absence) of particular variants encoded by the HDAC9, HDAC9a, HDAC9(ΔNLS), HDAC9a(NLS), or HDRP(ΔNLS) nucleic acid molecule.

In one embodiment of this method, the level or amount of HDAC9, HDAC9a, HDAC9(ΔNLS), HDAC9a(ΔNLS), or HDRP(ΔNLS) polypeptide in a test sample is compared with the level or amount of the HDAC9, HDAC9a, HDAC9 (ΔNLS), HDAC9a(ΔNLS), or HDRP(ΔNLS) polypeptide in a control sample. A level or amount of the polypeptide in the test sample that is higher or lower than the level or amount of the polypeptide in the control sample, such that the difference is statistically significant, is indicative of an alteration in the expression of the HDAC9, HDAC9a, HDAC9(ΔNLS), HDAC9a(ΔNLS), or HDRP(ΔNLS) polypeptide, and is diagnostic for a decreased susceptibility to a cell proliferation disease, an apoptotic disease, or a cell differentiation disease.

Alternatively, the composition of the HDAC9, HDAC9a, HDAC9(ΔNLS), HDAC9a(ΔNLS), or HDRP(ΔNLS) polypeptide in a test sample is compared with the composition of the HDAC9, HDAC9a, HDAC9(ΔNLS), HDAC9a (ΔNLS), or HDRP(ΔNLS) polypeptide in a control sample. A difference in the composition of the polypeptide in the test sample, as compared with the composition of the polypeptide in the control sample (e.g., the presence of different variants), is diagnostic for a decreased susceptibility to a cell proliferation disease, an apoptotic disease, or a cell differentiation disease. In another embodiment, both the level or amount and the composition of the polypeptide can be assessed in the test sample and in the control sample. A difference in the amount or level of the polypeptide in the test sample, compared to the control sample; a difference in composition in the test sample, compared to the control sample; or both a difference in the amount or level, and a difference in the composition, is indicative of a decreased susceptibility to a cell proliferation disease, an apoptotic disease, or a cell differentiation disease.

Kits (e.g., reagent kits) useful in the methods of diagnosis comprise components useful in any of the methods described herein, including, for example, hybridization probes or primers as described herein (e.g., labeled probes or primers), reagents for detection of labeled molecules, restriction enzymes (e.g., for RFLP analysis), allele-specific oligonucleotides, antibodies that bind to a mutant or to non-mutant (native) HDAC9, HDAC9a, HDAC9(ΔNLS), HDAC9a (ΔNLS), or HDRP(ΔNLS) polypeptide, means for amplification of nucleic acids comprising HDAC9, HDAC9a, HDAC9 (ΔNLS), HDAC9a(ΔNLS), or HDRP(ΔNLS), or means for analyzing the nucleic acid sequence of HDAC9, HDAC9a, HDAC9(ΔNLS), HDAC9a(ΔNLS), or HDRP(ΔNLS), or for analyzing the amino acid sequence of an HDAC9, HDAC9a, HDAC9(ΔNLS), HDAC9a(ΔNLS), or HDRP(ΔNLS) polypeptide, etc.

Screening Assays and Agents Identified Thereby

The invention provides methods (also referred to herein as "screening assays") for identifying the presence of a nucleotide that hybridizes to a nucleic acid of the invention, as well as for identifying the presence of a polypeptide encoded by a nucleic acid of the invention. In one embodiment, the presence (or absence) of a nucleic acid molecule of interest (e.g., a nucleic acid that has significant homology with a nucleic acid of HDAC9, HDAC9a, HDAC9(ΔNLS), HDAC9a (ΔNLS), or HDRP(ΔNLS)) in a sample can be assessed by contacting the sample with a nucleic acid comprising a nucleic acid of the invention (e.g., a nucleic acid having the sequence of SEQ ID NO: 1, SEQ ID NO: 3, SEQ ID NO: 5, SEQ ID NO: 7, or SEQ ID NO: 9, which may optionally comprise at least one polymorphism, or the complement thereof, or a nucleic acid encoding an amino acid having the sequence of SEQ ID NO: 2, SEQ ID NO:4, SEQ ID NO: 6, SEQ ID NO: 8, or SEQ ID NO: 10, or a fragment or variant of such nucleic acids), under stringent conditions as described above, and then assessing the sample for the presence (or absence) of hybridization. In a preferred embodiment, high stringency conditions are conditions appropriate for selective hybridization. In another embodiment, a sample containing the nucleic acid molecule of interest is contacted with a nucleic acid containing a contiguous nucleotide sequence (e.g., a primer or a probe as described above) that is at least partially complementary to a part of the nucleic acid molecule of interest (e.g., an HDAC9, HDAC9a, HDAC9(ΔNLS), HDAC9a(ΔNLS), or HDRP(ΔNLS) nucleic acid), and the contacted sample is assessed for the presence or absence of hybridization. In a preferred embodiment, the nucleic acid containing a contiguous nucleotide sequence is completely complementary to a part of the nucleic acid molecule of HDAC9, HDAC9a, HDAC9(ΔNLS), HDAC9a(ΔNLS), or HDRP(ΔNLS).

In any of the above embodiments, all or a portion of the nucleic acid of interest can be subjected to amplification prior to performing the hybridization.

In another embodiment, the presence (or absence) of an HDAC9, HDAC9a, HDAC9(ΔNLS), HDAC9a(ΔNLS), or HDRP(ΔNLS) polypeptide, such as a polypeptide of the invention or a fragment or variant thereof, in a sample can be assessed by contacting the sample with an antibody that specifically binds to the polypeptide of HDAC9, HDAC9a, HDAC9(ΔNLS), HDAC9a(ΔNLS), or HDRP(ΔNLS) (e.g., an antibody such as those described above), and then assessing the sample for the presence (or absence) of binding of the antibody to the HDAC9, HDAC9a, HDAC9(ΔNLS), HDAC9a(ΔNLS), or HDRP(ΔNLS) polypeptide.

In another embodiment, the invention provides methods for identifying agents or compounds (e.g., fusion proteins, polypeptides, peptidomimetics, prodrugs, receptors, binding agents, antibodies, small molecules or other drugs, or ribozymes) that alter or modulate (e.g., increase or decrease) the activity of the polypeptides described herein, or that otherwise interact with the polypeptides herein. For example, such compounds can be compounds or agents that bind to polypeptides described herein (e.g., HDAC9, HDAC9a, HDAC9(ΔNLS), HDAC9a(ΔNLS), or HDRP(ΔNLS) substrates or agents); that have a stimulatory or inhibitory effect on, for example, activity of polypeptides of the invention; or that change (e.g., enhance or inhibit) the ability of the polypeptides of the invention to interact with HDAC9, HDAC9a, HDAC9(ΔNLS), HDAC9a(ΔNLS), or HDRP (ΔNLS) binding agents; or that alter post-translational processing of the HDAC9, HDAC9a, HDAC9(ΔNLS), HDAC9a (ΔNLS), or HDRP(ΔNLS) polypeptide (e.g., agents that alter proteolytic processing to direct the polypeptide from where it is normally synthesized to another location in the cell, such as the cell surface; or agents that alter proteolytic processing such that more polypeptide is released from the cell, etc.). In one example, the binding agent is a cell proliferation disease binding agent, an apoptotic disease binding agent, or a cell differentiation disease binding agent. As used herein, by a "cell proliferation disease binding agent," an "apoptotic disease binding agent," or a "cell differentiation disease binding agent" is meant an agent as described herein that binds to a polypeptide of the present invention and modulates a cell proliferation disease, an apoptotic disease, or a cell differentiation disease. The modulation can be an increase or a decrease in the severity or progression of the disease. In addition, a cell proliferation disease binding agent, an apoptotic disease binding agent, or a cell differentiation disease binding agent includes an agent that binds to a polypeptide that is upstream (earlier) or downstream (later) of the cell signaling events mediated by a polypeptide of the present invention, and thereby modulates the overall activity of the signaling pathway; in turn, the disease state is modulated.

The candidate compound can cause an increase in the activity of the polypeptide. For example, the activity of the polypeptide can be increased by at least 1.5-fold to 2-fold, at least 3-fold, or, at least 5-fold, relative to the control. Alternatively, the polypeptide activity can be a decrease, for example, by at least 10%, at least 20%, 40%, 50%, or 75%, or by at least 90%, relative to the control.

In one embodiment, the invention provides assays for screening candidate compounds or test agents to identify compounds that bind to or modulate the activity of polypeptides described herein (or biologically active portion(s) thereof), as well as agents identifiable by the assays. As used herein, a "candidate compound" or "test agent" is a chemical molecule, be it naturally-occurring or artificially-derived, and includes, for example, peptides, proteins, synthesized molecules, for example, synthetic organic molecules, naturally-occurring molecule, for example, naturally occurring organic molecules, nucleic acid molecules, and components thereof.

In general, candidate compounds for uses in the present invention may be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. For example, candidate compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (Lam, Anticancer Drug Des., 12: 145 (1997)). Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activities should be employed whenever possible.

When a crude extract is found to modulate (i.e., stimulate or inhibit) the expression and/or activity of the nucleic acids and or polypeptides of the present invention, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits nucleic acid expression, polypeptide expression, or polypeptide biological activity. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases in which it is desirable to alter the activity or expression of the nucleic acids or polypeptides of the present invention.

In one embodiment, to identify candidate compounds that alter the biological activity, for example, the enzymatic activity or transcriptional repression activity of an HDAC9, HDAC9a, HDAC9(ΔNLS), HDAC9a(ΔNLS), or HDRP (ΔNLS) polypeptide, a cell, tissue, cell lysate, tissue lysate, or solution containing or expressing an HDAC9, HDAC9a, HDAC9(ΔNLS), HDAC9a(ΔNLS), or HDRP(ΔNLS) polypeptide (e.g., SEQ ID NO: 2, SEQ ID NO: 4, SEQ ID NO: 6, SE ID NO: 8, SEQ ID NO: 10, or another variant encoded by HDAC9, HDAC9a, HDAC9(ΔNLS), HDAC9a (ΔNLS), or HDRP(ΔNLS)), or a fragment or derivative thereof (as described above), can be contacted with a candidate compound to be tested under conditions suitable for enzymatic reaction or transcriptional repression reaction, as described herein.

Alternatively, the polypeptide can be contacted directly with the candidate compound to be tested. The level (amount) of HDAC9, HDAC9a, HDAC9(ΔNLS), HDAC9a(ΔNLS), or HDRP(ΔNLS) biological activity is assessed (e.g., the level (amount) of HDAC9, HDAC9a, HDAC9(ΔNLS), HDAC9a (ΔNLS), or HDRP(ΔNLS) biological activity is measured, either directly or indirectly), and is compared with the level of biological activity in a control (i.e., the level of activity of the HDAC9, HDAC9a, HDAC9(ΔNLS), HDAC9a(ΔNLS), or HDRP(ΔNLS) polypeptide or active fragment or derivative thereof in the absence of the candidate compound to be tested, or in the presence of the candidate compound vehicle only). If the level of the biological activity in the presence of the candidate compound differs, by an amount that is statistically significant, from the level of the biological activity in the absence of the candidate compound, or in the presence of the candidate compound vehicle only, then the candidate compound is a compound that alters the biological activity of an HDAC9, HDAC9a, HDAC9(ΔNLS), HDAC9a(ΔNLS), or HDRP(ΔNLS) polypeptide. For example, an increase in the level of HDAC9, HDAC9a, HDAC9(ΔNLS), HDAC9a (ΔNLS), or HDRP(ΔNLS) enzymatic or transcriptional repression activity relative to a control, indicates that the candidate compound is a compound that enhances (is an agonist of) HDAC9, HDAC9a, HDAC9(ΔNLS), HDAC9a (ΔNLS), or HDRP(ΔNLS) activity. Similarly, a decrease in the enzymatic level or transcriptional repression level of HDAC9, HDAC9a, HDAC9(ΔNLS), HDAC9a(ΔNLS), or HDRP(ΔNLS) activity relative to a control, indicates that the candidate compound is a compound that inhibits (is an antagonist of) HDAC9, HDAC9a, HDAC9(ΔNLS), HDAC9a (ΔNLS), or HDRP(ΔNLS) activity. In another embodiment, the level of biological activity of an HDAC9, HDAC9a, HDAC9(ΔNLS), HDAC9a(ΔNLS), or HDRP(ΔNLS) polypeptide or derivative or fragment thereof in the presence of the candidate compound to be tested, is compared with a control level that has previously been established. A level of the biological activity in the presence of the candidate compound that differs from the control level by an amount that is statistically significant indicates that the compound alters HDAC9, HDAC9a, HDAC9(ΔNLS), HDAC9a(ΔNLS), or HDRP(ΔNLS) biological activity.

The present invention also relates to an assay for identifying compounds that alter the expression of an HDAC9, HDAC9a, HDAC9(ΔNLS), HDAC9a(ΔNLS), or HDRP (ΔNLS) nucleic acid molecule (e.g., antisense nucleic acids, fusion proteins, polypeptides, peptidomimetics, prodrugs, receptors, binding agents, antibodies, small molecules or other drugs, or ribozymes) that alter (e.g., increase or decrease) expression (e.g., transcription or translation) of the nucleic acid molecule or that otherwise interact with the nucleic acids described herein, as well as compounds identifiable by the assays. For example, a solution containing a nucleic acid encoding an HDAC9, HDAC9a, HDAC9 (ΔNLS), HDAC9a(ΔNLS), or HDRP(ΔNLS) polypeptide can be contacted with a candidate compound to be tested. The solution can comprise, for example, cells containing the nucleic acid or cell lysate containing the nucleic acid; alternatively, the solution can be another solution that comprises elements necessary for transcription/translation of the nucleic acid. Cells not suspended in solution can also be employed, if desired. The level and/or pattern of HDAC9, HDAC9a, HDAC9(ΔNLS), HDAC9a(ΔNLS), or HDRP(ΔNLS) expression (e.g., the level and/or pattern of mRNA or of protein expressed, such as the level and/or pattern of different variants) is assessed, and is compared with the level and/or pattern of expression in a control (i.e., the level and/or pattern of HDAC9, HDAC9a, HDAC9(ΔNLS), HDAC9a(ΔNLS), or HDRP(ΔNLS) expression in the absence of the candidate compound, or in the presence of the candidate compound vehicle only). If the level and/or pattern in the presence of the candidate compound differs, by an amount or in a manner that is statistically significant, from the level and/or pattern in the absence of the candidate compound, or in the presence of the candidate compound vehicle only, then the candidate compound is a compound that alters the expression of HDAC9, HDAC9a, HDAC9(ΔNLS), HDAC9a(ΔNLS), or HDRP (ΔNLS). Enhancement of HDAC9, HDAC9a, HDAC9 (ΔNLS), HDAC9a(ΔNLS), or HDRP(ΔNLS) expression indicates that the candidate compound is an agonist of HDAC9, HDAC9a, HDAC9(ΔNLS), HDAC9a(ΔNLS), or HDRP(ΔNLS) activity. Similarly, inhibition of HDAC9, HDAC9a, HDAC9(ΔNLS), HDAC9a(ΔNLS), or HDRP (ΔNLS) expression indicates that the candidate compound is an antagonist of HDAC9, HDAC9a, HDAC9(ΔNLS), HDAC9a(ΔNLS), or HDRP(ΔNLS) activity. In another embodiment, the level and/or pattern of an HDAC9, HDAC9a, HDAC9(ΔNLS), HDAC9a(ΔNLS), or HDRP (ΔNLS) polypeptide(s) (e.g., different variants) in the presence of the candidate compound to be tested, is compared with a control level and/or pattern that has previously been established. A level and/or pattern in the presence of the candidate compound that differs from the control level and/or pattern by an amount or in a manner that is statistically significant indicates that the candidate compound alters HDAC9, HDAC9a, HDAC9(ΔNLS), HDAC9a(ΔNLS), or HDRP(ΔNLS) expression.

In another embodiment of the invention, compounds that alter the expression of an HDAC9, HDAC9a, HDAC9 (ΔNLS), HDAC9a(ΔNLS), or HDRP(ΔNLS) nucleic acid molecule or that otherwise interact with the nucleic acids described herein, can be identified using a cell, cell lysate, or solution containing a nucleic acid encoding the promoter region of the HDAC9, HDAC9a, HDAC9(ΔNLS), HDAC9a (ΔNLS), or HDRP(ΔNLS) gene operably linked to a reporter gene. After contact with a candidate compound to be tested, the level of expression of the reporter gene (e.g., the level of mRNA or of protein expressed) is assessed, and is compared with the level of expression in a control (i.e., the level of the expression of the reporter gene in the absence of the candidate compound, or in the presence of the candidate compound vehicle only). If the level in the presence of the candidate compound differs, by an amount or in a manner that is statistically significant, from the level in the absence of the candidate compound, or in the presence of the candidate compound vehicle only, then the candidate compound is a compound that alters the expression of HDAC9, HDAC9a, HDAC9 (ΔNLS), HDAC9a(ΔNLS), or HDRP(ΔNLS), as indicated by its ability to alter expression of a gene that is operably linked to the HDAC9, HDAC9a, HDAC9(ΔNLS), HDAC9a(ΔNLS), or HDRP(ΔNLS) gene promoter. Enhancement of the expression of the reporter indicates that the compound is an agonist of HDAC9, HDAC9a, HDAC9(ΔNLS), HDAC9a(ΔNLS), or HDRP(ΔNLS) activity. Similarly, inhibition of the expression of the reporter indicates that the compound is an antagonist of HDAC9, HDAC9a, HDAC9(ΔNLS), HDAC9a (ΔNLS), or HDRP(ΔNLS) activity. In another embodiment, the level of expression of the reporter in the presence of the candidate compound to be tested, is compared with a control level that has previously been established. A level in the presence of the candidate compound that differs from the control level by an amount or in a manner that is statistically significant indicates that the candidate compound alters HDAC9, HDAC9a, HDAC9(ΔNLS), HDAC9a(ΔNLS), or HDRP(ΔNLS) expression.

Compounds that alter the amounts of different variants encoded by HDAC9, HDAC9a, HDAC9(ΔNLS), HDAC9a (ΔNLS), or HDRP(ΔNLS) (e.g., a compound that enhances activity of a first variant, and that inhibits activity of a second variant), as well as compounds that are agonists of activity of a first variant and antagonists of activity of a second variant, can easily be identified using these methods described above.

In other embodiments of the invention, assays can be used to assess the impact of a candidate compound on the activity of a polypeptide in relation to an HDAC9, HDAC9a, HDAC9 (ΔNLS), HDAC9a(ΔNLS), or HDRP(ΔNLS) substrate, for example, an inhibitor of histone deacetylase activity. These inhibitors fall into four general classes: 1) short-chain fatty acids (e.g., 4-phenylbutyrate and valproic acid); 2) hydroxamic acids (e.g., SAHA, Pyroxamide, trichostatin A (TSA), oxamflatin and CHAPs, such as, CHAP1 and CHAP 31); 3) cyclic tetrapeptides (Trapoxin A, Apicidin and Depsipeptide (FK-228, also known as FR9011228); 4) benzamides (e.g., MS-275); and other compounds such as Scriptaid. Examples of such assays and compounds can be found in U.S. Pat. No. 5,369,108, issued on Nov. 29, 1994, U.S. Pat. No. 5,700,811, issued on Dec. 23, 1997, and U.S. Pat. No. 5,773,474, issued on Jun. 30, 1998 to Breslow et al., U.S. Pat. No. 5,055,608, issued on Oct. 8, 1991, and U.S. Pat. No. 5,175,191, issued on Dec. 29, 1992 to Marks et al., as well as, Yoshida et al., supra; Saito et al., supra; Furamai et al., supra; Komatsu et al., supra; Su et al., supra; Lee et al., supra and Suzuki et al. supra, the entire content of all of which are hereby incorporated by reference.

In one example, a cell or tissue that expresses or contains a compound that interacts with HDAC9, HDAC9a, HDAC9 (ΔNLS), HDAC9a(ΔNLS), or HDRP(ΔNLS) (herein referred to as an "HDAC9, HDAC9a, HDAC9(ΔNLS), HDAC9a (ΔNLS), or HDRP(ΔNLS) substrate," which can be a polypeptide or other molecule that interacts with HDAC9, HDAC9a, HDAC9(ΔNLS), HDAC9a(ΔNLS), or HDRP (ΔNLS)) is contacted with HDAC9, HDAC9a, HDAC9 (ΔNLS), HDAC9a(ΔNLS), or HDRP(ΔNLS) in the presence of a candidate compound, and the ability of the candidate compound to alter the interaction between HDAC9, HDAC9a, HDAC9(ΔNLS), HDAC9a(ΔNLS), or HDRP (ΔNLS) and the HDAC9, HDAC9a, HDAC9(ΔNLS), HDAC9a(ΔNLS), or HDRP (ΔNLS) substrate is determined, for example, by assaying activity of the polypeptide. Alternatively, a cell lysate or a solution containing the HDAC9, HDAC9a, HDAC9(ΔNLS), HDAC9a(ΔNLS), or HDRP (ΔNLS) substrate, can be used. A compound that binds to HDAC9, HDAC9a, HDAC9(ΔNLS), HDAC9a(ΔNLS), or HDRP(ΔNLS) or the HDAC9, HDAC9a, HDAC9(ΔNLS), HDAC9a(ΔNLS), or HDRP(ΔNLS) substrate can alter the interaction by interfering with, or enhancing the ability of HDAC9, HDAC9a, HDAC9(ΔNLS), HDAC9a(ΔNLS), or HDRP(ΔNLS) to bind to, associate with, or otherwise interact with the HDAC9, HDAC9a, HDAC9(ΔNLS), HDAC9a (ΔNLS), or HDRP(ΔNLS) substrate.

Determining the ability of the candidate compound to bind to HDAC9, HDAC9a, HDAC9(ΔNLS), HDAC9a(ΔNLS), or HDRP(ΔNLS) or an HDAC9, HDAC9a, HDAC9(ΔNLS), HDAC9a(ΔNLS), or HDRP(ΔNLS) substrate can be accomplished, for example, by coupling the candidate compound with a radioisotope or enzymatic label such that binding of the candidate compound to the polypeptide can be determined by detecting the labeled with $^{125}I$, $^{35}S$, $^{14}C$, or $^{3}H$, either directly or indirectly, and the radioisotope detected by direct counting of radioemmission or by scintillation counting. Alternatively, candidate compound can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a candidate compound to interact with the polypeptide without the labeling of any of the interactants. For example, a microphysiometer can be used to detect the interaction of a candidate compound with HDAC9, HDAC9a, HDAC9(ΔNLS), HDAC9a(ΔNLS), or HDRP(ΔNLS) or an HDAC9, HDAC9a, HDAC9(ΔNLS), HDAC9a(ΔNLS), or HDRP(ΔNLS) substrate without the labeling of either the candidate compound, HDAC9, HDAC9a, HDAC9(ΔNLS), HDAC9a(ΔNLS), or HDRP(ΔNLS), or the HDAC9, HDAC9a, HDAC9(ΔNLS), HDAC9a(ΔNLS), or HDRP (ΔNLS) substrate (McConnell et al., (1992) Science, 257: 1906-1912). As used herein, a "microphysiometer" (e.g., CYTOSENSOR) is an analytical instrument that measures the rate at which a cell acidifies its environment using a light-addressable potentiometric sensor (LAPS). Changes in this acidification rate can be used as an indicator of the interaction between ligand and polypeptide.

In another embodiment of the invention, assays can be used to identify polypeptides that interact with one or more HDAC9, HDAC9a, HDAC9(ΔNLS), HDAC9a(ΔNLS), or HDRP(ΔNLS) polypeptides, as described herein. For example, a yeast two-hybrid system such as that described by Fields and Song (Fields and Song, Nature 340: 245-246 (1989)) can be used to identify polypeptides that interact with one or more HDAC9, HDAC9a, HDAC9(ΔNLS), HDAC9a (ΔNLS), or HDRP(ΔNLS) polypeptides. In such a yeast two-hybrid system, vectors are constructed based on the flexibility of a transcription factor that has two functional domains (a DNA binding domain and a transcription activation domain). If the two domains are separated but fused to two different proteins that interact with one another, transcriptional activation can be achieved, and transcription of specific markers (e.g., nutritional markers such as His and Ade, or color markers such as lacZ) can be used to identify the presence of interaction and transcriptional activation. For example, in the methods of the invention, a first vector is used that includes a nucleic acid encoding a DNA binding domain and an HDAC9, HDAC9a, HDAC9(ΔNLS), HDAC9a(ΔNLS), or HDRP(ΔNLS) polypeptide, variant, or fragment or derivative thereof, and a second vector is used that includes a nucleic acid encoding a transcription activation domain and a nucleic acid encoding a polypeptide that potentially may interact with the HDAC9, HDAC9a, HDAC9(ΔNLS), HDAC9a(ΔNLS), or HDRP(ΔNLS) polypeptide, variant, or fragment or derivative thereof (e.g., an HDAC9, HDAC9a, HDAC9(ΔNLS), HDAC9a(ΔNLS), or HDRP(ΔNLS) polypeptide substrate or receptor). Incubation of yeast containing the first vector and the second vector under appropriate conditions (e.g., mating conditions such as used in the MATCHMAKER™ system from Clontech) allows identification of colonies that express the markers of HDAC9, HDAC9a, HDAC9(ΔNLS), HDAC9a (ΔNLS), or HDRP(ΔNLS). These colonies can be examined to identify the polypeptide(s) that interact with the HDAC9, HDAC9a, HDAC9(ΔNLS), HDAC9a(ΔNLS), or HDRP (ΔNLS) polypeptide or fragment or derivative thereof. Such polypeptides may be useful as compounds that alter the activity or expression of an HDAC9, HDAC9a, HDAC9(ΔNLS), HDAC9a(ΔNLS), or HDRP(ΔNLS) polypeptide, as described above.

In more than one embodiment of the above assay methods of the present invention, it may be desirable to immobilize an HDAC9, HDAC9a, HDAC9(ΔNLS), HDAC9a(ΔNLS), or HDRP(ΔNLS) polypeptide, or an HDAC9, HDAC9a, HDAC9(ΔNLS), HDAC9a(ΔNLS), or HDRP(ΔNLS) substrate, or other components of the assay on a solid support, in order to facilitate separation of complexed from uncomplexed forms of one or both of the polypeptides, as well as to accommodate automation of the assay. Binding of a candidate compound to the polypeptide, or interaction of the polypeptide with a substrate in the presence and absence of a candidate compound, can be accomplished in any vessel suitable for containing the reactants. Examples of such vessels include microtitre plates, test tubes, and micro-centrifuge tubes. In one embodiment, a fusion protein (e.g., a glutathione-S-transferase fusion protein) can be provided that adds a domain that allows HDAC9, HDAC9a, HDAC9(ΔNLS), HDAC9a (ΔNLS), or HDRP(ΔNLS) or an HDAC9, HDAC9a, HDAC9 (ΔNLS), HDAC9a(ΔNLS), or HDRP(ΔNLS) substrate to be bound to a matrix or other solid support.

In another embodiment, modulators of expression of nucleic acid molecules of the invention are identified in a method wherein a cell, cell lysate, tissue, tissue lysate, or solution containing a nucleic acid encoding HDAC9, HDAC9a, HDAC9(ΔNLS), HDAC9a(ΔNLS), or HDRP (ΔNLS) is contacted with a candidate compound and the expression of appropriate mRNA or polypeptide (e.g., variant(s)) in the cell, cell lysate, tissue, or tissue lysate, or solution, is determined. The level of expression of appropriate mRNA or polypeptide(s) in the presence of the candidate compound is compared to the level of expression of mRNA or polypeptide(s) in the absence of the candidate compound, or in the presence of the candidate compound vehicle only. The candidate compound can then be identified as a modulator of expression based on this comparison. For example, when expression of mRNA or polypeptide is greater (statistically significantly greater) in the presence of the candidate compound than in its absence, the candidate compound is identified as a stimulator or enhancer of the mRNA or polypeptide expression. Alternatively, when expression of the mRNA or polypeptide is less (statistically significantly less) in the presence of the candidate compound than in its absence, the candidate compound is identified as an inhibitor of the mRNA or polypeptide expression. The level of mRNA or polypeptide expression in the cells can be determined by methods described herein for detecting mRNA or polypeptide.

This invention further pertains to novel compounds identified by the above-described screening assays. Accordingly, it is within the scope of this invention to further use a compound identified as described herein in an appropriate animal model. For example, a compound identified as described herein (e.g., a candidate compound that is a modulating compound such as an antisense nucleic acid molecule, a specific antibody, or a polypeptide substrate) can be used in an animal model to determine the efficacy, toxicity, or side effects of treatment with such a compound. Alternatively, a compound identified as described herein can be used in an animal model to determine the mechanism of action of such a compound. Furthermore, this invention pertains to uses of novel compounds identified by the above-described screening assays for treatments as described herein. In addition, a compound identified as described herein can be used to alter activity of an HDAC9, HDAC9a, HDAC9(ΔNLS), HDAC9a(ΔNLS), or HDRP(ΔNLS) polypeptide, or to alter expression of HDAC9, HDAC9a, HDAC9(ΔNLS), HDAC9a(ΔNLS), or HDRP (ΔNLS), by contacting the polypeptide or the nucleic acid molecule (or contacting a cell comprising the polypeptide or the nucleic acid molecule) with the compound identified as described herein.

Pharmaceutical Compositions

The present invention also pertains to pharmaceutical compositions comprising nucleic acids described herein, particularly nucleotides encoding the polypeptides described herein; comprising polypeptides described herein (e.g., SEQ ID NO: 2, SEQ ID NO: 4, SEQ ID NO: 6, SEQ ID NO: 8, SEQ ID NO: 10, and/or other variants encoded by HDAC9, HDAC9a, HDAC9(ΔNLS), HDAC9a(ΔNLS), or HDRP(ΔNLS)); and/or comprising a compound that alters (e.g., increases or decreases) HDAC9, HDAC9a, HDAC9(ΔNLS), HDAC9a (ΔNLS), or HDRP(ΔNLS) expression or HDAC9, HDAC9a, HDAC9(ΔNLS), HDAC9a(ΔNLS), or HDRP(ΔNLS) polypeptide activity as described herein. For instance, a polypeptide, protein, fragment, fusion protein or prodrug thereof, or a nucleotide or nucleic acid construct (vector) comprising a nucleotide of the present invention, a compound that alters HDAC9, HDAC9a, HDAC9(ΔNLS), HDAC9a (ΔNLS), or HDRP(ΔNLS) polypeptide activity, a compound that alters HDAC9, HDAC9a, HDAC9(ΔNLS), HDAC9a (ΔNLS), or HDRP(ΔNLS) nucleic acid expression, or an HDAC9, HDAC9a, HDAC9(ΔNLS), HDAC9a(ΔNLS), or HDRP(ΔNLS) substrate or binding partner, can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. Other suitable methods of introduction can also include gene therapy (as described below), rechargeable or biodegradable devices, particle acceleration devises ("gene guns") and slow release polymeric devices. The pharmaceutical compositions of this invention can also be administered as part of a combinatorial therapy with other compounds.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The compound may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The compounds are administered in a therapeutically effective amount. The amount of compounds that will be therapeutically effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the symptoms of a cell proliferation disease, an apoptotic disease, or a cell differentiation disease, and should be decided according to the judgment of a practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, that notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the compounds can be separated, mixed together in any combination, present in a single vial or tablet. Compounds assembled in a blister pack or other dispensing means is preferred. For the purpose of this invention, unit dosage is intended to mean a dosage that is dependent on the individual pharmacodynamics of each compound and administered in FDA approved dosages in standard time courses.

Methods of Therapy

The present invention also pertains to methods of treatment (prophylactic, diagnostic, and/or therapeutic) for a cell proliferation disease, an apoptotic disease, or a cell differentiation disease, using an HDAC9, HDAC9a, HDAC9(ΔNLS), HDAC9a(ΔNLS), or HDRP(ΔNLS) therapeutic compound. An "HDAC9, HDAC9a, HDAC9(ΔNLS), HDAC9a(ΔNLS), or HDRP(ΔNLS) therapeutic compound" is a compound that alters (e.g., enhances or inhibits) HDAC9, HDAC9a, HDAC9(ΔNLS), HDAC9a(ΔNLS), or HDRP(ΔNLS) polypeptide activity and/or HDAC9, HDAC9a, HDAC9(ΔNLS), HDAC9a(ΔNLS), or HDRP(ΔNLS) nucleic acid molecule expression, as described herein (e.g., an HDAC9, HDAC9a, HDAC9(ΔNLS), HDAC9a(ΔNLS), or HDRP(ΔNLS) agonist or antagonist). HDAC9, HDAC9a, HDAC9(ΔNLS), HDAC9a(ΔNLS), or HDRP(ΔNLS) therapeutic compounds can alter HDAC9, HDAC9a, HDAC9(ΔNLS), HDAC9a(ΔNLS), or HDRP(ΔNLS) polypeptide activity or nucleic acid molecule expression by a variety of means, such as, for example, by providing additional HDAC9, HDAC9a, HDAC9(ΔNLS), HDAC9a(ΔNLS), or HDRP(ΔNLS) polypeptide or by upregulating the transcription or translation of the HDAC9, HDAC9a, HDAC9(ΔNLS), HDAC9a(ΔNLS), or HDRP(ΔNLS) nucleic acid molecule; by altering post-translational processing of the HDAC9, HDAC9a, HDAC9(ΔNLS), HDAC9a(ΔNLS), or HDRP(ΔNLS) polypeptide; by altering transcription of HDAC9, HDAC9a, HDAC9(ΔNLS), HDAC9a(ΔNLS), or HDRP(ΔNLS) variants; or by interfering with HDAC9, HDAC9a, HDAC9(ΔNLS), HDAC9a(ΔNLS), or HDRP(ΔNLS) polypeptide activity (e.g., by binding to an HDAC9, HDAC9a, HDAC9(ΔNLS), HDAC9a(ΔNLS), or HDRP(ΔNLS) polypeptide), or by downregulating the transcription or translation of the HDAC9, HDAC9a, HDAC9(ΔNLS), HDAC9a(ΔNLS), or HDRP(ΔNLS) nucleic acid molecule. Representative HDAC9, HDAC9a, HDAC9(ΔNLS), HDAC9a(ΔNLS), or HDRP(ΔNLS) therapeutic compounds include the following: nucleic acids or fragments or derivatives thereof described herein, particularly nucleotides encoding the polypeptides described herein and vectors comprising such nucleic acids (e.g., a nucleic acid molecule, cDNA, and/or RNA, such as a nucleic acid encoding an HDAC9, HDAC9a, HDAC9 (ΔNLS), HDAC9a(ΔNLS), or HDRP(ΔNLS) polypeptide or active fragment or derivative thereof, or an oligonucleotide; for example, SEQ ID NO: 1, SEQ ID NO: 3, SEQ ID NO: 5, SEQ ID NO: 7, or SEQ ID NO: 9, which may optionally comprise at least one polymorphism, or a nucleic acid encoding SEQ ID NO: 2, SEQ ID NO: 4, SEQ ID NO: 6, SEQ ID NO: 8, SEQ ID NO: 10, or fragments or derivatives thereof); polypeptides described herein (e.g., SEQ ID NO: 2, SEQ ID NO: 4, SEQ ID NO: 6, SEQ ID NO: 8 SEQ ID NO: 10 and/or other variants encoded by HDAC9, HDAC9a, HDAC9 (ΔNLS), HDAC9a(ΔNLS), or HDRP(ΔNLS), or fragments or derivatives thereof); HDAC9, HDAC9a, HDAC9(ΔNLS), HDAC9a(ΔNLS), or HDRP(ΔNLS) substrates; peptidomimetics; fusion proteins or prodrugs thereof; antibodies (e.g., an antibody to a mutant HDAC9, HDAC9a, HDAC9(ΔNLS), HDAC9a(ΔNLS), or HDRP(ΔNLS) polypeptide, or an antibody to a non-mutant HDAC9, HDAC9a, HDAC9(ΔNLS), HDAC9a(ΔNLS), or HDRP(ΔNLS) polypeptide, or an antibody to a particular variant encoded by HDAC9, HDAC9a, HDAC9(ΔNLS), HDAC9a(ΔNLS), or HDRP(ΔNLS), as described above); ribozymes; other small molecules; and other compounds that alter (e.g., enhance or inhibit) HDAC9, HDAC9a, HDAC9(ΔNLS), HDAC9a(ΔNLS), or HDRP (ΔNLS) nucleic acid expression or polypeptide activity, for example, those compounds identified in the screening methods described herein, or that regulate transcription of HDAC9, HDAC9a, HDAC9(ΔNLS), HDAC9a(ΔNLS), or HDRP(ΔNLS) variants (e.g., compounds that affect which variants are expressed, or that affect the amount of each variant that is expressed. More than one HDAC9, HDAC9a, HDAC9(ΔNLS), HDAC9a(ΔNLS), or HDRP(ΔNLS) therapeutic compound can be used concurrently, if desired.

The HDAC9, HDAC9a, HDAC9(ΔNLS), HDAC9a (ΔNLS), or HDRP(ΔNLS) therapeutic compound that is a nucleic acid is used in the treatment of a cell proliferation disease, an apoptotic disease, or a cell differentiation disease. The term, "treatment" as used herein, refers not only to ameliorating symptoms associated with the disease, but also preventing or delaying the onset of the disease, and also lessening the severity or frequency of symptoms of the disease. The therapy is designed to alter (e.g., inhibit or enhance), replace or supplement activity of an HDAC9, HDAC9a, HDAC9 (ΔNLS), HDAC9a(ΔNLS), or HDRP(ΔNLS) polypeptide in an individual. For example, an HDAC9, HDAC9a, HDAC9 (ΔNLS), HDAC9a(ΔNLS), or HDRP(ΔNLS) therapeutic compound can be administered in order to upregulate or increase the expression or availability of the HDAC9, HDAC9a, HDAC9(ΔNLS), HDAC9a(ΔNLS), or HDRP (ΔNLS) nucleic acid molecule or of specific variants of HDAC9, HDAC9a, HDAC9(ΔNLS), HDAC9a(ΔNLS), or HDRP(ΔNLS), or, conversely, to downregulate or decrease the expression or availability of the HDAC9, HDAC9a, HDAC9(ΔNLS), HDAC9a(ΔNLS), or HDRP(ΔNLS) nucleic acid molecule or specific variants of HDAC9, HDAC9a, HDAC9(ΔNLS), HDAC9a(ΔNLS), or HDRP(ΔNLS). Upregulation or increasing expression or availability of a native HDAC9, HDAC9a, HDAC9(ΔNLS), HDAC9a (ΔNLS), or HDRP(ΔNLS) nucleic acid molecule or of a particular variant could interfere with or compensate for the expression or activity of a defective gene or another variant; downregulation or decreasing expression or availability of a native HDAC9, HDAC9a, HDAC9(ΔNLS), HDAC9a (ΔNLS), or HDRP(ΔNLS) nucleic acid molecule or of a particular variant could minimize the expression or activity of a defective gene or the particular variant and thereby minimize the impact of the defective gene or the particular variant.

The HDAC9, HDAC9a, HDAC9(ΔNLS), HDAC9a (ΔNLS), or HDRP(ΔNLS) therapeutic compound(s) are administered in a therapeutically effective amount (i.e., an amount that is sufficient to treat the disease, such as by ameliorating symptoms associated with the disease, preventing or delaying the onset of the disease, and/or also lessening the severity or frequency of symptoms of the disease). The amount that will be therapeutically effective in the treatment of a particular individual's disorder or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

In one embodiment, a nucleic acid of the invention (e.g., a nucleic acid encoding an HDAC9, HDAC9a, HDAC9 (ΔNLS), HDAC9a(ΔNLS), or HDRP(ΔNLS) polypeptide, such as SEQ ID NO: 1, SEQ ID NO: 3, SEQ ID NO: 5, SEQ ID NO: 7, or SEQ ID NO: 9, which may optionally comprise at least one polymorphism, or a nucleic acid that encodes an HDAC9, HDAC9a, HDAC9(ΔNLS), HDAC9a(ΔNLS), or HDRP(ΔNLS) polypeptide or a variant, derivative or fragment thereof, such as a nucleic acid encoding the protein of SEQ ID NO: 2, SEQ ID NO: 4, SEQ ID NO: 6, SEQ ID NO: 8, or SEQ ID NO: 10) can be used, either alone or in a pharmaceutical composition as described above. For example, HDAC9, HDAC9a, HDAC9(ΔNLS), HDAC9a (ΔNLS), or HDRP(ΔNLS) or a cDNA encoding an HDAC9, HDAC9a, HDAC9(ΔNLS), HDAC9a(ΔNLS), or HDRP (ΔNLS) polypeptide, either by itself or included within a vector, can be introduced into cells (either in vitro or in vivo) such that the cells produce native HDAC9, HDAC9a, HDAC9 (ΔNLS), HDAC9a(ΔNLS), or HDRP(ΔNLS) polypeptide. If desired, cells that have been transformed with the gene or cDNA or a vector comprising the gene or cDNA can be introduced (or re-introduced) into an individual affected with the disease. Thus, cells that, in nature, lack native HDAC9, HDAC9a, HDAC9(ΔNLS), HDAC9a(ΔNLS), or HDRP (ΔNLS) expression and activity, or have mutant HDAC9, HDAC9a, HDAC9(ΔNLS), HDAC9a(ΔNLS), or HDRP (ΔNLS) expression and activity, or have expression of a disease-associated HDAC9, HDAC9a, HDAC9(ΔNLS), HDAC9a(ΔNLS), or HDRP(ΔNLS) variant, can be engineered to express an HDAC9, HDAC9a, HDAC9(ΔNLS), HDAC9a(ΔNLS), or HDRP(ΔNLS) polypeptide or an active fragment of an HDAC9, HDAC9a, HDAC9(ΔNLS), HDAC9a(ΔNLS), or HDRP(ΔNLS) polypeptide (or a different variant of an HDAC9, HDAC9a, HDAC9(ΔNLS), HDAC9a(ΔNLS), or HDRP(ΔNLS) polypeptide). In a preferred embodiment, nucleic acid encoding the HDAC9, HDAC9a, HDAC9(ΔNLS), HDAC9a(ΔNLS), or HDRP (ΔNLS) polypeptide, or an active fragment or derivative thereof, can be introduced into an expression vector, such as a viral vector, and the vector can be introduced into appropriate cells in an animal. Other gene transfer systems, including viral and nonviral transfer systems, can be used. Alternatively, nonviral gene transfer methods, such as calcium phosphate coprecipitation, mechanical techniques (e.g., microinjection); membrane fusion-mediated transfer via liposomes; or direct DNA uptake, can also be used to introduce the desired nucleic acid molecule into a cell.

Alternatively, in another embodiment of the invention, a nucleic acid of the invention; a nucleic acid complementary to a nucleic acid of the invention; or a portion of such a nucleic acid (e.g., an oligonucleotide as described below), can be used in "antisense" therapy, in which a nucleic acid (e.g., an oligonucleotide) that specifically hybridizes to the RNA and/or genomic DNA of HDAC9, HDAC9a, HDAC9(ΔNLS), HDAC9a(ΔNLS), or HDRP(ΔNLS) is administered or generated in situ. The antisense nucleic acid that specifically hybridizes to the RNA and/or DNA inhibits expression of the HDAC9, HDAC9a, HDAC9(ΔNLS), HDAC9a(ΔNLS), or HDRP(ΔNLS) nucleic acid molecule, e.g., by inhibiting translation and/or transcription. Binding of the antisense nucleic acid can be by conventional base pair complementarity, or, for example, in the case of binding to DNA duplexes, through specific interaction in the major groove of the double helix.

An antisense construct of the present invention can be delivered, for example, as an expression plasmid as described above. When the plasmid is transcribed in the cell, it produces RNA that is complementary to a portion of the mRNA and/or DNA that encodes an HDAC9, HDAC9a, HDAC9(ΔNLS), HDAC9a(ΔNLS), or HDRP(ΔNLS) polypeptide. Alternatively, the antisense construct can be an oligonucleotide probe which is generated ex vivo and introduced into cells; it then inhibits expression by hybridizing with the mRNA and/or genomic DNA of HDAC9, HDAC9a, HDAC9(ΔNLS), HDAC9a(ΔNLS), or HDRP(ΔNLS). In one embodiment, the oligonucleotide probes are modified oligonucleotides that are resistant to endogenous nucleases, e.g. exonucleases and/or endonucleases, thereby rendering them stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy are also described, for example, by Van der Krol et al., Biotechniques 6: 958-976 (1988); and Stein et al., Cancer Res 48: 2659-2668 (1988). With respect to antisense DNA, oligodeoxyribonucleotides derived from the translation initiation site, e.g. between the −10 and +10 regions of an HDAC9, HDAC9a, HDAC9(ΔNLS), HDAC9a(ΔNLS), or HDRP (ΔNLS) nucleic acid sequence, are preferred.

To perform antisense therapy, oligonucleotides (RNA, cDNA or DNA) are designed that are complementary to mRNA encoding an HDAC9, HDAC9a, HDAC9(ΔNLS), HDAC9a(ΔNLS), or HDRP(ΔNLS) polypeptide. The antisense oligonucleotides bind to HDAC9, HDAC9a, HDAC9 (ΔNLS), HDAC9a(ΔNLS), or HDRP(ΔNLS) mRNA transcripts and prevent translation. Absolute complementarity, although preferred, is not required. A sequence "complementary" to a portion of an RNA, as referred to herein, indicates that a sequence has sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid, as described in detail above. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures.

The oligonucleotides used in antisense therapy can be DNA, RNA, or chimeric mixtures or derivatives or modified versions thereof, single-stranded or double-stranded. The oligonucleotides can be modified at the base moiety, sugar moiety, or phosphate backbone, for example, to improve stability of the molecule, hybridization, etc. The oligonucleotides can include other appended groups such as peptides (e.g. for targeting host cell receptors in vivo), or compounds facilitating transport across the cell membrane (see, e.g., Letsinger et al., Proc. Natl. Acad. Sci. USA 86: 6553-6556 (1989); Lemaitre et al., Proc. Natl. Acad Sci. USA 84: 648-652 (1987); PCT International Publication No. WO88/09810)) or the blood-brain barrier (see, e.g., PCT International Publication No. WO89/10134), or hybridization-triggered cleavage agents (see, e.g., Krol et al., BioTechniques 6: 958-976 (1988)) or intercalating agents. (See, e.g., Zon, Pharm. Res. 5: 539-549 (1988)). To this end, the oligonucleotide may be conjugated to another molecule (e.g., a peptide, hybridization triggered cross-linking agent, transport agent, hybridization-triggered cleavage agent).

The antisense molecules are delivered to cells that express HDAC9, HDAC9a, HDAC9(ΔNLS), HDAC9a(ΔNLS), or HDRP(ΔNLS) in vivo. A number of methods can be used for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically. Alternatively, in a preferred embodiment, a recombinant DNA construct is utilized in which the antisense oligonucleotide is placed under the control of a strong promoter (e.g., pol III or pol II). The use of such a construct to transfect target cells in the patient results in the transcription of sufficient amounts of single stranded RNAs that will form complementary base pairs with the endogenous HDAC9, HDAC9a, HDAC9 (ΔNLS), HDAC9a(ΔNLS), or HDRP(ΔNLS) transcripts and thereby prevent translation of the HDAC9, HDAC9a, HDAC9 (ΔNLS), HDAC9a(ΔNLS), or HDRP(ΔNLS) mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art and described above. For example, a plasmid, cosmid, YAC, or viral vector can be used to prepare the recombinant DNA construct that can be introduced directly into the tissue site. Alternatively, viral vectors can be used that selectively infect the desired tissue, in which case administration may be accomplished by another route (e.g., systematically).

Endogenous HDAC9, HDAC9a, HDAC9(ΔNLS), HDAC9a(ΔNLS), or HDRP(ΔNLS) expression can also be reduced by inactivating or "knocking out" HDAC9, HDAC9a, HDAC9(ΔNLS), HDAC9a(ΔNLS), or HDRP (ΔNLS) nucleic acid sequences or their promoters using targeted homologous recombination (e.g., see Smithies et al., Nature 317: 230-234 (1985); Thomas and Capecchi, Cell 51: 503-512 (1987); Thompson et al., Cell 5: 313-321 (1989)). For example, a mutant, non-functional HDAC9, HDAC9a, HDAC9(ΔNLS), HDAC9a(ΔNLS), or HDRP(ΔNLS) (or a completely unrelated DNA sequence) flanked by DNA homologous to the endogenous HDAC9, HDAC9a, HDAC9

(ΔNLS), HDAC9a(ΔNLS), or HDRP(ΔNLS) (either the coding regions or regulatory regions of HDAC9, HDAC9a, HDAC9(ΔNLS), HDAC9a(ΔNLS), or HDRP(ΔNLS)) can be used, with or without a selectable marker and/or a negative selectable marker, to transfect cells that express HDAC9, HDAC9a, HDAC9(ΔNLS), HDAC9a(ΔNLS), or HDRP (ΔNLS) in vivo. Insertion of the DNA construct, via targeted homologous recombination, results in inactivation of HDAC9, HDAC9a, HDAC9(ΔNLS), HDAC9a(ΔNLS), or HDRP(ΔNLS). The recombinant DNA constructs can be directly administered or targeted to the required site in vivo using appropriate vectors, as described above. Alternatively, expression of non-mutant HDAC9, HDAC9a, HDAC9 (ΔNLS), HDAC9a(ΔNLS), or HDRP(ΔNLS) can be increased using a similar method: Targeted homologous recombination can be used to insert a DNA construct comprising a non-mutant, functional HDAC9, HDAC9a, HDAC9 (ΔNLS), HDAC9a(ΔNLS), or HDRP(ΔNLS) (e.g., a gene having SEQ ID NO: 1, SEQ ID NO: 3, SEQ ID NO: 5, SEQ ID NO: 7, or SEQ ID NO: 9, which may optionally comprise at least one polymorphism), or a portion thereof, in place of a mutant HDAC9, HDAC9a, HDAC9(ΔNLS), HDAC9a (ΔNLS), or HDRP(ΔNLS) in the cell, as described above. In another embodiment, targeted homologous recombination can be used to insert a DNA construct comprising a nucleic acid that encodes an HDAC9, HDAC9a, HDAC9(ΔNLS), HDAC9a(ΔNLS), or HDRP(ΔNLS) polypeptide variant that differs from that present in the cell.

Alternatively, endogenous HDAC9, HDAC9a, HDAC9 (ΔNLS), HDAC9a(ΔNLS), or HDRP(ΔNLS) expression can be reduced by targeting deoxyribonucleotide sequences complementary to the regulatory region of HDAC9, HDAC9a, HDAC9(ΔNLS), HDAC9a(ΔNLS), or HDRP (ΔNLS) (i.e., the HDAC9, HDAC9a, HDAC9(ΔNLS), HDAC9a(ΔNLS), or HDRP(ΔNLS) promoter and/or enhancers) to form triple helical structures that prevent transcription of HDAC9, HDAC9a, HDAC9(ΔNLS), HDAC9a(ΔNLS), or HDRP(ΔNLS) in target cells in the body. (See generally, Helene Anticancer Drug Des., 6(6): 569-84 (1991); Helene et al., Ann, N.Y. Acad. Sci., 660: 27-36 (1992); and Maher, Bioassays 14(12): 807-15 (1992)). Likewise, the antisense constructs described herein, by antagonizing the normal biological activity of one of the HDAC9, HDAC9a, HDAC9 (ΔNLS), HDAC9a(ΔNLS), or HDRP(ΔNLS) proteins, can be used in the manipulation of tissue, e.g., tissue differentiation, both in vivo and for ex vivo tissue cultures. Furthermore, the antisense techniques (e.g., microinjection of antisense molecules, or transfection with plasmids whose transcripts are anti-sense with regard to an HDAC9, HDAC9a, HDAC9 (ΔNLS), HDAC9a(ΔNLS), or HDRP(ΔNLS) mRNA or gene sequence) can be used to investigate role of HDAC9, HDAC9a, HDAC9(ΔNLS), HDAC9a(ΔNLS), or HDRP (ΔNLS) in developmental events, as well as the normal cellular function of HDAC9, HDAC9a, HDAC9(ΔNLS), HDAC9a(ΔNLS), or HDRP(ΔNLS) in adult tissue. Such techniques can be utilized in cell culture, but can also be used in the creation of transgenic animals.

In yet another embodiment of the invention, other HDAC9, HDAC9a, HDAC9(ΔNLS), HDAC9a(ΔNLS), or HDRP (ΔNLS) therapeutic compounds as described herein can also be used in the treatment or prevention of a cell proliferation disease, an apoptotic disease, or a cell differentiation disease. The therapeutic compounds can be delivered in a composition, as described above, or by themselves. They can be administered systemically, or can be targeted to a particular tissue. The therapeutic compounds can be produced by a variety of means, including chemical synthesis; recombinant production; in vivo production (e.g., a transgenic animal, such as U.S. Pat. No. 4,873,316 to Meade et al.), for example, and can be isolated using standard means such as those described herein.

A combination of any of the above methods of treatment (e.g., administration of non-mutant HDAC9, HDAC9a, HDAC9(ΔNLS), HDAC9a(ΔNLS), or HDRP(ΔNLS) polypeptide in conjunction with antisense therapy targeting mutant HDAC9, HDAC9a, HDAC9(ΔNLS), HDAC9a (ΔNLS), or HDRP(ΔNLS) mRNA; administration of a first variant encoded by HDAC9, HDAC9a, HDAC9(ΔNLS), HDAC9a(ΔNLS), or HDRP(ΔNLS) in conjunction with antisense therapy targeting a second encoded by HDAC9, HDAC9a, HDAC9(ΔNLS), HDAC9a(ΔNLS), or HDRP (ΔNLS), can also be used.

In another embodiment, the invention is directed to HDAC9, HDAC9a, HDAC9(ΔNLS), HDAC9a(ΔNLS), or HDRP(ΔNLS) nucleic acid molecules and HDAC9, HDAC9a, HDAC9(ΔNLS), HDAC9a(ΔNLS), or HDRP (ΔNLS) polypeptides for use as a medicament in therapy. For example, the nucleic acid molecules or polypeptides of the present invention can be used in the treatment of a cell proliferation disease, an apoptotic disease, or a cell differentiation disease. In addition, the HDAC9, HDAC9a, HDAC9 (ΔNLS), HDAC9a(ΔNLS), or HDRP(ΔNLS) nucleic acid molecules and HDAC9, HDAC9a, HDAC9(ΔNLS), HDAC9a(ΔNLS), or HDRP(ΔNLS) polypeptides described herein can be used in the manufacture of a medicament for the treatment of a cell proliferation disease, an apoptotic disease, or a cell differentiation disease.

The invention will be further described by the following non-limiting examples. The teachings of all publications cited herein are incorporated herein by reference in their entirety.

Exemplification

Cloning of cDNA Encodes a Novel HDAC, Designated HDAC9

HDAC9 was cloned by PCR and 3' rapid amplification of cDNA ends using primers designed from the sequence of human chromosome 7 whose translated product exhibited 80% identity to the HDAC domain of HDAC4, described in detail as follows.

Database analyses indicate that HDRP is located on chromosome 7 (7p15-p21). The human genome database (February 2001 release) of GenBank was searched using the human HDAC4 amino acid sequence. The TBLASTN program was used to identify open reading frames downstream of HDRP on chromosome 7 that exhibit significant homology to the HDAC domain of HDAC4. Several fragments whose translated products exhibit over 58% identity were retrieved. Two sense primers (OL486, 5'-CCATGGAAACGGTACCCAGCAGGC-3' (SEQ ID NO: 16) and OL487, 5'-CACTCCATCGCTATGATGAAGGG-3' (SEQ ID NO: 17)) and antisense primers (OL484, 5'-AGTTCCCTTCATCATAGCGATGG-3' (SEQ ID NO: 18) and OL485, 5'-AATGTACAGGATGCTGGGGT-3' (SEQ ID NO: 19)) each were designed based upon one of these fragments whose translated products matched amino acids 842-873 of HDAC4. RT-PCR was performed using each of the antisense primers and a sense primer (5'-CCCTTGTAGCTGGTGGAGTTCCCTT-3' (SEQ ID NO: 20)) from the coding region of HDRP and human brain cDNA as a template. PCR was performed in a Biometra TGRADIENT Thermocycler for 30 cycles at 95° C. for 20 seconds, 60° C. for 20 seconds, and 72° C. for 120 seconds.

3'-rapid amplification of cDNA ends was performed using the sense primer OL486 and adaptor primer 1 (Clontech), and marathon-ready cDNA from human brain (Clontech, Palo Alto, Calif.) according to the manufacturer's instruction. The products were re-amplified using nested sense primer OL487 and adaptor primer 2 (Clontech, Palo Alto, Calif.). PCR products were cloned into pGEM®-T-easy vector (Promega, Madison, Wis.) and sequenced using an automated DNA sequencer at the DNA Sequencing Core Facility of the Memorial Sloan-Kettering Cancer Center, using DNA sequencing methods known to one of skill in the art.

Two cDNAs were cloned from the above-described methods. One cDNA (SEQ ID NO:1) encodes an HDAC9 protein that is 1011 amino acids in length. The other cDNA (SEQ ID NO: 3) encodes an HDAC9a protein that is 879 amino acids long. The cDNA sequence and amino sequence of HDAC9 and HDAC9a are shown in FIGS. 1A-1G and FIGS. 2A-2B, respectively. Database analyses of these cDNAs against human genomic DNA sequences indicated that these two cDNAs are generated by alternatively splicing. An alignment of HDAC9, HDAC9a, HDRP, and HDAC4 is shown in FIGS. 3A-3C.

Each of the HDAC9 and HDAC9a nucleic acid sequences were cloned into the pFLAG-CMV-5b vector (Sigma) in frame with the C-terminal FLAG tag. Only the coding regions plus three extra base pairs (ACC) of cDNA of the HDAC9 and HDAC9a nucleic acid sequences were included in the constructs. These constructs are referred to herein as HDAC9-FLAG and HDAC9a-FLAG, respectively. These constructs are contained in *E. coli*, and can readily be expressed. For HDAC9, the insert is 3033 bp and for HDAC9a, the insert size is 2637 bp. Both HDAC9 and HDAC9a can be released with EcoRV and BamHI (whose sites have been incorporated in the primers to obtain HDAC9 and HDAC9a coding cDNA for cloning purpose) restriction enzyme digestion.

Figure 4:
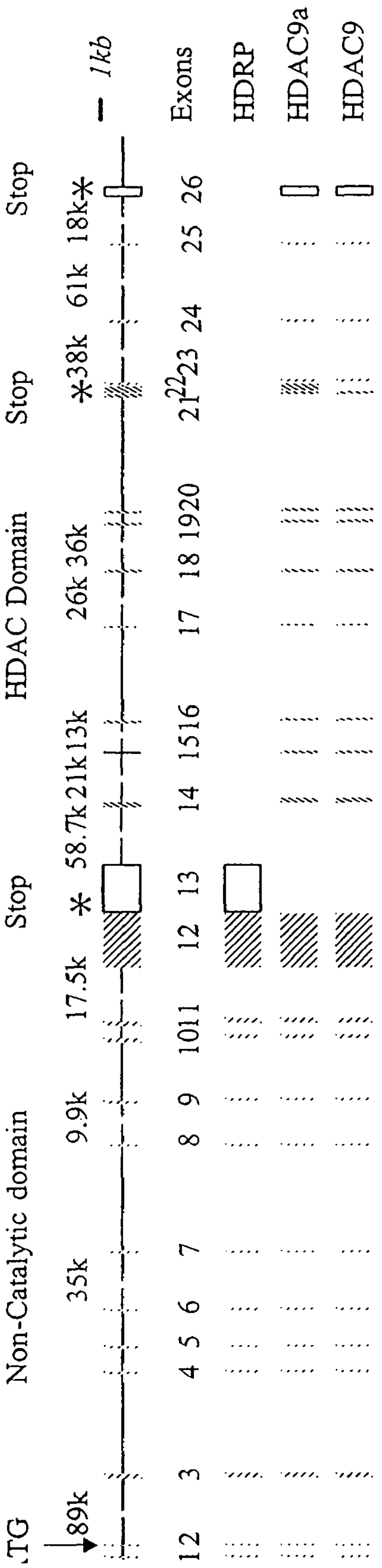
FIG. 4 shows a schematic representation of the human HDAC9 gene structure. The striped boxes represent exons present in isoforms HDRP, HDAC9a, and HDAC9. The lines represent introns. Broken lines are used for larger introns (with size in base pair on top). The 5' untranslated region cDNA and coding region cDNA are represented here. Exons 1-12 encode a non-catalytic domain of the polypeptides, and exons 14-21 encode the histone deacetylase catalytic domain of the polypeptides, which provide the polypeptides with deacetylase activity.
Figure 5:
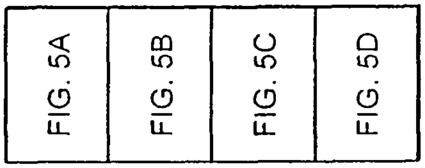
FIG. 5 is a schematic representation of the order in which FIGS. 5A-5D should be viewed.

The HDAC9 cDNA sequences from the known 5'-end of HDRP cDNA to the 3'-untranslated region cloned in this study cover over 511 kb of genomic DNA on chromosome 7. As shown in FIG. 4, the coding region cDNA of HDAC9 resides in 23 exons spanning 458 kb of genomic sequence. Exons 21, 22, and 23 are one single exon in HDAC9a, but the middle exon that is numbered exon 22 in FIG. 4, containing an in-frame stop codon, is spliced out in HDAC9. In addition, exons 12 and 13 are a single exon used by HDRP. Exon 13 is spliced as part of an intron in HDAC9 and HDAC9a.

Further analysis revealed that exon 7, which contains a nuclear localization signal (NLS) is alternatively spliced in an HDRP isoform, creating HDRP(ΔNLS). RT-PCR analyses using primers based on sequences from exon 6 and exon 14 indicate that this alternative splicing event also occurs in HDAC9 and/or HDAC9a. Thus, it is possible that at least 6 proteins can be generated from a single HDAC9 gene by alternatively splicing of its RNA. The cDNA sequences and amino acid sequences for HDAC9, HDAC9a, HDAC9 (ΔNLS), HDAC9a(ΔNLS), and HDRP(ΔNLS) are shown in FIGS. 1A-1O and 2A-2E, respectively.

HDAC9 mRNA is Differentially Expressed Among Human Tissues

Figure 6A:
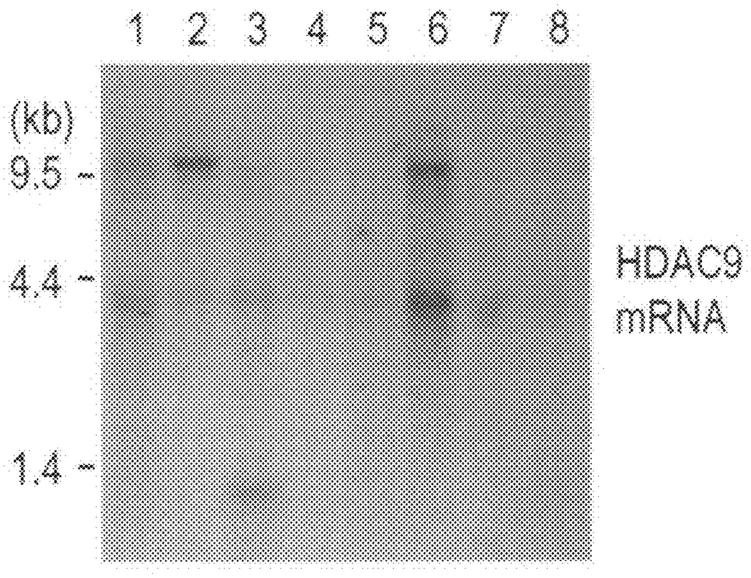
FIG. 6A is a scanned imaged of a multiple human tissue Northern blot that was probed to determine mRNA expression of HDAC9 using a cDNA probe that recognizes both HDAC9 and HDAC9a. The tissues examined are lane 1, heart; lane 2, brain; lane 3, placenta; lane 4, lung; lane 5, liver; lane 6, skeletal muscle; lane 7, kidney; and lane 8, pancreas. Positions of the RNA size marker in kilobases (kb) are indicated to the left of the blot.

The expression of HDAC9 mRNA was determined by Northern blot analysis using a human multiple tissue Northern blot (Clontech, Palo Alto, Calif.). Hybridization was performed according to the manufacturer's instruction using ExPressHyb solution (Clontech, Palo Alto, Calif.). The $^{32}P$-random priming labeled 3'-untranslated region common to both HDAC9 and HDAC9a that shares no significant sequence homology with HDRP was used as a probe. Two transcripts at 9.8 and 4.1 kb were detected in all tissues examined (FIG. 6A). The 4.1 kb transcript is shorter than the 4.4 kb HDRP transcript (See Zhou, et al., Proc. Natl. Acad. Sci. USA, 97: 1056-1061 (2000)). A third transcript at 1.2 kb was detected in placenta (FIG. 6A). Similar to HDRP (See Zhou, X., et al., Proc. Natl. Acad. Sci. USA, 97:1056-1061 (2000)), high levels of HDAC9 transcripts were detected in brain and skeletal muscle (FIG. 6A).

Figure 6B:
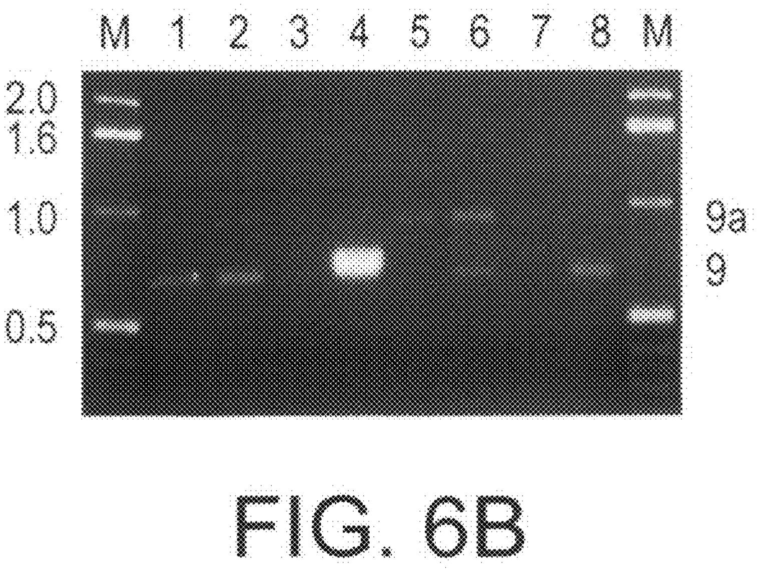
FIG. 6B is a scanned image of an electrophoretic gel showing the results of RT-PCR analyses of mRNA from the same tissues as examined in the Northern blot of FIG. 6A to determine the distribution of HDAC9 and HDAC9a mRNA among these tissues. PCR products were resolved by agarose gel electrophoresis and visualized by ethidium bromide under UV light. A 1-kb DNA ladder was run on both sides of the gel with the size (in kb) indicated on the left. On the right side, the expected products for HDAC9 and HDAC9a are indicated as 9 and 9a, respectively.

The distribution of alternatively spliced mRNA variants among tissues was examined by RT-PCR using primers (OL516 5'-TGTGTCATCGAGCTGGCTTC-3' (SEQ ID NO: 21) and OL517 5'-ATCTTCTGCAAGTGGCTCCA-3' (SEQ ID NO: 22)) spanning the alternatively spliced exon 22 and cDNA panel from the same tissues as the multiple tissue Northern blot. PCR was performed in a Biometra TGRADIENT Thermocycler for 30 cycles at 95° C. for 20 seconds, 60° C. for 20 seconds, and 72° C. for 60 seconds. The expected sizes of PCR products were 680 base pairs for HDAC9 and 993 base pairs for HDAC9a. The ratio of HDAC9 and HDAC9a transcripts differed among tissues (FIG. 6B). In the placenta and kidney, the levels of the two transcripts were about the same (FIG. 6B). In the brain, heart, and pancreas, there were more transcripts of HDAC9 than HDAC9a. In the other tissues examined, there were more HDAC9a transcripts than HDAC9 transcripts (FIG. 6B). Under the conditions tested, HDAC9 transcripts were undetectable in liver (FIG. 6B). The lung had an HDAC9 product that was larger than expected and abundant. The lung also had low levels of HDAC9 transcripts and HDAC9a transcripts (FIG. 6B). An additional PCR product was also amplified from cDNA of the pancreas; this product was than the expected products from HDAC9 and HDAC9a (FIG. 6B). The identity of the different sized transcripts is unknown.

HDAC9 and HDAC9a Possess Histone Deacetylase Activity

HDAC9 was named based on sequence homology to HDAC4 (FIGS. 3A-3C). To determine whether HDAC9 and HDAC9a possess HDAC activity, an HDAC enzymatic assay was performed using anti-FLAG immunoprecipitated HDAC9-FLAG and HDAC9a-FLAG.

C-terminal FLAG-tagged HDAC9 (HDAC9-FLAG) and HDAC9a (HDAC9a-FLAG) expression vectors were constructed using the pFLAG-CMV-5b vector (Sigma) and PCR amplified coding regions of HDAC9 and HDAC9a in frame with the FLAG-tag to form pFLAG-CMV-5b-HDAC9 (plasmid VR1) and pFLAG-CMV-5b-HDAC9a (plasmid VR2). All constructs were confirmed by DNA sequencing.

Transfection of human kidney 293T cells, immunoprecipitation using anti-FLAG M2 Agarose (Sigma), Western blot analyses and dual luciferase assays were performed essentially as previously described by Zhou et al. (Proc. Natl. Acad. Sci. USA, 97:1056-1061 (2000)). Briefly, the cells (American Type Culture Collection) were cultured in DME HG medium (GIBCO/BRL) supplemented with 10% (vol/vol) FBS at 37° C. in a 5% $CO_2$ atmosphere. Transient transfection was performed by using LIPOFECTAMINE® (GIBCO/BRL) or FUGENE® 6 (Roche Molecular Biochemicals) according to the manufacturers' instructions. Cells were harvested 24 to 48 hours after transfection and lysed in IP lysis buffer (50 mM Tris HCl, pH 7.5/120 mM NaCl/5 mM EDTA/0.5% NP-40) at $5\times10^7$ cells per ml. Immunoprecipitation with anti-FLAG M2-agarose (Sigma, St. Louis, Mo.) was performed according to the manufacturer's instructions. Immunoprecipitated proteins were released from the agarose beads by using FLAG-peptide and either used directly for HDAC enzymatic activity assays or resolved on SDS/PAGE for Western blot analyses. Anti-FLAG antibody was purchased from Sigma (St. Louis, Mo.). Western blot analyses were performed using standard methods.

HDAC9 and HDAC9a enzymatic activity were assessed with the HDAC Fluorescent Activity Assay/Drug Discovery Kit-AK-500 (BIOMOL Research Laboratories) using a FLUOR DE LYS™ that contains an acetylated lysine side chain as a substrate and immunoprecipitated HDAC9-FLAG and HDAC9a-FLAG polypeptides according to the manufacturer's instruction and a SPECTRAmax® GEMINI XS microplate spectrofluorometer using the SOFTmax® PRO system (Molecular Devices) at excitation 355 nm and emission 460 nm with a cut off filter of 455 nm. Briefly, HDAC9-FLAG and HDAC9a-FLAG were incubated with the substrate overnight at room temperature in a 96-well plate. The reaction was stopped by addition of Fluor De Lys™ Developer and samples were read with the fluorometer.

Figure 7:
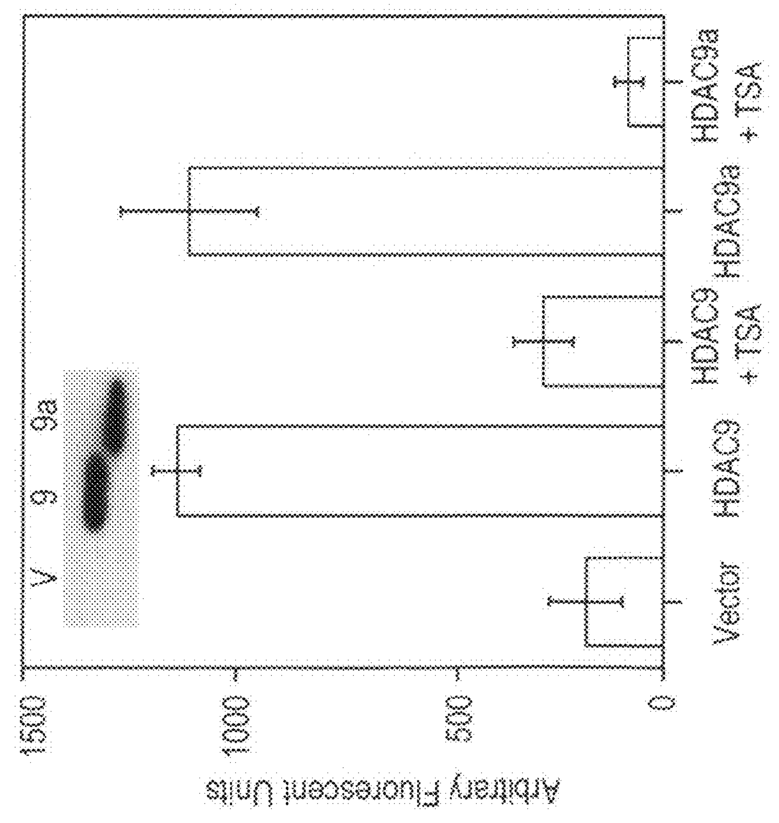
FIG. 7 is a graph of HDAC enzymatic activity of HDAC anti-FLAG-immunoprecipitated proteins isolated from vector control, HDAC9-FLAG, and HDAC9a-FLAG transfected 293T cells, as measured in fluorescence units using FLUOR DE LYS® as a substrate in the presence or absence of 1 μM TSA. Results are shown as the mean of three independent assays. The inset is a scanned image of an anti-FLAG Western blot showing the amount of proteins used in the assay. V, Vector control; 9, HDAC9-FLAG; and 9a, HDAC9a-FLAG.

As shown in FIG. 7, both HDAC9-FLAG and HDAC9a-FLAG deacetylated the acetylated lysine of FLUOR DE LYS® and the activity of HDAC9 and HDAC9a was comparable. To examine the activity of HDAC9 and HDAC9a, inhibition studies using TSA were carried out by preincubating HDAC9-FLAG and HDAC9a-FLAG with TSA for 15 minutes at room temperature. The assay was then carried out as stated above. As shown in FIG. 7, TSA inhibited HDAC9 and HDAC9a deacetylase activity. The inset gel in FIG. 7 shows the amount of protein used in the assay. SAHA, a potent HDAC inhibitor (Richon et al., Proc. Natl. Acad. Sci. USA, 95:3003-3007 (1998)) also completely inhibited the histone deacetylase activity of HDAC9-FLAG and HDAC9a-FLAG. The HDAC activity of HDAC9 and HDAC9a was about ten times lower than the deacetylase activity of HDAC4 when comparable amount of protein was used under conditions tested here.

HDAC9 and HDAC9a enzymatic activity was also determined through HDAC enzymatic assays using $^3$H-histones isolated from murine erythroleukemia cells as a substrate. This assay was performed essentially as described by Richon et al. (Proc. Natl. Acad. Sci. USA, 95:3003-3007 (1998)). Briefly, HDAC9-FLAG and HDAC9a-FLAG were incubated with $^3$H-histones overnight at 37° C. The reaction was stopped by the addition of 1M HCl/0.1 acetic acid. Released $^3$H-acetic acid was extracted with ethyl acetate and quantified by scintillation counting. For inhibition studies, the immunoprecipitated complexes were preincubated with the different HDAC inhibitors for 30 minutes at 4° C.

Figure 8:
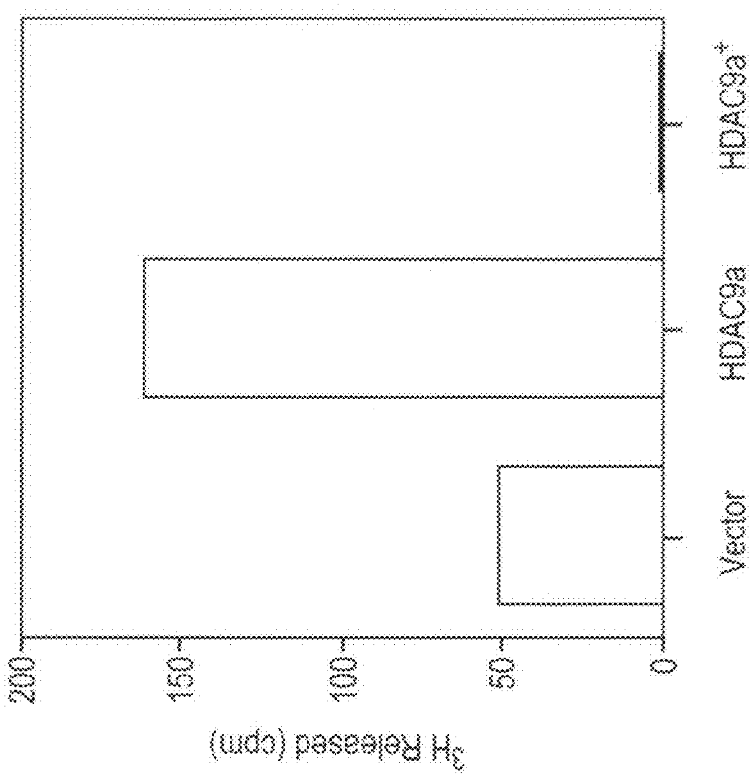
FIG. 8 is a graph of HDAC enzymatic activity of HDAC anti-FLAG-immunoprecipitated proteins isolated from vector control, and HDAC9a-FLAG (treated with 2 μM SAHA or left untreated) transfected 293T cells, as measured by $^{3}$H-acetic acid released from $^{3}$H-histones in the presence or absence of 2 μM SAHA. Vector control; HDAC9a, HDAC9a-FLAG; and HDAC9a+, HDAC9a-FLAG+SAHA.

As shown in FIG. 8, HDAC9a-FLAG deacetylated $^3$H-acetyl-histones. SAHA, a potent HDAC inhibitor also completely inhibited the histone deacetylase activity of HDAC9a-FLAG. TSA also inhibited HDAC9a deacetylase activity. Similar results were obtained when HDAC9 was used as the enzyme source.

HDAC9 and HDAC9a Repress MEF2-Mediated Transcription

Figure 9A:
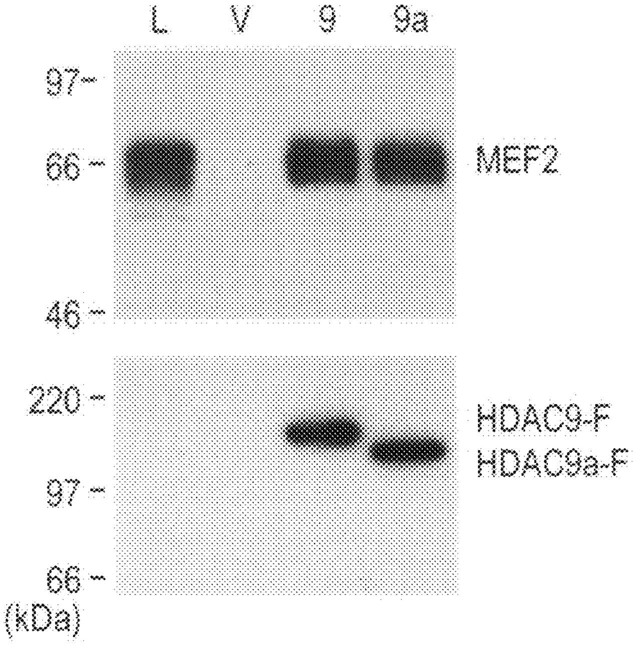
FIG. 9A shows a scanned image of a Western blot of 293T whole cell lysate and anti-FLAG immunoprecipitates from 293T cells transfected with vector, HDAC9-FLAG or HDAC9a-FLAG using antibodies against MEF2 and FLAG. Top panel, anti-MEF2 Western; bottom panel, anti-FLAG Western. L, 293T whole cell lysate; V, vector control IP; 9, HDAC9-FLAG IP; 9a, HDAC9a-FLAG IP.

The Xenopus homolog of HDRP, MITR, was identified as a MEF2 interacting transcriptional repressor (Sparrow et al., EMBO J. 18:5085-5098(1999)) and mouse HDRP also interacts with and represses MEF2 mediated transcription (Zhang et al., J. Biol. Chem. 276:35-39 (2001)). We first tested whether HDAC9-FLAG and HDAC9a-FLAG interact with MEF2. 293 cells were transfected with vector, HDAC9-FLAG, or HDAC9a-FLAG. The cells were subsequently lysed and HDAC9-FLAG and HDAC9a-FLAG proteins were immunoprecipitated with anti-FLAG antibodies. Western blot analysis of the immunoprecipitated proteins was carried out, using anti-MEF-2 antibody to probe the blot. As shown in FIG. 9A, both HDAC9 and HDAC9a interacted with MEF2 in 293T cells.

Figure 9B:
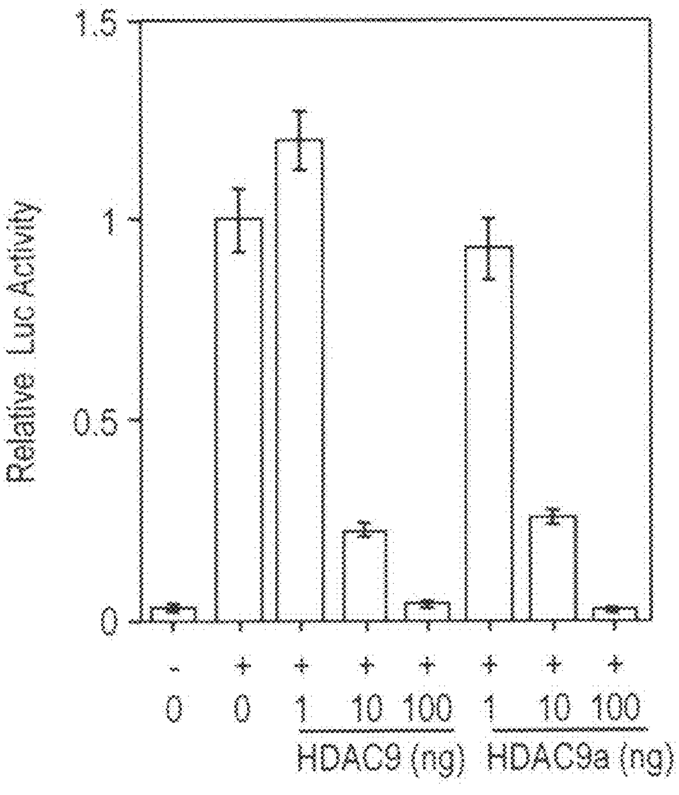
FIG. 9B is a graph showing the transcription level of p3XMEF2-Luc in the presence or absence of pcDNA3 empty vector (−), pCMV-MEF2C, and/or a vector encoding pFLAG-HDAC9 or pFLAG-HDAC9a. p3XMEF2-Luc (100 ng) and pRL-TK (5 ng) were transfected into 293T cells with pcDNA3 empty vector (−) or with pCMV-MEF2C (100 ng) (+) along with the indicated amount of pFLAG-HDAC9 or pFLAG-HDAC9a. pFLAG empty vector was used to adjust the DNA to an equal amount in each transfection. The firefly luciferase activity was first normalized to the co-transfected Renilla luciferase activity and the value for MEF2C alone was then set as 1. Results are shown as the mean of three independent transfections+/−standard deviation.

It was then determined whether HDAC9 and HDAC9a repress MEF2-mediated transcription. This determination was carried out as follows. The p3XMEF2-luciferase reporter gene (100 ng) and the vector pRL-TK (Promega) (5 ng) were co-transfected into 293T cells in the absence (pcDNA3 empty vector) or presence of MEF2C (100 ng of pCMV-MEF2C). HDAC9-F (1 ng, 10 ng, or 100 ng of pFLAG-HDAC9; pFLAG-HDAC9 and HDAC9-FLAG are different constructs, with the FLAG sequence located at opposite ends of the HDAC9 nucleotide, but are functionally equivalent) or HDAC9a-F (1 ng, 10 ng, or 100 ng of pFLAG-HDAC9a; pFLAG-HDAC9a and HDAC9a-FLAG are different constructs, with the FLAG sequence located at opposite ends of the HDAC9a nucleotide, but are functionally equivalent) was included in a subset of experimental groups with the MEF2C vector. pFLAG empty vector was used to adjust the DNA to an equal amount in each transfection. The cells were harvested 24 to 36 hours after transfection and the luciferase activities were measured using the Dual-Luciferase™ Reporter Assay System from Promega according to the manufacturer's instruction. The firefly luciferase activity was first normalized to the co-transfected Renilla luciferase activity (encoded by the pRL-TK vector), and the luciferase activity value for cells transfected with MEF2C alone was set at 1. MEF2C activated transcription over 30 times the basal level of transcription. As shown in FIG. 9B, HDAC9-FLAG and HDAC9a-FLAG repressed MEF2C mediated transcriptional activation in a dose-dependent manner and completely abolished the activation at the 100 ng dose for both HDAC9 and HDAC9a. The transcriptional repression effect of HDAC9 and HDAC9a on MEF2C mediated transcription was a specific effect since a co-transfected reporter gene for transfection efficiency containing a TK promoter was not repressed by HDAC9 or HDAC9a.

Described herein is the identification and characterization of a new class II HDAC, designated HDAC9. HDAC9 has several alternatively spliced isoforms, one of which is the previously identified HDRP (Zhou et al., Proc. Natl. Acad. Sci. USA 97:1056-1061 (2000)). HDAC9 and HDAC9a possess HDAC activity, which appears to have a lower specific enzymatic activity than HDAC4. While not wishing to be bound by any particular theory, it is possible that an essential co-factor is lost during immunoprecipitation or does not exist in 293T cells (for example, metastasis-associated protein 2 is essential for the assembly of a catalytically active HDAC1 (Zhang et al., Genes Dev. 13:1924-1935 (1999)), the substrates used are not its natural substrate, or the FLAG tag which interferes with the folding of the protein.

Figure 10:
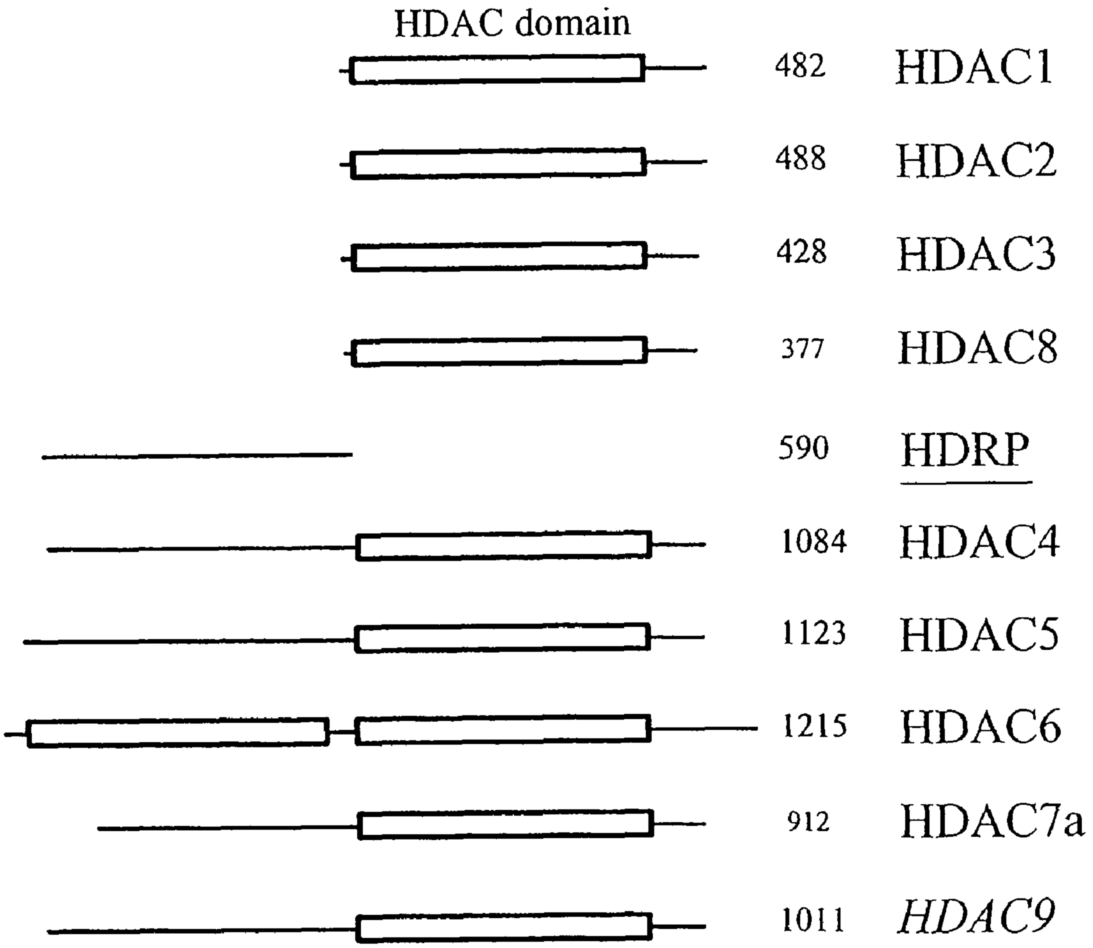
FIG. 10 shows a schematic representation of the HDAC domains of human non-Sir2 family HDACs and HDRP. The boxes represent histone deacetylase (HDAC) domains.
Figure 12:
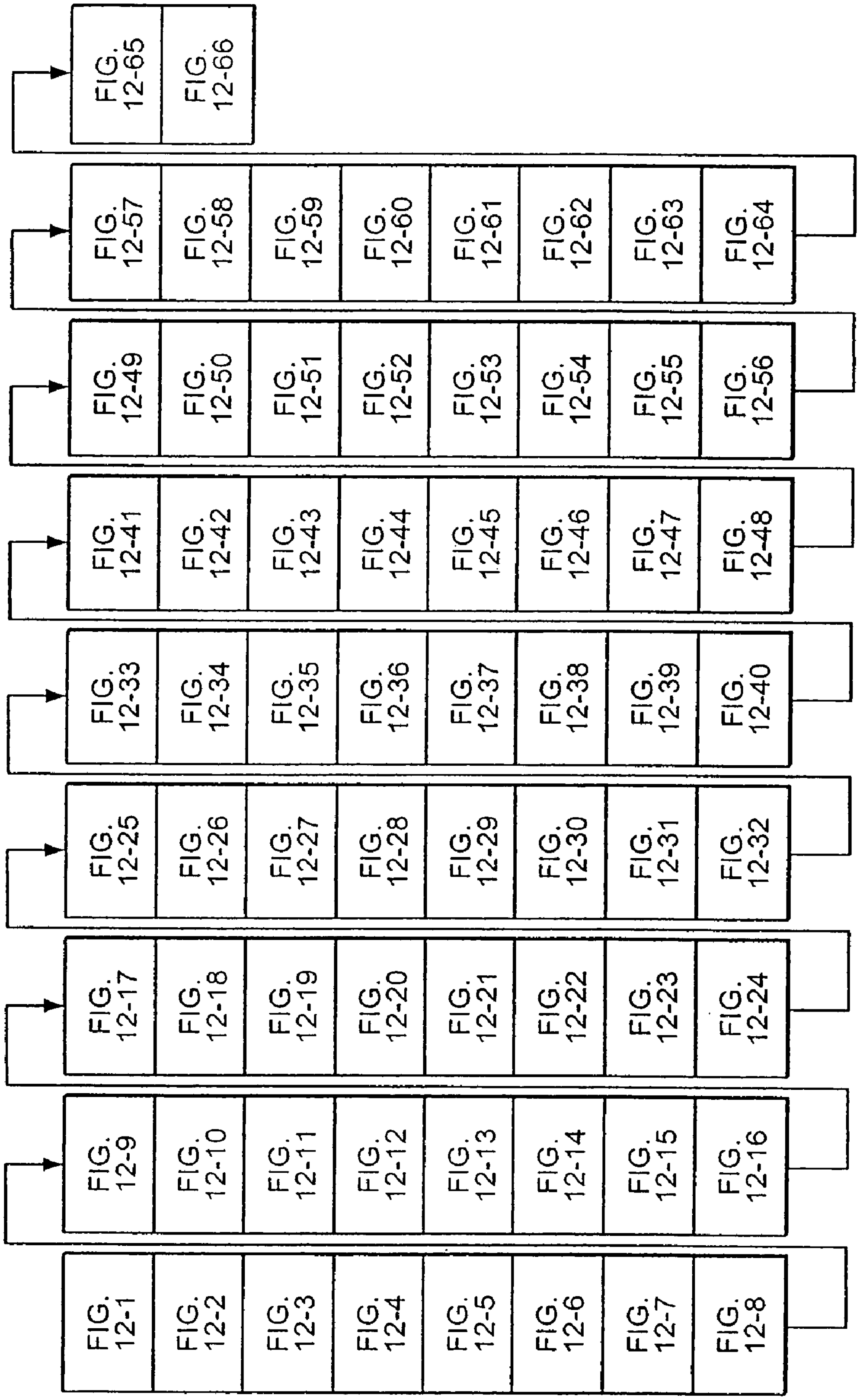
FIG. 12 is a schematic representation of the order in which FIGS. 12-1 through 12-66 should be viewed.
Figure 14:
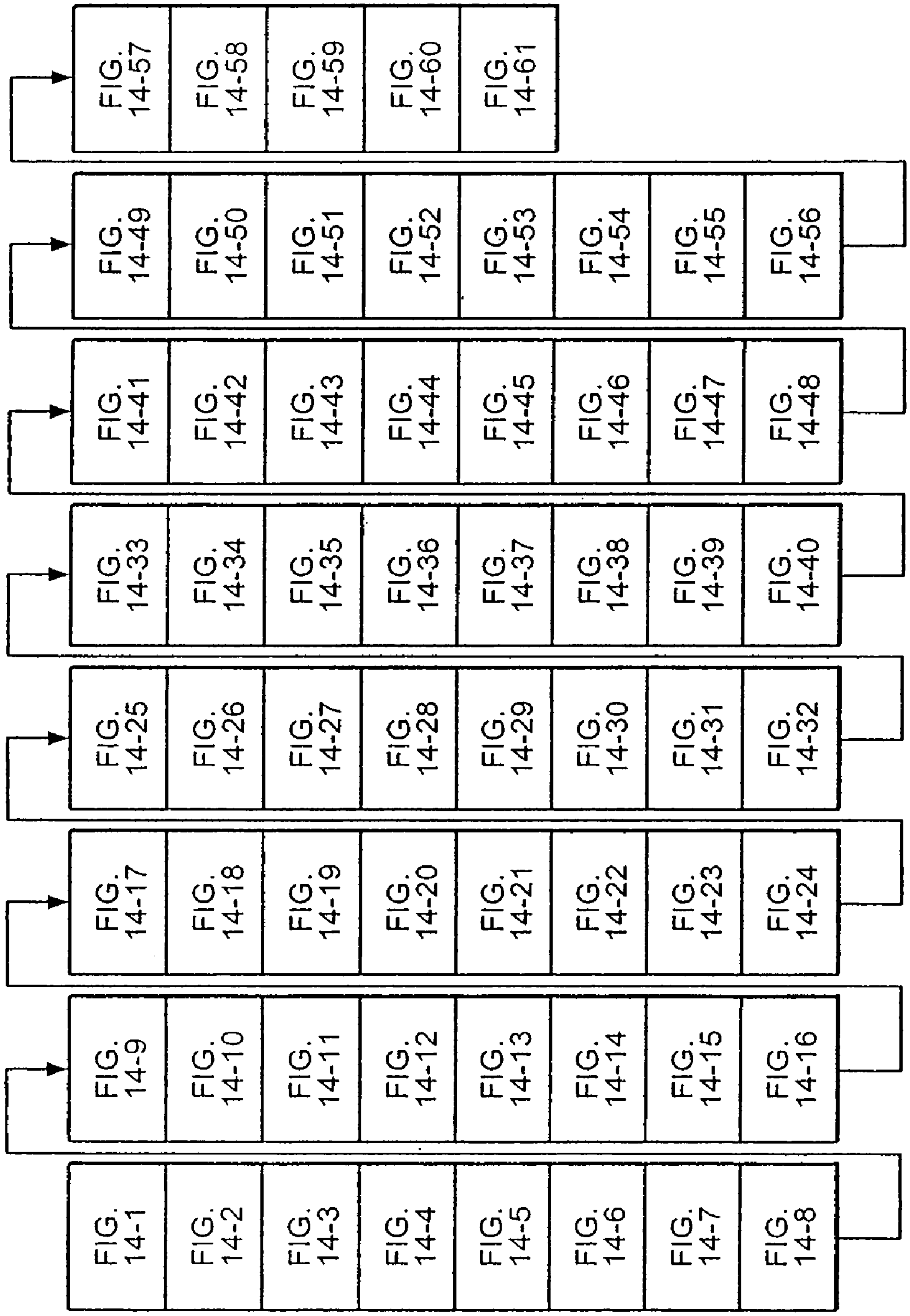
FIG. 14 is a schematic representation of the order in which FIGS. 14-1 through 14-61 should be viewed.

Searching the human genome with the HDAC domain from either HDAC1 or HDAC9 identified a total of 10 HDACs in the presently completed human genome sequence, a number of which are schematically represented in FIG. 10. HDACs 1, 2, 3, 8, 4, 5, 6, 7, 9, and 9a all have HDAC domains. HDRP, which is also schematically depicted in FIG. 10, does not have a catalytic domain.

All references described herein are incorporated by reference in their entirety. While this invention has been particularly shown and described with reference to preferred embodiment thereof, it will be understood by those skilled in the art that various changes in form and details may be made therein without departing from the spirit and scope of the invention as defined by the appended claims.

What is claimed is:

1. A purified antibody that selectively binds an isolated or recombinant histone deacetylase polypeptide consisting of the amino acid sequence set forth in SEQ ID NO: 2, wherein the antibody does not bind to HDRP consisting of the amino acid set forth in SEQ ID NO: 11.

2. A purified antibody that selectively binds an isolated or recombinant histone deacetylase polypeptide comprising the amino acid sequence as set forth in SEQ ID NO:2, wherein the antibody does not bind to HDRP consisting of the amino acid set forth in SEQ ID NO: 11.

3. A purified antibody that selectively binds an isolated or recombinant histone deacetylase polypeptide, wherein said polypeptide is encoded by a nucleotide sequence as set forth in SEQ ID NO: 1, wherein the antibody does not bind to HDRP consisting of the amino acid set forth in SEQ ID NO: 11.

4. The antibody of any one of claim 1, 2 or 3 wherein the antibody is monoclonal.

5. The antibody of any one of claim 1, 2 or 3, wherein the antibody is human or humanized.

* * * * *

UNITED STATES PATENT AND TRADEMARK OFFICE

CERTIFICATE OF CORRECTION

PATENT NO. : 7,816,499 B2
APPLICATION NO. : 11/809899
DATED : October 19, 2010
INVENTOR(S) : Victoria M. Richon et al.

It is certified that error appears in the above-identified patent and that said Letters Patent is hereby corrected as shown below:

On the cover page, item (56), under the section Foreign Patent Documents,

"WO WO 02/36786 A2 5/2002"

should read

--WO WO 02/36783 A2 5/2002--.

Signed and Sealed this
Eighth Day of March, 2011

David J. Kappos
*Director of the United States Patent and Trademark Office*

SEQUENCE LISTING

<160> NUMBER OF SEQ ID NOS: 22

<210> SEQ ID NO 1
<211> LENGTH: 3186
<212> TYPE: DNA
<213> ORGANISM: Homo sapiens

<400> SEQUENCE: 1
ggggaagaga ggcacagaca cagataggag aagggcaccg gctggagcca cttgcaggac 60
tgagggtttt tgcaacaaaa ccctagcagc ctgaagaact ctaagccaga tggggtggct 120
ggacgagagc agctcttggc tcagcaaaga atgcacagta tgatcagctc agtggatgtg 180
aagtcagaag ttcctgtggg cctggagccc atctcacctt tagacctaag gacagacctc 240
aggatgatga tgcccgtggt ggaccctgtt gtccgtgaga agcaattgca gcaggaatta 300
cttcttatcc agcagcagca acaaatccag aagcagcttc tgatagcaga gtttcagaaa 360
cagcatgaga acttgacacg gcagcaccag gctcagcttc aggagcatat caaggaactt 420
ctagccataa aacagcaaca agaactccta gaaaaggagc agaaactgga gcagcagagg 480
caagaacagg aagtagagag gcatcgcaga gaacagcagc ttcctcctct cagaggcaaa 540
gatagaggac gagaaagggc agtggcaagt acagaagtaa agcagaagct tcaagagttc 600
ctactgagta aatcagcaac gaaagacact ccaactaatg gaaaaaatca ttccgtgagc 660
cgccatccca agctctggta cacggctgcc caccacacat cattggatca aagctctcca 720
ccccttagtg gaacatctcc atcctacaag tacacattac caggagcaca agatgcaaag 780
gatgatttcc cccttcgaaa aactgcctct gagcccaact tgaaggtgcg gtccaggtta 840
aaacagaaag tggcagagag gagaagcagc cccttactca ggcggaagga tggaaatgtt 900
gtcacttcat tcaagaagcg aatgtttgag gtgacagaat cctcagtcag tagcagttct 960
ccaggctctg gtcccagttc accaaacaat gggccaactg gaagtgttac tgaaaatgag 1020
acttcggttt tgccccctac ccctcatgcc gagcaaatgg tttcacagca acgcattcta 1080
attcatgaag attccatgaa cctgctaagt ctttatacct ctccttcttt gcccaacatt 1140
accttggggc ttcccgcagt gccatcccag ctcaatgctt cgaattcact caaagaaaag 1200
cagaagtgtg agacgcagac gcttaggcaa ggtgttcctc tgcctgggca gtatggaggc 1260
agcatcccgg catcttccag ccaccctcat gttactttag agggaaagcc acccaacagc 1320
agccaccagg ctctcctgca gcatttatta ttgaaagaac aaatgcgaca gcaaaagctt 1380
cttgtagctg gtggagttcc cttacatcct cagtctccct tggcaacaaa agagagaatt 1440
tcacctggca ttagaggtac ccacaaattg ccccgtcaca gacccctgaa ccgaacccag 1500
tctgcacctt tgcctcagag cacgttggct cagctggtca ttcaacagca acaccagcaa 1560
ttcttggaga agcagaagca ataccagcag cagatccaca tgaacaaact gctttcgaaa 1620
tctattgaac aactgaagca accaggcagt caccttgagg aagcagagga agagcttcag 1680
ggggaccagg cgatgcagga agacagagcg ccctctagtg gcaacagcac taggagcgac 1740
agcagtgctt gtgtggatga cacactggga caagttgggg ctgtgaaggt caaggaggaa 1800
ccagtggaca gtgatgaaga tgctcagatc caggaaatgg aatctgggga gcaggctgct 1860
tttatgcaac agcctttcct ggaacccacg cacacacgtg cgctctctgt gcgccaagct 1920
ccgctggctg cggttggcat ggatggatta gagaaacacc gtctcgtctc caggactcac 1980
tcttcccctg ctgcctctgt tttacctcac ccagcaatgg accgccccct ccagcctggc 2040

-continued tctgcaactg gaattgccta tgaccccttg atgctgaaac accagtgcgt ttgtggcaat 2100
tccaccaccc accctgagca tgctggacga atacagagta tctggtcacg actgcaagaa 2160
actgggctgc taaataaatg tgagcgaatt caaggtcgaa aagccagcct ggaggaaata 2220
cagcttgttc attctgaaca tcactcactg ttgtatggca ccaacccccct ggacggacag 2280 aagctggacc ccaggatact cctaggtgat gactctcaaa agtttttttc ctcattacct 2340
tgtggtggac ttggggtgga cagtgacacc atttggaatg agctacactc gtccggtgct 2400
gcacgcatgg ctgttggctg tgtcatcgag ctggcttcca aagtggcctc aggagagctg 2460
aagaatgggt ttgctgttgt gaggccccct ggccatcacg ctgaagaatc cacagccatg 2520
gggttctgct tttttaattc agttgcaatt accgccaaat acttgagaga ccaactaaat 2580
ataagcaaga tattgattgt agatctggat gttcaccatg gaaacggtac ccagcaggcc 2640
ttttatgctg accccagcat cctgtacatt tcactccatc gctatgatga agggaacttt 2700
ttccctggca gtggagcccc aaatgaggtt ggaacaggcc ttggagaagg gtacaatata 2760
aatattgcct ggacaggtgg ccttgatcct cccatgggag atgttgagta ccttgaagca 2820
ttcaggacca tcgtgaagcc tgtggccaaa gagtttgatc cagacatggt cttagtatct 2880
gctggatttg atgcattgga aggccacacc cctcctctag gagggtacaa agtgacggca 2940
aaatgttttg gtcatttgac gaagcaattg atgacattgg ctgatggacg tgtggtgttg 3000
gctctagaag gaggacatga tctcacagcc atctgtgatg catcagaagc ctgtgtaaat 3060
gcccttctag gaaatgagct ggagccactt gcagaagata ttctccacca aagcccgaat 3120
atgaatgctg ttatttcttt acagaagatc attgaaattc aaagtatgtc tttaaagttc 3180
tcttaa 3186

<210> SEQ ID NO 2
<211> LENGTH: 1011
<212> TYPE: PRT
<213> ORGANISM: Homo sapiens

<400> SEQUENCE: 2

Met His Ser Met Ile Ser Ser Val Asp Val Lys Ser Glu Val Pro Val
1               5                   10                  15

Gly Leu Glu Pro Ile Ser Pro Leu Asp Leu Arg Thr Asp Leu Arg Met
            20                  25                  30

Met Met Pro Val Val Asp Pro Val Val Arg Glu Lys Gln Leu Gln Gln
        35                  40                  45

Glu Leu Leu Leu Ile Gln Gln Gln Gln Gln Ile Gln Lys Gln Leu Leu
    50                  55                  60

Ile Ala Glu Phe Gln Lys Gln His Glu Asn Leu Thr Arg Gln His Gln
65                  70                  75                  80

Ala Gln Leu Gln Glu His Ile Lys Glu Leu Leu Ala Ile Lys Gln Gln
                85                  90                  95

Gln Glu Leu Leu Glu Lys Glu Gln Lys Leu Glu Gln Gln Arg Gln Glu
            100                 105                 110

Gln Glu Val Glu Arg His Arg Arg Glu Gln Gln Leu Pro Pro Leu Arg
        115                 120                 125

Gly Lys Asp Arg Gly Arg Glu Arg Ala Val Ala Ser Thr Glu Val Lys
    130                 135                 140

Gln Lys Leu Gln Glu Phe Leu Leu Ser Lys Ser Ala Thr Lys Asp Thr
145                 150                 155                 160

-continued

```
Pro Thr Asn Gly Lys Asn His Ser Val Ser Arg His Pro Lys Leu Trp
                165                 170                 175

Tyr Thr Ala Ala His His Thr Ser Leu Asp Gln Ser Ser Pro Pro Leu
            180                 185                 190

Ser Gly Thr Ser Pro Ser Tyr Lys Tyr Thr Leu Pro Gly Ala Gln Asp
        195                 200                 205

Ala Lys Asp Asp Phe Pro Leu Arg Lys Thr Ala Ser Glu Pro Asn Leu
    210                 215                 220

Lys Val Arg Ser Arg Leu Lys Gln Lys Val Ala Glu Arg Arg Ser Ser
225                 230                 235                 240

Pro Leu Leu Arg Arg Lys Asp Gly Asn Val Val Thr Ser Phe Lys Lys
                245                 250                 255

Arg Met Phe Glu Val Thr Glu Ser Ser Val Ser Ser Ser Ser Pro Gly
            260                 265                 270

Ser Gly Pro Ser Ser Pro Asn Asn Gly Pro Thr Gly Ser Val Thr Glu
        275                 280                 285

Asn Glu Thr Ser Val Leu Pro Pro Thr Pro His Ala Glu Gln Met Val
    290                 295                 300

Ser Gln Gln Arg Ile Leu Ile His Glu Asp Ser Met Asn Leu Leu Ser
305                 310                 315                 320

Leu Tyr Thr Ser Pro Ser Leu Pro Asn Ile Thr Leu Gly Leu Pro Ala
                325                 330                 335

Val Pro Ser Gln Leu Asn Ala Ser Asn Ser Leu Lys Glu Lys Gln Lys
            340                 345                 350

Cys Glu Thr Gln Thr Leu Arg Gln Gly Val Pro Leu Pro Gly Gln Tyr
        355                 360                 365

Gly Gly Ser Ile Pro Ala Ser Ser Ser His Pro His Val Thr Leu Glu
    370                 375                 380

Gly Lys Pro Pro Asn Ser Ser His Gln Ala Leu Leu Gln His Leu Leu
385                 390                 395                 400

Leu Lys Glu Gln Met Arg Gln Gln Lys Leu Leu Val Ala Gly Gly Val
                405                 410                 415

Pro Leu His Pro Gln Ser Pro Leu Ala Thr Lys Glu Arg Ile Ser Pro
            420                 425                 430

Gly Ile Arg Gly Thr His Lys Leu Pro Arg His Arg Pro Leu Asn Arg
        435                 440                 445

Thr Gln Ser Ala Pro Leu Pro Gln Ser Thr Leu Ala Gln Leu Val Ile
    450                 455                 460

Gln Gln Gln His Gln Gln Phe Leu Glu Lys Gln Lys Gln Tyr Gln Gln
465                 470                 475                 480

Gln Ile His Met Asn Lys Leu Leu Ser Lys Ser Ile Glu Gln Leu Lys
                485                 490                 495

Gln Pro Gly Ser His Leu Glu Glu Ala Glu Glu Glu Leu Gln Gly Asp
            500                 505                 510

Gln Ala Met Gln Glu Asp Arg Ala Pro Ser Ser Gly Asn Ser Thr Arg
        515                 520                 525

Ser Asp Ser Ser Ala Cys Val Asp Asp Thr Leu Gly Gln Val Gly Ala
    530                 535                 540

Val Lys Val Lys Glu Glu Pro Val Asp Ser Asp Glu Asp Ala Gln Ile
545                 550                 555                 560

Gln Glu Met Glu Ser Gly Glu Gln Ala Ala Phe Met Gln Gln Pro Phe
                565                 570                 575

Leu Glu Pro Thr His Thr Arg Ala Leu Ser Val Arg Gln Ala Pro Leu
```

-continued

```
            580                 585                 590

Ala Ala Val Gly Met Asp Gly Leu Glu Lys His Arg Leu Val Ser Arg
        595                 600                 605

Thr His Ser Ser Pro Ala Ala Ser Val Leu Pro His Pro Ala Met Asp
    610                 615                 620

Arg Pro Leu Gln Pro Gly Ser Ala Thr Gly Ile Ala Tyr Asp Pro Leu
625                 630                 635                 640

Met Leu Lys His Gln Cys Val Cys Gly Asn Ser Thr Thr His Pro Glu
                645                 650                 655

His Ala Gly Arg Ile Gln Ser Ile Trp Ser Arg Leu Gln Glu Thr Gly
            660                 665                 670

Leu Leu Asn Lys Cys Glu Arg Ile Gln Gly Arg Lys Ala Ser Leu Glu
        675                 680                 685

Glu Ile Gln Leu Val His Ser Glu His His Ser Leu Leu Tyr Gly Thr
    690                 695                 700

Asn Pro Leu Asp Gly Gln Lys Leu Asp Pro Arg Ile Leu Leu Gly Asp
705                 710                 715                 720

Asp Ser Gln Lys Phe Phe Ser Ser Leu Pro Cys Gly Gly Leu Gly Val
                725                 730                 735

Asp Ser Asp Thr Ile Trp Asn Glu Leu His Ser Ser Gly Ala Ala Arg
            740                 745                 750

Met Ala Val Gly Cys Val Ile Glu Leu Ala Ser Lys Val Ala Ser Gly
        755                 760                 765

Glu Leu Lys Asn Gly Phe Ala Val Val Arg Pro Pro Gly His His Ala
    770                 775                 780

Glu Glu Ser Thr Ala Met Gly Phe Cys Phe Phe Asn Ser Val Ala Ile
785                 790                 795                 800

Thr Ala Lys Tyr Leu Arg Asp Gln Leu Asn Ile Ser Lys Ile Leu Ile
                805                 810                 815

Val Asp Leu Asp Val His His Gly Asn Gly Thr Gln Gln Ala Phe Tyr
            820                 825                 830

Ala Asp Pro Ser Ile Leu Tyr Ile Ser Leu His Arg Tyr Asp Glu Gly
        835                 840                 845

Asn Phe Phe Pro Gly Ser Gly Ala Pro Asn Glu Val Gly Thr Gly Leu
    850                 855                 860

Gly Glu Gly Tyr Asn Ile Asn Ile Ala Trp Thr Gly Gly Leu Asp Pro
865                 870                 875                 880

Pro Met Gly Asp Val Glu Tyr Leu Glu Ala Phe Arg Thr Ile Val Lys
                885                 890                 895

Pro Val Ala Lys Glu Phe Asp Pro Asp Met Val Leu Val Ser Ala Gly
            900                 905                 910

Phe Asp Ala Leu Glu Gly His Thr Pro Pro Leu Gly Gly Tyr Lys Val
        915                 920                 925

Thr Ala Lys Cys Phe Gly His Leu Thr Lys Gln Leu Met Thr Leu Ala
    930                 935                 940

Asp Gly Arg Val Val Leu Ala Leu Glu Gly Gly His Asp Leu Thr Ala
945                 950                 955                 960

Ile Cys Asp Ala Ser Glu Ala Cys Val Asn Ala Leu Leu Gly Asn Glu
                965                 970                 975

Leu Glu Pro Leu Ala Glu Asp Ile Leu His Gln Ser Pro Asn Met Asn
            980                 985                 990

Ala Val Ile Ser Leu Gln Lys Ile Ile Glu Ile Gln Ser Met Ser Leu
        995                 1000                1005
```

-continued

Lys Phe Ser
1010

<210> SEQ ID NO 3
<211> LENGTH: 3499
<212> TYPE: DNA
<213> ORGANISM: Homo sapiens

<400> SEQUENCE: 3
ggggaagaga ggcacagaca cagataggag aagggcaccg gctggagcca cttgcaggac 60
tgagggtttt tgcaacaaaa ccctagcagc ctgaagaact ctaagccaga tggggtggct 120
ggacgagagc agctcttggc tcagcaaaga atgcacagta tgatcagctc agtggatgtg 180
aagtcagaag ttcctgtggg cctggagccc atctcacctt tagacctaag gacagacctc 240
aggatgatga tgcccgtggt ggaccctgtt gtccgtgaga agcaattgca gcaggaatta 300
cttcttatcc agcagcagca acaaatccag aagcagcttc tgatagcaga gtttcagaaa 360
cagcatgaga acttgacacg gcagcaccag gctcagcttc aggagcatat caaggaactt 420
ctagccataa aacagcaaca agaactccta gaaaaggagc agaaactgga gcagcagagg 480
caagaacagg aagtagagag gcatcgcaga gaacagcagc ttcctcctct cagaggcaaa 540
gatagaggac gagaaagggc agtggcaagt acagaagtaa agcagaagct tcaagagttc 600
ctactgagta aatcagcaac gaaagacact ccaactaatg gaaaaaatca ttccgtgagc 660
cgccatccca agctctggta cacggctgcc caccacacat cattggatca aagctctcca 720
ccccttagtg gaacatctcc atcctacaag tacacattac caggagcaca agatgcaaag 780
gatgatttcc cccttcgaaa aactgcctct gagcccaact tgaaggtgcg gtccaggtta 840
aaacagaaag tggcagagag gagaagcagc cccttactca ggcggaagga tggaaatgtt 900
gtcacttcat tcaagaagcg aatgtttgag gtgacagaat cctcagtcag tagcagttct 960
ccaggctctg gtcccagttc accaaacaat gggccaactg gaagtgttac tgaaaatgag 1020
acttcggttt tgccccctac ccctcatgcc gagcaaatgg tttcacagca acgcattcta 1080
attcatgaag attccatgaa cctgctaagt ctttatacct ctccttcttt gcccaacatt 1140
accttggggc ttcccgcagt gccatcccag ctcaatgctt cgaattcact caaagaaaag 1200
cagaagtgtg agacgcagac gcttaggcaa ggtgttcctc tgcctgggca gtatggaggc 1260
agcatcccgg catcttccag ccaccctcat gttactttag agggaaagcc acccaacagc 1320
agccaccagg ctctcctgca gcatttatta ttgaaagaac aaatgcgaca gcaaaagctt 1380
cttgtagctg gtggagttcc cttacatcct cagtctccct tggcaacaaa agagagaatt 1440
tcacctggca ttagaggtac ccacaaattg ccccgtcaca gacccctgaa ccgaacccag 1500
tctgcacctt tgcctcagag cacgttggct cagctggtca ttcaacagca acaccagcaa 1560
ttcttggaga agcagaagca ataccagcag cagatccaca tgaacaaact gctttcgaaa 1620
tctattgaac aactgaagca accaggcagt caccttgagg aagcagagga agagcttcag 1680
ggggaccagg cgatgcagga agacagagcg ccctctagtg gcaacagcac taggagcgac 1740
agcagtgctt gtgtggatga cacactggga caagttgggg ctgtgaaggt caaggaggaa 1800
ccagtggaca gtgatgaaga tgctcagatc caggaaatgg aatctgggga gcaggctgct 1860
tttatgcaac agcctttcct ggaacccacg cacacacgtg cgctctctgt gcgccaagct 1920
ccgctggctg cggttggcat ggatggatta gagaaacacc gtctcgtctc caggactcac 1980
tcttcccctg ctgcctctgt tttacctcac ccagcaatgg accgccccct ccagcctggc 2040

-continued

```
tctgcaactg gaattgccta tgaccccttg atgctgaaac accagtgcgt ttgtggcaat   2100
tccaccaccc accctgagca tgctggacga atacagagta tctggtcacg actgcaagaa   2160
actgggctgc taaataaatg tgagcgaatt caaggtcgaa aagccagcct ggaggaaata   2220
cagcttgttc attctgaaca tcactcactg ttgtatggca ccaacccccct ggacggacag   2280
aagctggacc ccaggatact cctaggtgat gactctcaaa agttttttttc ctcattacct   2340
tgtggtggac ttggggtgga cagtgacacc atttggaatg agctacactc gtccggtgct   2400
gcacgcatgg ctgttggctg tgtcatcgag ctggcttcca aagtggcctc aggagagctg   2460
aagaatgggt ttgctgttgt gaggcccccct ggccatcacg ctgaagaatc cacagccatg   2520
gggttctgct tttttaattc agttgcaatt accgccaaat acttgagaga ccaactaaat   2580
ataagcaaga tattgattgt agatctggat gttcaccatg gaaacggtac ccagcaggcc   2640
ttttatgctg accccagcat cctgtacatt tcactccatc gctatgatga agggaacttt   2700
ttccctggca gtggagcccc aaatgaggtt cggtttattt ctttagagcc ccacttttat   2760
ttgtatcttt caggtaattg cattgcatga ttacccctaa ttttcttgtc ctttgctggt   2820
gttttaaatt acacgagatt actgaattgt cccatgggac caagaaccag tgcagaacaa   2880
gtgcataacc cagagcactg tttgtcaggg aaggttgggc tgatttgatg tgttgtttga   2940
tgtttatttc aagagctccc atgtgcttgt tttcctctct tcttgctttc ttccatttgc   3000
tctcttctct gcccaccgtg gtgtgtcttt ctcttcccag gttggaacag gccttggaga   3060
agggtacaat ataaatattg cctggacagg tggccttgat cctcccatgg gagatgttga   3120
gtaccttgaa gcattcagga ccatcgtgaa gcctgtggcc aaagagtttg atccagacat   3180
ggtcttagta tctgctggat ttgatgcatt ggaaggccac acccctcctc taggagggta   3240
caaagtgacg gcaaaatgtt ttggtcattt gacgaagcaa ttgatgacat tggctgatgg   3300
acgtgtggtg ttggctctag aaggaggaca tgatctcaca gccatctgtg atgcatcaga   3360
agcctgtgta aatgcccttc taggaaatga gctggagcca cttgcagaag atattctcca   3420
ccaaagcccg aatatgaatg ctgttatttc tttacagaag atcattgaaa ttcaaagtat   3480
gtctttaaag ttctcttaa                                                3499
```

<210> SEQ ID NO 4
<211> LENGTH: 879
<212> TYPE: PRT
<213> ORGANISM: Homo sapiens

<400> SEQUENCE: 4

```
Met His Ser Met Ile Ser Ser Val Asp Val Lys Ser Glu Val Pro Val
 1               5                   10                  15

Gly Leu Glu Pro Ile Ser Pro Leu Asp Leu Arg Thr Asp Leu Arg Met
            20                  25                  30

Met Met Pro Val Val Asp Pro Val Val Arg Glu Lys Gln Leu Gln Gln
        35                  40                  45

Glu Leu Leu Leu Ile Gln Gln Gln Gln Gln Ile Gln Lys Gln Leu Leu
    50                  55                  60

Ile Ala Glu Phe Gln Lys Gln His Glu Asn Leu Thr Arg Gln His Gln
65                  70                  75                  80

Ala Gln Leu Gln Glu His Ile Lys Glu Leu Leu Ala Ile Lys Gln Gln
                85                  90                  95

Gln Glu Leu Leu Glu Lys Glu Gln Lys Leu Glu Gln Gln Arg Gln Glu
            100                 105                 110
```

-continued

```
Gln Glu Val Glu Arg His Arg Arg Glu Gln Gln Leu Pro Pro Leu Arg
        115                 120                 125

Gly Lys Asp Arg Gly Arg Glu Arg Ala Val Ala Ser Thr Glu Val Lys
    130                 135                 140

Gln Lys Leu Gln Glu Phe Leu Leu Ser Lys Ser Ala Thr Lys Asp Thr
145                 150                 155                 160

Pro Thr Asn Gly Lys Asn His Ser Val Ser Arg His Pro Lys Leu Trp
                165                 170                 175

Tyr Thr Ala Ala His His Thr Ser Leu Asp Gln Ser Ser Pro Pro Leu
            180                 185                 190

Ser Gly Thr Ser Pro Ser Tyr Lys Tyr Thr Leu Pro Gly Ala Gln Asp
        195                 200                 205

Ala Lys Asp Asp Phe Pro Leu Arg Lys Thr Ala Ser Glu Pro Asn Leu
    210                 215                 220

Lys Val Arg Ser Arg Leu Lys Gln Lys Val Ala Glu Arg Arg Ser Ser
225                 230                 235                 240

Pro Leu Leu Arg Arg Lys Asp Gly Asn Val Val Thr Ser Phe Lys Lys
                245                 250                 255

Arg Met Phe Glu Val Thr Glu Ser Ser Val Ser Ser Ser Ser Pro Gly
            260                 265                 270

Ser Gly Pro Ser Ser Pro Asn Asn Gly Pro Thr Gly Ser Val Thr Glu
        275                 280                 285

Asn Glu Thr Ser Val Leu Pro Pro Thr Pro His Ala Glu Gln Met Val
    290                 295                 300

Ser Gln Gln Arg Ile Leu Ile His Glu Asp Ser Met Asn Leu Leu Ser
305                 310                 315                 320

Leu Tyr Thr Ser Pro Ser Leu Pro Asn Ile Thr Leu Gly Leu Pro Ala
                325                 330                 335

Val Pro Ser Gln Leu Asn Ala Ser Asn Ser Leu Lys Glu Lys Gln Lys
            340                 345                 350

Cys Glu Thr Gln Thr Leu Arg Gln Gly Val Pro Leu Pro Gly Gln Tyr
        355                 360                 365

Gly Gly Ser Ile Pro Ala Ser Ser Ser His Pro His Val Thr Leu Glu
    370                 375                 380

Gly Lys Pro Pro Asn Ser Ser His Gln Ala Leu Leu Gln His Leu Leu
385                 390                 395                 400

Leu Lys Glu Gln Met Arg Gln Gln Lys Leu Leu Val Ala Gly Gly Val
                405                 410                 415

Pro Leu His Pro Gln Ser Pro Leu Ala Thr Lys Glu Arg Ile Ser Pro
            420                 425                 430

Gly Ile Arg Gly Thr His Lys Leu Pro Arg His Arg Pro Leu Asn Arg
        435                 440                 445

Thr Gln Ser Ala Pro Leu Pro Gln Ser Thr Leu Ala Gln Leu Val Ile
    450                 455                 460

Gln Gln Gln His Gln Gln Phe Leu Glu Lys Gln Lys Gln Tyr Gln Gln
465                 470                 475                 480

Gln Ile His Met Asn Lys Leu Leu Ser Lys Ser Ile Glu Gln Leu Lys
                485                 490                 495

Gln Pro Gly Ser His Leu Glu Glu Ala Glu Glu Glu Leu Gln Gly Asp
            500                 505                 510

Gln Ala Met Gln Glu Asp Arg Ala Pro Ser Ser Gly Asn Ser Thr Arg
        515                 520                 525
```

-continued

```
Ser Asp Ser Ser Ala Cys Val Asp Asp Thr Leu Gly Gln Val Gly Ala
    530                 535                 540

Val Lys Val Lys Glu Glu Pro Val Asp Ser Asp Glu Asp Ala Gln Ile
545                 550                 555                 560

Gln Glu Met Glu Ser Gly Glu Gln Ala Ala Phe Met Gln Gln Pro Phe
                565                 570                 575

Leu Glu Pro Thr His Thr Arg Ala Leu Ser Val Arg Gln Ala Pro Leu
            580                 585                 590

Ala Ala Val Gly Met Asp Gly Leu Glu Lys His Arg Leu Val Ser Arg
        595                 600                 605

Thr His Ser Ser Pro Ala Ala Ser Val Leu Pro His Pro Ala Met Asp
    610                 615                 620

Arg Pro Leu Gln Pro Gly Ser Ala Thr Gly Ile Ala Tyr Asp Pro Leu
625                 630                 635                 640

Met Leu Lys His Gln Cys Val Cys Gly Asn Ser Thr Thr His Pro Glu
                645                 650                 655

His Ala Gly Arg Ile Gln Ser Ile Trp Ser Arg Leu Gln Glu Thr Gly
            660                 665                 670

Leu Leu Asn Lys Cys Glu Arg Ile Gln Gly Arg Lys Ala Ser Leu Glu
        675                 680                 685

Glu Ile Gln Leu Val His Ser Glu His His Ser Leu Leu Tyr Gly Thr
    690                 695                 700

Asn Pro Leu Asp Gly Gln Lys Leu Asp Pro Arg Ile Leu Leu Gly Asp
705                 710                 715                 720

Asp Ser Gln Lys Phe Phe Ser Ser Leu Pro Cys Gly Gly Leu Gly Val
                725                 730                 735

Asp Ser Asp Thr Ile Trp Asn Glu Leu His Ser Ser Gly Ala Ala Arg
            740                 745                 750

Met Ala Val Gly Cys Val Ile Glu Leu Ala Ser Lys Val Ala Ser Gly
        755                 760                 765

Glu Leu Lys Asn Gly Phe Ala Val Val Arg Pro Pro Gly His His Ala
    770                 775                 780

Glu Glu Ser Thr Ala Met Gly Phe Cys Phe Phe Asn Ser Val Ala Ile
785                 790                 795                 800

Thr Ala Lys Tyr Leu Arg Asp Gln Leu Asn Ile Ser Lys Ile Leu Ile
                805                 810                 815

Val Asp Leu Asp Val His His Gly Asn Gly Thr Gln Gln Ala Phe Tyr
            820                 825                 830

Ala Asp Pro Ser Ile Leu Tyr Ile Ser Leu His Arg Tyr Asp Glu Gly
        835                 840                 845

Asn Phe Phe Pro Gly Ser Gly Ala Pro Asn Glu Val Arg Phe Ile Ser
    850                 855                 860

Leu Glu Pro His Phe Tyr Leu Tyr Leu Ser Gly Asn Cys Ile Ala
865                 870                 875
```

<210> SEQ ID NO 5
<211> LENGTH: 3054
<212> TYPE: DNA
<213> ORGANISM: Homo sapiens

<400> SEQUENCE: 5

```
ggggaagaga ggcacagaca cagataggag aagggcaccg gctggagcca cttgcaggac      60

tgagggtttt tgcaacaaaa ccctagcagc ctgaagaact ctaagccaga tggggtggct     120

ggacgagagc agctcttggc tcagcaaaga atgcacagta tgatcagctc agtggatgtg     180
```

-continued

```
aagtcagaag ttcctgtggg cctggagccc atctcacctt tagacctaag gacagacctc    240
aggatgatga tgcccgtggt ggaccctgtt gtccgtgaga agcaattgca gcaggaatta    300
cttcttatcc agcagcagca acaaatccag aagcagcttc tgatagcaga gtttcagaaa    360
cagcatgaga acttgacacg gcagcaccag gctcagcttc aggagcatat caaggaactt    420
ctagccataa aacagcaaca agaactccta gaaaaggagc agaaactgga gcagcagagg    480
caagaacagg aagtagagag gcatcgcaga gaacagcagc ttcctcctct cagaggcaaa    540
gatagaggac gagaaagggc agtggcaagt acagaagtaa agcagaagct tcaagagttc    600
ctactgagta aatcagcaac gaaagacact ccaactaatg gaaaaaatca ttccgtgagc    660
cgccatccca agctctggta cacggctgcc caccacacat cattggatca aagctctcca    720
ccccttagtg gaacatctcc atcctacaag tacacattac caggagcaca agatgcaaag    780
gatgatttcc cccttcgaaa aactgaatcc tcagtcagta gcagttctcc aggctctggt    840
cccagttcac caaacaatgg gccaactgga agtgttactg aaaatgagac ttcggttttg    900
ccccctaccc ctcatgccga gcaaatggtt tcacagcaac gcattctaat tcatgaagat    960
tccatgaacc tgctaagtct ttatacctct ccttctttgc ccaacattac cttggggctt   1020
cccgcagtgc catcccagct caatgcttcg aattcactca aagaaaagca gaagtgtgag   1080
acgcagacgc ttaggcaagg tgttcctctg cctgggcagt atggaggcag catcccggca   1140
tcttccagcc accctcatgt tactttagag ggaaagccac ccaacagcag ccaccaggct   1200
ctcctgcagc atttattatt gaaagaacaa atgcgacagc aaaagcttct tgtagctggt   1260
ggagttccct tacatcctca gtctcccttg gcaacaaaag agagaatttc acctggcatt   1320
agaggtaccc acaaattgcc ccgtcacaga cccctgaacc gaacccagtc tgcacctttg   1380
cctcagagca cgttggctca gctggtcatt caacagcaac accagcaatt cttggagaag   1440
cagaagcaat accagcagca gatccacatg aacaaactgc tttcgaaatc tattgaacaa   1500
ctgaagcaac caggcagtca ccttgaggaa gcagaggaag agcttcaggg ggaccaggcg   1560
atgcaggaag acagagcgcc ctctagtggc aacagcacta ggagcgacag cagtgcttgt   1620
gtggatgaca cactgggaca agttggggct gtgaaggtca aggaggaacc agtggacagt   1680
gatgaagatg ctcagatcca ggaaatggaa tctggggagc aggctgcttt tatgcaacag   1740
cctttcctgg aacccacgca cacacgtgcg ctctctgtgc gccaagctcc gctggctgcg   1800
gttggcatgg atggattaga gaaacaccgt ctcgtctcca ggactcactc ttcccctgct   1860
gcctctgttt tacctcaccc agcaatggac cgcccccctcc agcctggctc tgcaactgga   1920
attgcctatg accccttgat gctgaaacac cagtgcgttt gtggcaattc caccacccac   1980
cctgagcatg ctggacgaat acagagtatc tggtcacgac tgcaagaaac tgggctgcta   2040
aataaatgtg agcgaattca aggtcgaaaa gccagcctgg aggaaataca gcttgttcat   2100
tctgaacatc actcactgtt gtatggcacc aacccccctgg acggacagaa gctggacccc   2160
aggatactcc taggtgatga ctctcaaaag ttttttttcct cattaccttg tggtggactt   2220
ggggtggaca gtgacaccat ttggaatgag ctacactcgt ccggtgctgc acgcatggct   2280
gttggctgtg tcatcgagct ggcttccaaa gtggcctcag gagagctgaa gaatgggttt   2340
gctgttgtga ggcccccctgg ccatcacgct gaagaatcca cagccatggg gttctgcttt   2400
tttaattcag ttgcaattac cgccaaatac ttgagagacc aactaaatat aagcaagata   2460
ttgattgtag atctggatgt tcaccatgga aacggtaccc agcaggcctt ttatgctgac   2520
```

-continued

```
cccagcatcc tgtacatttc actccatcgc tatgatgaag ggaacttttt ccctggcagt   2580

ggagccccaa atgaggttgg aacaggcctt ggagaagggt acaatataaa tattgcctgg   2640

acaggtggcc ttgatcctcc catgggagat gttgagtacc ttgaagcatt caggaccatc   2700

gtgaagcctg tggccaaaga gtttgatcca gacatggtct tagtatctgc tggatttgat   2760

gcattggaag gccacacccc tcctctagga gggtacaaag tgacggcaaa atgttttggt   2820

catttgacga agcaattgat gacattggct gatggacgtg tggtgttggc tctagaagga   2880

ggacatgatc tcacagccat ctgtgatgca tcagaagcct gtgtaaatgc ccttctagga   2940

aatgagctgg agccacttgc agaagatatt ctccaccaaa gcccgaatat gaatgctgtt   3000

atttctttac agaagatcat tgaaattcaa agtatgtctt taaagttctc ttaa         3054


<210> SEQ ID NO 6
<211> LENGTH: 967
<212> TYPE: PRT
<213> ORGANISM: Homo sapiens

<400> SEQUENCE: 6

Met His Ser Met Ile Ser Ser Val Asp Val Lys Ser Glu Val Pro Val
 1               5                  10                  15

Gly Leu Glu Pro Ile Ser Pro Leu Asp Leu Arg Thr Asp Leu Arg Met
            20                  25                  30

Met Met Pro Val Val Asp Pro Val Val Arg Glu Lys Gln Leu Gln Gln
        35                  40                  45

Glu Leu Leu Leu Ile Gln Gln Gln Gln Gln Ile Gln Lys Gln Leu Leu
    50                  55                  60

Ile Ala Glu Phe Gln Lys Gln His Glu Asn Leu Thr Arg Gln His Gln
65                  70                  75                  80

Ala Gln Leu Gln Glu His Ile Lys Glu Leu Leu Ala Ile Lys Gln Gln
                85                  90                  95

Gln Glu Leu Leu Glu Lys Glu Gln Lys Leu Glu Gln Gln Arg Gln Glu
            100                 105                 110

Gln Glu Val Glu Arg His Arg Arg Glu Gln Gln Leu Pro Pro Leu Arg
        115                 120                 125

Gly Lys Asp Arg Gly Arg Glu Arg Ala Val Ala Ser Thr Glu Val Lys
    130                 135                 140

Gln Lys Leu Gln Glu Phe Leu Leu Ser Lys Ser Ala Thr Lys Asp Thr
145                 150                 155                 160

Pro Thr Asn Gly Lys Asn His Ser Val Ser Arg His Pro Lys Leu Trp
                165                 170                 175

Tyr Thr Ala Ala His His Thr Ser Leu Asp Gln Ser Ser Pro Pro Leu
            180                 185                 190

Ser Gly Thr Ser Pro Ser Tyr Lys Tyr Thr Leu Pro Gly Ala Gln Asp
        195                 200                 205

Ala Lys Asp Asp Phe Pro Leu Arg Lys Thr Glu Ser Ser Val Ser Ser
    210                 215                 220

Ser Ser Pro Gly Ser Gly Pro Ser Ser Pro Asn Asn Gly Pro Thr Gly
225                 230                 235                 240

Ser Val Thr Glu Asn Glu Thr Ser Val Leu Pro Pro Thr Pro His Ala
                245                 250                 255

Glu Gln Met Val Ser Gln Gln Arg Ile Leu Ile His Glu Asp Ser Met
            260                 265                 270

Asn Leu Leu Ser Leu Tyr Thr Ser Pro Ser Leu Pro Asn Ile Thr Leu
        275                 280                 285
```

-continued

```
Gly Leu Pro Ala Val Pro Ser Gln Leu Asn Ala Ser Asn Ser Leu Lys
    290                 295                 300

Glu Lys Gln Lys Cys Glu Thr Gln Thr Leu Arg Gln Gly Val Pro Leu
305                 310                 315                 320

Pro Gly Gln Tyr Gly Gly Ser Ile Pro Ala Ser Ser Ser His Pro His
                325                 330                 335

Val Thr Leu Glu Gly Lys Pro Pro Asn Ser Ser His Gln Ala Leu Leu
            340                 345                 350

Gln His Leu Leu Leu Lys Glu Gln Met Arg Gln Gln Lys Leu Leu Val
        355                 360                 365

Ala Gly Gly Val Pro Leu His Pro Gln Ser Pro Leu Ala Thr Lys Glu
    370                 375                 380

Arg Ile Ser Pro Gly Ile Arg Gly Thr His Lys Leu Pro Arg His Arg
385                 390                 395                 400

Pro Leu Asn Arg Thr Gln Ser Ala Pro Leu Pro Gln Ser Thr Leu Ala
                405                 410                 415

Gln Leu Val Ile Gln Gln Gln His Gln Gln Phe Leu Glu Lys Gln Lys
            420                 425                 430

Gln Tyr Gln Gln Gln Ile His Met Asn Lys Leu Leu Ser Lys Ser Ile
        435                 440                 445

Glu Gln Leu Lys Gln Pro Gly Ser His Leu Glu Glu Ala Glu Glu Glu
    450                 455                 460

Leu Gln Gly Asp Gln Ala Met Gln Glu Asp Arg Ala Pro Ser Ser Gly
465                 470                 475                 480

Asn Ser Thr Arg Ser Asp Ser Ser Ala Cys Val Asp Asp Thr Leu Gly
                485                 490                 495

Gln Val Gly Ala Val Lys Val Lys Glu Glu Pro Val Asp Ser Asp Glu
            500                 505                 510

Asp Ala Gln Ile Gln Glu Met Glu Ser Gly Glu Gln Ala Ala Phe Met
        515                 520                 525

Gln Gln Pro Phe Leu Glu Pro Thr His Thr Arg Ala Leu Ser Val Arg
    530                 535                 540

Gln Ala Pro Leu Ala Ala Val Gly Met Asp Gly Leu Glu Lys His Arg
545                 550                 555                 560

Leu Val Ser Arg Thr His Ser Ser Pro Ala Ala Ser Val Leu Pro His
                565                 570                 575

Pro Ala Met Asp Arg Pro Leu Gln Pro Gly Ser Ala Thr Gly Ile Ala
            580                 585                 590

Tyr Asp Pro Leu Met Leu Lys His Gln Cys Val Cys Gly Asn Ser Thr
        595                 600                 605

Thr His Pro Glu His Ala Gly Arg Ile Gln Ser Ile Trp Ser Arg Leu
    610                 615                 620

Gln Glu Thr Gly Leu Leu Asn Lys Cys Glu Arg Ile Gln Gly Arg Lys
625                 630                 635                 640

Ala Ser Leu Glu Glu Ile Gln Leu Val His Ser Glu His His Ser Leu
                645                 650                 655

Leu Tyr Gly Thr Asn Pro Leu Asp Gly Gln Lys Leu Asp Pro Arg Ile
            660                 665                 670

Leu Leu Gly Asp Asp Ser Gln Lys Phe Phe Ser Ser Leu Pro Cys Gly
        675                 680                 685

Gly Leu Gly Val Asp Ser Asp Thr Ile Trp Asn Glu Leu His Ser Ser
    690                 695                 700
```

-continued

```
Gly Ala Ala Arg Met Ala Val Gly Cys Val Ile Glu Leu Ala Ser Lys
705                 710                 715                 720

Val Ala Ser Gly Glu Leu Lys Asn Gly Phe Ala Val Val Arg Pro Pro
                725                 730                 735

Gly His His Ala Glu Glu Ser Thr Ala Met Gly Phe Cys Phe Phe Asn
            740                 745                 750

Ser Val Ala Ile Thr Ala Lys Tyr Leu Arg Asp Gln Leu Asn Ile Ser
        755                 760                 765

Lys Ile Leu Ile Val Asp Leu Asp Val His His Gly Asn Gly Thr Gln
    770                 775                 780

Gln Ala Phe Tyr Ala Asp Pro Ser Ile Leu Tyr Ile Ser Leu His Arg
785                 790                 795                 800

Tyr Asp Glu Gly Asn Phe Phe Pro Gly Ser Gly Ala Pro Asn Glu Val
                805                 810                 815

Gly Thr Gly Leu Gly Glu Gly Tyr Asn Ile Asn Ile Ala Trp Thr Gly
            820                 825                 830

Gly Leu Asp Pro Pro Met Gly Asp Val Glu Tyr Leu Glu Ala Phe Arg
        835                 840                 845

Thr Ile Val Lys Pro Val Ala Lys Glu Phe Asp Pro Asp Met Val Leu
    850                 855                 860

Val Ser Ala Gly Phe Asp Ala Leu Glu Gly His Thr Pro Pro Leu Gly
865                 870                 875                 880

Gly Tyr Lys Val Thr Ala Lys Cys Phe Gly His Leu Thr Lys Gln Leu
                885                 890                 895

Met Thr Leu Ala Asp Gly Arg Val Val Leu Ala Leu Glu Gly Gly His
            900                 905                 910

Asp Leu Thr Ala Ile Cys Asp Ala Ser Glu Ala Cys Val Asn Ala Leu
        915                 920                 925

Leu Gly Asn Glu Leu Glu Pro Leu Ala Glu Asp Ile Leu His Gln Ser
    930                 935                 940

Pro Asn Met Asn Ala Val Ile Ser Leu Gln Lys Ile Ile Glu Ile Gln
945                 950                 955                 960

Ser Met Ser Leu Lys Phe Ser
                965


<210> SEQ ID NO 7
<211> LENGTH: 3367
<212> TYPE: DNA
<213> ORGANISM: Homo sapiens

<400> SEQUENCE: 7

ggggaagaga ggcacagaca cagataggag aagggcaccg gctggagcca cttgcaggac      60

tgagggtttt tgcaacaaaa ccctagcagc ctgaagaact ctaagccaga tggggtggct     120

ggacgagagc agctcttggc tcagcaaaga atgcacagta tgatcagctc agtggatgtg     180

aagtcagaag ttcctgtggg cctggagccc atctcacctt tagacctaag gacagacctc     240

aggatgatga tgcccgtggt ggaccctgtt gtccgtgaga agcaattgca gcaggaatta     300

cttcttatcc agcagcagca acaaatccag aagcagcttc tgatagcaga gtttcagaaa     360

cagcatgaga acttgacacg gcagcaccag gctcagcttc aggagcatat caaggaactt     420

ctagccataa aacagcaaca agaactccta gaaaaggagc agaaactgga gcagcagagg     480

caagaacagg aagtagagag gcatcgcaga gaacagcagc ttcctcctct cagaggcaaa     540

gatagaggac gagaaagggc agtggcaagt acagaagtaa agcagaagct tcaagagttc     600
```

-continued

```
ctactgagta aatcagcaac gaaagacact ccaactaatg gaaaaaatca ttccgtgagc    660
cgccatccca agctctggta cacggctgcc caccacacat cattggatca aagctctcca    720
ccccttagtg gaacatctcc atcctacaag tacacattac caggagcaca agatgcaaag    780
gatgatttcc cccttcgaaa aactgaatcc tcagtcagta gcagttctcc aggctctggt    840
cccagttcac caaacaatgg gccaactgga agtgttactg aaaatgagac ttcggttttg    900
ccccctaccc ctcatgccga gcaaatggtt tcacagcaac gcattctaat tcatgaagat    960
tccatgaacc tgctaagtct ttatacctct ccttctttgc ccaacattac cttggggctt   1020
cccgcagtgc catcccagct caatgcttcg aattcactca aagaaaagca gaagtgtgag   1080
acgcagacgc ttaggcaagg tgttcctctg cctgggcagt atggaggcag catcccggca   1140
tcttccagcc accctcatgt tactttagag ggaaagccac ccaacagcag ccaccaggct   1200
ctcctgcagc atttattatt gaaagaacaa atgcgacagc aaaagcttct tgtagctggt   1260
ggagttccct tacatcctca gtctcccttg gcaacaaaag agagaatttc acctggcatt   1320
agaggtaccc acaaattgcc ccgtcacaga cccctgaacc gaacccagtc tgcacctttg   1380
cctcagagca cgttggctca gctggtcatt caacagcaac accagcaatt cttggagaag   1440
cagaagcaat accagcagca gatccacatg aacaaactgc tttcgaaatc tattgaacaa   1500
ctgaagcaac caggcagtca ccttgaggaa gcagaggaag agcttcaggg ggaccaggcg   1560
atgcaggaag acagagcgcc ctctagtggc aacagcacta ggagcgacag cagtgcttgt   1620
gtggatgaca cactgggaca agttggggct gtgaaggtca aggaggaacc agtggacagt   1680
gatgaagatg ctcagatcca ggaaatggaa tctggggagc aggctgcttt tatgcaacag   1740
cctttcctgg aacccacgca cacacgtgcg ctctctgtgc gccaagctcc gctggctgcg   1800
gttggcatgg atggattaga gaaacaccgt ctcgtctcca ggactcactc ttcccctgct   1860
gcctctgttt tacctcaccc agcaatggac cgcccccctcc agcctggctc tgcaactgga   1920
attgcctatg accccttgat gctgaaacac cagtgcgttt gtggcaattc caccacccac   1980
cctgagcatg ctggacgaat acagagtatc tggtcacgac tgcaagaaac tgggctgcta   2040
aataaatgtg agcgaattca aggtcgaaaa gccagcctgg aggaaataca gcttgttcat   2100
tctgaacatc actcactgtt gtatggcacc aaccccctgg acggacagaa gctggacccc   2160
aggatactcc taggtgatga ctctcaaaag tttttttcct cattaccttg tggtggactt   2220
ggggtggaca gtgacaccat ttggaatgag ctacactcgt ccggtgctgc acgcatggct   2280
gttggctgtg tcatcgagct ggcttccaaa gtggcctcag gagagctgaa gaatgggttt   2340
gctgttgtga ggccccctgg ccatcacgct gaagaatcca cagccatggg gttctgcttt   2400
tttaattcag ttgcaattac cgccaaatac ttgagagacc aactaaatat aagcaagata   2460
ttgattgtag atctggatgt tcaccatgga aacggtaccc agcaggcctt ttatgctgac   2520
cccagcatcc tgtacatttc actccatcgc tatgatgaag ggaacttttt ccctggcagt   2580
ggagccccaa atgaggttcg gtttatttct ttagagcccc acttttattt gtatctttca   2640
ggtaattgca ttgcatgatt acccctaatt ttcttgtcct ttgctggtgt tttaaattac   2700
acgagattac tgaattgtcc catgggacca agaaccagtg cagaacaagt gcataaccca   2760
gagcactgtt tgtcagggaa ggttgggctg atttgatgtg ttgtttgatg tttatttcaa   2820
gagctcccat gtgcttgttt tcctctcttc ttgctttctt ccatttgctc tcttctctgc   2880
ccaccgtggt gtgtctttct cttcccaggt tggaacaggc cttggagaag ggtacaatat   2940
aaatattgcc tggacaggtg gccttgatcc tcccatggga gatgttgagt accttgaagc   3000
```

-continued

```
attcaggacc atcgtgaagc ctgtggccaa agagtttgat ccagacatgg tcttagtatc   3060

tgctggattt gatgcattgg aaggccacac ccctcctcta ggagggtaca aagtgacggc   3120

aaaatgtttt ggtcatttga cgaagcaatt gatgacattg gctgatggac gtgtggtgtt   3180

ggctctagaa ggaggacatg atctcacagc catctgtgat gcatcagaag cctgtgtaaa   3240

tgcccttcta ggaaatgagc tggagccact tgcagaagat attctccacc aaagcccgaa   3300

tatgaatgct gttatttctt tacagaagat cattgaaatt caaagtatgt ctttaaagtt   3360

ctcttaa                                                             3367
```

<210> SEQ ID NO 8
<211> LENGTH: 835
<212> TYPE: PRT
<213> ORGANISM: Homo sapiens

<400> SEQUENCE: 8

```
Met His Ser Met Ile Ser Ser Val Asp Val Lys Ser Glu Val Pro Val
 1               5                  10                  15

Gly Leu Glu Pro Ile Ser Pro Leu Asp Leu Arg Thr Asp Leu Arg Met
            20                  25                  30

Met Met Pro Val Val Asp Pro Val Val Arg Glu Lys Gln Leu Gln Gln
        35                  40                  45

Glu Leu Leu Leu Ile Gln Gln Gln Gln Gln Ile Gln Lys Gln Leu Leu
    50                  55                  60

Ile Ala Glu Phe Gln Lys Gln His Glu Asn Leu Thr Arg Gln His Gln
65                  70                  75                  80

Ala Gln Leu Gln Glu His Ile Lys Glu Leu Leu Ala Ile Lys Gln Gln
                85                  90                  95

Gln Glu Leu Leu Glu Lys Glu Gln Lys Leu Glu Gln Gln Arg Gln Glu
            100                 105                 110

Gln Glu Val Glu Arg His Arg Arg Glu Gln Gln Leu Pro Pro Leu Arg
        115                 120                 125

Gly Lys Asp Arg Gly Arg Glu Arg Ala Val Ala Ser Thr Glu Val Lys
    130                 135                 140

Gln Lys Leu Gln Glu Phe Leu Leu Ser Lys Ser Ala Thr Lys Asp Thr
145                 150                 155                 160

Pro Thr Asn Gly Lys Asn His Ser Val Ser Arg His Pro Lys Leu Trp
                165                 170                 175

Tyr Thr Ala Ala His His Thr Ser Leu Asp Gln Ser Ser Pro Pro Leu
            180                 185                 190

Ser Gly Thr Ser Pro Ser Tyr Lys Tyr Thr Leu Pro Gly Ala Gln Asp
        195                 200                 205

Ala Lys Asp Asp Phe Pro Leu Arg Lys Thr Glu Ser Ser Val Ser Ser
    210                 215                 220

Ser Ser Pro Gly Ser Gly Pro Ser Ser Pro Asn Asn Gly Pro Thr Gly
225                 230                 235                 240

Ser Val Thr Glu Asn Glu Thr Ser Val Leu Pro Pro Thr Pro His Ala
                245                 250                 255

Glu Gln Met Val Ser Gln Gln Arg Ile Leu Ile His Glu Asp Ser Met
            260                 265                 270

Asn Leu Leu Ser Leu Tyr Thr Ser Pro Ser Leu Pro Asn Ile Thr Leu
        275                 280                 285

Gly Leu Pro Ala Val Pro Ser Gln Leu Asn Ala Ser Asn Ser Leu Lys
    290                 295                 300
```

-continued

```
Glu Lys Gln Lys Cys Glu Thr Gln Thr Leu Arg Gln Gly Val Pro Leu
305                 310                 315                 320

Pro Gly Gln Tyr Gly Gly Ser Ile Pro Ala Ser Ser Ser His Pro His
                325                 330                 335

Val Thr Leu Glu Gly Lys Pro Pro Asn Ser Ser His Gln Ala Leu Leu
            340                 345                 350

Gln His Leu Leu Leu Lys Glu Gln Met Arg Gln Gln Lys Leu Leu Val
        355                 360                 365

Ala Gly Gly Val Pro Leu His Pro Gln Ser Pro Leu Ala Thr Lys Glu
    370                 375                 380

Arg Ile Ser Pro Gly Ile Arg Gly Thr His Lys Leu Pro Arg His Arg
385                 390                 395                 400

Pro Leu Asn Arg Thr Gln Ser Ala Pro Leu Pro Gln Ser Thr Leu Ala
                405                 410                 415

Gln Leu Val Ile Gln Gln Gln His Gln Gln Phe Leu Glu Lys Gln Lys
            420                 425                 430

Gln Tyr Gln Gln Gln Ile His Met Asn Lys Leu Leu Ser Lys Ser Ile
        435                 440                 445

Glu Gln Leu Lys Gln Pro Gly Ser His Leu Glu Glu Ala Glu Glu Glu
    450                 455                 460

Leu Gln Gly Asp Gln Ala Met Gln Glu Asp Arg Ala Pro Ser Ser Gly
465                 470                 475                 480

Asn Ser Thr Arg Ser Asp Ser Ser Ala Cys Val Asp Asp Thr Leu Gly
                485                 490                 495

Gln Val Gly Ala Val Lys Val Lys Glu Glu Pro Val Asp Ser Asp Glu
            500                 505                 510

Asp Ala Gln Ile Gln Glu Met Glu Ser Gly Glu Gln Ala Ala Phe Met
        515                 520                 525

Gln Gln Pro Phe Leu Glu Pro Thr His Thr Arg Ala Leu Ser Val Arg
    530                 535                 540

Gln Ala Pro Leu Ala Ala Val Gly Met Asp Gly Leu Glu Lys His Arg
545                 550                 555                 560

Leu Val Ser Arg Thr His Ser Ser Pro Ala Ala Ser Val Leu Pro His
                565                 570                 575

Pro Ala Met Asp Arg Pro Leu Gln Pro Gly Ser Ala Thr Gly Ile Ala
            580                 585                 590

Tyr Asp Pro Leu Met Leu Lys His Gln Cys Val Cys Gly Asn Ser Thr
        595                 600                 605

Thr His Pro Glu His Ala Gly Arg Ile Gln Ser Ile Trp Ser Arg Leu
    610                 615                 620

Gln Glu Thr Gly Leu Leu Asn Lys Cys Glu Arg Ile Gln Gly Arg Lys
625                 630                 635                 640

Ala Ser Leu Glu Glu Ile Gln Leu Val His Ser Glu His His Ser Leu
                645                 650                 655

Leu Tyr Gly Thr Asn Pro Leu Asp Gly Gln Lys Leu Asp Pro Arg Ile
            660                 665                 670

Leu Leu Gly Asp Asp Ser Gln Lys Phe Phe Ser Ser Leu Pro Cys Gly
        675                 680                 685

Gly Leu Gly Val Asp Ser Asp Thr Ile Trp Asn Glu Leu His Ser Ser
    690                 695                 700

Gly Ala Ala Arg Met Ala Val Gly Cys Val Ile Glu Leu Ala Ser Lys
705                 710                 715                 720
```

-continued

```
Val Ala Ser Gly Glu Leu Lys Asn Gly Phe Ala Val Val Arg Pro Pro
                725                 730                 735

Gly His His Ala Glu Glu Ser Thr Ala Met Gly Phe Cys Phe Phe Asn
            740                 745                 750

Ser Val Ala Ile Thr Ala Lys Tyr Leu Arg Asp Gln Leu Asn Ile Ser
        755                 760                 765

Lys Ile Leu Ile Val Asp Leu Asp Val His His Gly Asn Gly Thr Gln
    770                 775                 780

Gln Ala Phe Tyr Ala Asp Pro Ser Ile Leu Tyr Ile Ser Leu His Arg
785                 790                 795                 800

Tyr Asp Glu Gly Asn Phe Phe Pro Gly Ser Gly Ala Pro Asn Glu Val
                805                 810                 815

Arg Phe Ile Ser Leu Glu Pro His Phe Tyr Leu Tyr Leu Ser Gly Asn
            820                 825                 830

Cys Ile Ala
        835


<210> SEQ ID NO 9
<211> LENGTH: 1791
<212> TYPE: DNA
<213> ORGANISM: Homo sapiens

<400> SEQUENCE: 9

ggggaagaga ggcacagaca cagataggag aagggcaccg gctggagcca cttgcaggac      60

tgagggtttt tgcaacaaaa ccctagcagc ctgaagaact ctaagccaga tggggtggct     120

ggacgagagc agctcttggc tcagcaaaga atgcacagta tgatcagctc agtggatgtg     180

aagtcagaag ttcctgtggg cctggagccc atctcacctt tagacctaag gacagacctc     240

aggatgatga tgcccgtggt ggaccctgtt gtccgtgaga agcaattgca gcaggaatta     300

cttcttatcc agcagcagca acaaatccag aagcagcttc tgatagcaga gtttcagaaa     360

cagcatgaga acttgacacg gcagcaccag gctcagcttc aggagcatat caaggaactt     420

ctagccataa aacagcaaca agaactccta gaaaaggagc agaaactgga gcagcagagg     480

caagaacagg aagtagagag gcatcgcaga gaacagcagc ttcctcctct cagaggcaaa     540

gatagaggac gagaaagggc agtggcaagt acagaagtaa agcagaagct tcaagagttc     600

ctactgagta aatcagcaac gaaagacact ccaactaatg gaaaaaatca ttccgtgagc     660

cgccatccca agctctggta cacggctgcc caccacacat cattggatca aagctctcca     720

ccccttagtg gaacatctcc atcctacaag tacacattac caggagcaca agatgcaaag     780

gatgatttcc cccttcgaaa aactgaatcc tcagtcagta gcagttctcc aggctctggt     840

cccagttcac caaacaatgg gccaactgga agtgttactg aaaatgagac ttcggttttg     900

ccccctaccc ctcatgccga gcaaatggtt tcacagcaac gcattctaat tcatgaagat     960

tccatgaacc tgctaagtct ttatacctct ccttctttgc ccaacattac cttggggctt    1020

cccgcagtgc catcccagct caatgcttcg aattcactca aagaaaagca gaagtgtgag    1080

acgcagacgc ttaggcaagg tgttcctctg cctgggcagt atggaggcag catcccggca    1140

tcttccagcc accctcatgt tactttagag ggaaagccac ccaacagcag ccaccaggct    1200

ctcctgcagc atttattatt gaaagaacaa atgcgacagc aaaagcttct tgtagctggt    1260

ggagttccct tacatcctca gtctcccttg gcaacaaaag agagaatttc acctggcatt    1320

agaggtaccc acaaattgcc ccgtcacaga cccctgaacc gaacccagtc tgcacctttg    1380

cctcagagca cgttggctca gctggtcatt caacagcaac accagcaatt cttggagaag    1440
```

-continued

```
cagaagcaat accagcagca gatccacatg aacaaactgc tttcgaaatc tattgaacaa   1500

ctgaagcaac caggcagtca ccttgaggaa gcagaggaag agcttcaggg ggaccaggcg   1560

atgcaggaag acagagcgcc ctctagtggc aacagcacta ggagcgacag cagtgcttgt   1620

gtggatgaca cactgggaca agttggggct gtgaaggtca aggaggaacc agtggacagt   1680

gatgaagatg ctcagatcca ggaaatggaa tctggggagc aggctgcttt tatgcaacag   1740

gtaataggca aagatttagc tccaggattt gtaattaaag tcattatctg a            1791


<210> SEQ ID NO 10
<211> LENGTH: 546
<212> TYPE: PRT
<213> ORGANISM: Homo sapiens

<400> SEQUENCE: 10

Met His Ser Met Ile Ser Ser Val Asp Val Lys Ser Glu Val Pro Val
1               5                   10                  15

Gly Leu Glu Pro Ile Ser Pro Leu Asp Leu Arg Thr Asp Leu Arg Met
            20                  25                  30

Met Met Pro Val Val Asp Pro Val Val Arg Glu Lys Gln Leu Gln Gln
        35                  40                  45

Glu Leu Leu Leu Ile Gln Gln Gln Gln Gln Ile Gln Lys Gln Leu Leu
    50                  55                  60

Ile Ala Glu Phe Gln Lys Gln His Glu Asn Leu Thr Arg Gln His Gln
65                  70                  75                  80

Ala Gln Leu Gln Glu His Ile Lys Glu Leu Leu Ala Ile Lys Gln Gln
                85                  90                  95

Gln Glu Leu Leu Glu Lys Glu Gln Lys Leu Glu Gln Gln Arg Gln Glu
            100                 105                 110

Gln Glu Val Glu Arg His Arg Arg Glu Gln Gln Leu Pro Pro Leu Arg
        115                 120                 125

Gly Lys Asp Arg Gly Arg Glu Arg Ala Val Ala Ser Thr Glu Val Lys
    130                 135                 140

Gln Lys Leu Gln Glu Phe Leu Leu Ser Lys Ser Ala Thr Lys Asp Thr
145                 150                 155                 160

Pro Thr Asn Gly Lys Asn His Ser Val Ser Arg His Pro Lys Leu Trp
                165                 170                 175

Tyr Thr Ala Ala His His Thr Ser Leu Asp Gln Ser Ser Pro Pro Leu
            180                 185                 190

Ser Gly Thr Ser Pro Ser Tyr Lys Tyr Thr Leu Pro Gly Ala Gln Asp
        195                 200                 205

Ala Lys Asp Asp Phe Pro Leu Arg Lys Thr Glu Ser Ser Val Ser Ser
    210                 215                 220

Ser Ser Pro Gly Ser Gly Pro Ser Ser Pro Asn Asn Gly Pro Thr Gly
225                 230                 235                 240

Ser Val Thr Glu Asn Glu Thr Ser Val Leu Pro Pro Thr Pro His Ala
                245                 250                 255

Glu Gln Met Val Ser Gln Gln Arg Ile Leu Ile His Glu Asp Ser Met
            260                 265                 270

Asn Leu Leu Ser Leu Tyr Thr Ser Pro Ser Leu Pro Asn Ile Thr Leu
        275                 280                 285

Gly Leu Pro Ala Val Pro Ser Gln Leu Asn Ala Ser Asn Ser Leu Lys
    290                 295                 300

Glu Lys Gln Lys Cys Glu Thr Gln Thr Leu Arg Gln Gly Val Pro Leu
```

-continued 305 310 315 320

Pro Gly Gln Tyr Gly Gly Ser Ile Pro Ala Ser Ser Ser His Pro His
325 330 335

Val Thr Leu Glu Gly Lys Pro Pro Asn Ser Ser His Gln Ala Leu Leu
340 345 350

Gln His Leu Leu Leu Lys Glu Gln Met Arg Gln Gln Lys Leu Leu Val
355 360 365

Ala Gly Gly Val Pro Leu His Pro Gln Ser Pro Leu Ala Thr Lys Glu
370 375 380

Arg Ile Ser Pro Gly Ile Arg Gly Thr His Lys Leu Pro Arg His Arg
385 390 395 400

Pro Leu Asn Arg Thr Gln Ser Ala Pro Leu Pro Gln Ser Thr Leu Ala
405 410 415

Gln Leu Val Ile Gln Gln Gln His Gln Gln Phe Leu Glu Lys Gln Lys
420 425 430

Gln Tyr Gln Gln Gln Ile His Met Asn Lys Leu Leu Ser Lys Ser Ile
435 440 445

Glu Gln Leu Lys Gln Pro Gly Ser His Leu Glu Glu Ala Glu Glu Glu
450 455 460

Leu Gln Gly Asp Gln Ala Met Gln Glu Asp Arg Ala Pro Ser Ser Gly
465 470 475 480

Asn Ser Thr Arg Ser Asp Ser Ser Ala Cys Val Asp Asp Thr Leu Gly
485 490 495

Gln Val Gly Ala Val Lys Val Lys Glu Glu Pro Val Asp Ser Asp Glu
500 505 510

Asp Ala Gln Ile Gln Glu Met Glu Ser Gly Glu Gln Ala Ala Phe Met
515 520 525

Gln Gln Val Ile Gly Lys Asp Leu Ala Pro Gly Phe Val Ile Lys Val
530 535 540

Ile Ile
545

<210> SEQ ID NO 11
<211> LENGTH: 590
<212> TYPE: PRT
<213> ORGANISM: Homo sapiens

<400> SEQUENCE: 11

Met His Ser Met Ile Ser Ser Val Asp Val Lys Ser Glu Val Pro Val
1 5 10 15

Gly Leu Glu Pro Ile Ser Pro Leu Asp Leu Arg Thr Asp Leu Arg Met
20 25 30

Met Met Pro Val Val Asp Pro Val Val Arg Glu Lys Gln Leu Gln Gln
35 40 45

Glu Leu Leu Leu Ile Gln Gln Gln Gln Gln Ile Gln Lys Gln Leu Leu
50 55 60

Ile Ala Glu Phe Gln Lys Gln His Glu Asn Leu Thr Arg Gln His Gln
65 70 75 80

Ala Gln Leu Gln Glu His Ile Lys Glu Leu Leu Ala Ile Lys Gln Gln
85 90 95

Gln Glu Leu Leu Glu Lys Glu Gln Lys Leu Glu Gln Gln Arg Gln Glu
100 105 110

Gln Glu Val Glu Arg His Arg Arg Glu Gln Gln Leu Pro Pro Leu Arg
115 120 125

-continued

```
Gly Lys Asp Arg Gly Arg Glu Arg Ala Val Ala Ser Thr Glu Val Lys
    130                 135                 140

Gln Lys Leu Gln Glu Phe Leu Leu Ser Lys Ser Ala Thr Lys Asp Thr
145                 150                 155                 160

Pro Thr Asn Gly Lys Asn His Ser Val Ser Arg His Pro Lys Leu Trp
                165                 170                 175

Tyr Thr Ala Ala His His Thr Ser Leu Asp Gln Ser Ser Pro Pro Leu
            180                 185                 190

Ser Gly Thr Ser Pro Ser Tyr Lys Tyr Thr Leu Pro Gly Ala Gln Asp
        195                 200                 205

Ala Lys Asp Asp Phe Pro Leu Arg Lys Thr Ala Ser Glu Pro Asn Leu
    210                 215                 220

Lys Val Arg Ser Arg Leu Lys Gln Lys Val Ala Glu Arg Arg Ser Ser
225                 230                 235                 240

Pro Leu Leu Arg Arg Lys Asp Gly Asn Val Val Thr Ser Phe Lys Lys
                245                 250                 255

Arg Met Phe Glu Val Thr Glu Ser Ser Val Ser Ser Ser Ser Pro Gly
            260                 265                 270

Ser Gly Pro Ser Ser Pro Asn Asn Gly Pro Thr Gly Ser Val Thr Glu
        275                 280                 285

Asn Glu Thr Ser Val Leu Pro Pro Thr Pro His Ala Glu Gln Met Val
    290                 295                 300

Ser Gln Gln Arg Ile Leu Ile His Glu Asp Ser Met Asn Leu Leu Ser
305                 310                 315                 320

Leu Tyr Thr Ser Pro Ser Leu Pro Asn Ile Thr Leu Gly Leu Pro Ala
                325                 330                 335

Val Pro Ser Gln Leu Asn Ala Ser Asn Ser Leu Lys Glu Lys Gln Lys
            340                 345                 350

Cys Glu Thr Gln Thr Leu Arg Gln Gly Val Pro Leu Pro Gly Gln Tyr
        355                 360                 365

Gly Gly Ser Ile Pro Ala Ser Ser Ser His Pro His Val Thr Leu Glu
    370                 375                 380

Gly Lys Pro Pro Asn Ser Ser His Gln Ala Leu Leu Gln His Leu Leu
385                 390                 395                 400

Leu Lys Glu Gln Met Arg Gln Gln Lys Leu Leu Val Ala Gly Gly Val
                405                 410                 415

Pro Leu His Pro Gln Ser Pro Leu Ala Thr Lys Glu Arg Ile Ser Pro
            420                 425                 430

Gly Ile Arg Gly Thr His Lys Leu Pro Arg His Arg Pro Leu Asn Arg
        435                 440                 445

Thr Gln Ser Ala Pro Leu Pro Gln Ser Thr Leu Ala Gln Leu Val Ile
    450                 455                 460

Gln Gln Gln His Gln Gln Phe Leu Glu Lys Gln Lys Gln Tyr Gln Gln
465                 470                 475                 480

Gln Ile His Met Asn Lys Leu Leu Ser Lys Ser Ile Glu Gln Leu Lys
                485                 490                 495

Gln Pro Gly Ser His Leu Glu Glu Ala Glu Glu Glu Leu Gln Gly Asp
            500                 505                 510

Gln Ala Met Gln Glu Asp Arg Ala Pro Ser Ser Gly Asn Ser Thr Arg
        515                 520                 525

Ser Asp Ser Ser Ala Cys Val Asp Asp Thr Leu Gly Gln Val Gly Ala
    530                 535                 540

Val Lys Val Lys Glu Glu Pro Val Asp Ser Asp Glu Asp Ala Gln Ile
```

-continued 545 550 555 560

Gln Glu Met Glu Ser Gly Glu Gln Ala Ala Phe Met Gln Gln Val Ile
565 570 575

Gly Lys Asp Leu Ala Pro Gly Phe Val Ile Lys Val Ile Ile
580 585 590

<210> SEQ ID NO 12
<211> LENGTH: 1084
<212> TYPE: PRT
<213> ORGANISM: Homo sapiens

<400> SEQUENCE: 12

Met Ser Ser Gln Ser His Pro Asp Gly Leu Ser Gly Arg Asp Gln Pro
1 5 10 15

Val Glu Leu Leu Asn Pro Ala Arg Val Asn His Met Pro Ser Thr Val
20 25 30

Asp Val Ala Thr Ala Leu Pro Leu Gln Val Ala Pro Ser Ala Val Pro
35 40 45

Met Asp Leu Arg Leu Asp His Gln Phe Ser Leu Pro Val Ala Glu Pro
50 55 60

Ala Leu Arg Glu Gln Gln Leu Gln Gln Glu Leu Leu Ala Leu Lys Gln
65 70 75 80

Lys Gln Gln Ile Gln Arg Gln Ile Leu Ile Ala Glu Phe Gln Arg Gln
85 90 95

His Glu Gln Leu Ser Arg Gln His Glu Ala Gln Leu His Glu His Ile
100 105 110

Lys Gln Gln Gln Glu Met Leu Ala Met Lys His Gln Gln Glu Leu Leu
115 120 125

Glu His Gln Arg Lys Leu Glu Arg His Arg Gln Glu Gln Glu Leu Glu
130 135 140

Lys Gln His Arg Glu Gln Lys Leu Gln Gln Leu Lys Asn Lys Glu Lys
145 150 155 160

Gly Lys Glu Ser Ala Val Ala Ser Thr Glu Val Lys Met Lys Leu Gln
165 170 175

Glu Phe Val Leu Asn Lys Lys Lys Ala Leu Ala His Arg Asn Leu Asn
180 185 190

His Cys Ile Ser Ser Asp Pro Arg Tyr Trp Tyr Gly Lys Thr Gln His
195 200 205

Ser Ser Leu Asp Gln Ser Ser Pro Pro Gln Ser Gly Val Ser Thr Ser
210 215 220

Tyr Asn His Pro Val Leu Gly Met Tyr Asp Ala Lys Asp Asp Phe Pro
225 230 235 240

Leu Arg Lys Thr Ala Ser Glu Pro Asn Leu Lys Leu Arg Ser Arg Leu
245 250 255

Lys Gln Lys Val Ala Glu Arg Arg Ser Ser Pro Leu Leu Arg Arg Lys
260 265 270

Asp Gly Pro Val Val Thr Ala Leu Lys Lys Arg Pro Leu Asp Val Thr
275 280 285

Asp Ser Ala Cys Ser Ser Ala Pro Gly Ser Gly Pro Ser Ser Pro Asn
290 295 300

Asn Ser Ser Gly Ser Val Ser Ala Glu Asn Gly Ile Ala Pro Ala Val
305 310 315 320

Pro Ser Ile Pro Ala Glu Thr Ser Leu Ala His Arg Leu Val Ala Arg
325 330 335

-continued

```
Glu Gly Ser Ala Ala Pro Leu Pro Leu Tyr Thr Ser Pro Ser Leu Pro
            340                 345                 350

Asn Ile Thr Leu Gly Leu Pro Ala Thr Gly Pro Ser Ala Gly Thr Ala
        355                 360                 365

Gly Gln Gln Asp Thr Glu Arg Leu Thr Leu Pro Ala Leu Gln Gln Arg
    370                 375                 380

Leu Ser Leu Phe Pro Gly Thr His Leu Thr Pro Tyr Leu Ser Thr Ser
385                 390                 395                 400

Pro Leu Glu Arg Asp Gly Gly Ala Ala His Ser Pro Leu Leu Gln His
                405                 410                 415

Met Val Leu Leu Glu Gln Pro Pro Ala Gln Ala Pro Leu Val Thr Gly
            420                 425                 430

Leu Gly Ala Leu Pro Leu His Ala Gln Ser Leu Val Gly Ala Asp Arg
        435                 440                 445

Val Ser Pro Ser Ile His Lys Leu Arg Gln His Arg Pro Leu Gly Arg
    450                 455                 460

Thr Gln Ser Ala Pro Leu Pro Gln Asn Ala Gln Ala Leu Gln His Leu
465                 470                 475                 480

Val Ile Gln Gln Gln His Gln Gln Phe Leu Glu Lys His Lys Gln Gln
                485                 490                 495

Phe Gln Gln Gln Gln Leu Gln Met Asn Lys Ile Ile Pro Lys Pro Ser
            500                 505                 510

Glu Pro Ala Arg Gln Pro Glu Ser His Pro Glu Glu Thr Glu Glu Glu
        515                 520                 525

Leu Arg Glu His Gln Ala Leu Leu Asp Glu Pro Tyr Leu Asp Arg Leu
    530                 535                 540

Pro Gly Gln Lys Glu Ala His Ala Gln Ala Gly Val Gln Val Lys Gln
545                 550                 555                 560

Glu Pro Ile Glu Ser Asp Glu Glu Glu Ala Glu Pro Pro Arg Glu Val
                565                 570                 575

Glu Pro Gly Gln Arg Gln Pro Ser Glu Gln Glu Leu Leu Phe Arg Gln
            580                 585                 590

Gln Ala Leu Leu Leu Glu Gln Gln Arg Ile His Gln Leu Arg Asn Tyr
        595                 600                 605

Gln Ala Ser Met Glu Ala Ala Gly Ile Pro Val Ser Phe Gly Gly His
    610                 615                 620

Arg Pro Leu Ser Arg Ala Gln Ser Ser Pro Ala Ser Ala Thr Phe Pro
625                 630                 635                 640

Val Ser Val Gln Glu Pro Pro Thr Lys Pro Arg Phe Thr Thr Gly Leu
                645                 650                 655

Val Tyr Asp Thr Leu Met Leu Lys His Gln Cys Thr Cys Gly Ser Ser
            660                 665                 670

Ser Ser His Pro Glu His Ala Gly Arg Ile Gln Ser Ile Trp Ser Arg
        675                 680                 685

Leu Gln Glu Thr Gly Leu Arg Gly Lys Cys Glu Cys Ile Arg Gly Arg
    690                 695                 700

Lys Ala Thr Leu Glu Glu Leu Gln Thr Val His Ser Glu Ala His Thr
705                 710                 715                 720

Leu Leu Tyr Gly Thr Asn Pro Leu Asn Arg Gln Lys Leu Asp Ser Lys
                725                 730                 735

Lys Leu Leu Gly Ser Leu Ala Ser Val Phe Val Arg Leu Pro Cys Gly
            740                 745                 750

Gly Val Gly Val Asp Ser Asp Thr Ile Trp Asn Glu Val His Ser Ala
```

-continued

```
        755                 760                 765

Gly Ala Ala Arg Leu Ala Val Gly Cys Val Val Glu Leu Val Phe Lys
    770                 775                 780

Val Ala Thr Gly Glu Leu Lys Asn Gly Phe Ala Val Val Arg Pro Pro
785                 790                 795                 800

Gly His His Ala Glu Glu Ser Thr Pro Met Gly Phe Cys Tyr Phe Asn
                805                 810                 815

Ser Val Ala Val Ala Ala Lys Leu Leu Gln Gln Arg Leu Ser Val Ser
            820                 825                 830

Lys Ile Leu Ile Val Asp Trp Asp Val His His Gly Asn Gly Thr Gln
        835                 840                 845

Gln Ala Phe Tyr Ser Asp Pro Ser Val Leu Tyr Met Ser Leu His Arg
    850                 855                 860

Tyr Asp Asp Gly Asn Phe Phe Pro Gly Ser Gly Ala Pro Asp Glu Val
865                 870                 875                 880

Gly Thr Gly Pro Gly Val Gly Phe Asn Val Asn Met Ala Phe Thr Gly
                885                 890                 895

Gly Leu Asp Pro Pro Met Gly Asp Ala Glu Tyr Leu Ala Ala Phe Arg
            900                 905                 910

Thr Val Val Met Pro Ile Ala Ser Glu Phe Ala Pro Asp Val Val Leu
        915                 920                 925

Val Ser Ser Gly Phe Asp Ala Val Glu Gly His Pro Thr Pro Leu Gly
    930                 935                 940

Gly Tyr Asn Leu Ser Ala Arg Cys Phe Gly Tyr Leu Thr Lys Gln Leu
945                 950                 955                 960

Met Gly Leu Ala Gly Gly Arg Ile Val Leu Ala Leu Glu Gly Gly His
                965                 970                 975

Asp Leu Thr Ala Ile Cys Asp Ala Ser Glu Ala Cys Val Ser Ala Leu
            980                 985                 990

Leu Gly Asn Glu Leu Asp Pro Leu Pro Glu Lys Val Leu Gln Gln Arg
        995                 1000                1005

Pro Asn Ala Asn Ala Val Arg Ser Met Glu Lys Val Met Glu Ile His
    1010                1015                1020

Ser Lys Tyr Trp Arg Cys Leu Gln Arg Thr Thr Ser Thr Ala Gly Arg
1025                1030                1035                1040

Ser Leu Ile Glu Ala Gln Thr Cys Glu Asn Glu Glu Ala Glu Thr Val
                1045                1050                1055

Thr Ala Met Ala Ser Leu Ser Val Gly Val Lys Pro Ala Glu Lys Arg
            1060                1065                1070

Pro Asp Glu Glu Pro Met Glu Glu Glu Pro Pro Leu
        1075                1080
```

<210> SEQ ID NO 13
<211> LENGTH: 3550
<212> TYPE: DNA
<213> ORGANISM: Homo sapiens

<400> SEQUENCE: 13

```
ggggaagaga ggcacagaca cagataggag aagggcaccg gctggagcca cttgcaggac     60

tgagggtttt tgcaacaaaa ccctagcagc ctgaagaact ctaagccaga tggggtggct    120

ggacgagagc agctcttggc tcagcaaaga atgcacagta tgatcagctc agtggatgtg    180

aagtcagaag ttcctgtggg cctggagccc atctcacctt tagacctaag gacagacctc    240

aggatgatga tgcccgtggt ggaccctgtt gtccgtgaga agcaattgca gcaggaatta    300
```

-continued

```
cttcttatcc agcagcagca acaaatccag aagcagcttc tgatagcaga gtttcagaaa    360
cagcatgaga acttgacacg gcagcaccag gctcagcttc aggagcatat caaggaactt    420
ctagccataa aacagcaaca agaactccta gaaaaggagc agaaactgga gcagcagagg    480
caagaacagg aagtagagag gcatcgcaga gaacagcagc ttcctcctct cagaggcaaa    540
gatagaggac gagaaagggc agtggcaagt acagaagtaa agcagaagct tcaagagttc    600
ctactgagta aatcagcaac gaaagacact ccaactaatg gaaaaaatca ttccgtgagc    660
cgccatccca agctctggta cacggctgcc caccacacat cattggatca aagctctcca    720
ccccttagtg gaacatctcc atcctacaag tacacattac caggagcaca agatgcaaag    780
gatgatttcc cccttcgaaa aactgcctct gagcccaact tgaaggtgcg gtccaggtta    840
aaacagaaag tggcagagag gagaagcagc cccttactca ggcggaagga tggaaatgtt    900
gtcacttcat tcaagaagcg aatgtttgag gtgacagaat cctcagtcag tagcagttct    960
ccaggctctg gtcccagttc accaaacaat gggccaactg gaagtgttac tgaaaatgag   1020
acttcggttt tgccccctac ccctcatgcc gagcaaatgg tttcacagca acgcattcta   1080
attcatgaag attccatgaa cctgctaagt ctttatacct ctccttcttt gcccaacatt   1140
accttggggc ttcccgcagt gccatcccag ctcaatgctt cgaattcact caaagaaaag   1200
cagaagtgtg agacgcagac gcttaggcaa ggtgttcctc tgcctgggca gtatggaggc   1260
agcatcccgg catcttccag ccaccctcat gttactttag agggaaagcc acccaacagc   1320
agccaccagg ctctcctgca gcatttatta ttgaaagaac aaatgcgaca gcaaaagctt   1380
cttgtagctg gtggagttcc cttacatcct cagtctccct tggcaacaaa agagagaatt   1440
tcacctggca ttagaggtac ccacaaattg ccccgtcaca gacccctgaa ccgaacccag   1500
tctgcacctt tgcctcagag cacgttggct cagctggtca ttcaacagca acaccagcaa   1560
ttcttggaga agcagaagca ataccagcag cagatccaca tgaacaaact gctttcgaaa   1620
tctattgaac aactgaagca accaggcagt caccttgagg aagcagagga agagcttcag   1680
ggggaccagg cgatgcagga agacagagcg ccctctagtg gcaacagcac taggagcgac   1740
agcagtgctt gtgtggatga cacactggga caagttgggg ctgtgaaggt caaggaggaa   1800
ccagtggaca gtgatgaaga tgctcagatc caggaaatgg aatctgggga gcaggctgct   1860
tttatgcaac aggtaatagg caaagattta gctccaggat ttgtaattaa agtcattatc   1920
tgacctttcc tggaacccac gcacacacgt gcgctctctg tgcgccaagc tccgctggct   1980
gcggttggca tggatggatt agagaaacac cgtctcgtct ccaggactca ctcttcccct   2040
gctgcctctg ttttacctca cccagcaatg gaccgccccc tccagcctgg ctctgcaact   2100
ggaattgcct atgacccctt gatgctgaaa caccagtgcg tttgtggcaa ttccaccacc   2160
caccctgagc atgctggacg aatacagagt atctggtcac gactgcaaga aactgggctg   2220
ctaaataaat gtgagcgaat tcaaggtcga aaagccagcc tggaggaaat acagcttgtt   2280
cattctgaac atcactcact gttgtatggc accaaccccc tggacggaca gaagctggac   2340
cccaggatac tcctaggtga tgactctcaa aagttttttt cctcattacc ttgtggtgga   2400
cttggggtgg acagtgacac catttggaat gagctacact cgtccggtgc tgcacgcatg   2460
gctgttggct gtgtcatcga gctggcttcc aaagtggcct caggagagct gaagaatggg   2520
tttgctgttg tgaggccccc tggccatcac gctgaagaat ccacagccat ggggttctgc   2580
ttttttaatt cagttgcaat taccgccaaa tacttgagag accaactaaa tataagcaag   2640
```

-continued

```
atattgattg tagatctgga tgttcaccat ggaaacggta cccagcaggc cttttatgct   2700

gaccccagca tcctgtacat ttcactccat cgctatgatg aagggaactt tttccctggc   2760

agtggagccc caaatgaggt tcggtttatt tctttagagc cccactttta tttgtatctt   2820

tcaggtaatt gcattgcatg attacccta atttcttgt cctttgctgg tgttttaaat   2880

tacacgagat tactgaattg tcccatggga ccaagaacca gtgcagaaca agtgcataac   2940

ccagagcact gtttgtcagg gaaggttggg ctgatttgat gtgttgtttg atgtttattt   3000

caagagctcc catgtgcttg ttttcctctc ttcttgcttt cttccatttg ctctcttctc   3060

tgcccaccgt ggtgtgtctt tctcttccca ggttggaaca ggccttggag aagggtacaa   3120

tataaatatt gcctggacag gtggccttga tcctcccatg ggagatgttg agtaccttga   3180

agcattcagg accatcgtga agcctgtggc caaagagttt gatccagaca tggtcttagt   3240

atctgctgga tttgatgcat tggaaggcca cacccctcct ctaggagggt acaaagtgac   3300

ggcaaaatgt tttggtcatt tgacgaagca attgatgaca ttggctgatg gacgtgtggt   3360

gttggctcta gaaggaggac atgatctcac agccatctgt gatgcatcag aagcctgtgt   3420

aaatgccctt ctaggaaatg agctggagcc acttgcagaa gatattctcc accaaagccc   3480

gaatatgaat gctgttattt ctttacagaa gatcattgaa attcaaagta tgtctttaaa   3540

gttctcttaa                                                          3550
```

<210> SEQ ID NO 14
<211> LENGTH: 7699
<212> TYPE: DNA
<213> ORGANISM: Homo sapiens

<400> SEQUENCE: 14

```
cccattcgcc attcaggctg cgcaactgtt gggaagggcg atcggtgcgg gcctcttcgc     60

tattacgcca gctggcgaaa gggggatgtg ctgcaaggcg attaagttgg gtaacgccca    120

gggttttccc agtcacgacg ttgtaaaacg acggccagtg ccaagctgat ctaatcaata    180

ttggccatta gccatattat tcattggtta tatagcataa atcaatattg gctattggcc    240

attgcatacg ttgtatccat atcataatat gtacatttat attggctcat gtccaacatt    300

accgccatgt tgacattgat tattgactag ttattaatag taatcaatta cggggtcatt    360

agttcatagc ccatatatgg agttccgcgt tacataactt acggtaaatg gcccgcctgg    420

cgaccgccca gcgacccccg cccgttgacg tcaatagtga cgtatgttcc catagtaacg    480

ccaataggga ctttccattg acgtcaatgg gtggagtatt tacggtaaac tgcccacttg    540

gcagtacatc aagtgtatca tatgccaagt ccgcccccta ttgacgtcaa tgacggtaaa    600

tggcccgcct agcattatgc ccagtacatg accttacggg agtttcctac ttggcagtac    660

atctacgtat tagtcatcgc tattaccatg gtgatgcggt tttggcagta caccaatggg    720

cgtggatagc ggtttgactc acggggattt ccaagtctcc accccattga cgtcaatggg    780

agtttgtttt ggcaccaaaa tcaacgggac tttccaaaat gtcgtaataa ccccgccccg    840

ttgacgcaaa tgggcggtag gcgtgtacgg tgggaggtct atataagcag agctcgttta    900

gtgaaccgtc agaattcaag cttgcggccg cagatctatc gatctgcagg atatcaccat    960

gcacagtatg atcagctcag tggatgtgaa gtcagaagtt cctgtgggcc tggagcccat   1020

ctcaccttta gacctaagga cagacctcag gatgatgatg cccgtggtgg accctgttgt   1080

ccgtgagaag caattgcagc aggaattact tcttatccag cagcagcaac aaatccagaa   1140

gcagcttctg atagcagagt ttcagaaaca gcatgagaac ttgacacggc agcaccaggc   1200
```

-continued

```
tcagcttcag gagcatatca aggaacttct agccataaaa cagcaacaag aactcctaga   1260
aaaggagcag aaactggagc agcagaggca agaacaggaa gtagagaggc atcgcagaga   1320
acagcagctt cctcctctca gaggcaaaga tagaggacga gaaagggcag tggcaagtac   1380
agaagtaaag cagaagcttc aagagttcct actgagtaaa tcagcaacga aagacactcc   1440
aactaatgga aaaaatcatt ccgtgagccg ccatcccaag ctctggtaca cggctgccca   1500
ccacacatca ttggatcaaa gctctccacc ccttagtgga acatctccat cctacaagta   1560
cacattacca ggagcacaag atgcaaagga tgatttcccc cttcgaaaaa ctgcctctga   1620
gcccaacttg aaggtgcggt ccaggttaaa acagaaagtg gcagagagga gaagcagccc   1680
cttactcagg cggaaggatg gaaatgttgt cacttcattc aagaagcgaa tgtttgaggt   1740
gacagaatcc tcagtcagta gcagttctcc aggctctggt cccagttcac caaacaatgg   1800
gccaactgga agtgttactg aaaatgagac ttcggttttg ccccctaccc ctcatgccga   1860
gcaaatggtt tcacagcaac gcattctaat tcatgaagat tccatgaacc tgctaagtct   1920
ttatacctct ccttctttgc ccaacattac cttggggctt cccgcagtgc catcccagct   1980
caatgcttcg aattcactca aagaaaagca gaagtgtgag acgcagacgc ttaggcaagg   2040
tgttcctctg cctgggcagt atggaggcag catcccggca tcttccagcc accctcatgt   2100
tactttagag ggaaagccac ccaacagcag ccaccaggct ctcctgcagc atttattatt   2160
gaaagaacaa atgcgacagc aaaagcttct tgtagctggt ggagttccct tacatcctca   2220
gtctcccttg gcaacaaaag agagaatttc acctggcatt agaggtaccc acaaattgcc   2280
ccgtcacaga cccctgaacc gaacccagtc tgcacctttg cctcagagca cgttggctca   2340
gctggtcatt caacagcaac accagcaatt cttggagaag cagaagcaat accagcagca   2400
gatccacatg aacaaactgc tttcgaaatc tattgaacaa ctgaagcaac caggcagtca   2460
ccttgaggaa gcagaggaag agcttcaggg ggaccaggcg atgcaggaag acagagcgcc   2520
ctctagtggc aacagcacta ggagcgacag cagtgcttgt gtggatgaca cactgggaca   2580
agttggggct gtgaaggtca aggaggaacc agtggacagt gatgaagatg ctcagatcca   2640
ggaaatggaa tctggggagc aggctgcttt tatgcaacag cctttcctgg aacccacgca   2700
cacacgtgcg ctctctgtgc gccaagctcc gctggctgcg gttggcatgg atggattaga   2760
gaaacaccgt ctcgtctcca ggactcactc ttcccctgct gcctctgttt tacctcaccc   2820
agcaatggac cgcccccctcc agcctggctc tgcaactgga attgcctatg accccttgat   2880
gctgaaacac cagtgcgttt gtggcaattc caccacccac cctgagcatg ctggacgaat   2940
acagagtatc tggtcacgac tgcaagaaac tgggctgcta aataaatgtg agcgaattca   3000
aggtcgaaaa gccagcctgg aggaaataca gcttgttcat tctgaacatc actcactgtt   3060
gtatggcacc aacccccctgg acggacagaa gctggacccc aggatactcc taggtgatga   3120
ctctcaaaag tttttttcct cattaccttg tggtggactt ggggtggaca gtgacaccat   3180
ttggaatgag ctacactcgt ccggtgctgc acgcatggct gttggctgtg tcatcgagct   3240
ggcttccaaa gtggcctcag gagagctgaa gaatgggttt gctgttgtga ggcccccctgg   3300
ccatcacgct gaagaatcca cagccatggg gttctgcttt tttaattcag ttgcaattac   3360
cgccaaatac ttgagagacc aactaaatat aagcaagata ttgattgtag atctggatgt   3420
tcaccatgga aacggtaccc agcaggcctt ttatgctgac cccagcatcc tgtacatttc   3480
actccatcgc tatgatgaag ggaacttttt ccctggcagt ggagccccaa atgaggttgg   3540
```

-continued

```
aacaggcctt ggagaagggt acaatataaa tattgcctgg acaggtggcc ttgatcctcc   3600
catgggagat gttgagtacc ttgaagcatt caggaccatc gtgaagcctg tggccaaaga   3660
gtttgatcca gacatggtct tagtatctgc tggatttgat gcattggaag gccacacccc   3720
tcctctagga gggtacaaag tgacggcaaa atgttttggt catttgacga agcaattgat   3780
gacattggct gatggacgtg tggtgttggc tctagaagga ggacatgatc tcacagccat   3840
ctgtgatgca tcagaagcct gtgtaaatgc ccttctagga aatgagctgg agccacttgc   3900
agaagatatt ctccaccaaa gcccgaatat gaatgctgtt atttctttac agaagatcat   3960
tgaaattcaa agtatgtctt taaagttctc tggatccggt accagattac aaggacgacg   4020
atgacaagta gatcccgggt ggcatccctg tgacccctcc ccagtgcctc tcctggcctt   4080
ggaagttgcc actccagtgc ccaccagcct tgtcctaata aaattaagtt gcatcatttt   4140
gtctgactag gtgtcctcta taatattatg gggtggaggg gggtggtatg gagcaagggg   4200
cccaagttgg gaagacaacc tgtagggcct gcggggtcta ttcgggaacc aagctggagt   4260
gcagtggcac aatcttggct cactgcaatc tccgcctcct gggttcaagc gattctcctg   4320
cctcagcctc ccgagttgtt gggattccag gcatgcatga ccaggctcag ctaatttttg   4380
tttttttggt agagacgggg tttcaccata ttggccaggc tggtctccaa ctcctaatct   4440
caggtgatct acccaccttg gcctcccaaa ttgctgggat tacaggcgtg aaccactgct   4500
cccttccctg tccttctgat tttaaaataa ctataccagc aggaggacgt ccagacacag   4560
cataggctac ctgccatggc ccaaccggtg ggacatttga gttgcttgct tggcactgtc   4620
ctctcatgcg ttgggtccac tcagtagatg cctgttgaat tgggtacgcg gccagcttct   4680
gtggaatgtg tgtcagttag ggtgtggaaa gtccccaggc tccccagcag gcagaagtat   4740
gcaaagcatg catctcaatt agtcagcaac caggtgtgga aagtccccca ggctccccag   4800
caggcagaag tatgcaaagc atgcatctca attagtcagc aaccatagtc ccgcccctaa   4860
ctccgcccat cccgccccta actccgccca gttccgccca ttctccgccc catggctgac   4920
taattttttt tatttatgca gaggccgagg ccgcctcggc ctctgagcta ttccagaagt   4980
agtgaggagg cttttttgga ggcctaggct tttgcaaaaa gctcctcgag gaactgaaaa   5040
accagaaagt taattcccta tagtgagtcg tattaaattc gtaatcatgg tcatagctgt   5100
ttcctgtgtg aaattgttat ccgctcacaa ttccacacaa catacgagcc ggaagcataa   5160
agtgtaaagc ctggggtgcc taatgagtga gctaactcac attaattgcg ttgcgctcac   5220
tgcccgcttt ccagtcggga aacctgtcgt gccagctgca ttaatgaatc ggccaacgcg   5280
cggggagagg cggtttgcgt attgggcgct cttccgcttc ctcgctcact gactcgctgc   5340
gctcggtcgt tcggctgcgg cgagcggtat cagctcactc aaaggcggta atacggttat   5400
ccacagaatc aggggataac gcaggaaaga acatgtgagc aaaaggccag caaaaggcca   5460
ggaaccgtaa aaaggccgcg ttgctggcgt ttttccatag gctccgcccc cctgacgagc   5520
atcacaaaaa tcgacgctca agtcagaggt ggcgaaaccc gacaggacta taaagatacc   5580
aggcgtttcc ccctggaagc tccctcgtgc gctctcctgt tccgaccctg ccgcttaccg   5640
gatacctgtc cgcctttctc ccttcgggaa gcgtggcgct ttctcaatgc tcacgctgta   5700
ggtatctcag ttcggtgtag gtcgttcgct ccaagctggg ctgtgtgcac gaaccccccg   5760
ttcagcccga ccgctgcgcc ttatccggta actatcgtct tgagtccaac ccggtaagac   5820
acgacttatc gccactggca gcagccactg gtaacaggat tagcagagcg aggtatgtag   5880
gcggtgctac agagttcttg aagtggtggc ctaactacgg ctacactaga agaacagtat   5940
```

-continued

```
ttggtatctg cgctctgctg aagccagtta ccttcggaaa aagagttggt agctcttgat   6000
ccggcaaaca aaccaccgct ggtagcggtg gtttttttgt ttgcaagcag cagattacgc   6060
gcagaaaaaa aggatctcaa gaagatcctt tgatcttttc tacggggtct gacgctcagt   6120
ggaacgaaaa ctcacgttaa gggattttgg tcatgagatt atcaaaaagg atcttcacct   6180
agatcctttt aaattaaaaa tgaagtttta aatcaatcta aagtatatat gagtaaactt   6240
ggtctgacag ttaccaatgc ttaatcagtg aggcacctat ctcagcgatc tgtctatttc   6300
gttcatccat agttgcctga ctccccgtcg tgtagataac tacgatacgg gagggcttac   6360
catctggccc cagtgctgca atgataccgc gagacccacg ctcaccggct ccagatttat   6420
cagcaataaa ccagccagcc ggaagggccg agcgcagaag tggtcctgca actttatccg   6480
cctccatcca gtctattaat tgttgccggg aagctagagt aagtagttcg ccagttaata   6540
gtttgcgcaa cgttgttgcc attgctacag gcatcgtggt gtcacgctcg tcgtttggta   6600
tggcttcatt cagctccggt tcccaacgat caaggcgagt tacatgatcc cccatgttgt   6660
gcaaaaaagc ggttagctcc ttcggtcctc cgatcgttgt cagaagtaag ttggccgcag   6720
tgttatcact catggttatg gcagcactgc ataattctct tactgtcatg ccatccgtaa   6780
gatgcttttc tgtgactggt gagtactcaa ccaagtcatt ctgagaatag tgtatgcggc   6840
gaccgagttg ctcttgcccg gcgtcaatac gggataatac cgcgccacat agcagaactt   6900
taaaagtgct catcattgga aaacgttctt cggggcgaaa actctcaagg atcttaccgc   6960
tgttgagatc cagttcgatg taacccactc gtgcacccaa ctgatcttca gcatctttta   7020
ctttcaccag cgtttctggg tgagcaaaaa caggaaggca aaatgccgca aaaaagggaa   7080
taagggcgac acggaaatgt tgaatactca tactcttcct ttttcaatat tattgaagca   7140
tttatcaggg ttattgtctc atgagcggat acatatttga atgtatttag aaaaataaac   7200
aaataggggt tccgcgcaca tttccccgaa aagtgccacc tgacgcgccc tgtagcggcg   7260
cattaagcgc ggcgggtgtg gtggttacgc gcagcgtgac cgctacactt gccagcgccc   7320
tagcgcccgc tcctttcgct ttcttccctt cctttctcgc cacgttcgcc ggctttcccc   7380
gtcaagctct aaatcggggc atccctttag ggttccgatt tagtgcttta cggcacctcg   7440
accccaaaaa acttgattag ggtgatggtt cacgtagtgg gccatcgccc tgatagacgg   7500
tttttcgccc tttgacgttg gagtccacgt tctttaatag tggactcttg ttccaaactg   7560
gaacaacact caaccctatc tcggtctatt cttttgattt ataagggatt ttgccgattt   7620
cggcctattg gttaaaaaat gagctgattt aacaaaaatt taacgcgaat tttaacaaaa   7680
tattaaacgt ttacaattt                                                 7699
```

<210> SEQ ID NO 15
<211> LENGTH: 7303
<212> TYPE: DNA
<213> ORGANISM: Homo sapiens

<400> SEQUENCE: 15

```
cccattcgcc attcaggctg cgcaactgtt gggaagggcg atcggtgcgg gcctcttcgc     60
tattacgcca gctggcgaaa gggggatgtg ctgcaaggcg attaagttgg gtaacgccca    120
gggttttccc agtcacgacg ttgtaaaacg acggccagtg ccaagctgat ctaatcaata    180
ttggccatta gccatattat tcattggtta tatagcataa atcaatattg gctattggcc    240
attgcatacg ttgtatccat atcataatat gtacatttat attggctcat gtccaacatt    300
```

-continued

```
accgccatgt tgacattgat tattgactag ttattaatag taatcaatta cggggtcatt    360
agttcatagc ccatatatgg agttccgcgt tacataactt acggtaaatg gcccgcctgg    420
cgaccgccca gcgacccccg cccgttgacg tcaatagtga cgtatgttcc catagtaacg    480
ccaataggga ctttccattg acgtcaatgg gtggagtatt tacggtaaac tgcccacttg    540
gcagtacatc aagtgtatca tatgccaagt ccgcccccta ttgacgtcaa tgacggtaaa    600
tggcccgcct agcattatgc ccagtacatg accttacggg agtttcctac ttggcagtac    660
atctacgtat tagtcatcgc tattaccatg gtgatgcggt tttggcagta caccaatggg    720
cgtggatagc ggtttgactc acggggattt ccaagtctcc accccattga cgtcaatggg    780
agtttgtttt ggcaccaaaa tcaacgggac tttccaaaat gtcgtaataa ccccgccccg    840
ttgacgcaaa tgggcggtag gcgtgtacgg tgggaggtct atataagcag agctcgttta    900
gtgaaccgtc agaattcaag cttgcggccg cagatctatc gatctgcagg atatcaccat    960
gcacagtatg atcagctcag tggatgtgaa gtcagaagtt cctgtgggcc tggagcccat   1020
ctcaccttta gacctaagga cagacctcag gatgatgatg cccgtggtgg accctgttgt   1080
ccgtgagaag caattgcagc aggaattact tcttatccag cagcagcaac aaatccagaa   1140
gcagcttctg atagcagagt ttcagaaaca gcatgagaac ttgacacggc agcaccaggc   1200
tcagcttcag gagcatatca aggaacttct agccataaaa cagcaacaag aactcctaga   1260
aaaggagcag aaactggagc agcagaggca agaacaggaa gtagagaggc atcgcagaga   1320
acagcagctt cctcctctca gaggcaaaga tagaggacga gaaagggcag tggcaagtac   1380
agaagtaaag cagaagcttc aagagttcct actgagtaaa tcagcaacga aagacactcc   1440
aactaatgga aaaaatcatt ccgtgagccg ccatcccaag ctctggtaca cggctgccca   1500
ccacacatca ttggatcaaa gctctccacc ccttagtgga acatctccat cctacaagta   1560
cacattacca ggagcacaag atgcaaagga tgatttcccc cttcgaaaaa ctgcctctga   1620
gcccaacttg aaggtgcggt ccaggttaaa acagaaagtg gcagagagga gaagcagccc   1680
cttactcagg cggaaggatg gaaatgttgt cacttcattc aagaagcgaa tgtttgaggt   1740
gacagaatcc tcagtcagta gcagttctcc aggctctggt cccagttcac caaacaatgg   1800
gccaactgga agtgttactg aaaatgagac ttcggttttg ccccctaccc ctcatgccga   1860
gcaaatggtt tcacagcaac gcattctaat tcatgaagat tccatgaacc tgctaagtct   1920
ttatacctct ccttctttgc ccaacattac cttggggctt cccgcagtgc catcccagct   1980
caatgcttcg aattcactca aagaaaagca gaagtgtgag acgcagacgc ttaggcaagg   2040
tgttcctctg cctgggcagt atggaggcag catcccggca tcttccagcc accctcatgt   2100
tactttagag ggaaagccac ccaacagcag ccaccaggct ctcctgcagc atttattatt   2160
gaaagaacaa atgcgacagc aaaagcttct tgtagctggt ggagttccct tacatcctca   2220
gtctcccttg gcaacaaaag agagaatttc acctggcatt agaggtaccc acaaattgcc   2280
ccgtcacaga cccctgaacc gaacccagtc tgcacctttg cctcagagca cgttggctca   2340
gctggtcatt caacagcaac accagcaatt cttggagaag cagaagcaat accagcagca   2400
gatccacatg aacaaactgc tttcgaaatc tattgaacaa ctgaagcaac caggcagtca   2460
ccttgaggaa gcagaggaag agcttcaggg ggaccaggcg atgcaggaag acagagcgcc   2520
ctctagtggc aacagcacta ggagcgacag cagtgcttgt gtggatgaca cactgggaca   2580
agttggggct gtgaaggtca aggaggaacc agtggacagt gatgaagatg ctcagatcca   2640
ggaaatggaa tctggggagc aggctgcttt tatgcaacag cctttcctgg aacccacgca   2700
```

-continued

```
cacacgtgcg ctctctgtgc gccaagctcc gctggctgcg gttggcatgg atggattaga   2760
gaaacaccgt ctcgtctcca ggactcactc ttcccctgct gcctctgttt tacctcaccc   2820
agcaatggac cgccccctcc agcctggctc tgcaactgga attgcctatg accccttgat   2880
gctgaaacac cagtgcgttt gtggcaattc caccacccac cctgagcatg ctggacgaat   2940
acagagtatc tggtcacgac tgcaagaaac tgggctgcta aataaatgtg agcgaattca   3000
aggtcgaaaa gccagcctgg aggaaataca gcttgttcat tctgaacatc actcactgtt   3060
gtatggcacc aaccccctgg acggacagaa gctggacccc aggatactcc taggtgatga   3120
ctctcaaaag ttttttttcct cattaccttg tggtggactt ggggtggaca gtgacaccat   3180
ttggaatgag ctacactcgt ccggtgctgc acgcatggct gttggctgtg tcatcgagct   3240
ggcttccaaa gtggcctcag gagagctgaa gaatgggttt gctgttgtga ggccccctgg   3300
ccatcacgct gaagaatcca cagccatggg gttctgcttt tttaattcag ttgcaattac   3360
cgccaaatac ttgagagacc aactaaatat aagcaagata ttgattgtag atctggatgt   3420
tcaccatgga aacggtaccc agcaggcctt ttatgctgac cccagcatcc tgtacatttc   3480
actccatcgc tatgatgaag ggaacttttt ccctggcagt ggagccccaa atgaggttcg   3540
gtttatttct ttagagcccc acttttattt gtatctttca ggtaattgca ttgcaggatc   3600
cggtaccaga ttacaaggac gacgatgaca agtagatccc gggtggcatc cctgtgaccc   3660
ctccccagtg cctctcctgg ccttggaagt tgccactcca gtgcccacca gccttgtcct   3720
aataaaatta agttgcatca ttttgtctga ctaggtgtcc tctataatat tatggggtgg   3780
aggggggtgg tatggagcaa ggggcccaag ttgggaagac aacctgtagg gcctgcgggg   3840
tctattcggg aaccaagctg gagtgcagtg gcacaatctt ggctcactgc aatctccgcc   3900
tcctgggttc aagcgattct cctgcctcag cctcccgagt tgttgggatt ccaggcatgc   3960
atgaccaggc tcagctaatt tttgtttttt tggtagagac ggggtttcac catattggcc   4020
aggctggtct ccaactccta atctcaggtg atctacccac cttggcctcc caaattgctg   4080
ggattacagg cgtgaaccac tgctcccttc cctgtccttc tgattttaaa ataactatac   4140
cagcaggagg acgtccagac acagcatagg ctacctgcca tggcccaacc ggtgggacat   4200
ttgagttgct tgcttggcac tgtcctctca tgcgttgggt ccactcagta gatgcctgtt   4260
gaattgggta cgcggccagc ttctgtggaa tgtgtgtcag ttagggtgtg gaaagtcccc   4320
aggctcccca gcaggcagaa gtatgcaaag catgcatctc aattagtcag caaccaggtg   4380
tggaaagtc cccaggctcc ccagcaggca gaagtatgca aagcatgcat ctcaattagt   4440
cagcaaccat agtcccgccc ctaactccgc ccatcccgcc cctaactccg cccagttccg   4500
cccattctcc gccccatggc tgactaattt tttttattta tgcagaggcc gaggccgcct   4560
cggcctctga gctattccag aagtagtgag gaggcttttt tggaggccta ggcttttgca   4620
aaaagctcct cgaggaactg aaaaaccaga aagttaattc cctatagtga gtcgtattaa   4680
attcgtaatc atggtcatag ctgtttcctg tgtgaaattg ttatccgctc acaattccac   4740
acaacatacg agccggaagc ataaagtgta aagcctgggg tgcctaatga gtgagctaac   4800
tcacattaat tgcgttgcgc tcactgcccg ctttccagtc gggaaacctg tcgtgccagc   4860
tgcattaatg aatcggccaa cgcgcgggga gaggcggttt gcgtattggg cgctcttccg   4920
cttcctcgct cactgactcg ctgcgctcgg tcgttcggct gcggcgagcg gtatcagctc   4980
actcaaaggc ggtaatacgg ttatccacag aatcagggga taacgcagga aagaacatgt   5040
```

-continued

```
gagcaaaagg ccagcaaaag gccaggaacc gtaaaaaggc cgcgttgctg gcgtttttcc   5100
ataggctccg cccccctgac gagcatcaca aaaatcgacg ctcaagtcag aggtggcgaa   5160
acccgacagg actataaaga taccaggcgt ttccccctgg aagctccctc gtgcgctctc   5220
ctgttccgac cctgccgctt accggatacc tgtccgcctt tctcccttcg ggaagcgtgg   5280
cgctttctca atgctcacgc tgtaggtatc tcagttcggt gtaggtcgtt cgctccaagc   5340
tgggctgtgt gcacgaaccc cccgttcagc ccgaccgctg cgccttatcc ggtaactatc   5400
gtcttgagtc caacccggta agacacgact tatcgccact ggcagcagcc actggtaaca   5460
ggattagcag agcgaggtat gtaggcggtg ctacagagtt cttgaagtgg tggcctaact   5520
acggctacac tagaagaaca gtatttggta tctgcgctct gctgaagcca gttaccttcg   5580
gaaaaagagt tggtagctct tgatccggca aacaaaccac cgctggtagc ggtggttttt   5640
ttgtttgcaa gcagcagatt acgcgcagaa aaaaaggatc tcaagaagat cctttgatct   5700
tttctacggg gtctgacgct cagtggaacg aaaactcacg ttaagggatt ttggtcatga   5760
gattatcaaa aaggatcttc acctagatcc ttttaaatta aaaatgaagt tttaaatcaa   5820
tctaaagtat atatgagtaa acttggtctg acagttacca atgcttaatc agtgaggcac   5880
ctatctcagc gatctgtcta tttcgttcat ccatagttgc ctgactcccc gtcgtgtaga   5940
taactacgat acgggagggc ttaccatctg gccccagtgc tgcaatgata ccgcgagacc   6000
cacgctcacc ggctccagat ttatcagcaa taaaccagcc agccggaagg gccgagcgca   6060
gaagtggtcc tgcaacttta tccgcctcca tccagtctat taattgttgc cgggaagcta   6120
gagtaagtag ttcgccagtt aatagtttgc gcaacgttgt tgccattgct acaggcatcg   6180
tggtgtcacg ctcgtcgttt ggtatggctt cattcagctc cggttcccaa cgatcaaggc   6240
gagttacatg atcccccatg ttgtgcaaaa aagcggttag ctccttcggt cctccgatcg   6300
ttgtcagaag taagttggcc gcagtgttat cactcatggt tatggcagca ctgcataatt   6360
ctcttactgt catgccatcc gtaagatgct tttctgtgac tggtgagtac tcaaccaagt   6420
cattctgaga atagtgtatg cggcgaccga gttgctcttg cccggcgtca atacgggata   6480
ataccgcgcc acatagcaga actttaaaag tgctcatcat tggaaaacgt tcttcggggc   6540
gaaaactctc aaggatctta ccgctgttga gatccagttc gatgtaaccc actcgtgcac   6600
ccaactgatc ttcagcatct tttactttca ccagcgtttc tgggtgagca aaaacaggaa   6660
ggcaaaatgc cgcaaaaaag ggaataaggg cgacacggaa atgttgaata ctcatactct   6720
tcctttttca atattattga agcatttatc agggttattg tctcatgagc ggatacatat   6780
ttgaatgtat ttagaaaaat aaacaaatag gggttccgcg cacatttccc cgaaaagtgc   6840
cacctgacgc gccctgtagc ggcgcattaa gcgcggcggg tgtggtggtt acgcgcagcg   6900
tgaccgctac acttgccagc gccctagcgc ccgctccttt cgctttcttc ccttcctttc   6960
tcgccacgtt cgccggcttt ccccgtcaag ctctaaatcg ggcatccct ttagggttcc    7020
gatttagtgc tttacggcac ctcgacccca aaaaacttga ttagggtgat ggttcacgta   7080
gtgggccatc gccctgatag acggtttttc gccctttgac gttggagtcc acgttcttta   7140
atagtggact cttgttccaa actggaacaa cactcaaccc tatctcggtc tattcttttg   7200
atttataagg gattttgccg atttcggcct attggttaaa aaatgagctg atttaacaaa   7260
aatttaacgc gaattttaac aaaatattaa acgtttacaa ttt                    7303
```

<210> SEQ ID NO 16
<211> LENGTH: 24

-continued

<212> TYPE: DNA
<213> ORGANISM: Artificial Sequence
<220> FEATURE:
<223> OTHER INFORMATION: Primer used to amplify human DNA

<400> SEQUENCE: 16
ccatggaaac ggtacccagc aggc 24

<210> SEQ ID NO 17
<211> LENGTH: 23
<212> TYPE: DNA
<213> ORGANISM: Artificial Sequence
<220> FEATURE:
<223> OTHER INFORMATION: Primer used to amplify human DNA

<400> SEQUENCE: 17
cactccatcg ctatgatgaa ggg 23

<210> SEQ ID NO 18
<211> LENGTH: 23
<212> TYPE: DNA
<213> ORGANISM: Artificial Sequence
<220> FEATURE:
<223> OTHER INFORMATION: Primer used to amplify human DNA

<400> SEQUENCE: 18
agttcccttc atcatagcga tgg 23

<210> SEQ ID NO 19
<211> LENGTH: 20
<212> TYPE: DNA
<213> ORGANISM: Artificial Sequence
<220> FEATURE:
<223> OTHER INFORMATION: Primer used to amplify human DNA

<400> SEQUENCE: 19
aatgtacagg atgctggggt 20

<210> SEQ ID NO 20
<211> LENGTH: 25
<212> TYPE: DNA
<213> ORGANISM: Artificial Sequence
<220> FEATURE:
<223> OTHER INFORMATION: Primer used to amplify human DNA

<400> SEQUENCE: 20
cccttgtagc tggtggagtt ccctt 25

<210> SEQ ID NO 21
<211> LENGTH: 20
<212> TYPE: DNA
<213> ORGANISM: Artificial Sequence
<220> FEATURE:
<223> OTHER INFORMATION: Primer used to amplify human DNA

<400> SEQUENCE: 21
tgtgtcatcg agctggcttc 20

<210> SEQ ID NO 22
<211> LENGTH: 20
<212> TYPE: DNA
<213> ORGANISM: Artificial Sequence
<220> FEATURE:
<223> OTHER INFORMATION: Primer used to amplify human DNA -continued

<400> SEQUENCE: 22
atcttctgca agtggctcca 20